US009472763B2

(12) United States Patent
Yoshimura et al.

(10) Patent No.: US 9,472,763 B2
(45) **Date of Patent: *Oct. 18, 2016**

(54) MACROMOLECULAR COMPOUND

(75) Inventors: Ken Yoshimura, Tsukuba (JP); Kenichiro Ohya, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 539 days.

This patent is subject to a terminal disclaimer.

(21) Appl. No.: 13/502,673

(22) PCT Filed: Oct. 29, 2010

(86) PCT No.: PCT/JP2010/069256

§ 371 (c)(1), (2), (4) Date: Apr. 18, 2012

(87) PCT Pub. No.: WO2011/052709

PCT Pub. Date: May 5, 2011

(65) Prior Publication Data

US 2012/0205596 A1 Aug. 16, 2012

(30) Foreign Application Priority Data

| | | |
|---|---|---|
| Oct. 29, 2009 | (JP) | 2009-248792 |
| Mar. 11, 2010 | (JP) | 2010-054220 |
| Apr. 21, 2010 | (JP) | 2010-097604 |
| Apr. 28, 2010 | (JP) | 2010-104112 |
| Jul. 14, 2010 | (JP) | 2010-159414 |

(51) Int. Cl.

*H01L 51/00* (2006.01)
*C08G 61/12* (2006.01)
*H01L 51/05* (2006.01)

(52) U.S. Cl.

CPC ......... *H01L 51/0036* (2013.01); *C08G 61/126* (2013.01); *C08G 2261/3223* (2013.01); *C08G 2261/3246* (2013.01); *C08G 2261/344* (2013.01); *C08G 2261/364* (2013.01); *H01L 51/0043* (2013.01); *H01L 51/0545* (2013.01); *Y02E 10/549* (2013.01)

(58) Field of Classification Search

CPC .................... C08G 61/126; C08G 2261/3223; C08G 2261/3246; C08G 2261/344; C08G 2261/364; H01L 51/0036; H01L 51/0043; H01L 51/0545

USPC .................... 252/500, 501.1, 519.4; 528/373

See application file for complete search history.

(56) References Cited

U.S. PATENT DOCUMENTS

| | | | |
|---|---|---|---|
| 2007/0014939 | A1 | 1/2007 | Gaudiana et al. |
| 2007/0017571 | A1 | 1/2007 | Gaudiana et al. |
| 2007/0020526 | A1 | 1/2007 | Gaudiana et al. |
| 2007/0131270 | A1 | 6/2007 | Gaudiana et al. |
| 2007/0158620 | A1 | 7/2007 | Gaudiana et al. |
| 2007/0246094 | A1 | 10/2007 | Brabec et al. |
| 2007/0267055 | A1 | 11/2007 | Gaudiana et al. |
| 2008/0003422 | A1 | 1/2008 | Ueda |
| 2008/0006324 | A1 | 1/2008 | Berke et al. |
| 2008/0138651 | A1 | 6/2008 | Doi et al. |
| 2009/0065770 | A1 | 3/2009 | Miura et al. |
| 2010/0006154 | A1 | 1/2010 | Kitazawa et al. |

(Continued)

FOREIGN PATENT DOCUMENTS

| | | | | |
|---|---|---|---|---|
| CN | 1989169 A | | 6/2007 | |
| EP | 1571170 | * | 9/2005 | ............ C08G 61/00 |
| GB | 2432837 A | | 6/2007 | |

(Continued)

OTHER PUBLICATIONS

Office Action issued Jun. 3, 2014 in corresponding Japanese Patent Application No. 2010-243447 with English translation.

(Continued)

*Primary Examiner* — Brian P Mruk

(74) *Attorney, Agent, or Firm* — Sughrue Mion, PLLC

(57) ABSTRACT

The present invention provides a macromolecular compound by which the short-circuit current density and the photoelectric conversion efficiency are enhanced when the macromolecular compound is used in an organic layer contained in a photovoltaic cell. Specifically, the present invention provides a macromolecular compound having a structural unit represented by Formula (1):

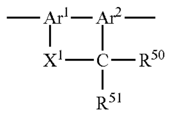

(1)

wherein $Ar^1$ and $Ar^2$ are the same as or different from each other and represent a trivalent heterocyclic group; $X^1$ represents —O—, —S—, —C(=O)—, —S(=O)—, —$SO_2$—, —$Si(R^3)(R^4)$—, —$N(R^5)$—, —$B(R^6)$—, —$P(R^7)$—, or —$P(=O)(R^8)$—; and $R^{51}$ represents an alkyl group having 6 or more carbon atoms, an alkyloxy group having 6 or more carbon atoms, an alkylthio group having 6 or more carbon atoms, an aryl group having 6 or more carbon atoms, an aryloxy group having 6 or more carbon atoms, an arylthio group having 6 or more carbon atoms, an arylalkyl group having 7 or more carbon atoms, an arylalkyloxy group having 7 or more carbon atoms, an arylalkylthio group having 7 or more carbon atoms, an acyl group having 6 or more carbon atoms, or an acyloxy group having 6 or more carbon atoms.

7 Claims, No Drawings

(56) References Cited

U.S. PATENT DOCUMENTS

| | | | |
|---|---|---|---|
| 2010/0084000 | A1 | 4/2010 | Ueda |
| 2010/0180944 | A1 | 7/2010 | Gaudiana et al. |

FOREIGN PATENT DOCUMENTS

| | | | |
|---|---|---|---|
| GB | 2466613 | A | 6/2010 |
| JP | 2004-168999 | A | 6/2004 |
| JP | 2006-063334 | A | 3/2006 |
| JP | 2008-109114 | A | 5/2008 |
| JP | 2009-506519 | A | 2/2009 |
| JP | 2009-096950 | A | 5/2009 |
| WO | 2007/105386 | A1 | 9/2007 |
| WO | 2008/044585 | A1 | 4/2008 |

OTHER PUBLICATIONS

First Office Action issued Jun. 26, 2013 in corresponding Chinese Patent Application No. 201080049149.9 with partial translation.

Communication from the State Intellectual Property Office of the People's Republic of China issue Aug. 28, 2014 in a counterpart Chinese Patent Application No. 201080049149.9.

Navacchia, M.L. et al., "Alkylenesulfanyl-Bridged Bithienyl Cores for Simultaneous Tuning of Electronic, Filming, and Thermal Properties of Oligothiophenes", Organic Letters, 2008, pp. 3665-3668, vol. 10, No. 17.

Huy, N. H., et al. "Dithienophosphinine", Organometallics, 2007, pp. 6497-6500, vol. 26, No. 25.

Huo L. et al., "Bandgap and Molecular Level Control of the Low-Bandgap Polymers Based on 3,6-Dithiophen-2-yl-2,5-dihydropyrrolo[3,4-c]pyrrole-1,4-dione toward Highly Efficient Polymer Solar Cells", Macromolecules, 2009; pp. 6564-6571, vol. 42, No. 17.

Xiao, S., et al., "Conjugated Polymers of Fused Bithiophenes with Enhanced π-Electron Delocalization for Photovoltaic Applications", Macromolecules, 2008, pp. 5688-5696, vol. 41, No. 15.

Second Office Action issued Feb. 17, 2014 in corresponding Chinese Patent Application No. 201080049149.9 with translation.

Chinese Office Action issued in corresponding CN Application No. 201080049149.9, dated Mar. 5, 2015.

* cited by examiner

MACROMOLECULAR COMPOUND

TECHNICAL FIELD

The present invention relates to a macromolecular compound having a specific structure.

BACKGROUND ART

In recent years, for the prevention of the global warming, the reduction of $CO_2$ discharged into the atmosphere is required. Therefore, for example, the adoption of a solar system using a PN junction-type silicon-based solar cell and the like is put forward. However, monocrystalline, multicrystalline, and amorphous silicon that are a material for a silicon-based solar cell require conditions of a high temperature and high vacuum in their production process.

By contrast, an organic thin film solar cell that is one example of the photovoltaic cell can omit a high temperature and high vacuum process used for a production process of a silicon-based solar cell and has the probability that it can be produced at low cost only by a coating process. Therefore, the organic thin film solar cell has been attracting attention in recent years. As the macromolecular compound used for an organic thin film solar cell, a macromolecular compound containing a repeated unit (A) and a repeated unit (B) is disclosed (Patent Literature 1).

[Chemical Formula 1]

Repeated Unit (A)

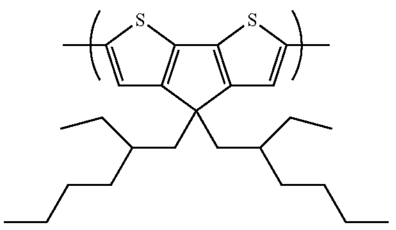

Repeated Unit (B)

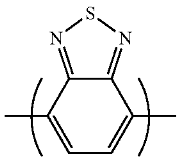

PRIOR ART LITERATURE

Patent Literature

Patent Literature 1: Japanese Patent Application Laid-open No. 2009-506519

SUMMARY OF THE INVENTION

Problem to be Solved by the Invention

However, a photovoltaic cell having an organic layer containing the macromolecular compound does not necessarily have a satisfactory short-circuit current density and a satisfactory photoelectric conversion efficiency.

It is an object of the present invention to provide a macromolecular compound by which the short-circuit current density and the photoelectric conversion efficiency of a photovoltaic cell are enhanced when the macromolecular compound is used for an organic layer contained in the photovoltaic cell.

Means for Solving Problem

Accordingly, the present invention firstly provides a macromolecular compound having a structural unit represented by Formula (1). The structural unit represented by Formula (1) is a divalent group.

[Chemical Formula 2]

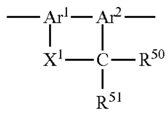

(1)

In the above Formula, $Ar^1$ and $Ar^2$ are the same as or different from each other and represent a trivalent heterocyclic group; $X^1$ represents —O—, —S—, —C(═O)—, —S(═O)—, —$SO_2$—, —$Si(R^3)(R^4)$—, —$N(R^5)$—, —$B(R^6)$—, —$P(R^7)$—, or —$P(=O)(R^8)$—; $R^3$, $R^4$, $R^5$, $R^6$, $R^7$, and $R^8$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $R^{50}$ represents a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $R^{51}$ represents an alkyl group having 6 or more carbon atoms, an alkyloxy group having 6 or more carbon atoms, an alkylthio group having 6 or more carbon atoms, an aryl group having 6 or more carbon atoms, an aryloxy group having 6 or more carbon atoms, an arylthio group having 6 or more carbon atoms, an arylalkyl group having 7 or more carbon atoms, an arylalkyloxy group having 7 or more carbon atoms, an arylalkylthio group having 7 or more carbon atoms, an acyl group having 6 or more carbon atoms, or an acyloxy group having 6 or more carbon atoms; and $X^1$ and $Ar^2$ are bonded with atoms adjacent to each other on the heterocycle that constitutes $Ar^1$, and $C(R^{50})(R^{51})$ and $Ar^1$ are bonded with atoms adjacent to each other on the heterocycle that constitutes $Ar^2$.

The present invention secondly provides a thin film comprising the above macromolecular compound.

The present invention thirdly provides a composition comprising the above macromolecular compound, and an electron acceptor compound.

The present invention fourthly provides a thin film comprising the above composition.

The present invention fifthly provides an ink comprising the above composition, and a solvent.

The present invention sixthly provides a compound represented by Formula (3).

[Chemical Formula 3]

(3)

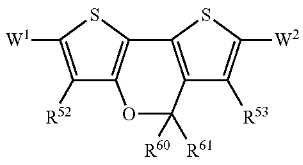

In the above Formula, $R^{52}$, $R^{53}$, $R^{60}$, and $R^{61}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; and $W^1$ and $W^2$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue.

The present invention seventhly provides a compound represented by Formula (4).

[Chemical Formula 4]

(4)

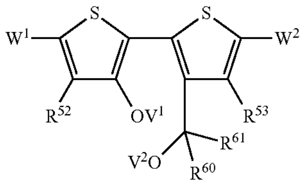

In the above Formula, $R^{60}$, $R^{61}$, $R^{52}$, and $R^{53}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $W^1$ and $W^2$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue; and $V^1$ and $V^2$ are the same as or different from each other and represent a hydrogen atom, an alkali metal, an alkyl group, an aryl group, or an arylalkyl group.

The present invention eighthly provides a compound represented by Formula (5).

[Chemical Formula 5]

(5)

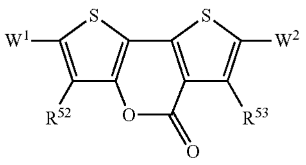

In the above Formula, $R^{52}$ and $R^{53}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; and $W^1$ and $W^2$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue.

The present invention ninthly provides a compound represented by Formula (5-1).

[Chemical Formula 6]

(5-1)

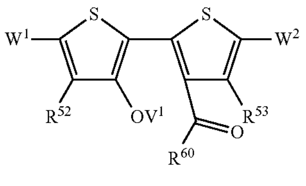

In the above Formula, $R^{60}$, $R^{52}$ and $R^{53}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $W^1$ and $W^2$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue; and $V^1$ represents a hydrogen atom, an alkali metal, an alkyl group, an aryl group or arylalkyl group.

The present invention tenthly provides compounds represented by Formula (8-1) and (8-2).

[Chemical Formula 7]

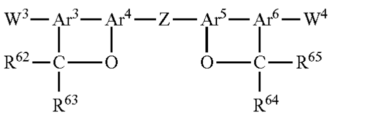

(8-1)

In the above Formula, $R^{62}$ to $R^{65}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $Ar^3$ to $Ar^6$ are the same as or different from each other and represent a trivalent heterocyclic group; $W^3$ and $W^4$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue; and Z represents an arylene group or a divalent heterocyclic group.

[Chemical Formula 8]

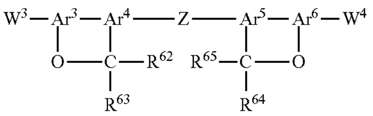

(8-2)

In the above Formula, $R^{62}$ to $R^{65}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $Ar^3$ to $Ar^6$ are the same as or different from each other and represent a trivalent heterocyclic group; $W^3$ and $W^4$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue; and Z represents an arylene group or a divalent heterocyclic group.

Effects of the Invention

The present invention is extremely useful since a photovoltaic cell having an organic layer containing the macromolecular compound of the present invention has a large short-circuit current density and a large photoelectric conversion efficiency.

EMBODIMENTS FOR CARRYING OUT THE INVENTION

Hereinafter, the present invention is described in detail.

The macromolecular compound of the present invention has a structural unit represented by Formula (1).

[Chemical Formula 9]

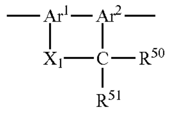

(1)

In Formula (1), $X^1$ represents —O—, —S—, —C(=O)—, —S(=O)—, —$SO_2$—, —Si($R^3$)($R^4$)—, —N($R^5$)—, —B($R^6$)—, —P($R^7$)—, or —P(=O) ($R^8$)—.

Here, $R^3$, $R^4$, $R^5$, $R^6$, $R^7$, and $R^8$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group.

Here, the alkyl group may be linear or branched, or a cycloalkyl group. The number of carbon atoms of the alkyl group is generally 1 to 30. Specific examples of the alkyl group may include a chain alkyl group such as a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a 1-methylbutyl group, an n-hexyl group, an isohexyl group, a 3-methylpentyl group, a 2-methylpentyl group, a 1-methylpentyl group, a heptyl group, an octyl group, an isooctyl group, a 2-ethylhexyl group, a 3,7-dimethyloctyl group, a nonyl group, a decyl group, an undecyl group, a dodecyl group, a tetradecyl group, a hexadecyl group, an octadecyl group and an eicosyl group, and a cycloalkyl group such as a cyclopentyl group, a cyclohexyl group and an adamantyl group.

The alkyloxy group may be linear or branched, or a cycloalkyloxy group. The alkyloxy group optionally has a substituent. The number of carbon atoms of the alkyloxy group is generally around 1 to 20. Specific examples of the alkyloxy group optionally having a substituent may include a methoxy group, an ethoxy group, a propoxy group, an iso-propoxy group, a butoxy group, an iso-butoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyl group, a perfluorooctyl group, a methoxymethyloxy group, and a 2-methoxyethyloxy group.

Here, in the present specification, the term "optionally has (having) a substituent" for a certain group means that a part or all of hydrogen atoms that the certain group has is (are) optionally substituted with a substituent. The term "optionally has a substituent" may be rephrased as "is optionally substituted." For example, a "divalent organic group optionally having a substituent" refers to a divalent organic group in which a part or all of hydrogen atoms in the divalent organic group is (are) optionally substituted with a substituent or substituents, and may be rephrased as a "divalent organic group that is optionally substituted". For example, a "hydrocarbon group optionally having a substituent" refers to a hydrocarbon group in which a part or all of hydrogen atoms in the hydrocarbon group is (are) optionally substituted with a substituent or substituents, and may be rephrased as a "hydrocarbon group that is optionally substituted."

The alkylthio group may be linear or branched, or a cycloalkylthio group. The alkylthio group optionally has a substituent. The number of carbon atoms of the alkylthio group is generally around 1 to 20. Specific examples of the alkylthio group optionally having a substituent may include a methylthio group, an ethylthio group, a propylthio group, an iso-propylthio group, a butylthio group, an iso-butylthio group, a tert-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group, and a trifluoromethylthio group.

For the aryl group, the number of carbon atoms thereof is generally around 6 to 60, and the aryl group optionally has a substituent. Specific examples of the aryl group optionally having a substituent may include a phenyl group, a C1-C12 alkyloxyphenyl group (C1-C12 alkyl means that the number of carbon atoms of the alkyl is 1 to 12; the C1-C12 alkyl is preferably C1-C8 alkyl, more preferably C1-C6 alkyl; the C1-C8 alkyl means alkyl having 1 to 8 carbon atoms and the C1-C6 alkyl means alkyl having 1 to 6 carbon atoms; and specific examples of the C1-C12 alkyl, the C1-C8 alkyl, and the C1-C6 alkyl may include the alkyl groups explained and exemplified above with respect to the alkyl group and the same hereinafter), a C1-C12 alkylphenyl group, a 1-naphthyl group, a 2-naphthyl group, and a pentafluorophenyl group.

For the aryloxy group, the number of carbon atoms thereof is generally around 6 to 60, and carbon atoms contained in its aromatic ring optionally have a substituent. Specific examples of the aryloxy group optionally having a substituent may include a phenoxy group, a C1-C12 alkyloxyphenoxy group, a C1-C12 alkylphenoxy group, a 1-naphthyloxy group, a 2-naphthyloxy group, and a pentafluorophenyloxy group.

For the arylthio group, the number of carbon atoms thereof is generally around 6 to 60, and carbon atoms contained in its aromatic ring optionally have a substituent. Specific examples of the arylthio group optionally having a substituent may include a phenylthio group, a C1-C12 alkyloxyphenylthio group, a C1-C12 alkylphenylthio group, a 1-naphthylthio group, a 2-naphthylthio group, and a pentafluorophenylthio group.

For the arylalkyl group, the number of carbon atoms thereof is generally around 7 to 60, and the arylalkyl group optionally has a substituent. Specific examples of the arylalkyl group optionally having a substituent may include a phenyl C1-C12 alkyl group, a C1-C12 alkyloxyphenyl C1-C12 alkyl group, a C1-C12 alkylphenyl C1-C12 alkyl group, a 1-naphthyl C1-C12 alkyl group, and a 2-naphthyl C1-C12 alkyl group.

For the arylalkyloxy group, the number of carbon atoms thereof is generally around 7 to 60, and the arylalkyloxy group optionally has a substituent. Specific examples of the arylalkyloxy group optionally having a substituent may include a phenyl C1-C12 alkyloxy group, a C1-C12 alkyloxyphenyl C1-C12 alkyloxy group, a C1-C12 alkylphenyl C1-C12 alkyloxy group, a 1-naphthyl C1-C12 alkyloxy group, and a 2-naphthyl C1-C12 alkyloxy group.

For the arylalkylthio group, the number of carbon atoms thereof is generally around 7 to 60, and the arylalkylthio group optionally has a substituent. Specific examples of the arylalkylthio group optionally having a substituent may include a phenyl C1-C12 alkylthio group, a C1-C12 alkyloxyphenyl C1-C12 alkylthio group, a C1-C12 alkylphenyl C1-C12 alkylthio group, a 1-naphthyl C1-C12 alkylthio group, and a 2-naphthyl C1-C12 alkylthio group.

For the acyl group, the number of carbon atoms thereof is generally around 2 to 20. Specific examples of the acyl group may include an acetyl group, a propionyl group, a butyryl group, an isobutyryl group, a pivaloyl group, a benzoyl group, a trifluoroacetyl group, and a pentafluorobenzoyl group.

For the acyloxy group, the number of carbon atoms thereof is generally around 2 to 20. Specific examples of the acyloxy group may include an acetoxy group, a propionyloxy group, a butyryloxy group, an isobutyryloxy group, a pivaloyloxy group, a benzoyloxy group, a trifluoroacetyloxy group, and a pentafluorobenzoyloxy group.

For the amido group, the number of carbon atoms thereof is generally around 1 to 20. The amido group refers to a group obtained by removing hydrogen atoms bonded to a nitrogen atom from an amide. Specific examples of the amido group may include a formamido group, an acetamido group, a propionamido group, a butyramido group, a benzamido group, a trifluoroacetamido group, a pentafluorobenzamido group, a diformamido group, a diacetamido group, a dipropionamido group, a dibutyramido group, a dibenzamido group, a ditrifluoroacetamido group, and a dipentafluorobenzamido group.

The acid imido group refers to a group obtained by removing hydrogen atoms bonded to a nitrogen atom from an acid imide. Specific examples of the acid imido group may include a succinimido group and a phthalic acid imido group.

For the substituted amino group, the number of carbon atoms thereof is generally around 1 to 40. Specific examples of the substituted amino group may include a methylamino group, a dimethylamino group, an ethylamino group, a diethylamino group, a propylamino group, a dipropylamino group, an isopropylamino group, a diisopropylamino group, a butylamino group, an isobutylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a C1-C12 alkyloxyphenylamino group, a di(C1-C12 alkyloxyphenyl)amino group, a di(C1-C12 alkylphenyl)amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl C1-C12 alkylamino group, a C1-C12 alkyloxyphenyl C1-C12 alkylamino group, a C1-C12 alkylphenyl C1-C12 alkylamino group, a di(C1-C12 alkyloxyphenyl C1-C12 alkyl)amino group, a di(C1-C12 alkylphenyl C1-C12 alkyl)amino group, a 1-naphthyl C1-C12 alkylamino group, and a 2-naphthyl C1-C12 alkylamino group.

Specific examples of the substituted silyl group may include a trimethylsilyl group, a triethylsilyl group, a tri-n-propylsilyl group, a triisopropylsilyl group, a tert-butyldimethylsilyl group, a triphenylsilyl group, a tri-p-xylylsilyl group, a tribenzylsilyl group, a diphenylmethylsilyl group, a tert-butyldiphenylsilyl group, and a dimethylphenylsilyl group.

Specific examples of the substituted silyloxy group may include a trimethylsilyloxy group, a triethylsilyloxy group, a tri-n-propylsilyloxy group, a tri-isopropylsilyloxy group, a tert-butyldimethylsilyloxy group, a triphenylsilyloxy group, a tri-p-xylylsilyloxy group, a tribenzylsilyloxy group, a diphenylmethylsilyloxy group, a tert-butyldiphenylsilyloxy group, and a dimethylphenylsilyloxy group.

Specific examples of the substituted silylthio group may include a trimethylsilylthio group, a triethylsilylthio group, a tri-n-propylsilylthio group, a tri-iso-propylsilylthio group, a tert-butyldimethylsilylthio group, a triphenylsilylthio group, a tri-p-xylylsilylthio group, a tribenzylsilylthio group, a diphenylmethylsilylthio group, a tert-butyldiphenylsilylthio group, and a dimethylphenylsilylthio group.

Specific examples of the substituted silylamino group may include a trimethylsilylamino group, a triethylsilylamino group, a tri-n-propylsilylamino group, a tri-isopropylsilylamino group, a tert-butyldimethylsilylamino group, a triphenylsilylamino group, a tri-p-xylylsilylamino group, a tribenzylsilylamino group, a diphenylmethylsilylamino group, a tert-butyldiphenylsilylamino group, a dimethylphenylsilylamino group, a di(trimethylsilyl)amino group, a di(triethylsilyl)amino group, a di(tri-n-propylsilyl)amino group, a di(tri-iso-propylsilyl)amino group, a di(tert-butyldimethylsilyl)amino group, a di(triphenylsilyl)amino group, a di(tri-p-xylylsilyl)amino group, a di(tribenzylsilyl)amino group, a di(diphenylmethylsilyl)amino group, a di(tert-butyldiphenylsilyl)amino group, and a di(dimethylphenylsilyl)amino group.

Examples of the monovalent heterocyclic group may include groups obtained by removing one hydrogen atom from a heterocyclic compound such as furan, thiophene, pyrrole, pyrroline, pyrrolidine, oxazole, isoxazole, thiazole, isothiazole, imidazole, imidazoline, imidazolidine, pyrazole, pyrazoline, pyrazolidine, furazan, triazole, thiadiazole, oxadiazole, tetrazole, pyran, pyridine, piperidine, thiopyran, pyridazine, pyrimidine, pyrazine, piperazine, morpholine, triazine, benzofuran, isobenzofuran, benzothiophene, indole, isoindole, indolizine, indoline, isoindoline, chromene, chromane, isochromane, benzopyran, quinoline, isoquinoline, quinolizine, benzimidazole, benzothiazole, indazole, naphthyridine, quinoxaline, quinazoline, quinazolidine, cinnoline, phthalazine, purine, pteridine, carbazole, xanthene, phenanthridine, acridine, β-carboline, perimidine, phenanthroline, thianthrene, phenoxathiin, phenoxazine, phenothiazine, and phenazine. The monovalent heterocyclic group optionally has a substituent. As the monovalent heterocyclic group, a monovalent aromatic heterocyclic group is preferred.

The heterocyclyloxy groups may include groups represented by Formula (11) in which an oxygen atom is bonded to the above monovalent heterocyclic group. The heterocyclylthio groups may include groups represented by Formula (12) in which a sulfur atom is bonded to the above monovalent heterocyclic group.

[Chemical Formula 10]

$$Ar^7—O— \quad (11)$$

$$Ar^7—S— \quad (12)$$

In Formula (11) and Formula (12), $Ar^7$ represents a monovalent heterocyclic group.

For the heterocyclyloxy group, the number of carbon atoms thereof is generally around 2 to 60. The heterocyclyloxy group optionally has a substituent. Specific examples of the heterocyclyloxy group optionally having a substituent may include a thienyloxy group, a C1-C12 alkylthienyloxy group, a pyrrolyloxy group, a furyloxy group, a pyridyloxy group, a C1-C12 alkylpyridyloxy group, an imidazolyloxy group, a pyrazolyloxy group, a triazolyloxy group, an oxazolyloxy group, a thiazoloxy group, and a thiadiazoleoxy group.

For the heterocyclylthio group, the number of carbon atoms thereof is generally around 2 to 60. The heterocyclylthio group optionally has a substituent. Specific examples of the heterocyclylthio group optionally having a substituent may include a thienylmercapto group, a C1-C12 alkylthienylmercapto group, a pyrrolylmercapto group, a furylmercapto group, a pyridylmercapto group, a C1-C12 alkylpyridylmercapto group, an imidazolylmercapto group, a pyrazolylmercapto group, a triazolylmercapto group, an oxazolylmercapto group, a thiazolemercapto group, and a thiadiazolemercapto group.

For the arylalkenyl group, the number of carbon atoms thereof is generally 8 to 20, and specific examples of the arylalkenyl group may include a styryl group.

For the arylalkynyl group, the number of carbon atoms thereof is generally 8 to 20, and specific examples of the arylalkynyl group may include a phenylacetylenyl group.

Specific examples of the halogen atom may include a fluorine atom, a chlorine atom, a bromine atom, and an iodine atom.

From the viewpoint of the easiness of the production of the monomer, $X^1$ is preferably —O—, —S—, or —C(═O)—, more preferably —O— or —C(═O)—, further preferably —O—.

In Formula (1), $Ar^1$ and $Ar^2$ are the same as or different from each other and represent a trivalent heterocyclic group. As illustrated in Formula (1), $Ar^1$ has three bonding sites and one of them is a bonding site with $Ar^2$, another is a bonding site with $X^1$, and the other is a bonding site with a hydrogen atom or other atoms. These other atoms may be a part of atoms constituting another constitutional unit. As illustrated in Formula (1), $Ar^2$ has three bonding sites and one of them is a bonding site with $Ar^1$, another is a bonding site with $X^2$, and the other is a bonding site with a hydrogen atom or other atoms. These other atoms may be a part of atoms constituting another constitutional unit.

The trivalent heterocyclic group refers to an atomic group obtained by removing three hydrogen atoms from a heterocyclic compound, and the number of carbon atoms of the trivalent heterocyclic group is generally 2 to 60, preferably 4 to 60, more preferably 4 to 20. The trivalent heterocyclic group optionally has a substituent on the heterocyclic group and the number of carbon atoms of the substituent is not included in the number of carbon atoms of the heterocyclic group. When the trivalent heterocyclic group has a substituent and the substituent contains carbon atoms, the number of carbon atoms of the substituent is preferably 1 to 40, more preferably 1 to 20, further preferably 1 to 6.

Here, the heterocyclic compound refers to an organic compound containing, in the ring thereof, as an element constituting the ring, not only a carbon atom, but also a heteroatom such as an oxygen atom, a sulfur atom, a nitrogen atom, a phosphorus atom, and a boron atom, among organic compounds having a cyclic structure.

Examples of the trivalent heterocyclic group may include trivalent groups below.

[Chemical Formula 11]

(201)

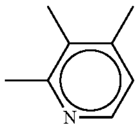

(202)

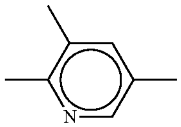

(203)

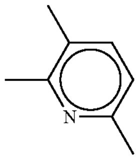

(204)

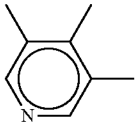

(205)

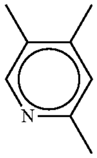

[Chemical Formula 12]

(206)

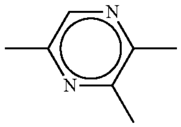

-continued (207)

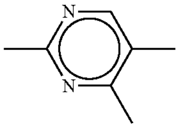

(208)

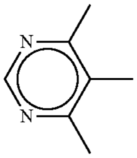

(209)

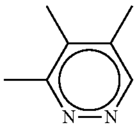

(210)

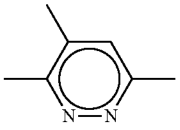

[Chemical Formula 13]

(211)

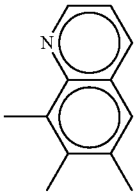

(212)

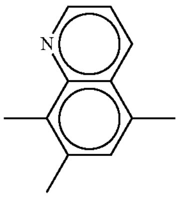

(213)

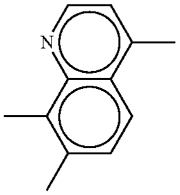

(214)

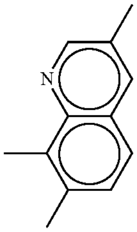

-continued
(215)
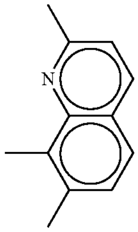
(216)
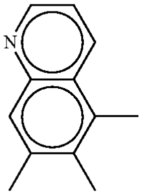
(217)
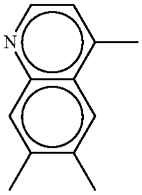
(218)
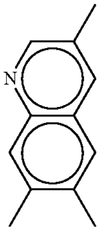
(219)
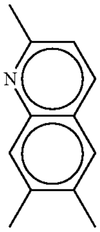
[Chemical Formula 14]
(220)
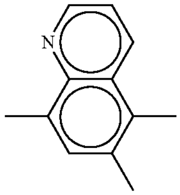
(221)
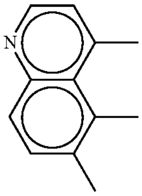
-continued
(222)
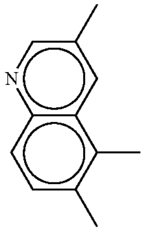
(223)
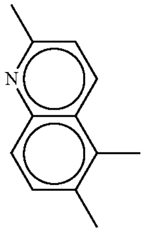
(224)
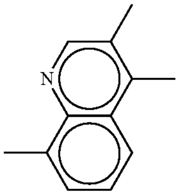
(225)
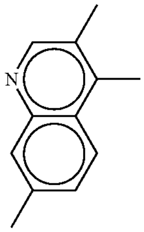
(226)
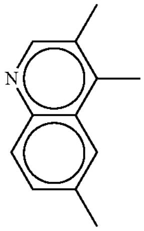
(227)
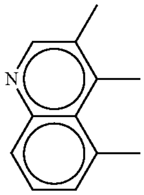
(228)
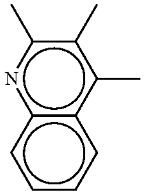

-continued
(229)
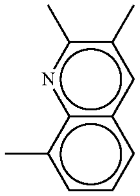
(230)
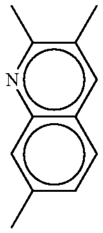
(231)
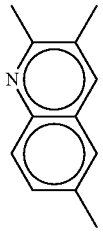
(232)
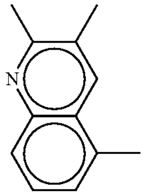
[Chemical Formula 15]
(233)
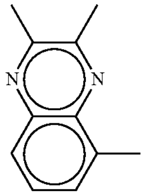
(234)
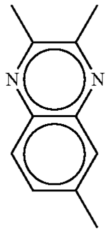
(235)
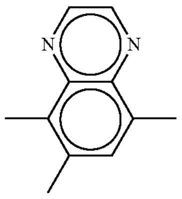
-continued
(236)
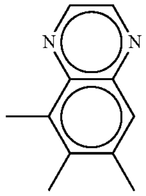
(237)
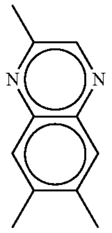
[Chemical Formula 16]
(238)
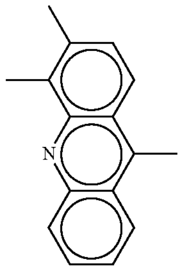
(239)
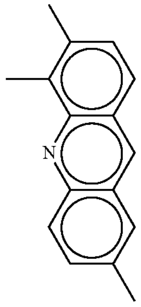
(240)
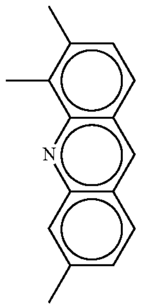

-continued
(241)
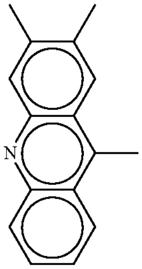
(242)
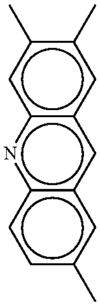
(243)
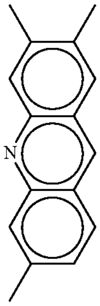
[Chemical Formula 17]
(244)
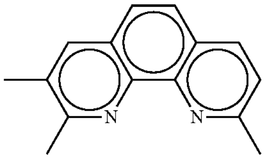
(245)
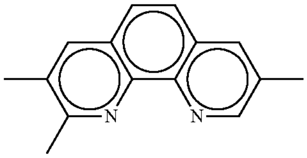
(246)
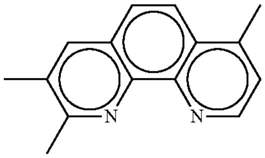
(247)
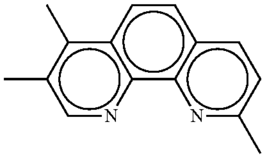
-continued
(248)
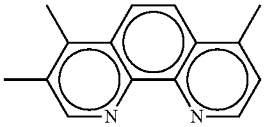
(249)
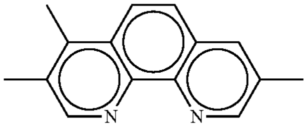
[Chemical Formula 18]
(250)
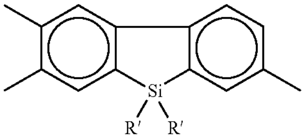
(251)
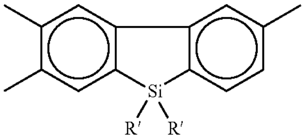
(252)
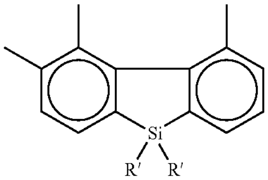
(253)
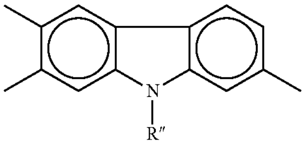
(254)
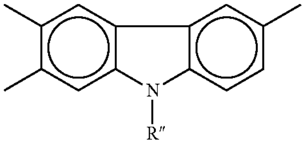
(255)
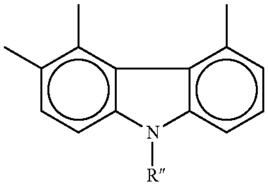
(256)
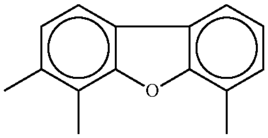
(257)
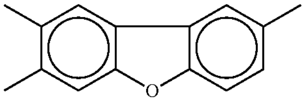

-continued
(258)
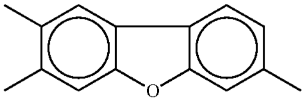
[Chemical Formula 19]
(259)
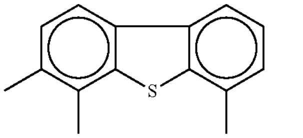
(260)
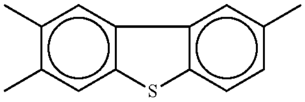
(261)
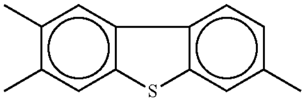
(262)
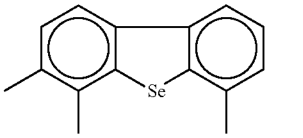
(263)
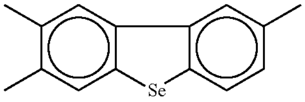
(264)
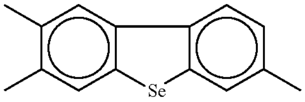
[Chemical Formula 20]
(265)
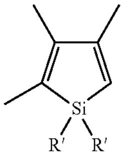
(266)
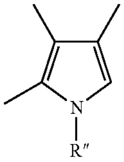
(267)
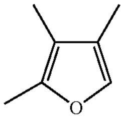
(268)
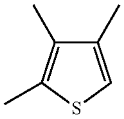
-continued
(269)
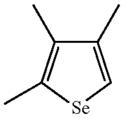
(270)
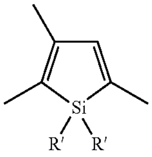
(271)
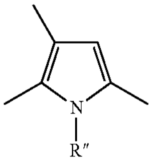
(272)
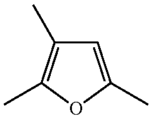
(273)
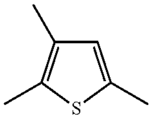
(274)
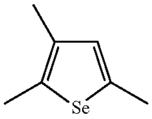
[Chemical Formula 21]
(275)
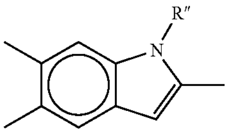
(276)
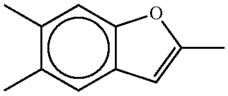
(277)
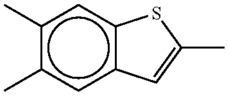
(278)
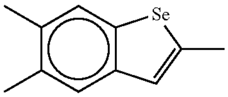
(279)
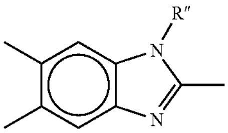
(280)
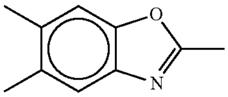

-continued (281)

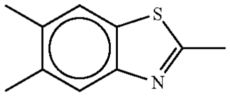

(282)

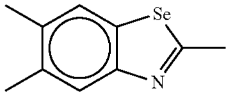

(283)

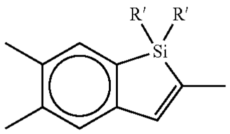

(284)

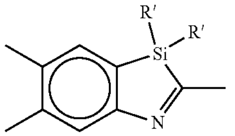

In Formula (201) to Formula (284), R's are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, a substituted amino group, an acyloxy group, an amido group, an arylalkenyl group, an arylalkynyl group, a monovalent heterocyclic group, or a cyano group.

R"s are the same as or different from each other and represent a hydrogen atom, an alkyl group, an aryl group, an arylalkyl group, a substituted silyl group, an acyl group, or a monovalent heterocyclic group.

The definition and specific examples of the halogen atom, the alkyl group, the alkyloxy group, the alkylthio group, the aryl group, the aryloxy group, the arylthio group, the arylalkyl group, the arylalkyloxy group, the arylalkylthio group, the substituted amino group, the acyloxy group, the amido group, the arylalkenyl group, the arylalkynyl group, or the monovalent heterocyclic group represented by R' are the same as the definition and specific examples of the halogen atom, the alkyl group, the alkyloxy group, the alkylthio group, the aryl group, the aryloxy group, the arylthio group, the arylalkyl group, the arylalkyloxy group, the arylalkylthio group, the substituted amino group, the acyloxy group, the amido group, the arylalkenyl group, the arylalkynyl group, or the monovalent heterocyclic group represented by the above $R^3$.

The definition and specific examples of the alkyl group, the aryl group, the arylalkyl group, the substituted silyl group, or the monovalent heterocyclic group represented by R" are the same as the definition and specific examples of the alkyl group, the aryl group, the arylalkyl group, the substituted silyl group, or the monovalent heterocyclic group represented by the above $R^3$.

In Formula (1), it is preferred that at least one of $Ar^1$ and $Ar^2$ is a group obtained by removing three hydrogen atoms from a thiophene ring, and it is more preferred that both of them are a group obtained by removing three hydrogen atoms from a thiophene ring.

In Formula (201) to Formula (284), the trivalent heterocyclic group is preferably a heterocyclic group containing a sulfur atom, more preferably a group represented by Formula (268) or Formula (273), further preferably a group represented by Formula (273).

In Formula (1), $R^{50}$ represents a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group. $R^{51}$ represents an alkyl group having 6 or more carbon atoms, an alkyloxy group having 6 or more carbon atoms, an alkylthio group having 6 or more carbon atoms, an aryl group having 6 or more carbon atoms, an aryloxy group having 6 or more carbon atoms, an arylthio group having 6 or more carbon atoms, an arylalkyl group having 7 or more carbon atoms, an arylalkyloxy group having 7 or more carbon atoms, an arylalkylthio group having 7 or more carbon atoms, an acyl group having 6 or more carbon atoms, or an acyloxy group having 6 or more carbon atoms.

The definition and specific examples of the halogen atom, the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the monovalent heterocyclic group, the heterocyclyloxy group, the heterocyclylthio group, the arylalkenyl group, or the arylalkynyl group represented by $R^{50}$ are the same as the definition and specific examples of the halogen atom, the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the monovalent heterocyclic group, the heterocyclyloxy group, the heterocyclylthio group, the arylalkenyl group, or the arylalkynyl group represented by the above $R^3$.

The definition and specific examples of the alkyl group, the alkyloxy group, the alkylthio group, the aryl group, the aryloxy group, the arylthio group, the acyl group, or the acyloxy group represented by $R^{51}$ are the same as the definition and specific examples of a group having 6 or more carbon atoms among the alkyl group, the alkyloxy group, the alkylthio group, the aryl group, the aryloxy group, the arylthio group, the acyl group, and the acyloxy group represented by the above $R^3$. The definition and specific examples of the arylalkyl group, the arylalkyloxy group, or the arylalkylthio group represented by $R^{51}$ are the same as the arylalkyl group, the arylalkyloxy group, or the arylalkylthio group represented by the above $R^3$.

$R^{50}$ and $R^{51}$ are the same as or different from each other and both of them are preferably an alkyl group having 6 or more carbon atoms, an alkyloxy group having 6 or more carbon atoms, an alkylthio group having 6 or more carbon atoms, an aryl group having 6 or more carbon atoms, an aryloxy group having 6 or more carbon atoms, an arylthio group having 6 or more carbon atoms, an arylalkyl group having 7 or more carbon atoms, an arylalkyloxy group having 7 or more carbon atoms, an arylalkylthio group having 7 or more carbon atoms, an acyl group having 6 or more carbon atoms, or an acyloxy group having 6 or more carbon atoms, more preferably an alkyl group having 6 or more carbon atoms, an alkyloxy group having 6 or more carbon atoms, an aryl group having 6 or more carbon atoms, or an aryloxy group having 6 or more carbon atoms, particularly preferably an alkyl group having 6 or more carbon atoms.

The alkyl groups having 6 or more carbon atoms may include a linear alkyl group such as a hexyl group, a heptyl group, an octyl group, a nonyl group, a decyl group, a undecyl group, a dodecyl group, a tridecyl group, a pentadecyl group, a hexadecyl group, a heptadecyl group, an octadecyl group, a nonadecyl group, an icosyl group, a triacontyl group, a tetracontyl group, and a pentacontyl group; and a branched alkyl group such as a 1,1,3,3-tetramethylbutyl group, a 1-methylheptyl group, a 2-ethylhexyl group, a 3,7-dimethyloctyl group, a 1-propylpentyl group, a 2-hexyldecyl group, a 2-heptylundecyl group, a 2-octyldodecyl group, a 3,7,11-trimethyldodecyl group, a 3,7,11,15-tetramethylhexadecyl group, and a 3,5,5-trimethylhexyl group.

Although the alkyl group having 6 or more carbon atoms is appropriately selected while taking into consideration the solubility and the like of a macromolecular compound having the group, the alkyl group having 6 or more carbon atoms is preferably a hexyl group, a heptyl group, an octyl group, a nonyl group, a decyl group, a undecyl group, a dodecyl group, a tridecyl group, a tetradecyl group, a pentadecyl group, a hexadecyl group, a 2-ethylhexyl group, a 3,7-dimethyloctyl group, a 1-propylpentyl group, or a 2-hexyldecyl group, further preferably a hexyl group, a heptyl group, an octyl group, a dodecyl group, a tetradecyl group, a hexadecyl group, a 2-ethylhexyl group, a 3,7-dimethyloctyl group, or a 2-hexyldecyl group, particularly preferably a hexyl group, an octyl group, a hexadecyl group, a 2-ethylhexyl group, or a 3,7-dimethyloctyl group.

In Formula (1), $X^1$ and $Ar^2$ are bonded with atoms (positions) adjacent to each other on a heterocycle that constitutes $Ar^1$, and $C(R^{50})(R^{51})$ and $Ar^1$ are bonded with atoms (positions) adjacent to each other on a heterocycle that constitutes $Ar^2$.

One preferred aspect of the structural unit represented by Formula (1) is a structural unit (a divalent group) represented by Formula (2).

[Chemical Formula 22]

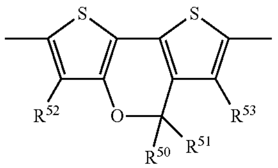

(2)

In the above formula, $R^{50}$ and $R^{51}$ represent the same as defined above; and $R^{52}$ and $R^{53}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group.

The definition and specific examples of the halogen atom, the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the monovalent heterocyclic group, the heterocyclyloxy group, the heterocyclylthio group, the arylalkenyl group, or the arylalkynyl group represented by $R^{52}$ and $R^{53}$ are the same as the definition and specific examples of the halogen atom, the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the monovalent heterocyclic group, the heterocyclyloxy group, the heterocyclylthio group, the arylalkenyl group, or the arylalkynyl group represented by the above $R^3$.

The structural unit represented by Formula (1) is preferably a structural unit represented by Formula (301) to Formula (356) or a structural unit further having a substituent on an aromatic hydrocarbon ring or a heterocycle that is contained in the structural unit. In the formulae, $R^{50}$ and $R^{51}$ represent the same as defined above.

[Chemical Formula 23]

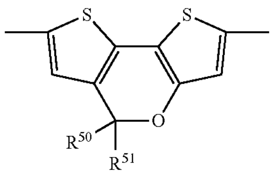

(301)

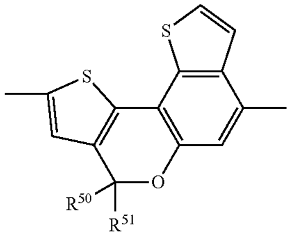

(302)

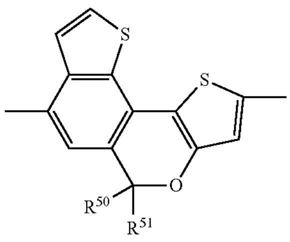

(303)

-continued
(304)
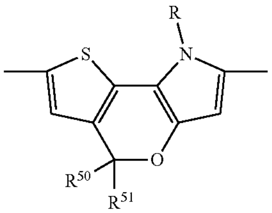
(305)
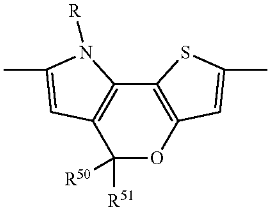
(306)
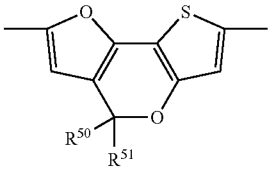
(307)
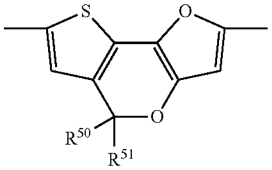
(308)
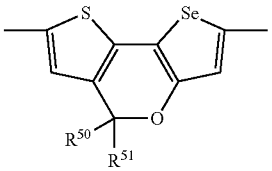
(309)
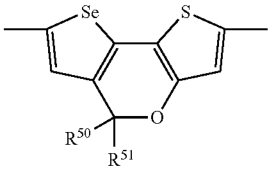
(310)
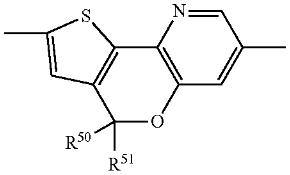
(311)
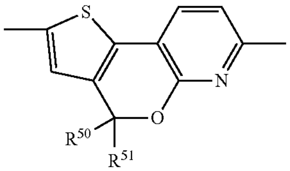
-continued
(312)
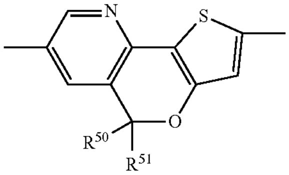
(313)
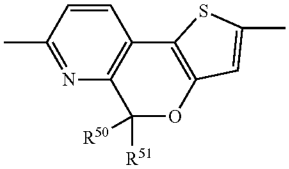
(314)
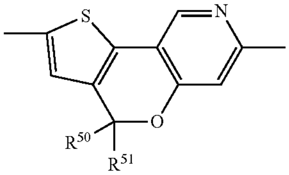
(315)
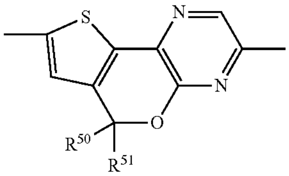
(316)
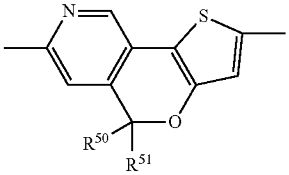
(317)
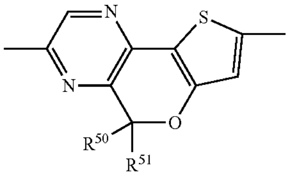
[Chemical Formula 24]
(318)
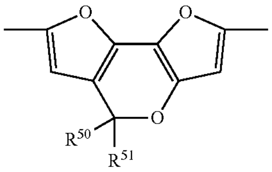
(319)
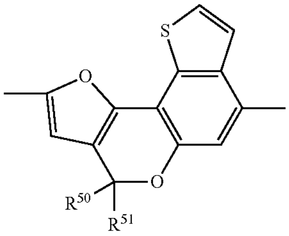

-continued
(320)
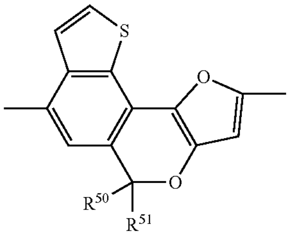
(321)
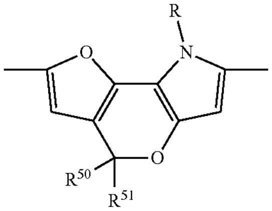
(322)
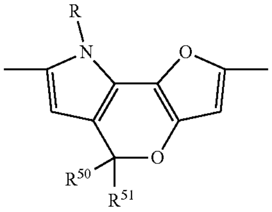
(323)
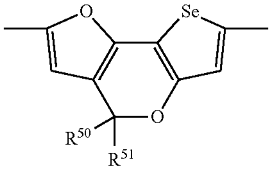
(324)
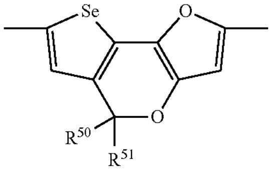
(325)
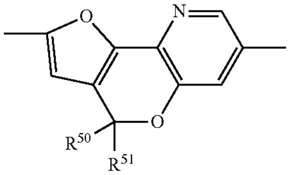
(326)
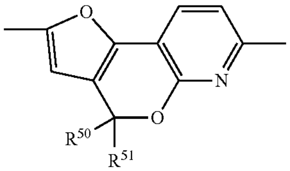
(327)
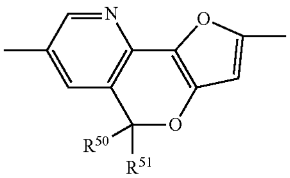
-continued
(328)
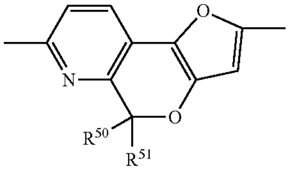
(329)
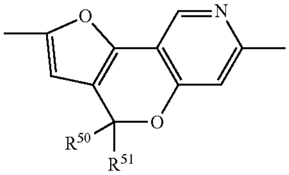
(330)
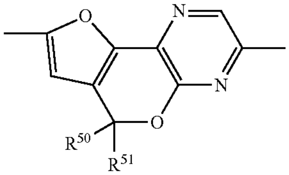
(331)
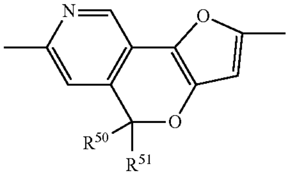
(332)
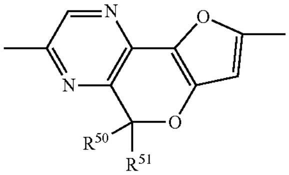
[Chemical Formula 25]
(333)
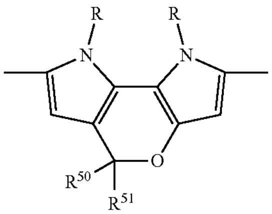
(334)
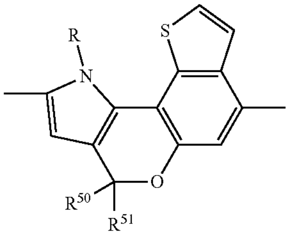

-continued
(335)
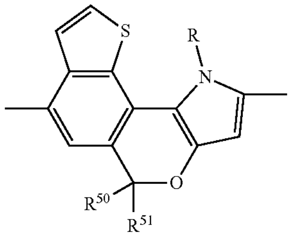
(336)
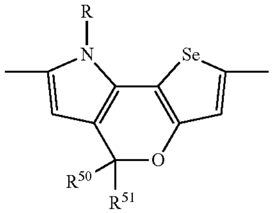
(337)
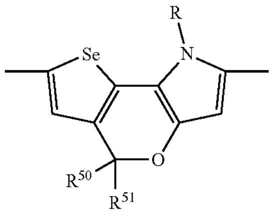
(338)
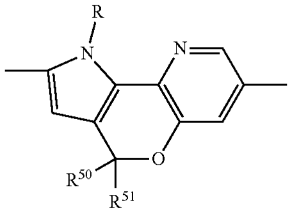
(339)
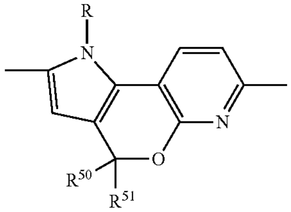
(340)
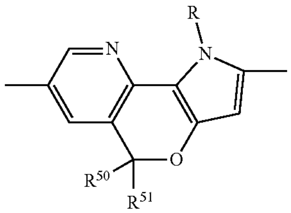
(341)
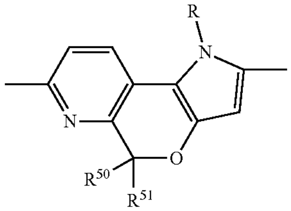
-continued
(342)
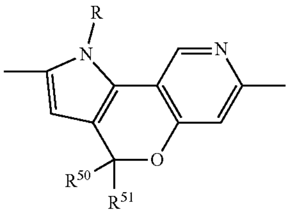
(343)
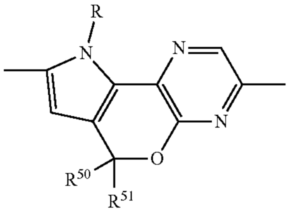
(344)
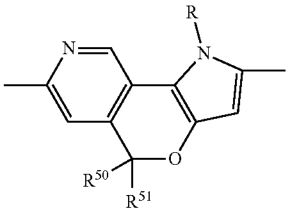
(345)
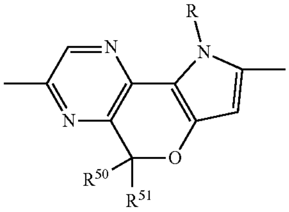
[Chemical Formula 26]
(346)
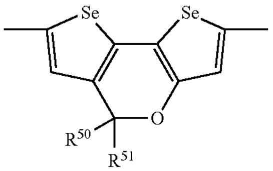
(347)
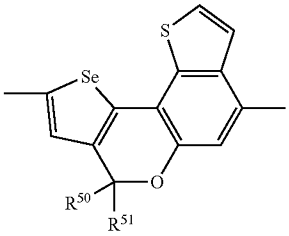
(348)
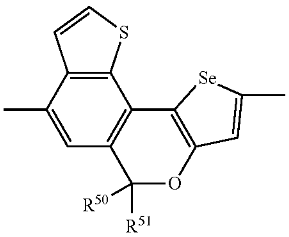

-continued (349)

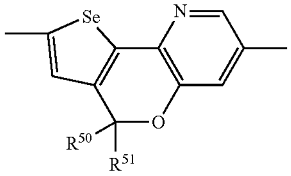

(350)

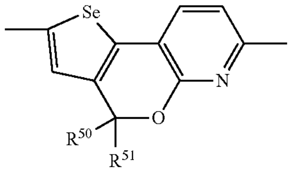

(351)

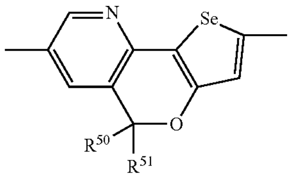

(352)

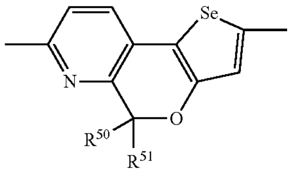

(353)

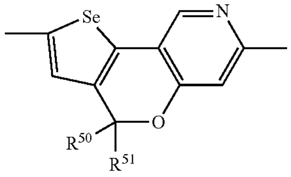

(354)

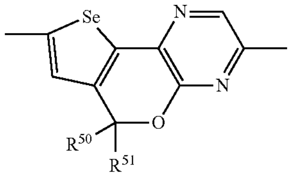

(355)

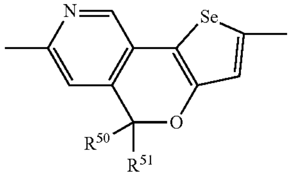

(356)

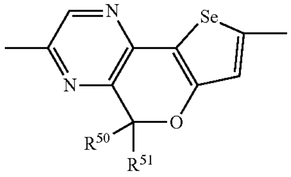

In the formulae, R represents a hydrogen atom or a substituent. A plurality of Rs may be the same as or different from each other and may be bonded with each other to form a ring. When R is a substituent, examples of the substituent may include a group selected from an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an amido group, a monovalent heterocyclic group, a carboxyl group, a substituted carboxyl group, a nitro group, and a cyano group. A hydrogen atom contained in these substituents is optionally substituted with a fluorine atom.

The definition and specific examples of the alkyl group, the alkyloxy group, the alkylthio group, the aryl group, the aryloxy group, the arylthio group, the arylalkyl group, the arylalkyloxy group, the arylalkylthio group, the arylalkenyl group, the arylalkynyl group, the substituted amino group, the substituted silyl group, the halogen atom, the acyl group, the acyloxy group, the amido group, or the monovalent heterocyclic group represented by R are the same as the definition and specific examples of the alkyl group, the alkyloxy group, the alkylthio group, the aryl group, the aryloxy group, the arylthio group, the arylalkyl group, the arylalkyloxy group, the arylalkylthio group, the arylalkenyl group, the arylalkynyl group, the substituted amino group, the substituted silyl group, the halogen atom, the acyl group, the acyloxy group, the amido group, or the monovalent heterocyclic group represented by the above $R^3$.

The substituted carboxyl group which generally has 2 to 20 carbon atoms is used and examples thereof may include a group having a methyl ester structure, a group having an ethyl ester structure, and a group having a butyl ester structure.

Among the structural units represented by Formula (301) to Formula (356), preferred are structural units represented by Formula (301) to Formula (317), more preferred are structural units represented by Formula (301) to Formula (303), particularly preferred is a structural unit represented by Formula (301).

The macromolecular compound of the present invention has preferably a structural unit different from the structural unit represented by Formula (1), in addition to the structural unit represented by Formula (1). In this case, it is preferred that the structural unit represented by Formula (1) and the structural unit different from the structural unit represented by Formula (1) form a conjugation. The conjugation in the present invention refers to a state in which: unsaturated bonds and single bonds are chained in the order of an unsaturated bond—a single bond—an unsaturated bond; two π bonds of π orbitals are adjacent to each other and π electrons of π bonds are arranged in parallel; and π electrons are not localized over a double bond or a triple bond, but spread over an adjacent single bond to be delocalized. Here, the unsaturated bond refers to a double bond or a triple bond.

The structural units different from the structural unit represented by Formula (1) may include divalent groups and examples of the divalent group may include an arylene group and a divalent heterocyclic group.

Here, the arylene group is an atomic group obtained by removing two hydrogen atoms from an aromatic hydrocarbon, and the number of carbon atoms constituting a ring of arylene group is generally around 6 to 60, preferably 6 to 20. Here, the aromatic hydrocarbons include an aromatic hydrocarbon having a benzene ring, an aromatic hydrocarbon having a condensed ring, and an aromatic hydrocarbon in which two or more of independent benzene rings or condensed rings are bonded with each other either directly or through a group such as vinylene.

Examples of the arylene group may include a phenylene group (for example, Formulae 1 to 3 below), a naphthalene-diyl group (Formulae 4 to 13 below), an anthracene-diyl group (Formulae 14 to 19 below), a biphenyl-diyl group (Formulae 20 to 25 below), a terphenyl-diyl group (Formulae 26 to 28 below), and a condensed ring compound group (Formulae 29 to 38 below). The condensed ring compound group may include a fluorene-diyl group (Formulae 36 to 38 below).

The divalent heterocyclic group refers to an atomic group obtained by removing two hydrogen atoms from a heterocyclic compound, and the number of carbon atoms constituting a ring of the divalent heterocyclic group is generally around 3 to 60.

Here, the heterocyclic compound refers to an organic compound containing, in the ring thereof, as an element constituting the ring, not only a carbon atom, but also a heteroatom such as oxygen, sulfur, nitrogen, phosphorus, boron, and arsenic, among organic compounds having a cyclic structure.

Examples of the divalent heterocyclic group may include the followings:

- a divalent heterocyclic group containing nitrogen as the heteroatom, including a pyridine-diyl group (Formulae 39 to 44 below), a diazaphenylene group (Formulae 45 to 48 below), a quinoline-diyl group (Formulae 49 to 63 below), a quinoxaline-diyl group (Formulae 64 to 68 below), an acridine-diyl group (Formulae 69 to 72 below), a bipyridyl-diyl group (Formulae 73 to 75 below), and a phenanthroline-diyl group (Formulae 76 to 78 below);
- a group containing a silicon atom, a nitrogen atom, a sulfur atom, a selenium atom or the like as the heteroatom and having a fluorene structure (Formulae 79 to 93 below);
- a 5-membered heterocyclic group containing a silicon atom, a nitrogen atom, a sulfur atom, a selenium atom or the like as the heteroatom (Formulae 94 to 98 below);
- a 5-membered ring-condensed heterocyclic group containing a silicon atom, a nitrogen atom, a sulfur atom, a selenium atom or the like as the heteroatom (Formulae 99 to 110 below);
- a 5-membered heterocyclic group containing a silicon atom, a nitrogen atom, a sulfur atom, a selenium atom or the like as the heteroatom that is bonded with other 5-membered heterocycles at an α-position of the heteroatom to form a dimer or an oligomer (Formulae 111 and 112 below);
- a 5-membered heterocyclic group containing a silicon atom, a nitrogen atom, a sulfur atom, a selenium atom or the like as the heteroatom that is bonded with phenyl groups at an α-position of the heteroatom (Formulae 113 to 119 below);
- a group in which a 5-membered ring-condensed heterocyclic group containing an oxygen atom, a nitrogen atom, a sulfur atom, a selenium atom or the like as the heteroatom is substituted with a phenyl group, a furyl group, or a thienyl group (Formulae 120 to 127 below);
- a group in which 5-membered heterocycles containing a nitrogen atom, a sulfur atom, a selenium atom or the like as the heteroatom are condensed with each other (Formulae 128 to 139 below); a group in which benzene rings and thiophene rings are condensed with each other (Formulae 140 to 143 below); and the like.

[Chemical Formula 27]

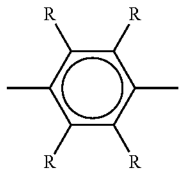

1

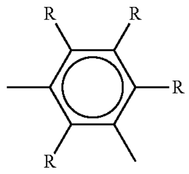

2

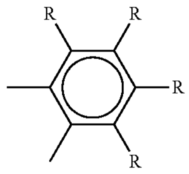

3

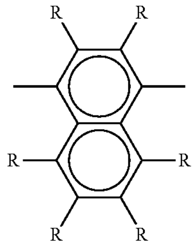

4

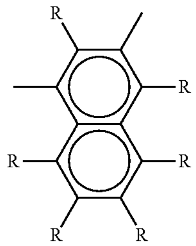

5

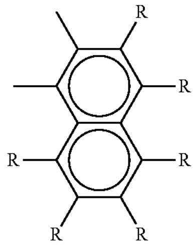

6

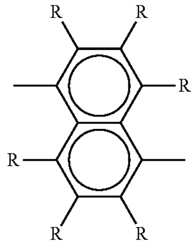

7

-continued
[Chemical Formula 28]
8
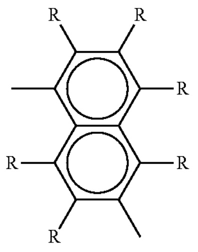
9
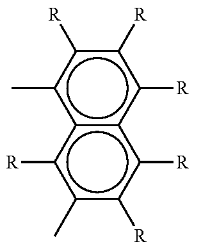
10
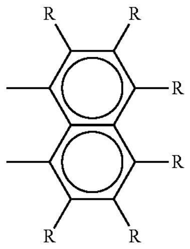
11
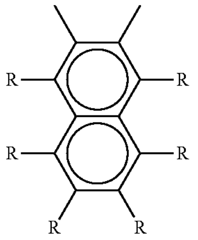
12
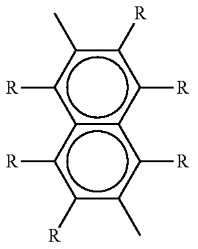
13
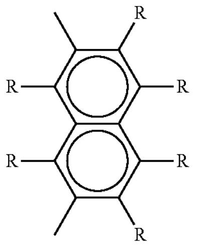
-continued
14
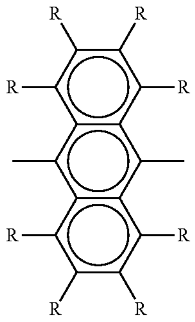
15
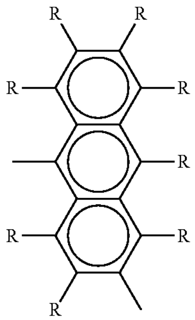
[Chemical Formula 29]
16
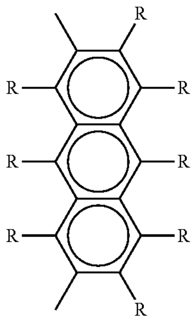
17
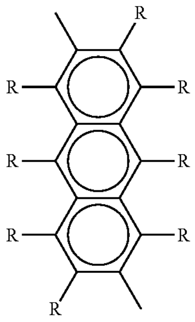
18
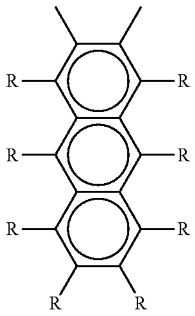

-continued
19
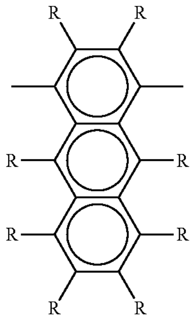
20
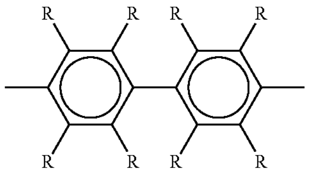
21
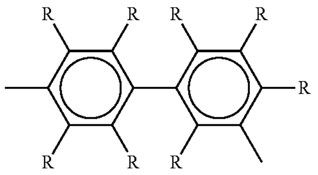
22
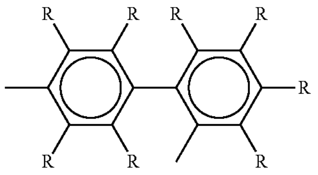
23
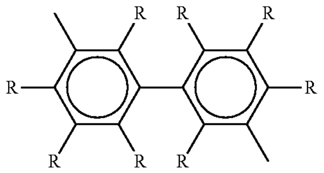
24
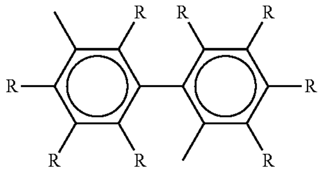
25
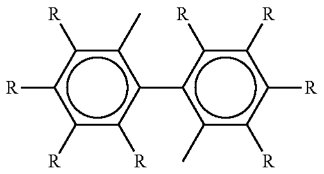
[Chemical Formula 30]
26
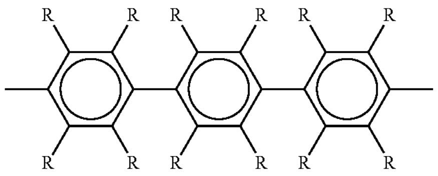
-continued
27
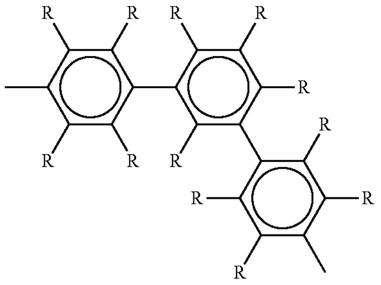
28
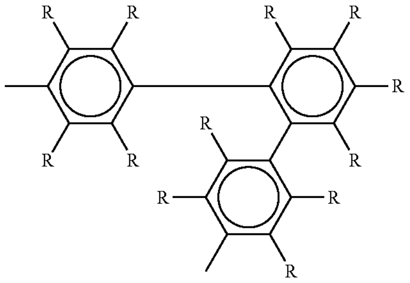
29
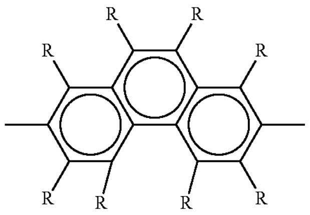
[Chemical Formula 31]
30
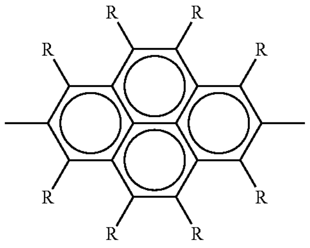
31
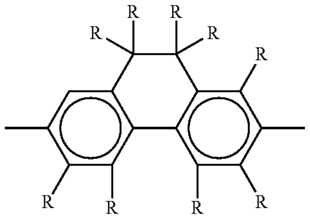
32
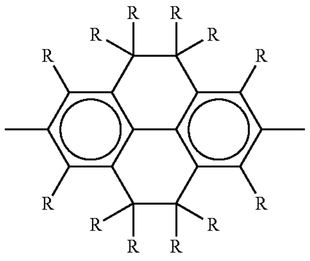

-continued
33
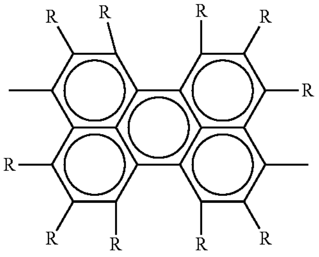
34
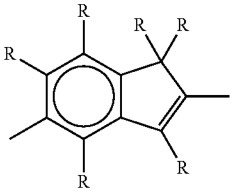
35
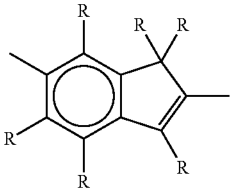
36
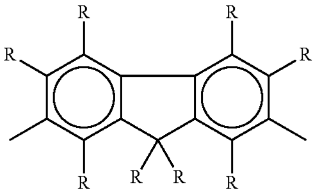
37
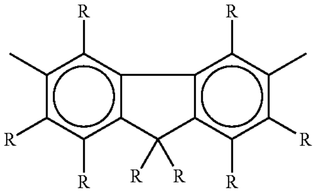
38
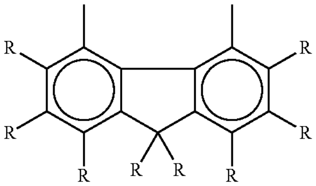
[Chemical Formula 32]
39
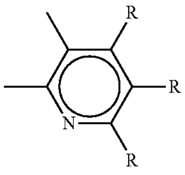
-continued
40
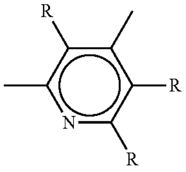
41
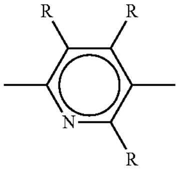
42
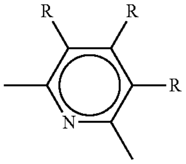
43
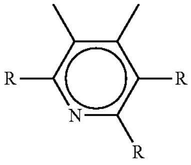
44
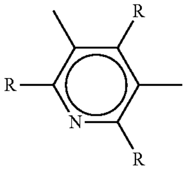
45
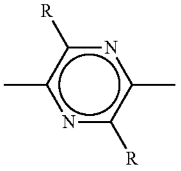
46
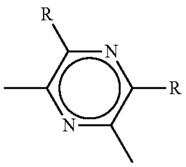
47
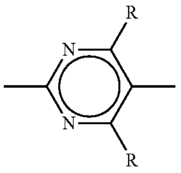

-continued
48
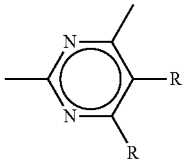
[Chemical Formula 33]
49
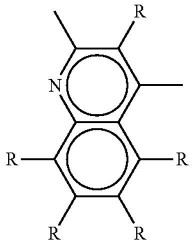
50
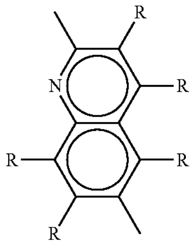
51
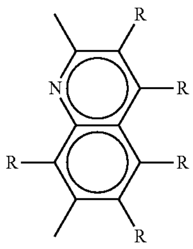
52
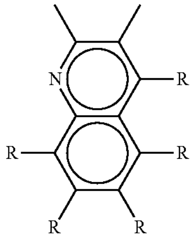
53
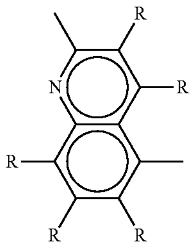
-continued
54
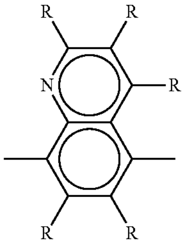
55
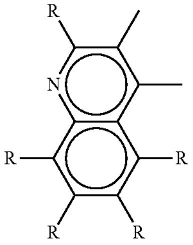
56
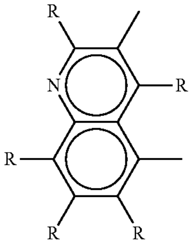
57
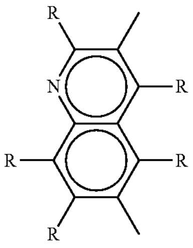
58
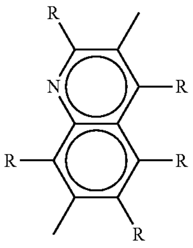
[Chemical Formula 34]
59
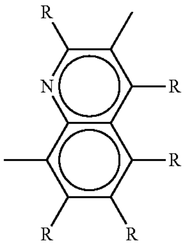

-continued
60
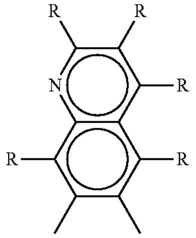
61
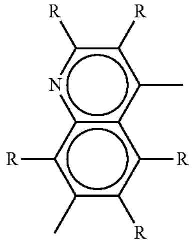
62
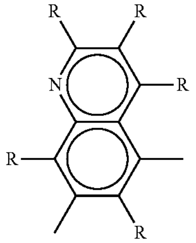
63
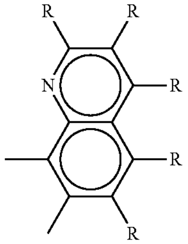
64
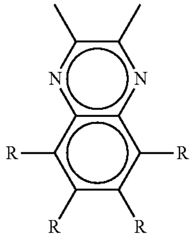
65
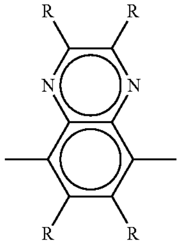
-continued
66
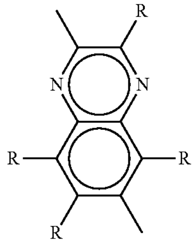
67
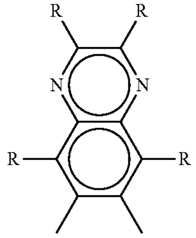
68
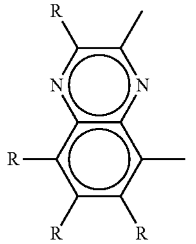
[Chemical Formula 35]
69
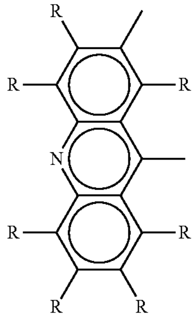
70
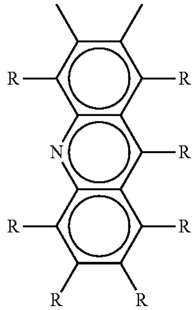

-continued
71
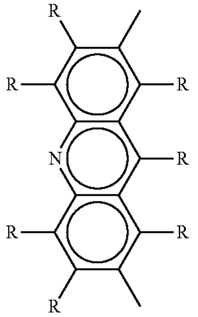
72
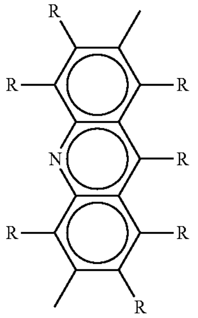
[Chemical Formula 36]
73
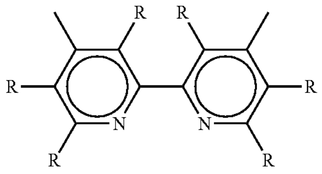
74
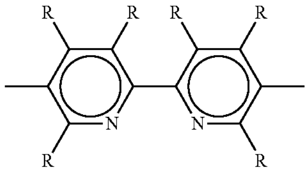
75
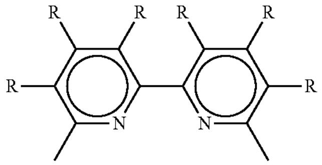
76
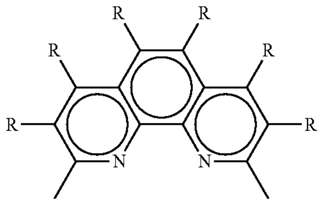
77
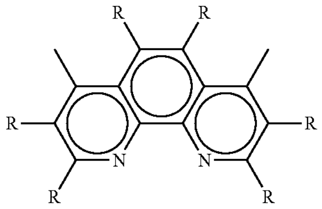
-continued
78
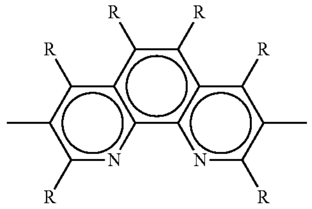
[Chemical Formula 37]
79
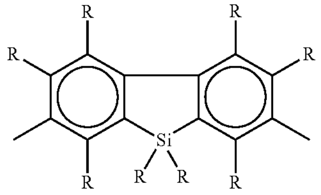
80
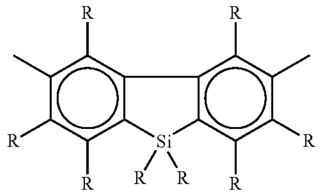
81
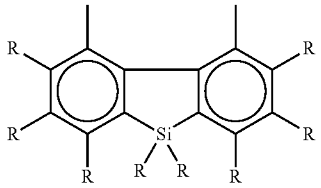
82
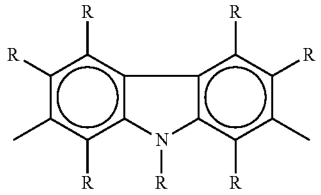
83
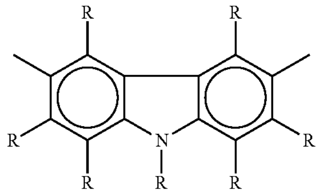
84
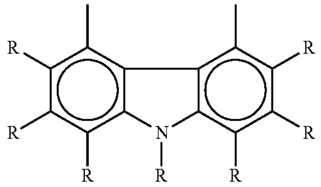

-continued
[Chemical Formula 38]
88
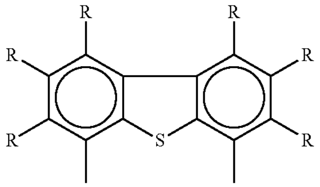
89
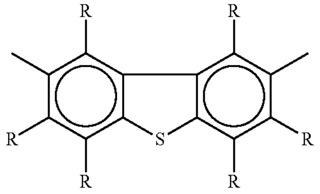
90
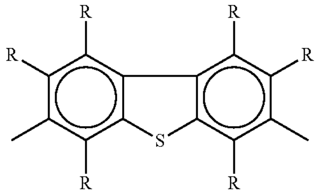
91
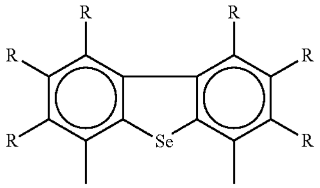
92
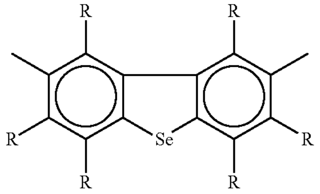
93
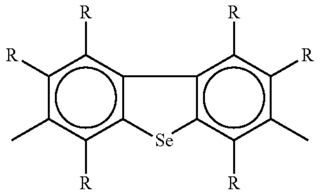
[Chemical Formula 39]
94
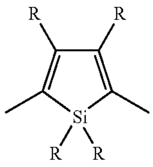
95
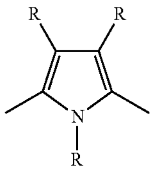
-continued
96
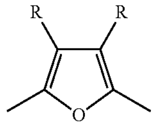
97
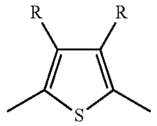
98
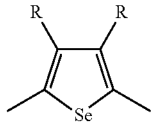
99
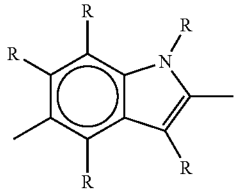
100
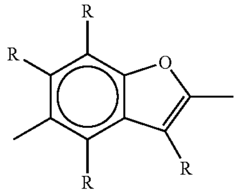
101
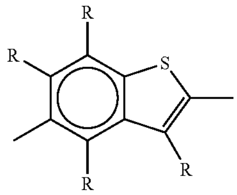
102
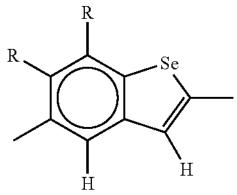
103
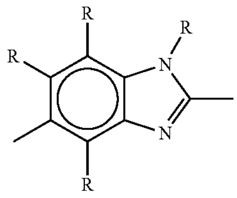
104
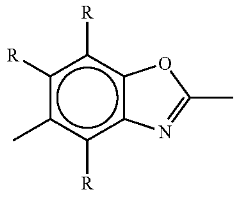

-continued
105
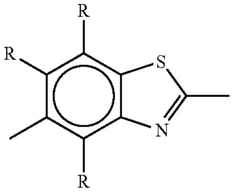
106
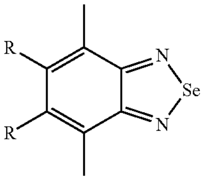
107
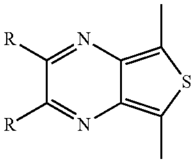
108
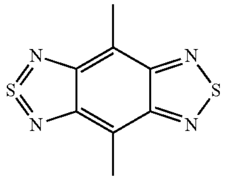
109
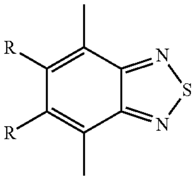
110
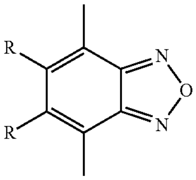
[Chemical Formula 40]
111
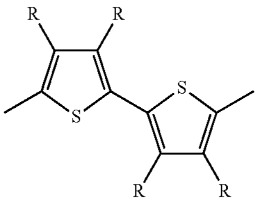
112
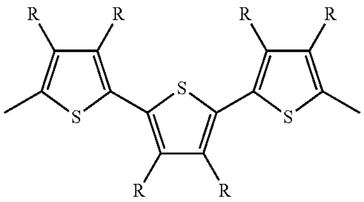
-continued
113
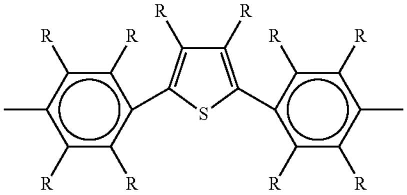
114
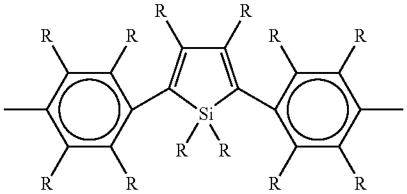
115
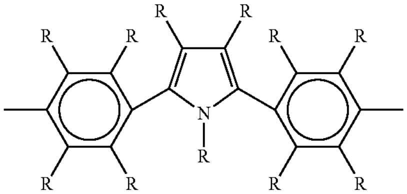
116
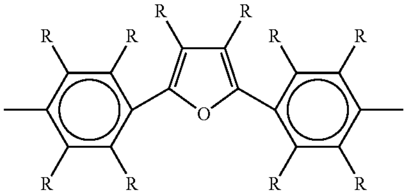
117
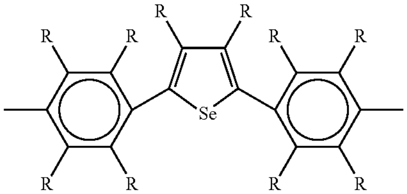
118
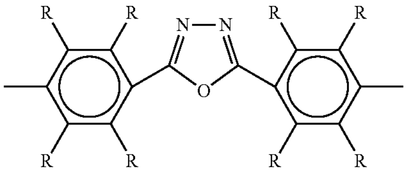
119
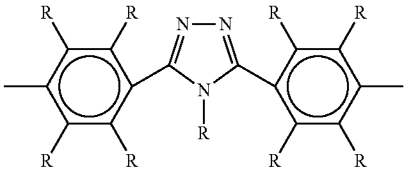
[Chemical Formula 41]
120
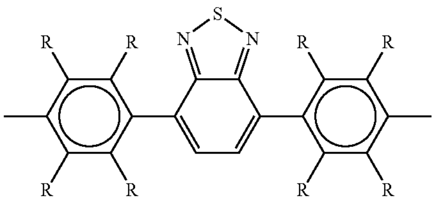

-continued
121
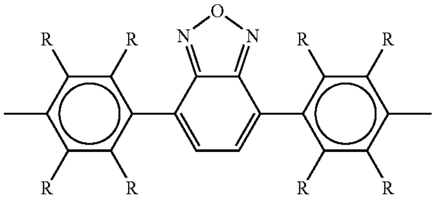
122
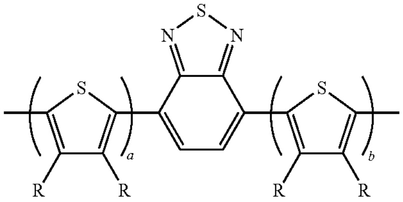
123
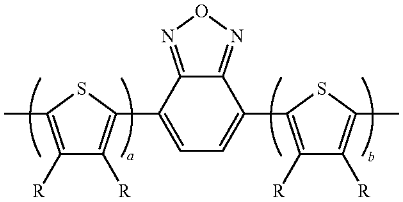
124
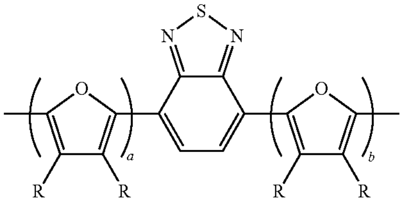
125
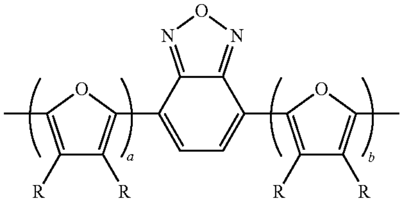
[Chemical Formula 42]
126
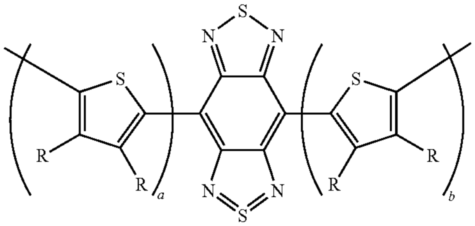
127
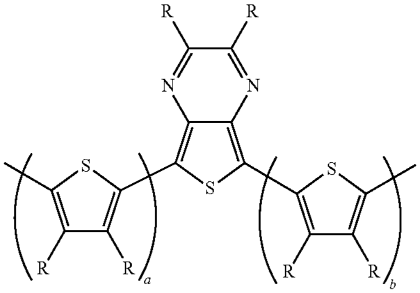
-continued
[Chemical Formula 43]
128
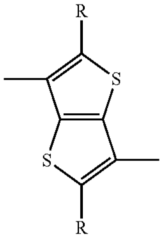
129
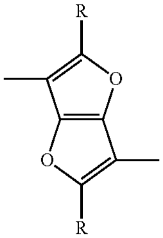
130
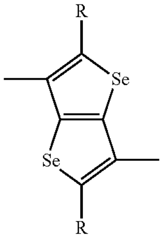
131
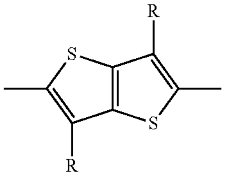
132
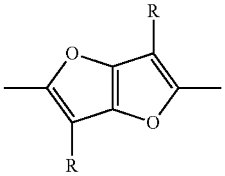
133
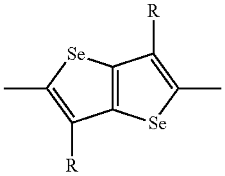
134
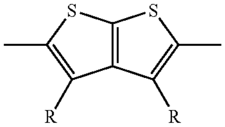
135
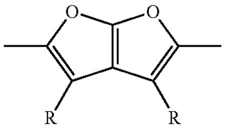

-continued

136

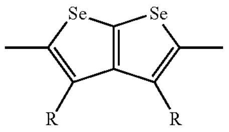

137

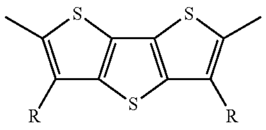

138

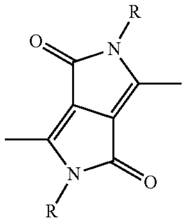

139

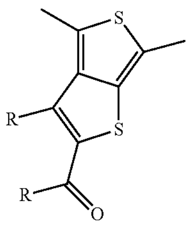

140

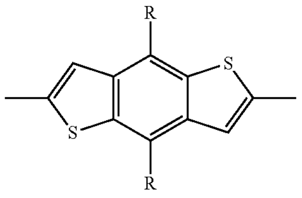

141

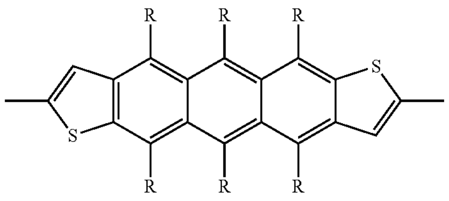

142

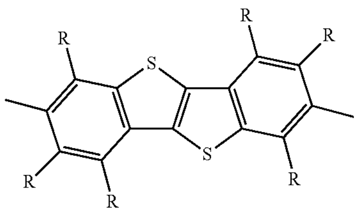

143

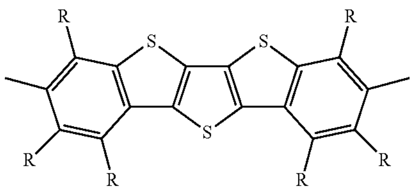

In Formula 1 to Formula 143, R represents the same as defined above. The symbols, a and b are the same as or different from each other and represent the number of repeating that is generally 1 to 5, preferably 1 to 3, particularly preferably 1.

As the structural unit different from the structural unit represented by Formula (1), the structural units represented by Formula (A-1) to Formula (E-1) in Group 1 below are preferred from the viewpoint of the photoelectric conversion efficiency.

[Chemical Formula 44]

(Group 1)

(A-1)

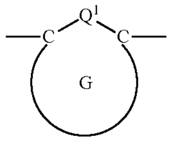

(B-1)

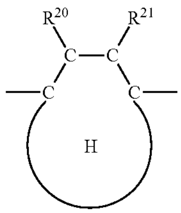

(C-1)

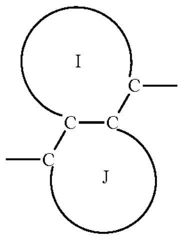

(D-1)

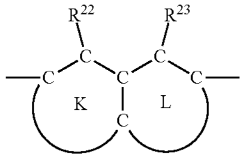

(E-1)

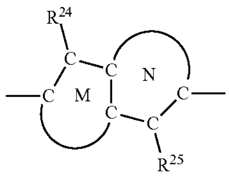

In Group 1, $Q^1$ represents a sulfur atom, an oxygen atom, a selenium atom, $—N(R^{30})—$, or $—CR^{31}═CR^{32}—$ wherein $R^{30}$, $R^{31}$, and $R^{32}$ are the same as or different from each other and represent a hydrogen atom or a substituent; $R^{20}$ to $R^{25}$ are the same as or different from each other and represent a hydrogen atom or a substituent wherein $R^{20}$ and $R^{21}$ may be coupled with each other to form a cyclic structure; and a ring G to a ring N are the same as or different from each other and represent an aromatic ring.

The aromatic rings represented by the ring G to the ring N may be a monocyclic aromatic ring or a multicyclic aromatic ring. Examples of the monocyclic aromatic ring may include aromatic rings such as a benzene ring, a pyrrole ring, a furan ring, a thiophene ring, an oxazole ring, a thiazole ring, a thiadiazole ring, a pyrazole ring, a pyridine ring, a pyrazine ring, an imidazole ring, a triazole ring, an isoxazole ring, an isothiazole ring, a pyrimidine ring, a pyridazine ring, and a triazine ring. However, the ring G is not a benzene ring. In Formula (B-1) to Formula (E-1), the bond represented by C—C includes a carbon-carbon single bond and a carbon-carbon double bond.

Examples of the multicyclic aromatic ring may include aromatic rings in which an arbitrary ring is condensed to the above monocyclic aromatic rings. Examples of the ring condensed to the monocyclic aromatic ring may include a furan ring, a thiophene ring, a pyrrole ring, a pyrroline ring, a pyrrolidine ring, an oxazole ring, an isoxazole ring, a thiazole ring, an isothiazole ring, a thiadiazole ring, an imidazole ring, an imidazoline ring, an imidazolidine ring, a pyrazole ring, a pyrazoline ring, a pyrazolidine ring, a furazan ring, a triazole ring, a thiadiazole ring, an oxadiazole ring, a tetrazole ring, a pyran ring, a pyridine ring, a piperidine ring, a thiopyran ring, a pyridazine ring, a pyrimidine ring, a pyrazine ring, a piperazine ring, a morpholine ring, a triazine ring, a benzofuran ring, an isobenzofuran ring, a benzothiophene ring, an indole ring, an isoindole ring, an indolizine ring, an indoline ring, an isoindoline ring, a chromene ring, a chromane ring, an isochromane ring, a benzopyran ring, a quinoline ring, an isoquinoline ring, a quinolizine ring, a benzimidazole ring, a benzothiazole ring, an indazole ring, a naphthyridine ring, a quinoxaline ring, a quinazoline ring, a quinazolidine ring, a cinnoline ring, a phthalazine ring, a purine ring, a pteridine ring, a carbazole ring, a xanthene ring, a phenanthridine ring, an acridine ring, a β-carboline ring, a perimidine ring, a phenanthroline ring, a thianthrene ring, a phenoxathiin ring, a phenoxazine ring, a phenothiazine ring, and a phenazine ring.

When $R^{30}$, $R^{31}$, and $R^{32}$ are a substituent, they represent a hydrogen atom or a substituent. Preferred examples of the substituent may include a halogen atom such as a fluorine atom, a bromine atom, and a chlorine atom, and a group having 1 to 30 carbon atoms. Examples of the group having 1 to 30 carbon atoms may include an alkyl group such as a methyl group, an ethyl group, a butyl group, a hexyl group, an octyl group, and a dodecyl group; an alkyloxy group such as a methoxy group, an ethoxy group, a butoxy group, a hexyloxy group, an octyloxy group, and a dodecyloxy group; and an aryl group such as a phenyl group and a naphthyl group.

In Group 1, $R^{20}$ to $R^{25}$ represent a hydrogen atom or a substituent. When $R^{20}$ to $R^{25}$ are a substituent, they are preferably a halogen atom such as a fluorine atom, a bromine atom, and a chlorine atom, or a group having 1 to 30 carbon atoms. Examples of the group having 1 to 30 carbon atoms may include an alkyl group such as a methyl group, an ethyl group, a butyl group, a hexyl group, an octyl group, and a dodecyl group; an alkyloxy group such as a methoxy group, an ethoxy group, a butoxy group, a hexyloxy group, an octyloxy group, and a dodecyloxy group; and an aryl group such as a phenyl group and a naphthyl group.

$R^{20}$ and $R^{21}$ may be coupled with each other to form a cyclic structure. Specific examples of the cyclic structure formed by coupling may include the structures represented by Formula (I) to Formula (III) below.

[Chemical Formula 45]

(I)

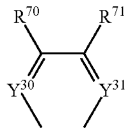

(II)

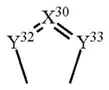

(III)

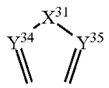

In Formula (I) to Formula (III), $R^{70}$ and $R^{71}$ are the same as or different from each other and represent a hydrogen atom or a substituent. When $R^{70}$ and $R^{71}$ are a substituent, preferred examples of the substituent may include a halogen atom such as a fluorine atom, a bromine atom, and a chlorine atom, and a group having 1 to 30 carbon atoms. Examples of the substituent may include an alkyl group such as a methyl group, an ethyl group, a butyl group, a hexyl group, an octyl group, and a dodecyl group; an alkyloxy group such as a methoxy group, an ethoxy group, a butoxy group, a hexyloxy group, an octyloxy group, and a dodecyloxy group; and an aryl group such as a phenyl group and a naphthyl group.

$X^{30}$ and $X^{31}$ are the same as or different from each other and represent a sulfur atom or a selenium atom. $X^{30}$ and $X^{31}$ are preferably a sulfur atom. $Y^{30}$ to $Y^{35}$ are the same as or different from each other and represent a nitrogen atom or $=CH-$. $Y^{30}$ to $Y^{35}$ are preferably a nitrogen atom.

The ring G to the ring N optionally have a substituent other than $R^{20}$ to $R^{25}$, and examples of the substituent may include a halogen atom such as a fluorine atom, a bromine atom, and a chlorine atom; an alkyl group such as a methyl group, an ethyl group, a butyl group, a hexyl group, an octyl group, and a dodecyl group; an alkyloxy group such as a methoxy group, an ethoxy group, a butoxy group, a hexyloxy group, an octyloxy group, and a dodecyloxy group; and an aryl group such as a phenyl group and a naphthyl group.

Among the structural units included in Group 1, the structural units represented by Formula (A-2) to Formula (E-2) in Group 2 below are more preferred from the viewpoint of the photoelectric conversion efficiency.

[Chemical Formula 46]

(Group 2)

(A-2)

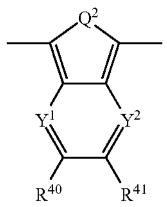

-continued (B-2)

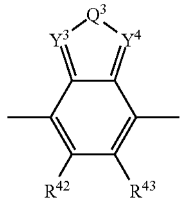

(C-2)

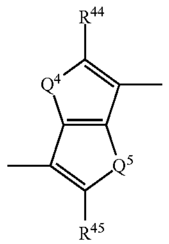

[Chemical Formula 47]

(D-2)

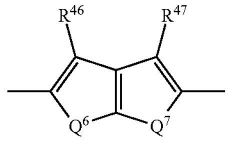

(E-2)

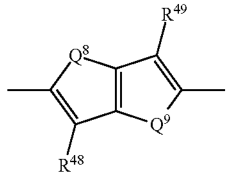

In Formula (A-2) to Formula (E-2), $Q^2$ to $Q^9$ are the same as or different from each other and represent a sulfur atom, an oxygen atom, a selenium atom, —N($R^{30}$)—, or —$CR^{31}$=$CR^{32}$—. $R^{30}$, $R^{31}$, and $R^{32}$ represent the same as defined above. $Q^2$ to $Q^9$ are preferably a sulfur atom. $Y^1$ to $Y^4$ are the same as or different from each other and represent a nitrogen atom or =CH—. $Y^1$ to $Y^4$ are preferably a nitrogen atom.

$R^{40}$ to $R^{49}$ are the same as or different from each other and represent a hydrogen atom or a substituent. When $R^{40}$ to $R^{49}$ are a substituent, preferred examples of the substituent may include a halogen atom such as a fluorine atom, a bromine atom, and a chlorine atom, and a group having 1 to 30 carbon atoms. Examples of the group having 1 to 30 carbon atoms may include an alkyl group such as a methyl group, an ethyl group, a butyl group, a hexyl group, an octyl group, and a dodecyl group; an alkyloxy group such as a methoxy group, an ethoxy group, a butoxy group, a hexyloxy group, an octyloxy group, and a dodecyloxy group; and an aryl group such as a phenyl group and a naphthyl group. $R^{40}$ and $R^{41}$, and $R^{42}$ and $R^{43}$ individually may be coupled with each other to form a cyclic structure.

Specific examples of the cyclic structures formed by coupling of $R^{40}$ and $R^{41}$, and $R^{42}$ and $R^{43}$ may include cyclic structures represented by Formula (I) and cyclic structures represented by Formula (II).

Preferred examples of the structural units represented by Formula (A-2) to Formula (E-2) may include groups represented by Formula (500) to Formula (522).

[Chemical Formula 48]

(500)

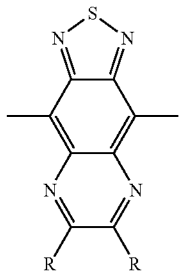

(501)

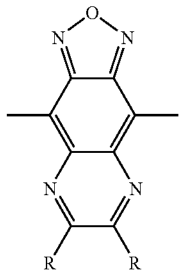

(502)

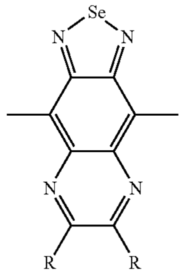

(503)

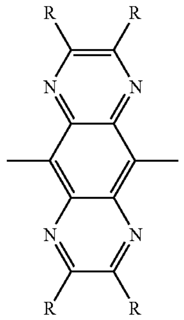

(504)

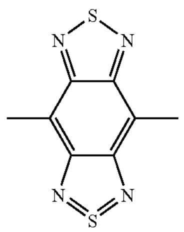

(505)

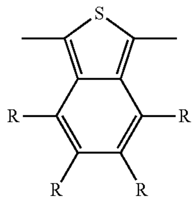

-continued
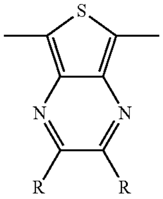
(506)
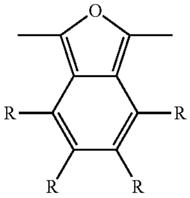
(507)
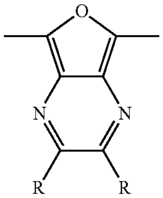
(508)
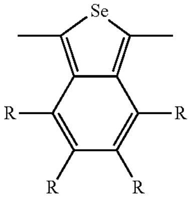
(509)
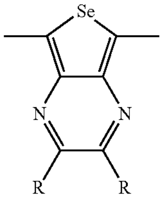
(510)
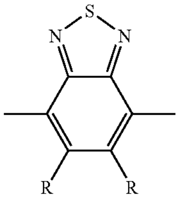
(511)
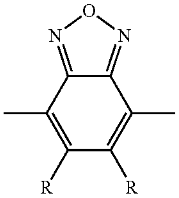
(512)
-continued
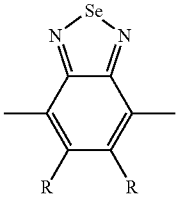
(513)
[Chemical Formula 49]
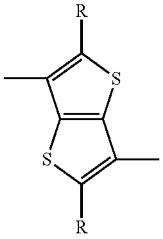
(514)
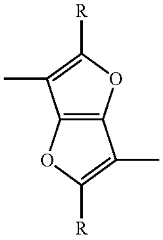
(515)
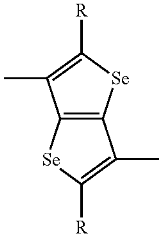
(516)
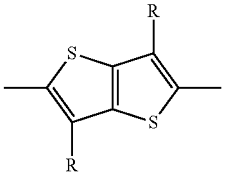
(517)
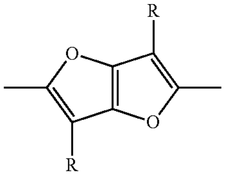
(518)
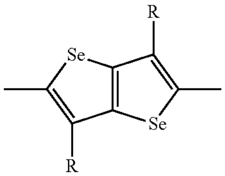
(519)

-continued
(520)
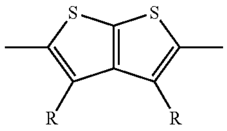
(521)
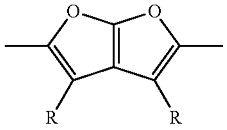
(522)
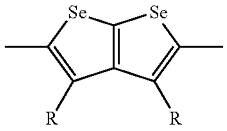
In the above formula, R represents the same as defined above.
Examples of the structural unit contained in the macromolecular compound of the present invention may include structural units represented by Formula (601) to Formula (640).
[Chemical Formula 50]
(601)
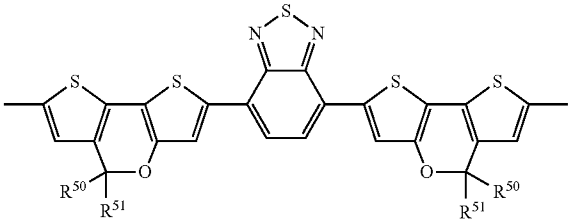
(602)
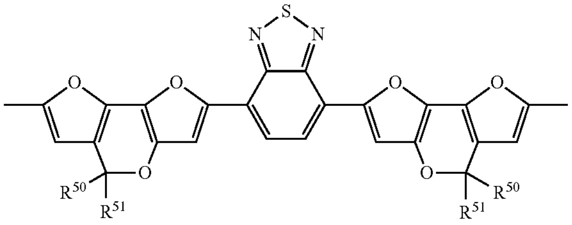
(603)
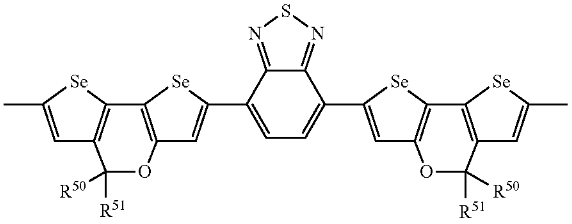
-continued
(604)
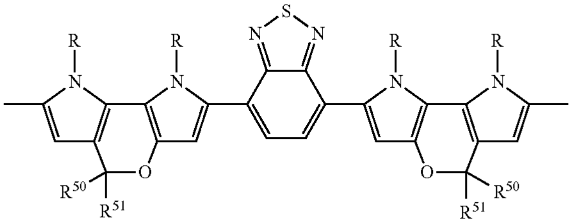
(605)
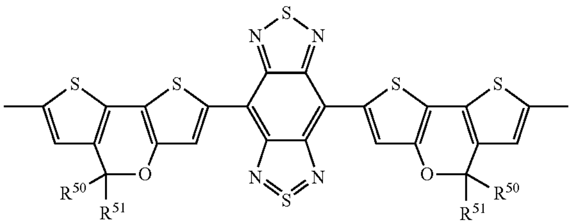
(606)
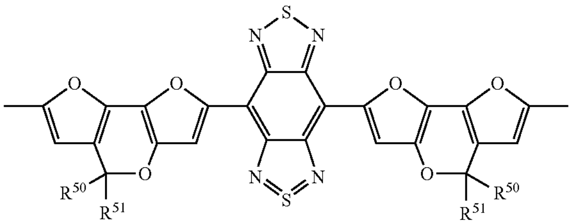
(607)
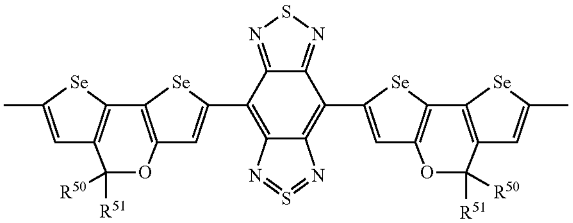
(608)
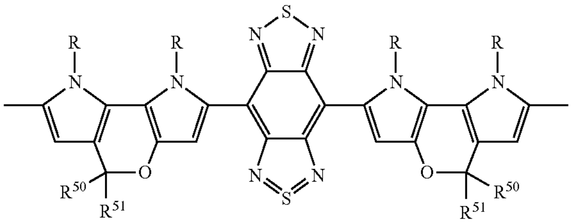
(609)
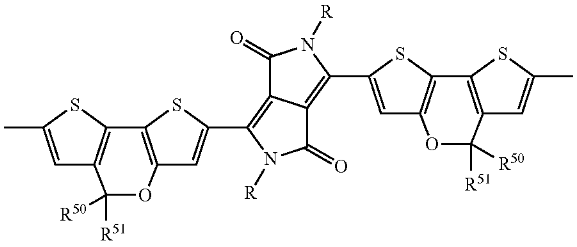

-continued
(610)
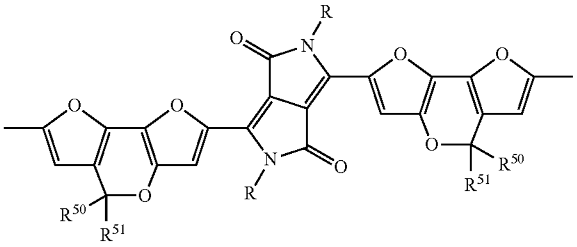
(611)
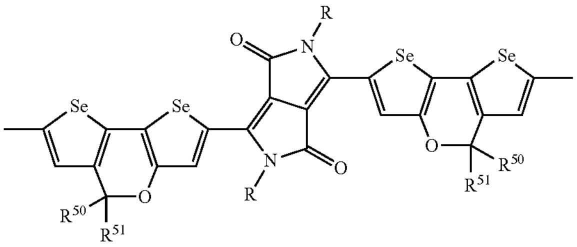
(612)
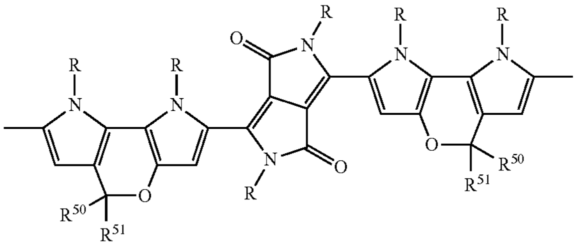
(613)
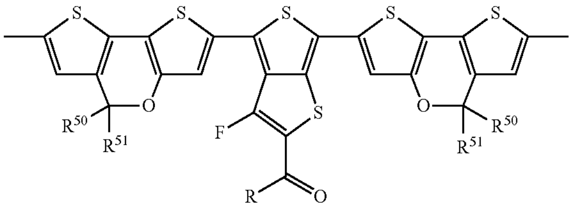
(614)
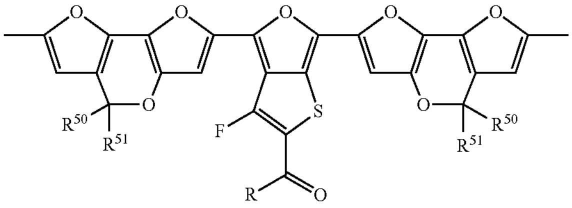
(615)
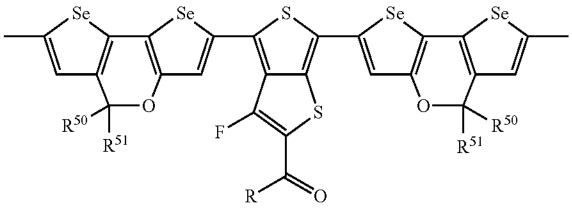
-continued
(616)
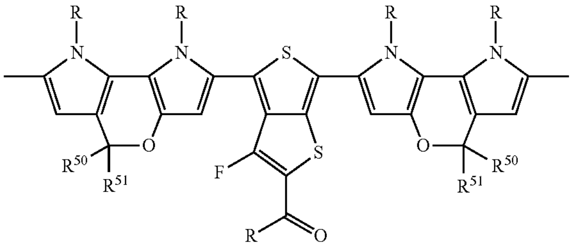
(617)
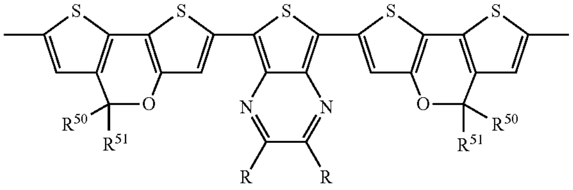
(618)
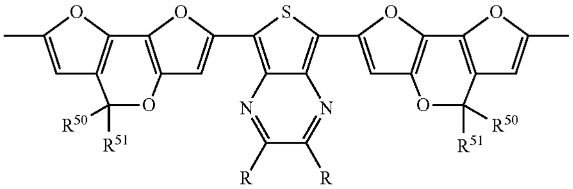
(619)
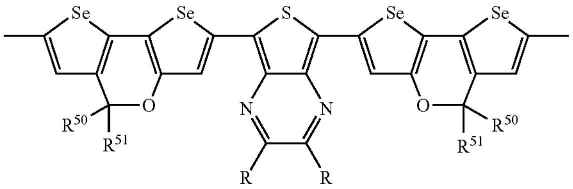
(620)
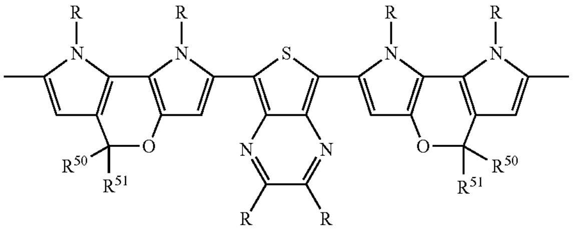
[Chemical Formula 51]
(621)
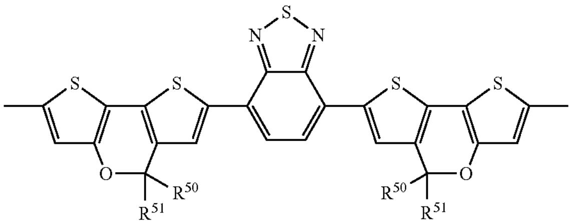

-continued
(622)
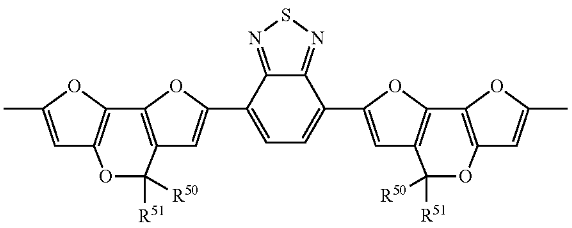
(623)
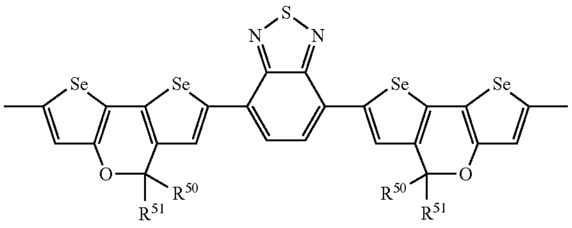
(624)
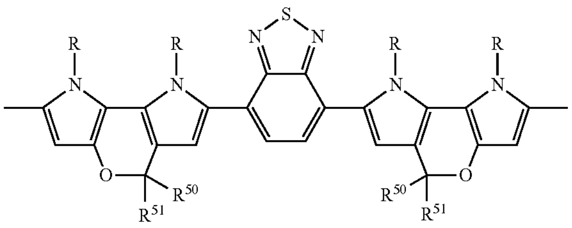
(625)
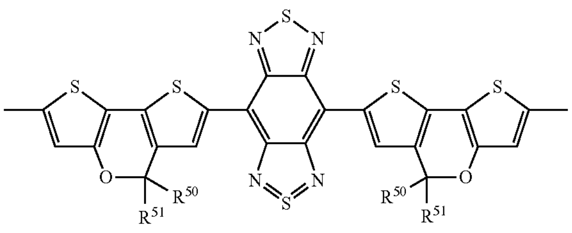
(626)
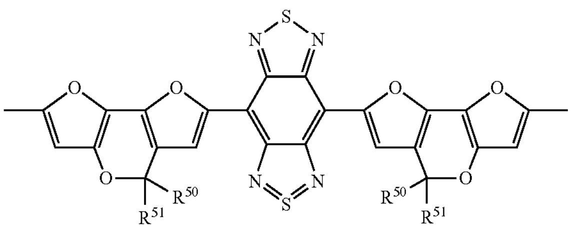
(627)
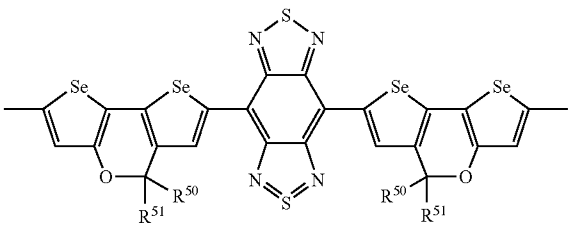
-continued
(628)
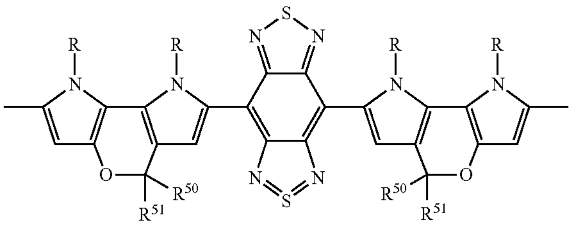
(629)
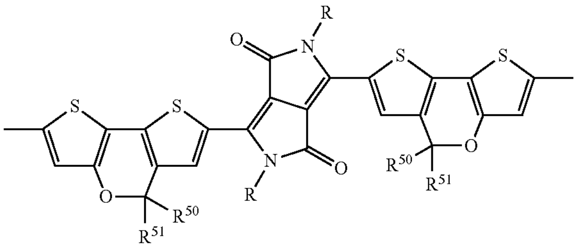
(630)
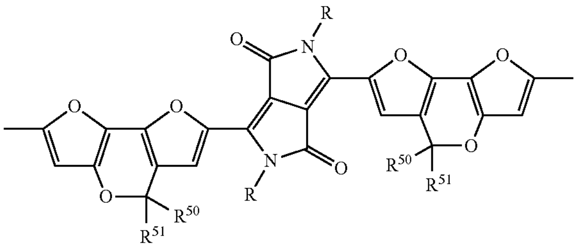
(631)
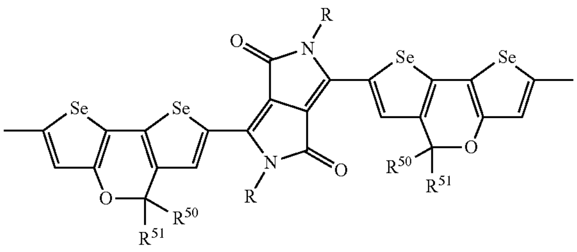
(632)
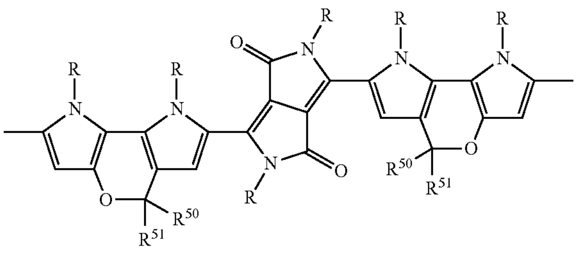
(633)
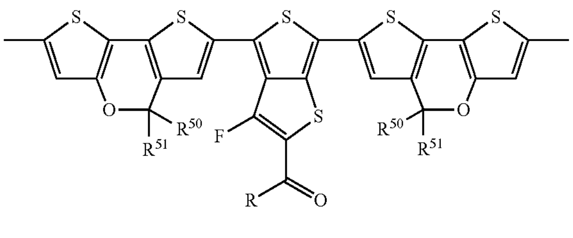

-continued (634)

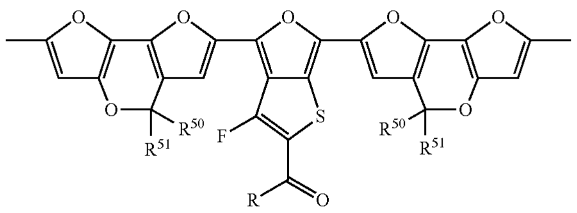

(635)

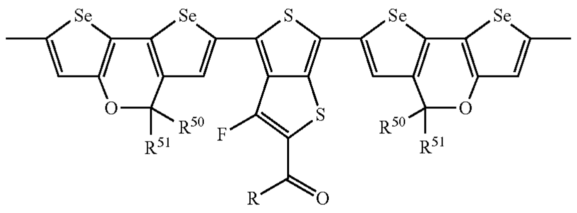

(636)

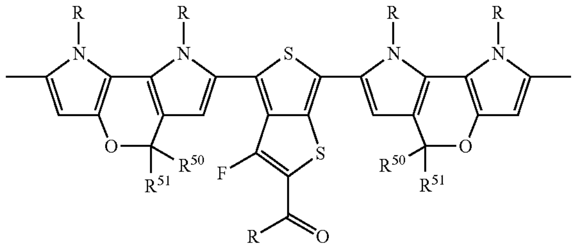

(637)

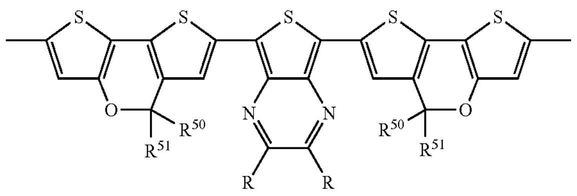

(638)

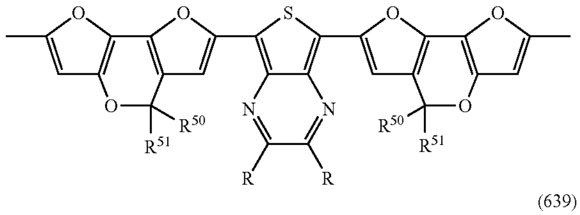

(639)

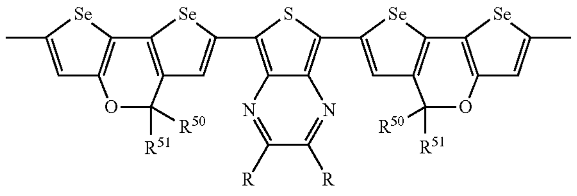

(640)

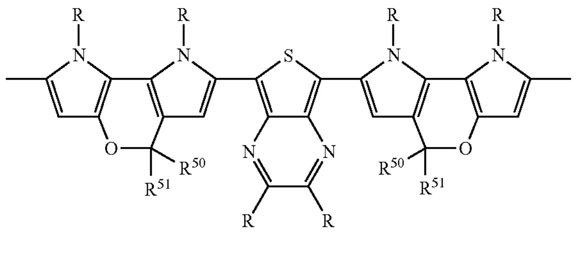

In the above formula, $R^{50}$, $R^{51}$, and R are the same as defined above.

The macromolecular compound of the present invention may have the structural units represented by Formula (601) to Formula (640) as a repeated unit or may have a chain of the structural units. The macromolecular compound of the present invention may also have a divalent organic group in which the structural units are bonded with each other through an arylene group or a divalent heterocyclic group as a repeated unit, or may have a chain of the divalent organic group. Examples of the arylene group and the divalent heterocyclic group may include groups represented by Formula 1 to Formula 143.

The macromolecular compound of the present invention refers to a compound having a weight-average molecular weight (Mw) of 1,000 or more. A macromolecular compound having a weight-average molecular weight of 3,000 to 10,000,000 is preferred. When the weight-average molecular weight is less than 3,000, there may be caused a defect of film formation during the production of a cell, a device or an element. When the weight-average molecular weight is more than 10,000,000, there may fall the solubility of the macromolecular compound in a solvent or the applicability of the macromolecular compound during the production of a cell, a device or an element. The weight-average molecular weight of the macromolecular compound is further preferably 8,000 to 5,000,000, particularly preferably 10,000 to 1,000,000.

The weight-average molecular weight in the present invention refers to a weight-average molecular weight in terms of polystyrene which is measured using gel permeation chromatography (GPC) with a standard sample of polystyrene.

As the content of the structural unit represented by Formula (1) in the macromolecular compound of the present invention, it is satisfactory that at least one structural unit is contained in the compound. In the macromolecular compound, 2 or more structural units in average per one macromolecule chain are preferably contained. Further preferably, 3 or more structural units in average per one macromolecule chain are contained.

When the macromolecular compound of the present invention is utilized in a cell, a device or an element, it is desired that the macromolecular compound has a high solubility in a solvent in terms of the easiness of the production of a cell, a device or an element. Specifically, the macromolecular compound of the present invention has preferably a solubility capable of preparing a solution containing 0.01% by weight (wt) or more of the macromolecular compound, more preferably a solubility capable of preparing a solution containing 0.1 wt % or more of the macromolecular compound, further preferably a solubility capable of preparing a solution containing 0.4 wt % or more of the macromolecular compound.

Although the production method of the macromolecular compound of the present invention is not particularly limited, a method using the Suzuki coupling reaction and a method using the Stille coupling reaction are preferred in terms of the easiness of the synthesis of the macromolecular compound.

Examples of the method using the Suzuki coupling reaction may include a production method having a process of reacting one or more type(s) of compound represented by Formula (100):

$$Q^{100}\text{-}E^{1}\text{-}Q^{200} \quad (100)$$

In the above Formula, $E^1$ represents a divalent group containing an aromatic ring, and $Q^{100}$ and $Q^{200}$ are the same as or different from each other and represent a boronic acid residue (—$B(OH)_2$) or a boric acid ester residue; with one or more type(s) of compound represented by Formula (200):

$$T^1\text{-}E^2\text{-}T^2 \quad (200)$$

In the above Formula, $E^2$ represents a structural unit represented by Formula (1), and $T^1$ and $T^2$ are the same as or different from each other and represent a halogen atom, an alkyl sulfonate group, an aryl sulfonate group, or an arylalkyl sulfonate group;

in the presence of a palladium catalyst and a base. $E^1$ is preferably a divalent aromatic group, further preferably a group represented by the above Formula 1 to Formula 143.

In this case, the total number of moles of one or more type(s) of compound represented by Formula (200) used for the reaction is preferably excessive relative to the total number of moles of one or more type(s) of compound represented by Formula (100) used for the reaction. When the total number of moles of one or more type(s) of compound represented by Formula (200) used for the reaction is assumed to be 1 mole, the total number of moles of one or more type(s) of compound represented by Formula (100) is preferably 0.6 to 0.99 mole, further preferably 0.7 to 0.95 mole.

Examples of the boric acid ester residue may include groups represented below:

[Chemical Formula 52]

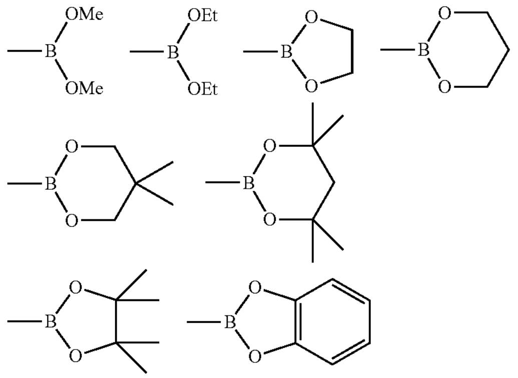

In the above Formula, Me represents a methyl group and Et represents an ethyl group.

Examples of the halogen atom represented by $T^1$ and $T^2$ in Formula (200) may include a fluorine atom, a chlorine atom, a bromine atom, and an iodine atom. In terms of the easiness of the synthesis of the macromolecular compound, the halogen atom is preferably a bromine atom or an iodine atom, further preferably a bromine atom.

Examples of the alkyl sulfonate group represented by $T^1$ and $T^2$ in Formula (200) may include a methane sulfonate group, an ethane sulfonate group, and a trifluoromethane sulfonate group. Examples of the aryl sulfonate group may include a benzene sulfonate group and a p-toluene sulfonate group. Examples of the arylalkyl sulfonate group may include a benzyl sulfonate group.

Specific examples of the method for carring out the Suzuki coupling reaction may include a method for carrying out the reaction using a palladium catalyst as a catalyst in any solvent in the presence of a base.

Examples of the palladium catalyst used for the Suzuki coupling reaction may include a Pd(0) catalyst and a Pd(II) catalyst. Specifically, examples of the palladium catalyst may include palladium [tetrakis(triphenylphosphine)], palladium acetates, dichlorobis(triphenylphosphine)palladium, palladium acetate, tris(dibenzylideneacetone)dipalladium, and bis(dibenzylideneacetone)palladium. From the viewpoint of the easiness of the reaction (polymerization) operation and the reaction (polymerization) rate, dichlorobis(triphenylphosphine)palladium, palladium acetate, and tris(dibenzylideneacetone)dipalladium are preferred.

The additive amount of the palladium catalyst is not particularly limited so long as it is an amount effective as the catalyst. It is generally 0.0001 mole to 0.5 mole, preferably 0.0003 mole to 0.1 mole, relative to 1 mole of the compound represented by Formula (100).

When palladium acetates are used as a palladium catalyst used for the Suzuki coupling reaction, for example, a phosphorus compound such as triphenylphosphine, tri(o-tolyl)phosphine, and tri(o-methoxyphenyl)phosphine can be added as a ligand. In this case, the additive amount of the ligand is generally 0.5 mole to 100 moles, preferably 0.9 mole to 20 moles, further preferably 1 mole to 10 moles, relative to 1 mole of the palladium catalyst.

Examples of the base used for the Suzuki coupling reaction may include inorganic bases, organic bases, and inorganic salts. Examples of the inorganic base may include potassium carbonate, sodium carbonate, and barium hydroxide. Examples of the organic base may include triethylamine and tributylamine. Examples of the inorganic salt may include cesium fluoride.

The additive amount of the base is generally 0.5 mole to 100 moles, preferably 0.9 mole to 20 moles, further preferably 1 mole to 10 moles, relative to 1 mole of the compound represented by Formula (100).

The Suzuki coupling reaction is generally carried out in a solvent. Examples of the solvent may include N,N-dimethylformamide, toluene, dimethoxyethane, and tetrahydrofuran. From the viewpoint of the solubility of the macromolecular compound used for the present invention, toluene and tetrahydrofuran are preferred. The base may be added as an aqueous solution to carry out the reaction in a two phases-system. When an inorganic salt is used as the base, the inorganic salt is generally added in a state of an aqueous solution for the reaction from the viewpoint of the solubility of the inorganic salt.

When the base is added in a state of an aqueous solution to carry out the reaction in a two phases-system, a phase-transfer catalyst such as a quaternary ammonium salt may be added, if necessary.

Although the temperature for carrying out the Suzuki coupling reaction depends on the solvent, the temperature is generally around 50 to 160° C. Preferably it is 60 to 120° C. from the viewpoint of making the molecular weight of the macromolecular compound higher. It is also possible to elevate the temperature to the near of the boiling point of the solvent for reflux. Although the reaction time may be terminated when the polymerization degree has reached an objective polymerization degree, the reaction time is generally around 0.1 to 200 hours. Preferably, it is around 1 to 30 hours for effeciency.

The Suzuki coupling reaction is carried out under an inactive atmosphere such as an argon gas and a nitrogen gas in a reaction system in which a Pd(O) catalyst is not inactivated. For example, the reaction is carried out in a system that is fully deaerated with an argon gas, a nitrogen gas or the like. Specifically, the reaction is carried out by:

fully purging the inside of a polymerization vessel (reaction system) with a nitrogen gas to deaerate the reaction system; then pouring the compound represented by Formula (100), the compound represented by Formula (200), and dicyclobis (triphenylphosphine) palladium (II) into the polymerization vessel; further purging fully the inside of the polymerization vessel with a nitrogen gas to deaerate the reaction system; then adding a solvent such as toluene that has been deaerated by bubbling the solvent with a nitrogen gas beforehand into the reaction system; then dropping, into the resultant reaction solution, an aqueous solution of a base such as sodium carbonate that has been deaerated by bubbling the solution with a nitrogen gas beforehand; then heating the resultant reaction mixture to elevate the temperature of the reaction mixture; and performing the polymerization, for example, at a reflux temperature for 8 hours while maintaining the inactive atmosphere.

Examples of the method using the Stille coupling reaction may include a production method having a process of reacting one or more type(s) of compound represented by Formula (300):

$$Q^{300}\text{-}E^{3}\text{-}Q^{400} \qquad (300)$$

In the above Formula, $E^3$ represents a divalent group containing an aromatic ring, and $Q^{300}$ and $Q^{400}$ are the same as or different from each other and represent an organotin residue;

with one or more type(s) of compound represented by the above Formula (200) in the presence of a palladium catalyst. $E^3$ is preferably a divalent aromatic group, further preferably a group represented by the aforementioned Formula 1 to Formula 143.

Examples of the organotin residue may include a group represented by $—SnR^{100}_3$. Here, $R^{100}$ represents a monovalent organic group. Examples of the monovalent organic group may include an alkyl group and an aryl group.

Examples of the alkyl group may include a linear alkyl group such as a methyl group, an ethyl group, an n-propyl group, an isopropyl group, an n-butyl group, an isobutyl group, an sec-butyl group, a tert-butyl group, an n-pentyl group, an isopentyl group, a 2-methylbutyl group, a 1-methylbutyl group, an n-hexyl group, an isohexyl group, a 3-methylpentyl group, a 2-methylpentyl group, a 1-methylpentyl group, a heptyl group, an octyl group, an isooctyl group, a 2-ethylhexyl group, a nonyl group, a decyl group, an undecyl group, a dodecyl group, a tetradecyl group, a hexadecyl group, an octadecyl group, and an eicosyl group; and a cycloalkyl group such as a cyclopentyl group, a cyclohexyl group, and an adamantyl group. Examples of the aryl group may include a phenyl group and a naphthyl group. The organotin residue is preferably $—SnMe_3$, $—SnEt_3$, $—SnBu_3$, or $—SnPh_3$, more preferably $—SnMe_3$, $—SnEt_3$, or $—SnBu_3$. In the above preferred examples, Me represents a methyl group, Et represents an ethyl group, Bu represents a butyl group, and Ph represents a phenyl group.

Examples of the halogen atom represented by $T^1$ and $T^2$ in Formula (200) may include a fluorine atom, a chlorine atom, a bromine atom, and an iodine atom. In terms of the easiness of the synthesis of the macromolecular compound, the halogen atom is preferably a bromine atom or an iodine atom.

Examples of the alkyl sulfonate group represented by $T^1$ and $T^2$ in Formula (200) may include a methane sulfonate group, an ethane sulfonate group, and a trifluoromethane sulfonate group. Examples of the aryl sulfonate group may include a benzene sulfonate group and a p-toluene sulfonate group. Examples of the aryl sulfonate group may include a benzyl sulfonate group.

Specifically, examples of the method may include a method for carrying out the reaction in the presence of, for example, a palladium catalyst as a catalyst in any solvent.

Examples of the palladium catalyst used for the Stille coupling reaction may include a Pd(0) catalyst and a Pd(II) catalyst. Specifically, examples of the palladium catalyst may include palladium [tetrakis(triphenylphosphine)], palladium acetates, dichlorobis(triphenylphosphine)palladium, palladium acetate, tris(dibenzylideneacetone)dipalladium, and bis(dibenzylideneacetone)palladium. Palladium [tetrakis(triphenylphosphine)] and tris(dibenzylideneacetone)dipalladium are preferred from the viewpoint of the easiness of the reaction (polymerization) operation and the reaction (polymerization) rate.

The additive amount of the palladium catalyst used for the Stille coupling reaction is not particularly limited so long as the additive amount is an amount effective as the catalyst. It is generally 0.0001 mole to 0.5 mole, preferably 0.0003 mole to 0.2 mole, relative to 1 mole of the compound represented by Formula (100).

In the Stille coupling reaction, a ligand and a co-catalyst can also be used, if necessary. Examples of the ligand may include a phosphorus compound such as triphenylphosphine, tri(o-tolyl)phosphine, tri(o-methoxyphenyl)phosphine, and tris(2-furyl)phosphine, and an arsenic compound such as triphenyl arsine and triphenoxy arsine. Examples of the co-catalyst may include copper iodide, copper bromide, copper chloride, and copper (I) 2-thenoate.

When the ligand or the co-catalyst is used, the additive amount of the ligand or the co-catalyst is generally 0.5 mole to 100 moles, preferably 0.9 mole to 20 moles, further preferably 1 mole to 10 moles, relative to 1 mole of the palladium catalyst.

The Stille coupling reaction is generally carried out in a solvent. Examples of the solvent may include N,N-dimethylformamide, N,N-dimethylacetamide, toluene, dimethoxyethane, and tetrahydrofuran. From the viewpoint of the solubility of the macromolecular compound used for the present invention, toluene and tetrahydrofuran are preferred.

Although the temperature for carrying out the Stille coupling reaction depends on the solvent, the temperature is generally around 50 to 160° C. Preferably, it is 60 to 120° C. from the viewpoint of making the molecular weight of the macromolecular compound higher. It is also possible to elevate the temperature to the near to the boiling point of the solvent for reflux.

Although the time for carrying out the reaction (reaction time) may be terminated when the polymerization degree has reached an objective polymerization degree, the reaction time is generally around 0.1 to 200 hours. Preferably, it is around 1 to 30 hours for efficiency.

The Stille coupling reaction is carried out under an inactive atmosphere such as an argon gas and a nitrogen gas in a reaction system in which a Pd catalyst is not inactivated. For example, the reaction is carried out in a system that is fully deaerated with an argon gas, a nitrogen gas or the like. Specifically, the reaction is carried out by: fully purging the inside of a polymerization vessel (reaction system) with a nitrogen gas to deaerate the reaction system; then pouring the compound represented by Formula (300), the compound represented by Formula (200), and a palladium catalyst into the polymerization vessel; further purging fully the inside of the polymerization vessel with a nitrogen gas to deaerate the reaction system; then adding a solvent such as toluene that has been deaerated by bubbling with a nitrogen gas beforehand to the reaction system; then adding a ligand or a co-catalyst to the reaction system, if necessary; then heating the resultant reaction mixture to elevate the temperature of the reaction mixture; and performing the polymerization, for example, at a reflux temperature for 8 hours while maintaining the inactive atmosphere.

The number average molecular weight (Mn) in terms of polystyrene of the macromolecular compound is preferably $1\times10^3$ to $1\times10^8$. When the number average molecular weight in terms of polystyrene is $1\times10^3$ or more, a rigid thin film can easily be obtained. By contrast, when the number average molecular weight is $10^8$ or less, the solubility of the macromolecular compound becomes high, so that the production of a thin film becomes easier.

A terminal group of the macromolecular compound of the present invention may be protected with a stable group, since there is the probability that the property or the life of a cell, a device or an element obtained by using such a macromolecular compound for the production of the cell, device or element might be lowered if a polymerization active group remains. The terminal group preferably has a conjugated bond continuing from a conjugation structure of the main chain, or may have a structure having, for example, a bonding with an aryl group or a heterocyclic group through a vinylene group.

Although the macromolecular compound of the present invention has a structural unit represented by Formula (1), the macromolecular compound can be synthesized, for example, by using a compound represented by Formula (1-3) as one of the raw materials.

[Chemical Formula 53]

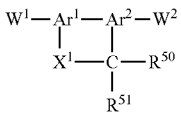

(1-3)

In Formula (1-3), $Ar^1$, $A^2$, $X^1$, $R^{50}$, and $R^{51}$ represent the same as defined above. $W^1$ and $W^2$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue.

When $W^1$ and $W^2$ are a hydrogen atom, by performing an oxidation polymerization, a macromolecular compound having a structural unit represented by Formula (1) can be produced. In the oxidation polymerization, a catalyst is used generally. As such a catalyst, a publicly known catalyst can be used. For example, a metal halide or a mixture of a metal halide and an amine complex (metal halide/amine complex) is used. Here, as the metal halide, for example, a monovalent-, divalent-, or trivalent-halide of a metal such as copper, iron, vanadium, and chromium can be used. Examples of the amine used for the production of the amine complex may include pyridine, lutidine, 2-methylimidazole, and N,N,N',N'-tetramethylethylenediamine. The metal halide/amine complex can be produced by mixing a metal halide with an amine in a solvent in the presence of oxygen and the mixing molar ratio of the metal halide and the amine is, for example, metal halide/amine=1/0.1 to 1/200, preferably around 1/0.3 to 1/100.

As the catalyst, iron chloride can also be used (Polym. Prep. Japan, Vol. 48, 309 (1999)). Furthermore, by using a copper/amine catalyst system (J. Org. Chem., 64, 2264 (1999), J. Polym. Sci. Part A, Polym. Chem., 37, 3702 (1999)), the molecular weight of the macromolecular compound can be enhanced.

The solvent for the oxidation polymerization is not particularly limited to be used so long as the solvent is a solvent from which the catalyst does not suffer poisoning. Examples of such a solvent may include hydrocarbon solvents, ether solvents, and alcohols. Here, examples of the hydrocarbon solvents may include toluene, benzene, xylene, trimethylbenzene, tetramethylbenzene, naphthalene, and tetralin. Examples of the ether solvent may include diethyl ether, diisopropyl ether, tetrahydrofuran, 1,4-dioxane, diphenyl ether, and tert-butyl methyl ether. Examples of the alcohols may include methanol, ethanol, isopropanol, and 2-methoxyethanol.

The reaction temperature for the oxidation polymerization is generally −100° C. to 100° C., preferably around −50 to 50° C.

Examples of the method for producing a copolymer may include a method of mixing two or more types of monomers to polymerize them and a method of polymerizing one type of monomer and then adding, to the reaction, a second monomer. By using or combining these methods, a block copolymer, a random copolymer, an alternate copolymer, a multiblock copolymer, a graft copolymer and the like can be produced.

From the viewpoint of the easiness of exchanging a functional group, $W^1$ and $W^2$ in Formula (1-3) are the same as or different from each other and are preferably a halogen atom, an alkyl sulfonate group, an aryl sulfonate group, an arylalkyl sulfonate group, a boric acid ester residue, a boronic acid residue; or an organotin residue.

Although when $W^1$ and $W^2$ are a hydrogen atom, as the method for converting $W^1$ and $W^2$ into a bromine atom, a publicly known method can be used, examples of the method may include a method of contacting a compound represented by Formula (1-3) in which $W^1$ and $W^2$ are a hydrogen atom with bromine or N-bromosuccinimide (NBS) to brominate $W^1$ and $W^2$. Although the conditions for the bromination can optionally be set, for example, a method of reacting with NBS in a solvent is desired since it exhibits a high brominaion rate and high selectivity of a position into which a bromine atom is introduced. Examples of the solvent used in this case may include N,N-dimethylformamide, chloroform, methylene chloride, and carbon tetrachloride. The reaction time is generally around 1 to 10 hours and the reaction temperature is generally around −50 to 50° C. The used amount of bromine is preferably around 1 to 5 moles relative to 1 mole of compound represented by Formula (1-3) in which $W^1$ and $W^2$ are a hydrogen atom. After the reaction, for example, ordinary post-treatment is carried out including, for example, extraction of the product with an organic solvent and evaporation of the soluvent after termination of the reaction by adding water. By the treatment, a compound represented by Formula (1-3) in which $W^1$ and $W^2$ are a bromine atom can be obtained. The isolation and the purification of the product can be performed by a method such as preparative isolation by chromatography and recrystallization.

A compound represented by Formula (3) that is one aspect of the compound represented by Formula (1-3) can be produced by reacting a compound represented by Formula (4) in the presence of an acid.

[Chemical Formula 54]

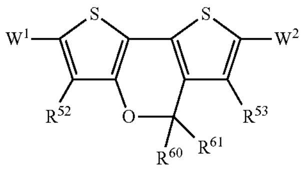

(3)

In the above Formula, $R^{52}$, $R^{53}$, $R^{60}$, and $R^{61}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; and $W^1$ and $W^2$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue.

[Chemical Formula 55]

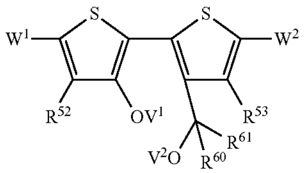

(4)

In the above Formula, $R^{60}$, $R^{61}$, $R^{52}$, $R^{53}$, $W^1$, and $W^2$ represent the same as defined above; and $V^1$ and $V^2$ are the same as or different from each other and represent a hydrogen atom, an alkali metal, an alkyl group, an aryl group, or an arylalkyl group.

The definition and specific examples of the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the halogen atom, the monovalent heterocyclic group, the heterocyclyloxy group, the heterocyclylthio group, the arylalkenyl group, or the arylalkynyl group represented by $R^{52}$, $R^{52}$, $R^{50}$, and $R^{61}$ are the same as the definition and specific examples of the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the halogen atom, the monovalent heterocyclic group, the heterocyclyloxy group, the heterocyclylthio group, the arylalkenyl group, or the arylalkynyl group represented by the above $R^3$.

The definition and specific examples of the alkyl group, the aryl group, or the arylalkyl group represented by $V^1$ and $V^2$ are the same as the definition and specific examples of the alkyl group, the aryl group, or the arylalkyl group represented by the above $R^3$.

$R^{61}$ is preferably an alkyl group having 6 or more carbon atoms, an alkyloxy group having 6 or more carbon atoms, an alkylthio group having 6 or more carbon atoms, an aryl group having 6 or more carbon atoms, an aryloxy group having 6 or more carbon atoms, an arylthio group having 6 or more carbon atoms, an arylalkyl group having 7 or more carbon atoms, an arylalkyloxy group having 7 or more carbon atoms, an arylalkylthio group having 7 or more carbon atoms, an acyl group having 6 or more carbon atoms, or an acyloxy group having 6 or more carbon atoms.

The acid used for the synthesis of the compound represented by Formula (3) from the compound represented by Formula (4) may be any one of a Lewis acid and a Bronsted acid and examples thereof may include hydrochloric acid, bromic acid, hydrofluoric acid, sulfuric acid, nitric acid, formic acid, acetic acid, propionic acid, oxalic acid, benzoic acid, boron fluoride, aluminum chloride, tin (IV) chloride, iron (II) chloride, titanium tetrachloride, benzenesulfonic acid, p-toluenesulfonic acid, and a mixture thereof.

The reaction can be carried out in the presence of a solvent. The reaction temperature is preferably −80° C. to a boiling point of the solvent.

Examples of the solvent used for the reaction may include a saturated hydrocarbon such as pentane, hexane, heptane, octane, and cyclohexane; an unsaturated hydrocarbon such as benzene, toluene, ethylbenzene, and xylene; a halogenated saturated hydrocarbon such as carbon tetrachloride, chloroform, dichloromethane, chlorobutane, bromobutane, chloropentane, bromopentane, chlorohexane, bromohexane, chlorocyclohexane, and bromocyclohexane; a halogenated unsaturated hydrocarbon such as chlorobenzene, dichlorobenzene, and trichlorobenzene; alcohols such as methanol, ethanol, propanol, isopropanol, butanol, and tert-butyl alcohol; carboxylic acids such as formic acid, acetic acid, and propionic acid; ethers such as dimethyl ether, diethyl ether, methyl tert-butyl ether, tetrahydrofuran, tetrahydropyran, and dioxane; and an inorganic acid such as hydrochloric acid, bromic acid, hydrofluoric acid, sulfuric acid, and nitric acid. These solvent may be used individually or in combination thereof.

After the reaction, for example, ordinary post-treatment is carried out including, for example, extraction of the product with an organic solvent and evaporation of the soluvent after termination of the reaction by adding water. By the treatment, a compound represented by Formula (3) can be obtained. The isolation and the purification of the product can be performed by a method such as preparative isolation by chromatography and recrystallization.

In the compound represented by Formula (4), from the viewpoint of the easiness of exchanging a functional group, it is preferred that $W^1$ and $W^2$ are the same as or different from each other and are a hydrogen atom, a halogen atom, an alkyl sulfonate group, an aryl sulfonate group, an arylalkyl sulfonate group, a boric acid ester residue, a boronic acid residue, or an organotin residue.

The compound represented by Formula (4) can be synthesized by reacting a compound represented by Formula (5) with a Grignard reagent or an organolithium (Li) compound.

[Chemical Formula 56]

(5)

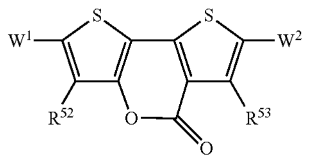

In the above Formula, $R^{52}$, $R^{53}$, $W^1$, and $W^2$ represent the same as defined above.

Examples of the Grignard reagent used for the above reaction may include methylmagnesium chloride, methylmagnesium bromide, ethylmagnesium chloride, ethylmagnesium bromide, propylmagnesium chloride, propylmagnesium bromide, butylmagnesium chloride, butylmagnesium bromide, hexylmagnesium bromide, octylmagnesium bromide, decylmagnesium bromide, allylmagnesium chloride, allylmagnesium bromide, benzylmagnesium chloride, phenylmagnesium bromide, naphthylmagnesium bromide, and tolylmagnesium bromide.

Examples of the organic Li compound may include methyl lithium, ethyl lithium, propyl lithium, butyl lithium, phenyl lithium, naphthyl lithium, benzyl lithium, and tolyl lithium.

The reaction can be carried out under an inert gas atmosphere such as nitrogen and argon in the presence of a solvent. The reaction temperature is preferably −80° C. to a boiling point of the solvent.

Examples of the solvent used for the reaction may include a saturated hydrocarbon such as pentane, hexane, heptane, octane, and cyclohexane; an unsaturated hydrocarbon such as benzene, toluene, ethylbenzene, and xylene; and ethers such as dimethyl ether, diethyl ether, methyl tert-butyl ether, tetrahydrofuran, tetrahydropyran, and dioxane. These solvents may be used individually or in combination thereof.

After the reaction, for example, ordinary post-treatment is carried out including, for example, extraction of the product with an organic solvent and evaporation of the soluvent after termination of the reaction by adding water. By the treatment, a compound represented by Formula (4) can be obtained. The isolation and the purification of the product can be performed by a method such as preparative isolation by chromatography and recrystallization.

Another synthetic method of the compound represented by Formula (4) includes a method of reacting a compound represented by Formula (5-1) with a Grignard reagent or an organolithium compound.

[Chemical Formula 57]

(5-1)

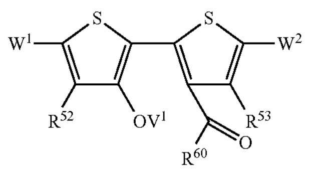

In the above Formula, $R^{52}$, $R^{53}$, $W^1$, $W^2$, $V^1$, and $R^{60}$ represent the same as defined above.

For the Grignard reagent, organic Li compound, reaction conditions, solvent, and treatment method after the reaction which are used above, the same compounds, conditions, and method as the compounds, conditions, and method described in the above method for synthesizing the compound represented by Formula (4) from the compound represented by Formula (5) can be used.

The compound represented by Formula (5-1) can be synthesized by reacting the compound represented by Formula (5) with 1 equivalent of a Grignard reagent or an organic Li compound. For the Grignard reagent, organic Li compound, reaction conditions, solvent, and treatment method after the reaction which are used above, the same compounds, conditions, and method as the compounds, conditions, and method described in the above method for synthesizing the compound represented by Formula (4) from the compound represented by Formula (5) can be used. When the reactivity of a Grignard reagent or an organic Li compound is low, more than 1 equivalent of a Grignard reagent or an organic Li compound relative to the compound represented by Formula (5) can be used. On the other hand, when the reactivity of a Grignard reagent or an organic Li compound is high, it is preferred that 1 equivalent of a Grignard reagent or an organic Li compound relative to the compound represented by Formula (5) is used.

A compound represented by Formula (7) among the compounds represented by Formula (5) can be produced by reacting a compound represented by Formula (6) with a peroxide.

[Chemical Formula 58]

(6)

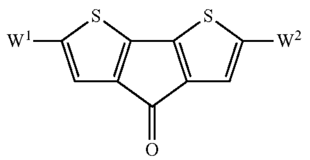

(7)

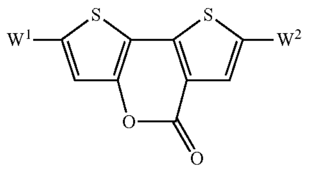

In Formula (6) and Formula (7), $W^1$ and $W^2$ represent the same as defined above.

Examples of the peroxide may include sodium perborate, m-chloro perbenzoic acid, hydrogen peroxide, and benzoyl peroxide. Preferred are sodium perborate and m-chloro perbenzoic acid and particularly preferred is sodium perborate.

The reaction can be carried out in the presence of a carboxylic acid solvent such as acetic acid, trifluoroacetic acid, propionic acid, and butyric acid. For enhancing the solubility of the compound represented by Formula (6), the reaction is preferably carried out in a solvent system which is mixture of carbon tetrachloride, chloroform, dichloromethane, benzene, toluene or the like. The reaction temperature is preferably 0° C. to a boiling point of the solvent.

After the reaction, for example, ordinary post-treatment is carried out including extraction of the product with an organic solvent and evaporation of the soluvent after termination of the reaction by adding water. By the treatment, a compound represented by Formula (7) can be obtained. The isolation and the purification of the product can be performed by a method such as preparative isolation by chromatography and recrystallization.

The macromolecular compound of the present invention can also be produced using a compound represented by Formula (8-1) or a compound represented by Formula (8-2).

[Chemical Formula 59]

(8-1)

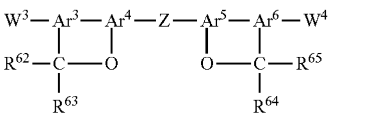

(8-2)

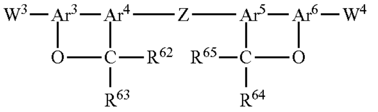

In the above Formula, $R^{62}$ to $R^{65}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group; $Ar^3$ to $Ar^6$ are the same as or different from each other and represent a trivalent heterocyclic group; $W^3$ and $W^4$ are the same as or different from each other and represent a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, a boronic acid residue, a formyl group, a vinyl group, or an organotin residue; and Z represents an arylene group or a divalent heterocyclic group.

The definition and specific examples of the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the halogen atom, the monovalent heterocyclic group, the heterocyclyloxy group, the heterocyclylthio group, the arylalkenyl group, or the arylalkynyl group represented by $R^{62}$ to $R^{65}$ are the same as the definition and specific examples of the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the halogen atom, the monovalent heterocyclic group, the heterocyclyloxy group, the heterocyclylthio group, the arylalkenyl group, or the arylalkynyl group represented by the above $R^3$. $R^{62}$ and $R^{65}$ are preferably an alkyl group having 6 or more carbon atoms, an alkyloxy group having 6 or more carbon atoms, an alkylthio group having 6 or more carbon atoms, an aryl group having 6 or more carbon atoms, an aryloxy group having 6 or more carbon atoms, an arylthio group having 6 or more carbon atoms, an arylalkyl group having 7 or more carbon atoms, an arylalkyloxy group having 7 or more carbon atoms, an arylalkylthio group having 7 or more carbon atoms, an acyl group having 6 or more carbon atoms, or an acyloxy group having 6 or more carbon atoms.

The definition and specific examples of the trivalent heterocycle represented by $Ar^3$ to $Ar^6$ are the same as the above definition and specific examples of $Ar^1$ and $Ar^2$.

Specific examples of the halogen atom, the alkyl sulfonate group, the aryl sulfonate group, the arylalkyl sulfonate group, the boric acid ester residue, the sulfonium methyl group, the phosphonium methyl group, the phosphonate methyl group, the monohalogenated methyl group, the boronic acid residue, the formyl group, the vinyl group, or the organotin residue represented by $W^3$ and $W^4$ may include the same groups as the groups exemplified for the above $W^1$ and $W^2$. Specific examples of the arylene group and the divalent heterocyclic group represented by Z may include the groups represented by Formula 1 to Formula 143.

Among the compounds represented by Formula (8-1), a compound represented by Formula (9-1) is preferred. Among the compounds represented by Formula (8-2), a compound represented by Formula (9-2) is preferred.

[Chemical Formula 60]

(9-1)

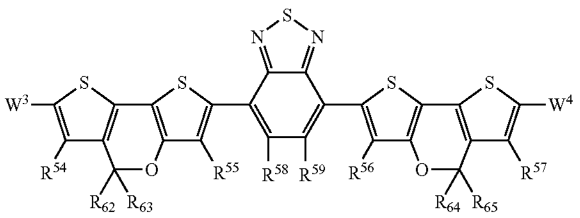

(9-2)

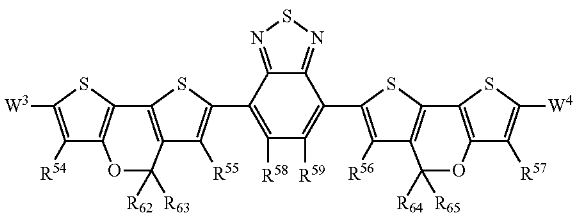

In the above Formula, $R^{62}$ to $R^{65}$, $W^3$, and $W^4$ represent the same as defined above. $R^{54}$ to $R^{59}$ are the same as or different from each other and represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amido group, an acid imido group, an amino group, a substituted amino group, a substituted silyl group, a substituted silyloxy group, a substituted silylthio group, a substituted silylamino group, a monovalent heterocyclic group, a heterocyclyloxy group, a heterocyclylthio group, an arylalkenyl group, an arylalkynyl group, a carboxyl group, or a cyano group.

The definition and specific examples of the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the halogen atom, the monovalent heterocyclic group, the heterocyclyloxy group, the heterocyclylthio group, the arylalkenyl group, or the arylalkynyl group represented by $R^{54}$ to $R^{59}$ are the same as the definition and specific examples of the alkyl group, the alkyloxy group, the alkylthio group, the aryl group, the aryloxy group, the arylthio group, the arylalkyl group, the arylalkyloxy group, the arylalkylthio group, the acyl group, the acyloxy group, the amido group, the acid imido group, the substituted amino group, the substituted silyl group, the substituted silyloxy group, the substituted silylthio group, the substituted silylamino group, the halogen atom, the monovalent heterocyclic group, the heterocyclyloxy group, the heterocyclylthio group, the arylalkenyl group, or the arylalkynyl group represented by the above $R^3$.

The compound represented by Formula (9-1) and the compound represented by Formula (9-2) can be obtained, for example, by reacting a compound represented by Formula (3) in which $W^1$ is a bromine atom and $W^2$ is a hydrogen atom or a compound represented by Formula (3) in which $W^1$ is a hydrogen atom and $W^2$ is a bromine atom with a compound represented by Formula (10) through the above Suzuki coupling method.

[Chemical Formula 61]

(10)

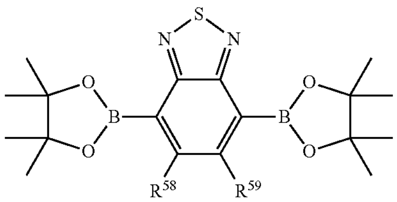

In the above Formula, $R^{58}$ and $R^{59}$ represent the same as defined above.

A compound represented by Formula (9-1) in which $W^3$ and $W^4$ are a hydrogen atom and a compound represented by Formula (9-2) in which $W^3$ and $W^4$ are a hydrogen atom can also be polymerized by oxidation polymerization or the like. A compound represented by Formula (9-1) in which $W^3$ and $W^4$ are the same as or different from each other and are a halogen atom, boric acid, a boric acid ester residue, or an organotin residue and a compound represented by Formula (9-2) in which $W^3$ and $W^4$ are the same as or different from each other and are a halogen atom, boric acid, a boric acid ester residue, or an organotin residue can be polymerized using the above Suzuki coupling or Stille coupling reaction.

The macromolecular compound of the present invention has preferably a light absorbing terminal wavelength that is a longer wavelength. The light absorbing terminal wavelength can be measured by the following method.

For the measurement, a spectrophotometer operating in wavelength regions of ultraviolet, visible, and near-infrared (for example, an ultraviolet-visible-near infrared spectrophotometer: JASCO-V670; manufactured by JASCO Corporation) is used. When JASCO-V670 is used, a range of measurable wavelength thereof is 200 to 1,500 nm. Therefore, the measurement is performed in this wavelength region. First, an absorption spectrum of a substrate used for the measurement is measured. The substrate such as a quartz substrate or a glass substrate is used. Next, on the substrate, a thin film comprising a first compound is formed from a solution containing the first compound or a melt containing the first compound. In the film formation from the solution, drying is performed after the film formation. Then, an absorption spectrum of the layered body of the thin film and the substrate is measured. The difference between the absorption spectrum of the layered body of the thin film and the substrate and the absorption spectrum of the substrate is obtained as the absorption spectrum of the thin film.

In the absorption spectrum of the thin film, the absorbance of the first compound is assigned on the ordinate axis and the wavelength is assigned on the abscissa axis. It is desired to control the film thickness of the thin film so that absorbance of the largest absorption peak becomes around 0.5 to 2. The absorbance of an absorption peak at the longest wavelength among absorption peaks is assumed to be 100%, and an intersection point of the absorption peak with a line parallel to the abscissa axis (wavelength axis) that passes through 50% of the absorbance, the intersection point being in a longer wavelength side than a peak wavelength of the absorption peak, is assumed to be a first point. An intersection point of the absorption peak with a line parallel to the wavelength axis that passes through 25% of the absorbance, the intersection point being in a longer wavelength side than a peak wavelength of the absorption peak, is assumed to be a second point. A wavelength for an intersection point of a line connecting the first point and the second point with the following standard line is defined as the light absorbing terminal wavelength. Here, the standard line refers to a line connecting a third point with a fourth point, which are defined as follows: the third point refers to a point on the absorption spectrum at a wavelength longer by 100 nm than the following standard wavelength; the fourth point refers to a point on the absorption spectrum at a wavelength longer by 150 nm than the following standard wavelength; and the standard wavelength refers to, when the standard wavelength is, when the absorbance of the absorption peak at the longest wavelength is assumed to be 100%, a wavelength for an intersection point of the absorption peak with a line parallel to the wavelength axis that passes through 10% of the absorbance, the intersection point being in a longer wavelength side than a peak wavelength of the absorption peak.

The macromolecular compound of the present invention can exhibit high electron and/or hole transport properties. Therefore, the macromolecular compound of the present invention can transport electrons or holes injected from an electrode or charges generated by light absorption, when an organic thin film containing the compound is used in a cell, a device or an element. Taking advantage of these properties, the macromolecular compound of the present invention can suitably be used in various cells, devices or elements such as a photovoltaic cell, an organic thin film transistor, and an organic electroluminescent device. Hereinafter, these cells, devices or elements are individually described.

<Photovoltaic Cell>

A photovoltaic cell having the macromolecular compound of the present invention has one or more activated layer(s) containing the macromolecular compound of the present invention between a pair of electrodes at least one of which is transparent or translucent.

A preferred form of the photovoltaic cell having the macromolecular compound of the present invention has a pair of electrodes at least one of which is transparent or translucent and an activated layer formed from an organic composition of a p-type organic semiconductor and an n-type organic semiconductor. The macromolecular compound of the present invention is preferably used as a p-type organic semiconductor. The action mechanism of the photovoltaic cell in this form is described. A light energy entering through a transparent or translucent electrode is absorbed by an electron acceptor compound (n-type organic semiconductor) such as fullerene derivatives and/or an electron donor compound (p-type organic semiconductor) such as the macromolecular compound of the present invention to generate an exciton in which an electron and a hole are bonded with each other. When the generated exciton moves and reaches a heterojunction interface where an electron acceptor compound and an electron donor compound are adjacent to each other, due to the difference of an HOMO energy and a LUMO energy of the electron acceptor compound and the electron donor compound at the interface, an electron and a hole are separated to generate electric charges (an electron and a hole) that can independently move. Each of the generated electric charges moves to an electrode to become able to be taken out as an electric energy (current) to the outside.

The photovoltaic cell produced using the macromolecular compound of the present invention is generally formed on a substrate. This substrate may be a substrate that does not chemically changed when an electrode and an organic layer is formed on the substrate. Examples of the material for the substrate may include a glass, a plastic, a macromolecule film, and silicon. When the substrate is opaque, it is preferred that an opposite electrode (that is, an electrode more distant from the substrate) is transparent or translucent.

Another aspect of the photovoltaic cell having the macromolecular compound of the present invention is a photovoltaic cell containing, between a pair of electrodes at least one of which is transparent or translucent, a first activated layer containing the macromolecular compound of the present invention and a second activated layer adjacent to the first activated layer that contains an electron acceptor compound such as fullerene derivatives.

Examples of the transparent or translucent electrode material may include a conductive metal oxide film and a translucent metal thin film. Specifically, a film produced using a conductive material such as indium oxide, zinc oxide, tin oxide, and a complex thereof such as indium-tin-oxide (ITO) and indium-zinc-oxide, NESA, gold, platinum, silver, copper and the like are used, and among them, ITO, indium-zinc-oxide, and tin oxide are preferred. Examples of the production method of the electrode may include a vacuum deposition method, a sputtering method, an ion plating method, and a plating method.

As the electrode material, an organic transparent conductive film of a polyaniline or a derivative thereof, a polythiophene or a derivative thereof or the like may also be used.

One of the electrodes may be not transparent, and as the material for this electrode, a metal, a conductive macromolecule or the like may be used. Specific examples of the electrode material may include a metal such as lithium, sodium, potassium, rubidium, cesium, magnesium, calcium, strontium, barium, aluminum, scandium, vanadium, zinc, yttrium, indium, cerium, samarium, europium, terbium, and ytterbium; an alloy of two or more types of these metals; an alloy of one or more type(s) of these metals with one or more type(s) of metal selected from the group consisting of gold, silver, platinum, copper, manganese, titanium, cobalt, nickel, tungsten, and tin; graphite; a graphite intercalation compound; a polyaniline and a derivative thereof; and a polythiophene and a derivative thereof. Examples of the alloy may include a magnesium-silver alloy, a magnesium-indium alloy, a magnesium-aluminum alloy, an indium-silver alloy, a lithium-aluminum alloy, a lithium-magnesium alloy, a lithium-indium alloy, and a calcium-aluminum alloy.

As a means for enhancing the photoelectric conversion efficiency, an additional intermediate layer other than the activated layer may also be used. Examples of the material used for the intermediate layer may include a halide of an alkali metal or an alkaline earth metal such as lithium fluoride, an oxide such as titanium oxide, and PEDOT (poly-3,4-ethylenedioxythiophene).

<Activated Layer>

The activated layer may contain one type of the macromolecular compounds of the present invention individually or in a combination of two or more types of the macromolecular compounds of the present invention. For enhancing the hole transport property of the activated layer, as the electron donor compound and/or the electron acceptor compound, a compound other than the macromolecular compound of the present invention may be blended in the activated layer to be used. Here, the electron donor compound and the electron acceptor compound are relatively determined from the energy level of energy order of these compounds.

Examples of the electron donor compound may include, in addition to the macromolecular compound of the present invention, a pyrazoline derivative, an arylamine derivative, a stilbene derivative, a triphenyldiamine derivative, oligothiophene and a derivative thereof, polyvinyl carbazole and a derivative thereof, polysilane and a derivative thereof, a polysiloxane derivative having an aromatic amine residue in a side chain or main chain, polyaniline and a derivative thereof, polythiophene and a derivative thereof, polypyrrole and a derivative thereof, polyphenylenevinylene and a derivative thereof, and polythienylenevinylene and a derivative thereof.

Examples of the electron acceptor compound may include, in addition to the macromolecular compound of the present invention, a carbon material, a metal oxide such as titanium oxide, an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, metal complexes of 8-hydroxyquinoline and a derivative thereof, polyquinoline and a derivative thereof, polyquinoxaline and a derivative thereof, polyfluorene and a derivative thereof, a phenanthroline derivative such as 2,9-dimethyl-4,7-diphenyl-1,10-phenanthroline (bathocuproine), fullerene, and a fullerene derivative, and among them, preferred are titanium oxide, a carbon nanotube, fullerene, and a fullerene derivative, particularly preferred are fullerene and a fullerene derivative.

Examples of fullerene and a fullerene derivative may include $C_{60}$, $C_{70}$, $C_{76}$, $C_{78}$, $C_{84}$, and a derivative thereof. A fullerene derivative refers to a compound in which at least a part of fullerene is modified.

Examples of the fullerene derivative may include a compound represented by Formula (13), a compound represented by Formula (14), a compound represented by Formula (15), and a compound represented by Formula (16).

[Chemical Formula 62]

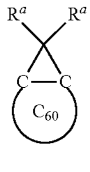

(13)

-continued (14)

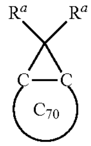

(15)

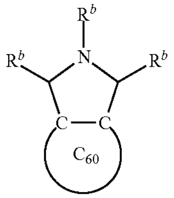

(16)

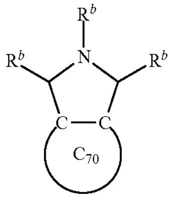

In Formulae (13) to (16), $R^a$ is an alkyl group, an aryl group, a heteroaryl group, or a group having an ester structure wherein a plurality of $R^a$s may be the same as or different from each other; and $R^b$ represents an alkyl group or an aryl group wherein a plurality of $R^b$s may be the same as or different from each other.

The definitions and specific examples of the alkyl group and the aryl group represented by $R^a$ and $R^b$ are the same as the definitions and specific examples of the alkyl group and the aryl group represented by $R^3$.

The heteroaryl group represented by $R^a$ generally has 3 to 60 carbon atoms and examples thereof may include a thienyl group, a pyrrolyl group, a furyl group, a pyridyl group, a quinolyl group, and an isoquinolyl group.

Examples of the group having an ester structure represented by $R^a$ may include a group represented by Formula (17).

[Chemical Formula 63]

(17)

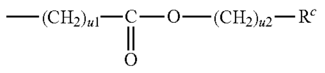

In the above Formula, u1 represents an integer of 1 to 6; u2 represents an integer of 0 to 6; and $R^c$ represents an alkyl group, an aryl group, or a heteroaryl group.

The definitions and specific examples of the alkyl group, the aryl group, and the heteroaryl group represented by $R^c$ are the same as the definitions and specific examples of the alkyl group, the aryl group, and the heteroaryl group represented by $R^a$.

Specific examples of the $C_{60}$ fullerene derivative may include the following compounds.

[Chemical Formula 64]

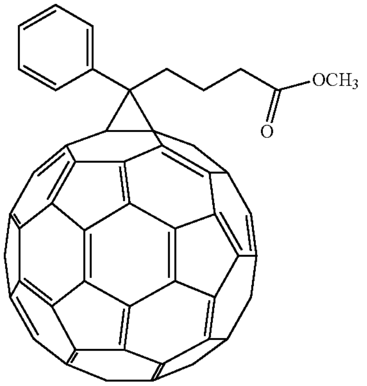

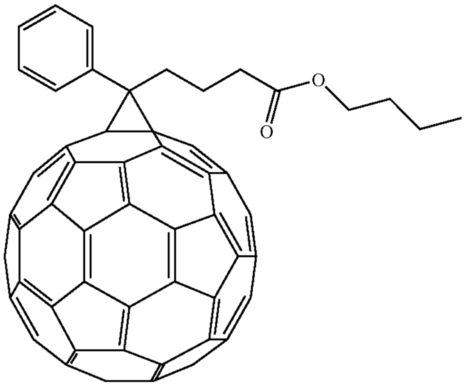

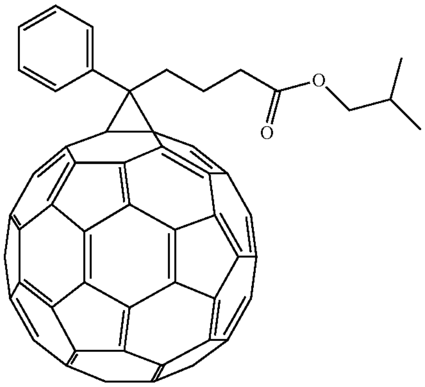

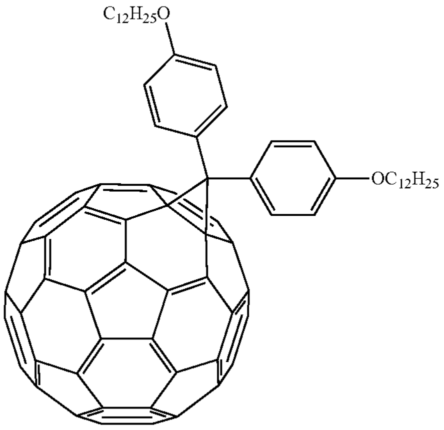

-continued

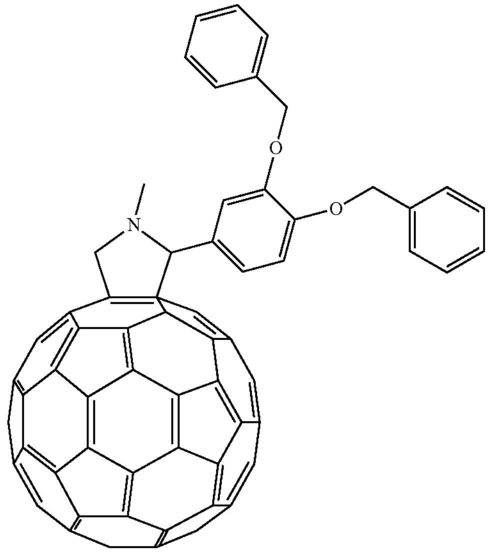

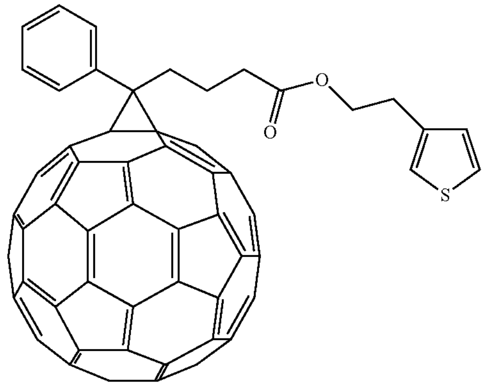

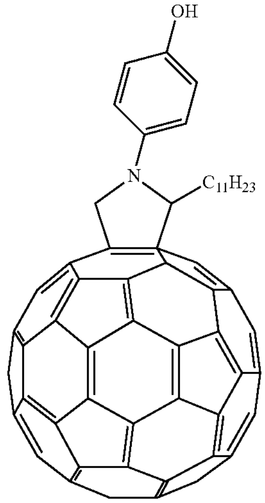

Specific examples of the $C_{70}$ fullerene derivative may include the following compounds.

[Chemical Formula 65]

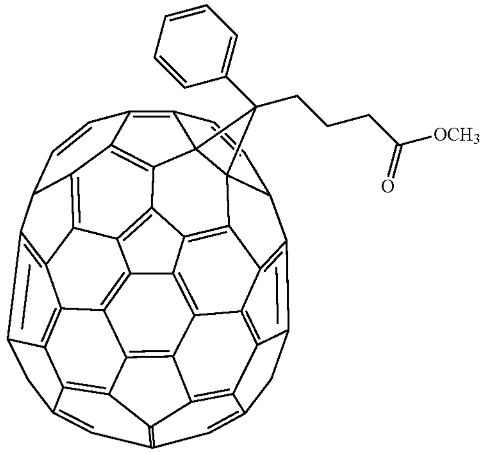

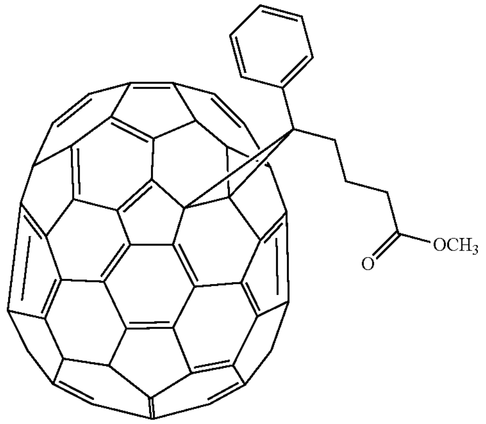

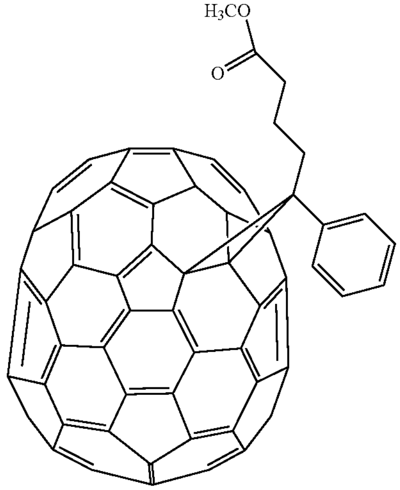

In addition, examples of the fullerene derivative may include [6,6]-phenyl C61 butyric acid methyl ester (C60 PCBM), [6,6]-phenyl C71 butyric acid methyl ester (C70 PCBM), [6,6]-phenyl C85 butyric acid methyl ester (C84 PCBM), and [6,6]-thienyl C61 butyric acid methyl ester.

When the macromolecular compound of the present invention and the fullerene derivative are'contained in the activated layer, the ratio of the fullerene derivative is preferably 10 to 1,000 parts by weight, more preferably 20 to 500 parts by weight, relative to 100 parts by weight of the macromolecular compound of the present invention.

The activated layer generally has a thickness of preferably 1 nm to 100 μm, more preferably 2 nm to 1,000 nm, further preferably 5 nm to 500 nm, more preferably 20 nm to 200 nm.

The production method of the activated layer may be any production method and examples thereof may include a film forming method from a solution containing the macromolecular compound and a film forming method by a vacuum deposition method.

<Production Method of Photovoltaic Cell>

A preferred production method of a photovoltaic cell is a production method of a cell having a first electrode and a second electrode and having an activated layer between the first electrode and the second electrode, which has a process of applying a solution (ink) containing the macromolecular compound of the present invention and a solvent on the first electrode by a coating method to form an activated layer and a process of forming the second electrode on the activated layer.

The solvent used for the film formation from the solution may be any solvent so long as the solvent dissolves the macromolecular compound of the present invention. Examples of the solvent may include an unsaturated hydrocarbon solvent such as toluene, xylene, mesitylene, tetralin, decalin, bicyclohexyl, n-butylbenzene, sec-butylbenzene, and tert-butylbenzene; a halogenated saturated hydrocarbon solvent such as carbon tetrachloride, chloroform, dichloromethane, dichloroethane, chlorobutane, bromobutane, chloropentane, bromopentane, chlorohexane, bromohexane, chlorocyclohexane, and bromocyclohexane; a halogenated unsaturated hydrocarbon solvent such as chlorobenzene, dichlorobenzene, and trichlorobenzene; and an ether solvent such as tetrahydrofuran and tetrahydropyran. The macromolecular compound of the present invention can generally be dissolved in these solvents or a solvent mixture containing one or more type(s) of these solvents. The macromolecular compound of the present invention can generally be dissolved in these solvents in a concentration of 0.1% by weight or more.

When the film formation is performed using the solution, examples of the coating method applicable to the film formation may include a slit coating method, a knife coating method, a spin coating method, a casting method, a micro gravure coating method, a gravure coating method, a bar coating method, a roll coating method, a wire bar coating method, a dip coating method, a spray coating method, a screen printing method, a gravure printing method, a flexo printing method, an offset printing method, an inkjet coating method, a dispenser printing method, a nozzle coating method, and a capillary coating method, and among them, preferred are a slit coating method, a capillary coating method, a gravure coating method, a micro gravure coating method, a bar coating method, a knife coating method, a nozzle coating method, an inkjet coating method, and a spin coating method.

From the viewpoint of film forming property, the surface tension of the solvent at 25° C. is preferably more than 15 mN/m, more preferably more than 15 mN/m and less than 100 mN/m, further preferably more than 25 mN/m and less than 60 mN/m.

<Organic Transistor>

The macromolecular compound of the present invention can also be used in an organic thin film transistor. Examples of the organic thin film transistor may include an organic thin film transistor having a constitution containing a source electrode and a drain electrode, an organic semiconductor layer (activated layer) acting as a current path between these electrodes, and a gate electrode for controlling a current amount passing through the current path, in which the organic semiconductor layer comprises the above-described organic thin film. Examples of such an organic thin film transistor may include an electric field effect-type organic thin film transistor and an electrostatic induction-type organic thin film transistor.

The electric field effect-type organic thin film transistor preferably comprises a source electrode and a drain electrode, an organic semiconductor layer (activated layer) acting as a current path between these electrodes, a gate electrode for controlling a current amount passing, through the current path, and an insulating layer disposed between the organic semiconductor layer and the gate electrode. Particularly, it is preferred that the source electrode and the drain electrode are provided as contacted with the organic semiconductor layer (activated layer), and further, the gate electrode is provided as sandwiching the insulating layer contacted with the organic semiconductor layer. In the electric field effect-type organic thin film transistor, the organic semiconductor layer comprises an organic thin film containing the macromolecular compound of the present invention.

The electrostatic induction-type organic thin film transistor has a source electrode and a drain electrode, an organic semiconductor layer (activated layer) acting as a current path between these electrodes, and a gate electrode for controlling a current amount passing through the current path, and the gate electrode is preferably provided in the organic semiconductor layer. Particularly, it is preferred the source electrode, the drain electrode, and the gate electrode provided in the organic semiconductor layer are provided as contacted with the organic semiconductor layer. Here, the structure of the gate electrode may be a structure by which a current path through which the current passes from the source electrode to the drain electrode is formed and the amount of the current passing through the current path can be controlled by a voltage applied to the gate electrode, and examples thereof may include an interdigitated electrode. Also in the electrostatic induction-type organic thin film transistor, the organic semiconductor layer comprises an organic thin film containing the macromolecular compound of the present invention.

When the macromolecular compound of the present invention is used in the activated layer of the electrostatic induction-type organic thin film transistor, from the viewpoint of transistor properties, the macromolecular compound of the present invention preferably has at least one type of structural unit selected from the group consisting of a structural unit represented by Formula (18), a structural unit represented by Formula (19), and a structural unit represented by Formula (20). From the viewpoint of the easiness of the synthesis, it is preferred that the macromolecular compound of the present invention has at least one type of structural unit selected from the group consisting of a structural unit represented by Formula (18) and a structural unit represented by Formula (19).

[Chemical Formula 66]

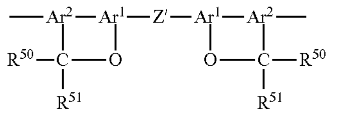

(18)

-continued

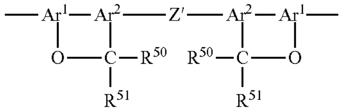

(19)

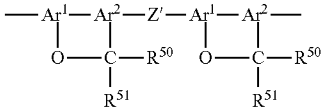

(20)

In Formula (18), Formula (19), and Formula (20), $Ar^1$, $Ar^2$, $X^1$, $R^{50}$, and $R^{51}$ represent the same as defined above; and Z' represents a single bond, an arylene group, or a divalent heterocyclic group.

Examples of the arylene group and the divalent heterocyclic group represented by Z' may include the above groups represented by Formula 1 to Formula 143.

When the macromolecular compound of the present invention contains at least one type of structural unit selected from the group consisting of a structural unit represented by Formula (18), a structural unit represented by Formula (19), and a structural unit represented by Formula (20), both of $R^{50}$ and $R^{51}$ are preferably a linear alkyl group from the viewpoint of transistor properties. Among linear alkyl groups, a linear alkyl group having 3 to 20 carbon atoms is preferred and a linear alkyl group having 6 to 18 carbon atoms is more preferred.

The macromolecular compound having a structural unit represented by Formula (18) can be produced, for example, by polymerizing a compound represented by Formula (8-1). The macromolecular compound having a structural unit represented by Formula (19) can be produced, for example, by polymerizing a compound represented by Formula (8-2).

<Organic Electroluminescent Device>

The macromolecular compound of the present invention can also be used in an organic electroluminescent device (organic EL device). The organic EL device has a light-emitting layer between a pair of electrodes at least one of which is transparent or translucent. The organic EL device may contain a hole transport layer and an electron transport layer in addition to the light-emitting layer. In any one layer of the light-emitting layer, the hole transport layer, and the electron transport layer, the macromolecular compound of the present invention is contained. The light-emitting layer may contain an electric charge transport material (which means a general term for the electron transport material and the hole transport material) in addition to the macromolecular compound of the present invention. Examples of the organic EL device may include an device having an anode, a light-emitting layer, and a cathode; an device having an anode, a light-emitting layer, an electron transport layer, and a cathode in which the anode further has an electron transport layer containing an electron transport material and is provided between the cathode and the light-emitting layer and adjacent to the light-emitting layer; an device having an anode, a hole transport layer, a light-emitting layer, and a cathode in which the anode further has a hole transport layer containing a hole transport material and is provided between the anode and the light-emitting layer and adjacent to the light-emitting layer; and an device having an anode, a hole transport layer, a light-emitting layer, an electron transport layer, and a cathode.

<Use of Cell>

By irradiating the photovoltaic cell using the macromolecular compound of the present invention with a light such as a solar, light from the transparent or translucent electrode, a photoelectromotive force is generated between the electrodes, so that the photovoltaic cell can act as an organic thin film solar cell. By integrating a plurality of organic thin film solar cells, the photovoltaic cell can also be used as an organic thin film solar cell module.

By irradiating the photovoltaic cell with a light from the transparent or translucent electrode in a state in which a voltage is applied to between the electrodes or in a state in which a voltage is not applied, a photocurrent is flowed, so that the photovoltaic cell can act as an organic optical sensor. By integrating a plurality of organic optical sensors, the photovoltaic cell can also be used as an organic image sensor.

The above organic thin film transistor can be used as a pixel driving element used for controlling the pixel of, for example, an electrophoresis display, a liquid crystal display, or an organic electroluminescent display or for controlling homogeneity of the screen brightness or a screen rewrite speed.

<Solar Cell Module>

The organic thin film solar cell can fundamentally take the same module structure as that of a conventional solar cell module. The solar cell module generally takes a structure in which a cell is provided on a supporting substrate such as a metal and a ceramic, and the cell is covered with filling resin, protective glass or the like to take in light from an opposite side of the supporting substrate. However, such a structure is also possible that a transparent material such as a toughened glass is used as the supporting substrate, and on the supporting substrate, a cell is provided to take in light from the side of the transparent supporting substrate. Specific known examples of such a structure may include a module structure called a superstrate type, a substrate type, or a potting type, and a substrate built-in-type module structure used in an amorphous silicon solar cell or the like. The organic thin film solar cell produced using the macromolecular compound of the present invention can also accordingly select these module structures according to the intended purpose, the using space, and the environment.

A representative module of the superstrate type or the substrate type has a structure in which: cells are provided at a constant interval between supporting substrates that are transparent in one side or both sides thereof and have been subjected to reflection preventing treatment; adjacent cells are connected with each other by a metal lead, a flexible wiring or the like; and in an outer edge part, a power-collecting electrode is provided to take out a generated electric power to the outside. Between the substrate and the cell, various plastic materials such as ethylenevinyl acetate (EVA) may be used in a shape of a film or a filling resin according to the purpose for protecting the cell or enhancing the power-collecting efficiency.

When the module is used at a position at which the surface of the module is not necessary to be coated with a hard material (for example, a position at which an impact from the outside is small), it is possible to compose the surface protecting layer with a transparent plastic film or to cure the above filling resin to impart a protecting function, for the purpose of omitting a supporting substrate on one side. The periphery of the supporting substrate is fixed by a metal frame in a sandwich-shape for securing the sealing of the inside and the rigidity of the module and between the supporting substrate and the frame is hermetically sealed with a sealing material. When a flexible material is used for the cell itself, the supporting substrate, the filling material, and the sealing material, a solar cell can also be provided on a curved surface.

In the case of a solar cell using a flexible supporter such as a polymer film, a cell main body can be produced by forming cells sequentially while letting out the supporter in a roll-shape, cutting the supporter in a desired size, and then sealing the penumbra of the supporter with a moisture-resistant flexible material. In addition, there can also be prepared a module structure called "SCAF" described in "Solar Energy Materials and Solar Cells, 48, pp. 383-391." Furthermore, a solar cell using a flexible supporter can also be adhered and fixed on a curved surface glass or the like to be used.

EXAMPLES

Hereinafter, Examples will be described for further explaining the present invention in detail. However, the present invention is not limited to the following Examples.

(NMR Measurement)

The NMR measurement was performed by dissolving an objective compound in deuterated chloroform and using an NMR apparatus (manufactured by Varian Inc.; INOVA 300).

(Measurement of Number Average Molecular Weight and Weight-average Molecular Weight)

As the number average molecular weight and the weight-average molecular weight, a number average molecular weight and a weight-average molecular weight in terms of polystyrene were measured by gel permeation chromatography (GPC) (manufactured by Shimadzu Corporation; trade name: LC-10Avp). The macromolecular compound to be measured was dissolved in tetrahydrofuran so that the concentration of the macromolecular compound became about 0.5% by weight and 30 μL of the resultant solution was injected into GPC. As the mobile phase of GPC, tetrahydrofuran was used and the mobile phase was flowed at a flow rate of 0.6 mL/min. As the column, two TSKgel SuperHM-H (manufactured by Tosoh Corporation) and one TSKgel SuperH2000 (manufactured by Tosoh Corporation) were connected in series. As the detector, a differential refractive index detector (manufactured by Shimadzu Corporation; trade name: RID-10A) was used.

Reference Example 1

Synthesis of Compound 1

[Chemical Formula 67]

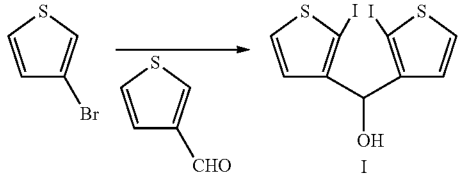

I

Into a 1,000 mL four-neck flask in which a gas in the flask was replaced by argon, 13.0 g (80.0 mmol) of 3-bromothiophene and 80 mL of diethyl ether were charged to prepare a homogeneous solution. While maintaining the solution at −78° C., 31 mL (80.6 mmol) of solution of n-butyl lithium (n-BuLi) (2.6 M) in hexane was dropped into the solution. At −78° C., the reaction was carried out for 2 hours and then into the resultant reaction mixture, a solution in which 8.96 g (80.0 mmol) of 3-thiophenealdehyde was dissolved in 20 mL of diethyl ether, was dropped. After the dropping, the resultant reaction mixture was stirred at −78° C. for 30 minutes and further at room temperature (25° C.) for 30 minutes. The reaction solution was cooled again to −78° C. and into the reaction solution, 62 mL (161 mmol) of solution of n-BuLi (2.6 M) in hexane was dropped over 15 minutes. After the dropping, the reaction solution was stirred at −25° C. for 2 hours and further at room temperature (25° C.) for 1 hour. Then, the reaction solution was cooled to −25° C. and into the reaction mixture, a solution in which 60 g (236 mmol) of iodine was dissolved in 1,000 mL of diethyl ether, was dropped over 30 minutes. After the dropping, the reaction mixture was stirred at room temperature (25° C.) for 2 hours and to the reaction mixture, 50 mL of a 1N sodium thiosulfate aqueous solution was added to terminate the reaction. The reaction product was extracted with diethyl ether, was then dried over magnesium sulfate, and was filtered. The filtrate was then concentrated to obtain 35 g of a crude product. The crude product was purified by recrystallization with chloroform to obtain 28 g of compound 1.

Reference Example 2

Synthesis of Compound 2

[Chemical Formula 68]

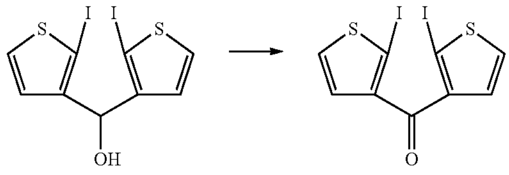

1 2

Into a 300 mL four-neck flask, 10.5 g (23.4 mmol) of bisiodothienyl methanol (compound 1) and 150 mL of methylene chloride were charged to prepare a homogeneous solution. To the solution, 7.50 g (34.8 mmol) of pyridinium chlorochromate was added and the resultant reaction mixture was stirred at room temperature (25° C.) for 10 hours. The reaction solution was filtered to remove insoluble matters and the filtrate was then concentrated to obtain 10.0 g (22.4 mmol) of compound 2.

Reference Example 3

Synthesis of Compound 3

[Chemical Formula 69]

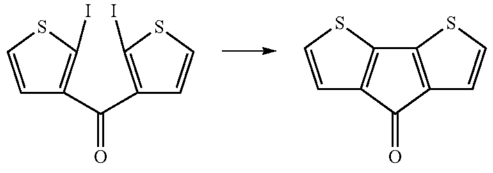

2 3

Into a 300 mL flask in which a gas in the flask was replaced by argon, 10.0 g (22.4 mmol) of the compound 2, 6.0 g (94.5 mmol) of a copper powder, and 120 mL of anhydrous N,N-dimethylformamide (hereinafter, which may be called DMF) were charged and the resultant reaction mixture was stirred at 120° C. for 4 hours. After the reaction, the flask was cooled to room temperature (25° C.) and the reaction solution was passed through a silica gel column to remove insoluble components. Then, 500 mL of water was added to the reaction solution and the reaction product was extracted with chloroform. The oil phase that was a chloroform solution was dried over magnesium sulfate and the oil phase was filtered, followed by concentrating the filtrate to obtain a crude product. The composition was purified by a silica gel column (developing solution: chloroform) to obtain 3.26 g of compound 3. The operations up to here were repeated by a plurality of times.

Example 1

Synthesis of Compound 4

[Chemical Formula 70]

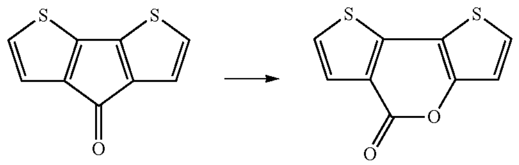

3 4

Into a 300 mL four-neck flask equipped with a mechanical stirrer in which a gas in the flask was replaced by argon, 3.85 g (20.0 mmol) of the compound 3, 50 mL of chloroform, and 50 mL of trifluoroacetic acid were charged to prepare a homogeneous solution. To the solution, 5.99 g (60 mmol) of sodium perborate monohydrate was added and the resultant reaction mixture was stirred at room temperature (25° C.) for 45 minutes. Then, to the reaction mixture, 200 mL of water was added and the reaction product was extracted with chloroform, followed by passing the organic phase that was a chloroform solution through a silica gel column and evaporating the solvent of the filtrate using an evaporator. Using methanol, the residue was recrystallized to obtain 534 mg of compound 4.

$^1$H NMR in $CDCl_3$ (ppm): 7.64 (d, 1H), 7.43 (d, 1H), 7.27 (d, 1H), 7.10 (d, 1H)

Example 2

Synthesis of Compound 5

[Chemical Formula 71]

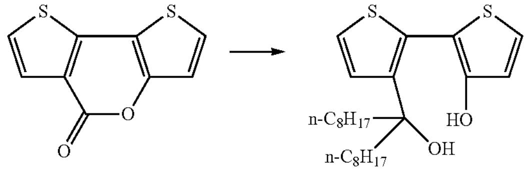

4 5

Into a 200 mL four-neck flask in which a gas in the flask was replaced by argon, 534 mg (2.56 mmol) of the compound 4 and 25 mL of anhydrous tetrahydrofuran (THF) were charged to prepare a homogeneous solution. The solution was cooled to −20° C. and thereto, 10.3 mL (10.3 mmol) of solution of n-octylmagnesium bromide (1 M) in THF was added. Then, the temperature of the resultant reaction mixture was elevated to room temperature (25° C.) and the reaction mixture was stirred at room temperature (25° C.) for 1.5 hours. Then, to the reaction mixture, 50 mL of water was added to terminate the reaction and the reaction product was extracted with ethyl acetate. The organic phase that was an ethyl acetate solution was dried over sodium sulfate and the ethyl acetate solution was then passed through a silica gel column, followed by evaporating the solvent of the filtrate to obtain 433 mg of compound 5.

$^1$H NMR in $CDCl_3$ (ppm): 7.24 (d, 1H), 7.19 (d, 1H), 6.98 (d, 1H), 6.76 (d, 1H), 1.79 (b, 4H), 1.32 (b, 24H), 0.86 (s, 6H)

Example 3

Synthesis of Compound 6

[Chemical Formula 72]

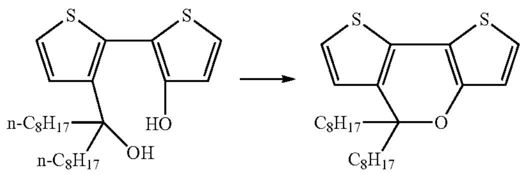

5 6

Into a 200 mL flask in which a gas in the flask was replaced by argon, 433 mg (0.992 mmol) of the compound 5 and 15 mL of toluene were charged to prepare a homogeneous solution. To the solution, 57 mg of sodium p-toluenesulfonate monohydrate was added and the resultant reaction mixture was stirred at 100° C. for 4 hours. The reaction solution was cooled to room temperature (25° C.) and thereto, 50 mL of water was added, followed by extracting the reaction product with toluene. The organic phase that was a toluene solution was dried over sodium sulfate and was filtered, and then the solvent was evaporated. The resultant crude product was purified by a silica gel column (solvent: hexane) to obtain 389 mg of compound 6 (yield: 93.7%).

$^1$H NMR in $CDCl_3$ (ppm): 6.99 (d, 1H), 6.94 (d, 1H), 6.69 (d, 1H), 6.60 (d, 1H), 1.80 (b, 4H), 1.32 (b, 24H), 0.86 (s, 6H)

Example 4

Synthesis of Compound 7

[Chemical Formula 73]

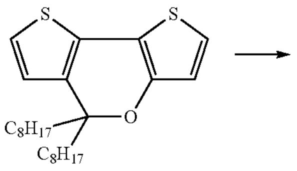

6

-continued

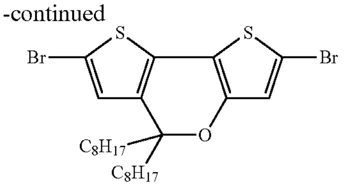

7

Into a 200 mL flask in which a gas in the flask was replaced by argon, 389 mg (0.929 mmol) of the compound 6 and 12 mL of anhydrous DMF were charged to prepare a homogeneous solution. The solution was maintained at −20° C. and thereto, 339 mg (1.90 mmol) of N-bromosuccinimide (hereinafter, which may be called NBS) was added. The reaction was carried out at −20° C. for 3 hours and then, at 0° C. for 1 hour. After the reaction, to the reaction mixture, 50 mL of a 1N sodium thiosulfate aqueous solution was added to terminate the reaction and the reaction product was extracted with ether. The organic phase that was an ether solution was dried over magnesium sulfate and was filtered, and from the filtrate, the solvent was evaporated to obtain a crude product. The crude product was purified by a silica gel column (solvent: hexane) to obtain 315 mg of compound 7 (yield: 58.9%).

$^1$H NMR in $CDCl_3$ (ppm): 6.65 (s, 1H), 6.63 (s, 1H), 1.81 (b, 4H), 1.33 (b, 24H), 0.87 (s, 6H)

Example 5

Synthesis of Polymer A

[Chemical Formula 74]

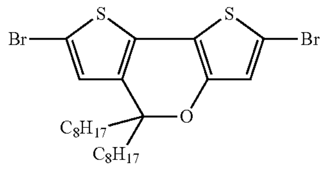

7

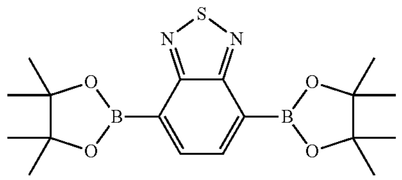

8

Into a 100 mL flask in which a gas in the flask was replaced by argon, 115.3 mg (0.200 mmol) of the compound 7, 77.6 mg (0.200 mmol) of compound 8 (4,7-bis(4,4,5,5-tetramethyl-1,3,2-dioxaborolan-2-yl)-2,1,3-benzothiadiazole) (manufactured by Aldrich Corp.), and 60.6 mg of methyltrialkylammonium chloride (trade name: Aliquat 336 (registered trademark); manufactured by Aldrich Corp.) were charged and the resultant reaction mixture was dissolved in 10 mL of toluene. The resultant toluene solution was bubbled with argon for 30 minutes. Then thereto, 0.67 mg of palladium acetate, 3.7 mg of tris(2-methoxyphenyl) phosphine, and 2 mL of a sodium carbonate aqueous solution (16.7% by weight) were added and the resultant reaction mixture was stirred at 100° C. for 1.5 hours. Then, to the reaction solution, 1 g of sodium diethyldithiocarbamate and 10 mL of water were added and the resultant reaction mixture was stirred under reflux for 2 hours. After the completion of the reaction, the reaction solution was cooled to around room temperature (25° C.) and the resultant reaction solution was left stand still to recover the separated toluene phase. The toluene phase was washed with 10 mL of water twice, with 10 mL of a 3% acetic acid water twice, and further with 10 mL of water twice and the resultant toluene phase was added into methanol to recover a deposited precipitate. The precipitate was dried under reduced pressure and was then dissolved in chloroform. Next, the resultant chloroform solution was filtered to remove insoluble matters and was then passed through an alumina column to be purified. The resultant chloroform solution was concentrated under reduced pressure and was then added into methanol to generate a precipitate and to recover the generated precipitate. The precipitate was washed with methanol and was then dried under reduced pressure to obtain 40 mg of polymer. Hereinafter, the polymer is called polymer A. The polymer A had a weight-average molecular weight in terms of polystyrene of 17,000 and a number average molecular weight in terms of polystyrene of 5,000.

The light absorbing terminal wavelength of the polymer A was 925 nm.

Example 6

Synthesis of Compound 5b

[Chemical Formula 75]

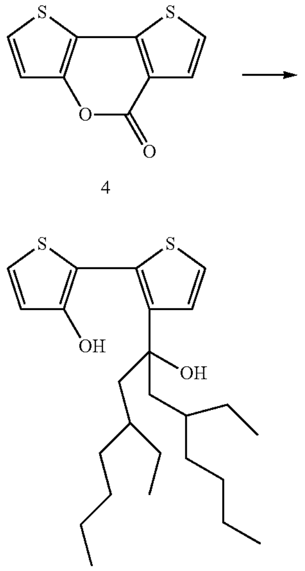

4

5b

Into a 100 mL four-neck flask in which a gas in the flask was replaced by argon, 1.06 g (5.09 mmol) of the compound 4 and 30 mL of anhydrous THF were charged to prepare a homogeneous solution. While maintaining the flask at −20° C., 12.7 mL of solution of 2-ethylhexylmagnesium bromide (1 M) in ether was added to the solution. Then, the temperature of the resultant reaction mixture was elevated to −5° C. over 30 minutes and the reaction mixture as it was stirred for 30 minutes. Then, the temperature of the reaction mixture was elevated to 0° C. over 10 minutes and the reaction mixture as it was was stirred for 1.5 hours. Then, to the reaction mixture, water was added to terminate the reaction and the reaction product was extracted with ethyl acetate. The organic phase that was an ethyl acetate solution was dried over sodium sulfate and was filtered and then the ethyl acetate solution was passed through a silica gel column, followed by evaporating the solvent of the filtrate to obtain 1.28 g of compound 5b. The operations up to here were repeated by a plurality of times.

$^{1}H$ NMR in $CDCl_3$ (ppm): 7.25 (d, 1H), 7.20 (d, 1H), 6.99 (d, 1H), 6.76 (d, 1H), 1.76 (s, 4H), 1.49 (b, 2H), 1.29-1.04 (m, 16H), 0.80 (s, 6H), 0.71 (s, 6H)

Example 7

Synthesis of Compound 6b

[Chemical Formula 76]

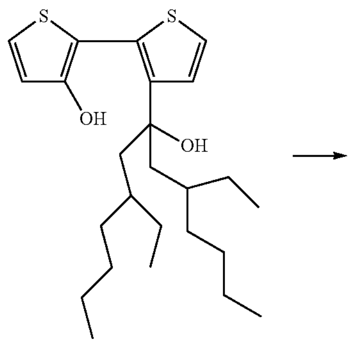

5b

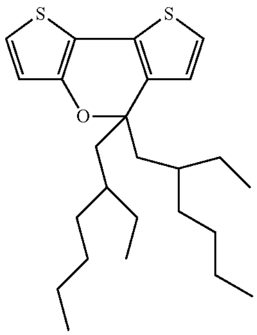

6b

Into a 200 mL flask in which a gas in the flask was replaced by argon, 2.58 g of the compound 5b and 30 mL of toluene were charged to prepare a homogeneous solution. To the solution, 100 mg of sodium p-toluenesulfonate monohydrate was added and the resultant reaction mixture was stirred at 100° C. for 1.5 hours. The resultant reaction solution was cooled to room temperature (25° C.) and to the reaction solution, 50 mL of water was then added, followed by extracting the reaction product with toluene. The organic phase that was a toluene solution was dried over sodium sulfate and was filtered and then the solvent was evaporated. The resultant crude product was purified by a silica gel column (solvent: hexane) to obtain 741 mg of compound 6b.

$^{1}H$ NMR in $CDCl_3$ (ppm): 6.98 (d, 1H), 6.93 (d, 1H), 6.68 (d, 1H), 6.59 (d, 1H), 1.78 (s, 4H), 1.50 (b, 2H), 1.30-1.05 (m, 16H), 0.81 (s, 6H), 0.72 (s, 6H)

Example 8

Synthesis of Compound 7b

[Chemical Formula 77]

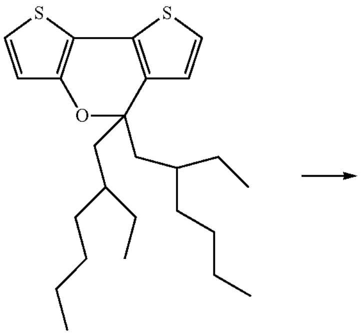

6b

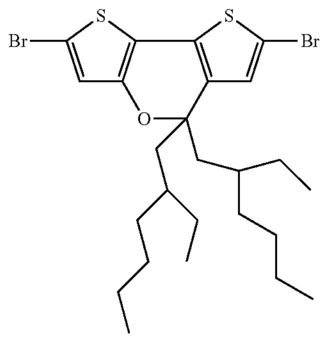

7b

Into a 200 mL flask in which a gas in the flask was replaced by argon, 741 mg (1.77 mmol) of the compound 6b and 20 mL of anhydrous DMF were charged to prepare a homogeneous solution. While maintaining the solution at −30° C., to the solution, 646 mg (3.63 mmol) of NBS was added and the temperature of the resultant reaction mixture was elevated from −30° C. to −10° C. over 30 minutes. After the confirmation of the disappearance of the compound 6b by liquid chromatography (LC), water and sodium thiosulfate were added to the reaction mixture to terminate the reaction and the reaction product was extracted with ether. The organic phase that was an ether solution was washed with a saturated sodium chloride aqueous solution, was dried over magnesium sulfate, and was filtered and then the solvent was evaporated to obtain a crude product. The crude product was purified by a silica gel column (solvent: hexane) to obtain 892 mg of compound 7b (yield: 87.4%).

$^{1}H$ NMR in $CDCl_3$ (ppm): 6.63 (1H), 6.59 (1H), 1.74 (s, 4H), 1.50 (b, 2H), 1.37-1.01 (m, 16H), 0.87 (s, 6H), 0.77 (s, 6H)

Example 9

Synthesis of Polymer B

[Chemical Formula 78]

7b

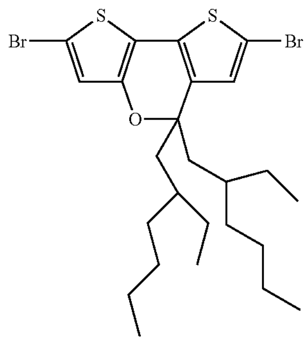

8

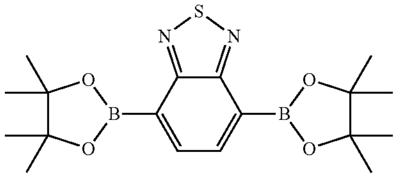

Into a 200 mL flask in which a gas in the flask was replaced by argon, 890 mg (1.54 mmol) of the compound 7b, 571.8 mg (1.47 mmol) of the compound 8 (4,7-bis(4,4,5,5-tetramethyl-1,3,2-dioxaborolan-2-yl)-2,1,3-benzothiadiazole) (manufactured by Aldrich Corp.), and 250 mg of methyltrialkylammonium chloride (trade name: Aliquat 336 (registered trademark); manufactured by Aldrich Corp.) were charged and the resultant reaction mixture was dissolved in 60 mL of toluene. The resultant toluene solution was bubbled with argon for 30 minutes. Then thereto, 3.74 mg of palladium acetate, 19.0 mg of tris(2-methoxyphenyl) phosphine, and 7.5 mL of a sodium carbonate aqueous solution (16.7% by weight) were added and the resultant reaction mixture was stirred at 70° C. for 4 hours. Then, to the reaction solution, 50 mg of phenylboric acid was added and the reaction was further carried out at 70° C. for 2 hours. Then, to the reaction solution, 2 g of sodium diethyldithiocarbamate and 20 mL of water were added and the resultant reaction mixture was stirred under reflux for 2 hours. The aqueous phase was removed and the organic phase was washed with 20 mL of water twice, with 20 mL of a 3% by weight acetic acid aqueous solution twice, and further with 20 mL of water twice, followed by pouring the resultant solution into methanol to precipitate polymer. The polymer was filtered and then dried and the resultant polymer was dissolved in 30 mL of o-dichlorobenzene again. The resultant solution was passed through an alumina/silica gel column and the resultant solution was added into methanol to precipitate polymer, followed by filtering and then drying the polymer to obtain 380 mg of purified polymer. Hereinafter, the polymer is called polymer B. The molecular weight of the polymer B measured by GPC (in terms of polystyrene) corresponded to Mw=77,000 and Mn=15,000. The light absorbing terminal wavelength of the polymer B was 930 nm.

Reference Example 4

Synthesis of Polymer C

[Chemical Formula 79]

9

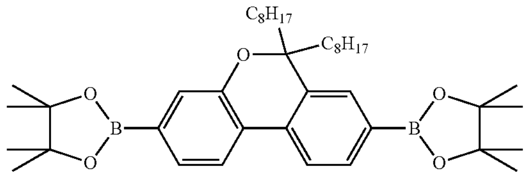

10

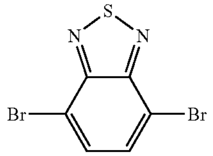

Into a 100 mL flask, 398.7 mg (0.605 mmol) of the above compound 9 synthesized according to the description in Example 10 of Japanese Patent Application Laid-open No. 2004-168999, 160.3 mg (0.5451 mmol) of compound 10 (4,7-dibromo-2,1,3-benzothiadiazole) (manufactured by Aldrich Corp.), and 200 mg of methyltrialkylammonium chloride (trade name: Aliquat 336 (registered trademark); manufactured by Aldrich Corp.) were charged and the resultant reaction mixture was dissolved in 40 mL of toluene. The resultant toluene solution was bubbled with argon for 30 minutes. Then thereto, 2.4 mg of palladium acetate, 12.2 mg of tris(2-methoxyphenyl)phosphine, and 2 mL of a sodium carbonate aqueous solution (16.7% by weight) were added and the resultant reaction mixture was stirred under reflux for 3 hours. Then, to the reaction solution, 50 mg of phenylboric acid was added and the reaction mixture was further stirred under reflux for 2 hours. Then, to the reaction solution, 2 g of sodium diethyldithiocarbamate and 20 mL of water were added and the resultant reaction mixture was stirred under reflux for 2 hours. After the completion of the reaction, the reaction solution was cooled to around room temperature (25° C.) and then the resultant reaction solution was left stand still to recover the separated toluene phase. The toluene phase was washed with 10 mL of water twice, with 10 mL of 3% acetic acid water twice, and further with 10 mL of water twice and the resultant toluene phase was added into methanol to recover a deposited precipitate. The precipitate was dried under reduced pressure and was then dissolved in chloroform. Next, the resultant chloroform solution was filtered to remove insoluble matters and was then passed through an alumina column to be purified. The resultant chloroform solution was concentrated under reduced pressure and was then poured into methanol to generate a precipitate and to recover the generated precipitate. The precipitate was washed with methanol and was then dried under reduced pressure to obtain 320 mg of polymer. Hereinafter, the polymer is called polymer C. The polymer C had a weight-average molecular weight in terms of polystyrene of 446,000 and a number average molecular weight in terms of polystyrene of 169,000. The light absorbing terminal wavelength of the polymer C was 550 nm.

Example 10

(Production and Evaluation of Ink and Organic Thin Film Solar Cell)

A glass substrate on which an ITO film was formed by a sputtering method in a thickness of 150 nm was subjected to surface treatment by ozone UV treatment. Next, the polymer B and fullerene C60PCBM (phenyl C61-butyric acid methyl ester; manufactured by Frontier Carbon Corporation) (weight ratio of the polymer B/C60PCBM was 1/3) were dissolved in o-dichlorobenzene (total weight of the polymer B and C60PCBM was 2.0% by weight) to produce an ink 1. The ink 1 was applied on the substrate by spin-coating to prepare an organic film containing the polymer B (film thickness: about 100 nm). The thus prepared organic film had the light absorbing terminal wavelength of 920 nm. Then, on the organic film, lithium fluoride was deposited by a vacuum deposition machine in a thickness of 2 nm and next thereon, Al was deposited in a thickness of 100 nm. The obtained organic thin film solar cell had a shape of a 2 mm×2 mm square. The obtained organic thin film solar cell was irradiated with a constant light using a solar simulator (manufactured by BUNKOUKEIKI Co., Ltd.; trade name: OTENTO-SUNII; AM 1.5G filter, irradiance: 100 $mW/cm^2$) and the generated current and voltage were measured to calculate the photoelectric conversion efficiency, the short-circuit current density, the open-circuit voltage, and the fill factor. $J_{sc}$ (short-circuit current density) was 5.64 $mA/cm^2$; Voc (open-circuit voltage) was 0.58 V; ff (fill factor) was 0.36; and photoelectric conversion efficiency (η) was 1.18%.

Example 11

In the same manner as in Example 10, except that xylene was used instead of o-dichlorobenzene, the preparation and evalutation of the cell were carried out. The result is listed in Table 1.

Comparative Example 1

In the same manner as in Example 10, except that the polymer C was used instead of the polymer B, the preparation and evalutation of the cell were carried out. The result is listed in Table 1.

Example 12

Synthesis of Compound 5c

[Chemical Formula 80]

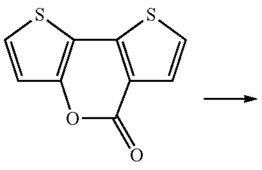

4

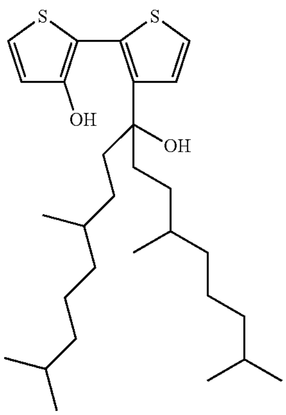

5c

Into a 100 mL four-neck flask in which a gas in the flask was replaced by argon, 1.00 g (4.80 mmol) of the compound 4 and 30 mL of anhydrous THF were charged to prepare a homogeneous solution. While maintaining the flask at −20° C., 12.7 mL of solution of 3,7-dimethyloctylmagnesium bromide (1 M) in ether was added to the solution. Then, the temperature of the resultant reaction mixture was elevated to −5° C. over 30 minutes and the reaction mixture as it was stirred for 30 minutes. Then, the temperature of the reaction mixture was elevated to 0° C. over 10 minutes and the reaction mixture as it was was stirred for 1.5 hours. Then, to the reaction mixture, water was added to terminate the reaction and the reaction product was extracted with ethyl acetate. The organic phase that was an ethyl acetate solution was dried over sodium sulfate and was filtered and then the ethyl acetate solution was passed through a silica gel column, followed by evaporating the solvent of the filtrate to obtain 1.50 g of compound 5c.

$^1$H NMR in $CDCl_3$ (ppm): 8.42 (b, 1H), 7.25 (d, 1H), 7.20 (d, 1H), 6.99 (d, 1H), 6.76 (d, 1H), 2.73 (b, 1H), 1.90 (m, 4H), 1.58-1.02 (b, 20H), 0.92 (s, 6H), 0.88 (s, 12H)

Example 13

Synthesis of Compound 6c

[Chemical Formula 81]

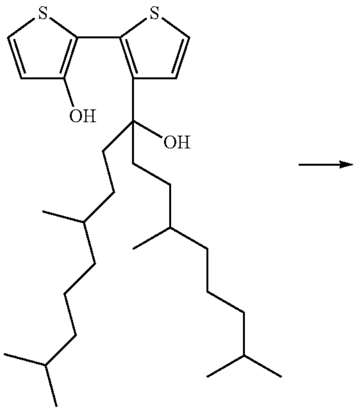

5c

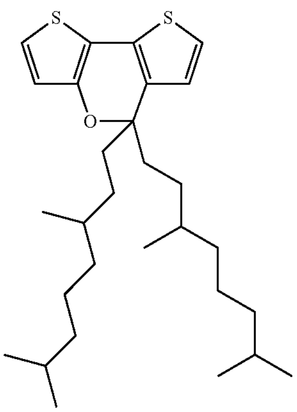

6c

Into a 200 mL flask in which a gas in the flask was replaced by argon, 1.50 g of the compound 5c and 30 mL of toluene were charged to prepare a homogeneous solution. To the solution, 100 mg of sodium p-toluenesulfonate monohydrate was added and the resultant reaction mixture was stirred at 100° C. for 1.5 hours. The resultant reaction solution was cooled to room temperature (25° C.) and to the reaction solution, 50 mL of water was added, followed by extracting the reaction product with toluene. The organic phase that was a toluene solution was dried over sodium sulfate and was filtered and then the solvent was evaporated. The resultant crude product was purified by a silica gel column (solvent: hexane) to obtain 1.33 g of compound 6c. The operations up to here were repeated by a plurality of times.

$^1$H NMR in $CDCl_3$ (ppm): 6.98 (d, 1H), 6.93 (d, 1H), 6.68 (d, 1H), 6.59 (d, 1H), 1.89 (m, 4H), 1.58-1.00 (b, 20H), 0.87 (s, 6H), 0.86 (s, 12H)

Example 14

Synthesis of Compound 11

[Chemical Formula 82]

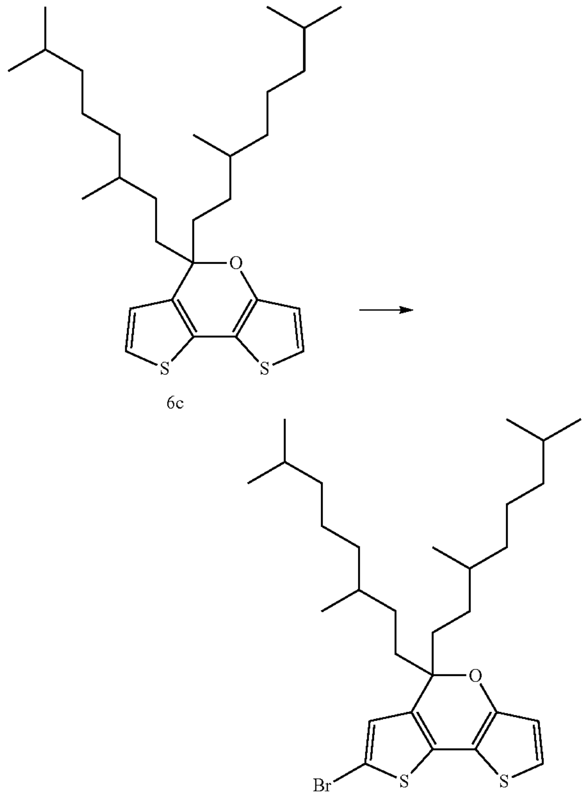

6c

11

Into a 300 mL flask in which a gas in the flask was replaced by argon, the compound 6c (3.52 g, 7.41 mmol) and N,N-dimethylformamide (DMF) (100 mL) were charged to prepare a homogeneous solution. The solution was subjected to argon bubbling at 25° C. for 30 minutes and the solution was cooled to −50° C. To the solution, NBS (1.20 g, 6.74 mmol) was added and the temperature of the resultant reaction mixture was elevated to 25° C. over 5.5 hours. To the reaction solution, 50 mL of water was added and the reaction solution was extracted with diethyl ether. The extract was dried over sodium sulfate and was then filtered, and the solvent was evaporated. The resultant crude product was purified by a silica gel column containing hexane as the solvent to obtain 3.30 g of compound 11.

$^1$H NMR ($CDCl_3$ (ppm)): 0.826 (m, 18H), 1.08-1.47 (m, 20H), 1.95 (m, 4H), 6.65 (d, 1H), 6.66 (s, 1H), 6.98 (s, 1H)

Example 15

Synthesis of Compound 12

[Chemical Formula 83]

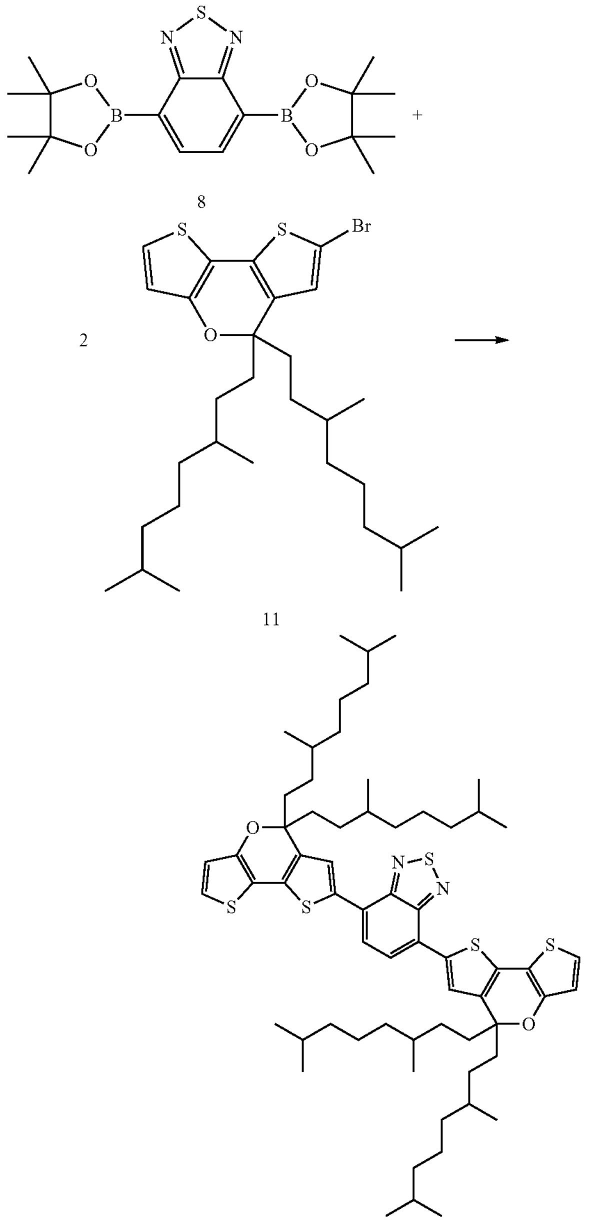

8

2

11

12

Into a 300 mL flask in which a gas in the flask was replaced by argon, the compound 8 (1.11 g, 2.85 mmol), the compound 11 (3.16 g, 5.70 mmol), toluene (90 mL), and methyltrialkylammonium chloride (trade name: Aliquat 336 (registered trademark); manufactured by Aldrich Corp.) (606 mg, 1.50 mmol) were charged to prepare a homogeneous solution and the resultant reaction mixture was subjected to argon bubbling at 25° C. for 30 minutes. The temperature of the reaction mixture was elevated to 90° C. and thereto, palladium acetate (6.7 mg, 1% by mole) and tris(2-methoxyphenyl)phosphine (37.0 mg, 3.5% by mole) were added. Then, while stirring the reaction mixture at 100° C., a sodium carbonate aqueous solution (16.7% by weight, 19.0 g, 30.0 mmol) was dropped into the reaction mixture over 30 minutes. After the dropping, the resultant reaction mixture was stirred at 100° C. for 2 hours. Then, to the reaction solution, pure water was added to separate the toluene phase and then the toluene phase was dried over sodium sulfate to obtain a crude product. The crude product was purified by a silica gel column using hexane as a developing solution to obtain 2.25 g of compound 12.

$^1$H NMR ($CDCl_3$ (ppm)): 0.826 (m, 36H), 1.08-1.47 (m, 40H), 1.95 (m, 8H), 6.71 (d, 2H), 7.04 (d, 2H), 7.77 (s, 2H), 7.79 (s, 2H)

Example 16

Synthesis of Compound 13

[Chemical Formula 84]

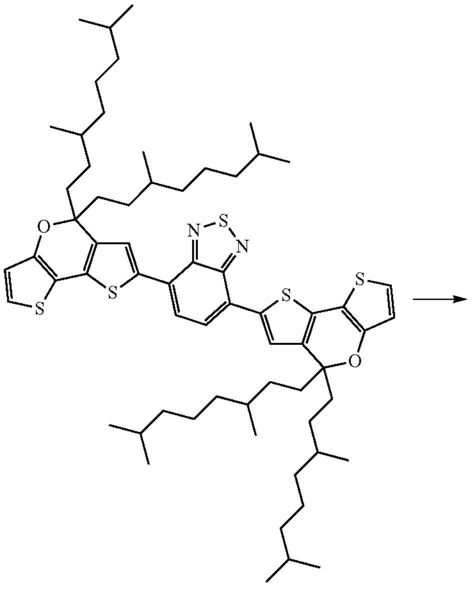

12

-continued

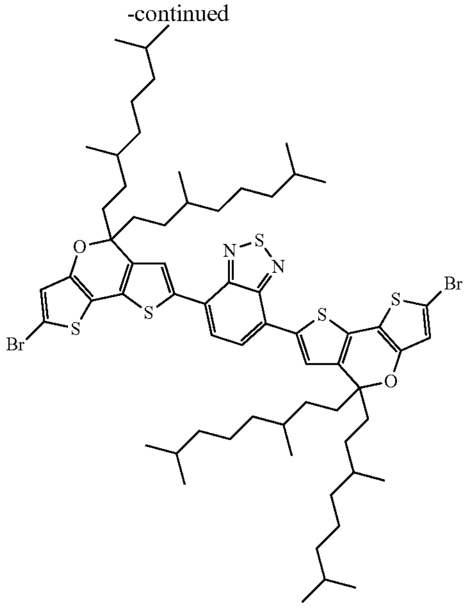

13

Into a 200 mL flask in which a gas in the flask was replaced by argon, the compound 12 (2.25 g, 2.08 mmol), DMF (40 mL), and tetrahydrofuran (THF) (40 mL) were charged to prepare a homogeneous solution. The resultant reaction mixture was cooled to −50° C. and thereto, NBS (814 mg, 4.58 mmol) was added, followed by elevating the temperature of the reaction mixture to 0° C. over 2.5 hours.

Then, to the reaction solution, pure water was added and the reaction solution was extracted using hexane into an organic phase. Then, to the reaction solution, pure water was added to separate a toluene phase and then the toluene phase was dried over sodium sulfate to obtain a crude product. The crude product was purified by a silica gel column using hexane as a developing solution to obtain 2.11 g of compound 13.

$^1$H-NMR ($CDCl_3$ (ppm)): 0.826 (m, 36H), 1.08-1.47 (m, 40H), 1.95 (m, 8H), 6.72 (s, 2H), 7.75 (s, 2H), 7.77 (s, 2H)

Example 17

Synthesis of Polymer D

[Chemical Formula 85]

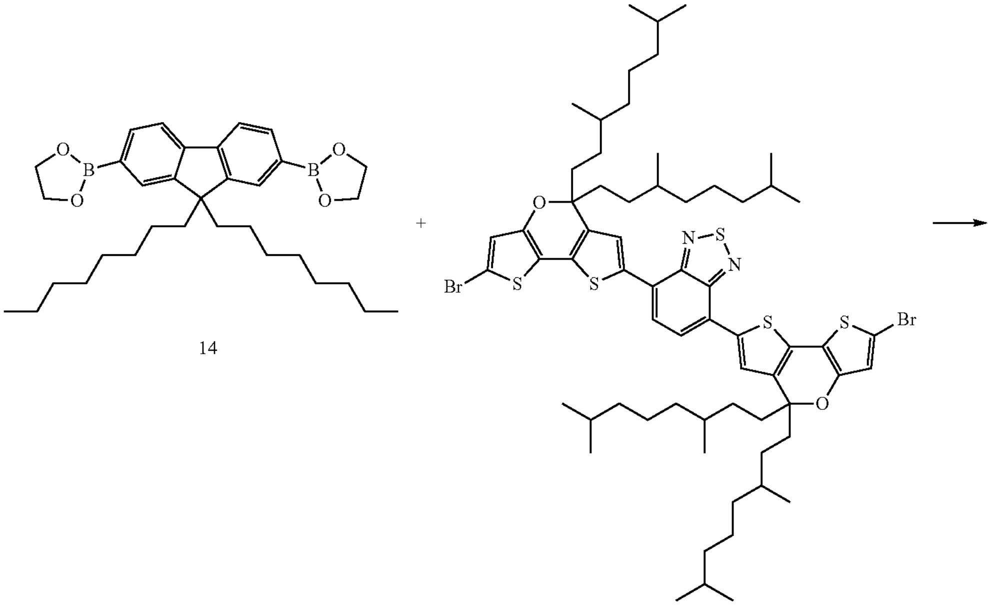

14

13

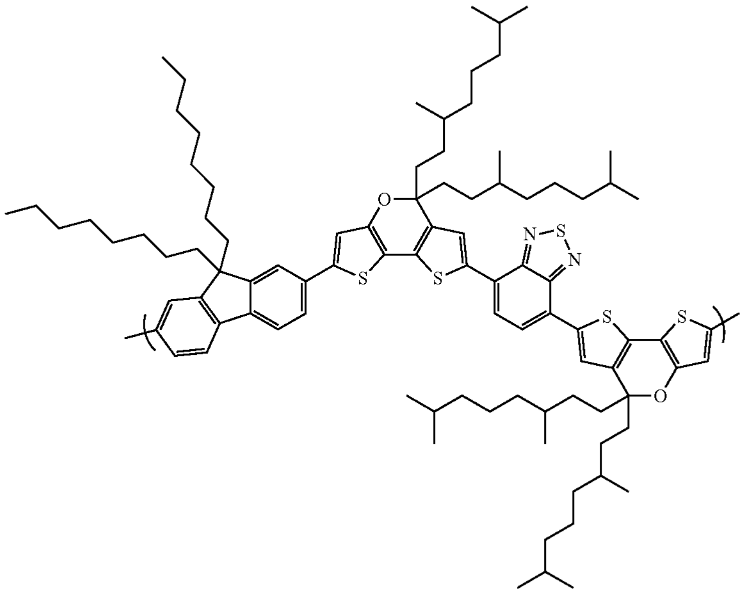

Polymer D

Into a 200 mL flask in which a gas in the flask was replaced by argon, compound 14 (manufactured by American Dye Source, Inc.) (96.9 mg, 0.183 mmol), the compound 13 (238.6 mg, 0.192 mmol), toluene (10 mL), and methyltrialkylammonium chloride (trade name: Aliquat 336 (registered trademark); manufactured by Aldrich Corp.) (60.6 mg, 0.15 mmol) were charged to prepare a homogeneous solution and the resultant reaction mixture was subjected to argon bubbling at 25° C. for 30 minutes. The temperature of the reaction mixture was elevated to 90° C. and thereto, palladium acetate (0.67 mg, 1% by mole) and tris(2-methoxyphenyl)phosphine (3.70 mg, 3.5% by mole) were added. Then, while stirring the reaction mixture at 100° C., a sodium carbonate aqueous solution (16.7% by weight, 1.90 g, 3.00 mmol) was dropped into the reaction mixture over 30 minutes. After 4 hours, to the reaction solution, phenylboric acid (3.66 mg, 0.03 mmol), palladium acetate (0.67 mg, 1% by mole), and tris(2-methoxyphenyl)phosphine (3.70 mg, 3.5% by mole) were added, the resultant reaction mixture was stirred further for 1 hour, and then the reaction was terminated. Then, to the reaction solution, 2 g of sodium diethyldithiocarbamate and 20 mL of water were added and the resultant reaction mixture was stirred under reflux for 2 hours. The aqueous phase was removed and then the organic phase was washed with 20 mL of water twice, with 20 mL of a 3% by weight acetic acid aqueous solution twice, and further with 20 mL of water twice, followed by pouring the resultant solution into methanol to precipitate polymer. The polymer was filtered and then dried and the resultant polymer was dissolved in 30 mL of o-dichlorobenzene again. The resultant solution was passed through an alumina/silica gel column and the resultant solution was added into methanol to precipitate polymer, followed by filtering and then drying the polymer to obtain 280 mg of purified polymer. Hereinafter, the polymer is called polymer D. The molecular weight of the polymer D measured by GPC (in terms of polystyrene) corresponded to Mw=116,000 and Mn=49,000. The light absorbing terminal wavelength of the polymer D was 755 nm.

Reference Example 5

Synthesis of Compound 16

[Chemical Formula 86]

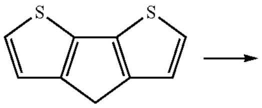

15

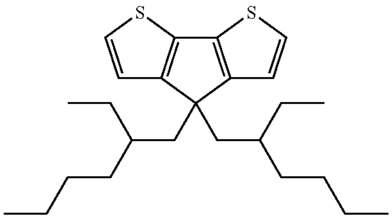

16

Into a 200 mL flask in which a gas in the flask was replaced by argon, compound 15 (1.78 g, 10.0 mmol), 2-ethylhexyl bromide (5.83 g, 25.0 mmol), potassium iodide (41.5 mg, 0.25 mmol), and potassium hydroxide (1.68 g, 30.0 mmol) were charged and the resultant reaction mixture was dissolved in dimethylsulfoxide (35 mL), followed by stirring the resultant reaction mixture at room temperature (25° C.) for 24 hours. After the reaction, 100 mL of water was added to the reaction mixture and the product was extract with hexane, followed by purifying the extract by a silica gel column (developing solution: hexane) to obtain 2.61 g of compound 16.

Reference Example 6

Synthesis of Compound 17

[Chemical Formula 87]

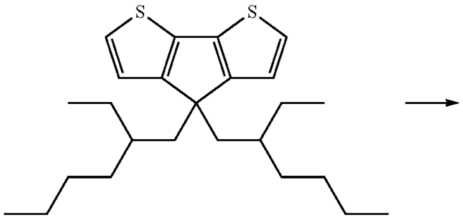

16

-continued

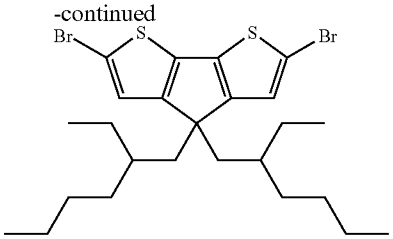

17

Into a 200 mL flask in which a gas in the flask was replaced by argon, the compound 16 (1.31 g, 3.25 mmol) and DMF (25 mL) were charged and the flask was cooled to 0° C., followed by adding NBS (1.21 g) to the resultant reaction mixture and stirring the resultant reaction mixture for 12 hours. Into the reaction solution, 100 mL of water was added to terminate the reaction and the product was extracted with ether. The extract was purified by a silica gel column (developing solution: hexane) to obtain 1.70 g of compound 17.

Reference Example 7

Synthesis of Polymer E

[Chemical Formula 88]

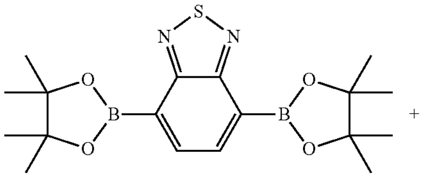

8

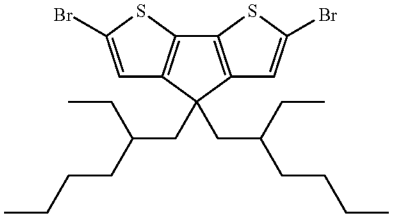

17

Into a 200 mL flask in which a gas in the flask was replaced by argon, 561 mg (1.00 mmol) of the compound 17, 388.1 mg (1.00 mmol) of the compound 8 (4,7-bis(4,4,5,5-tetramethyl-1,3,2-dioxaborolan-2-yl)-2,1,3-benzothiadiazole) (manufactured by Aldrich Corp.), and 202 mg of methyltrialkylammonium chloride (trade name: Aliquat 336 (registered trademark); manufactured by Aldrich Corp.) were charged to dissolve the resultant reaction mixture in 20 mL of toluene and the resultant toluene solution was subjected to argon bubbling for 30 minutes. Then, to the reaction mixture, 2.25 mg of palladium acetate, 12.3 mg of tris(2-methoxyphenyl)phosphine, and 6.5 mL of a sodium carbonate aqueous solution (16.7% by weight) were added and the resultant reaction mixture was stirred at 100° C. for 5 hours. Then, to the reaction solution, 50 mg of phenylboric acid was added and further, the reaction was carried out at 70° C. for 2 hours. Then, to the reaction solution, 2 g of sodium diethyldithiocarbamate and 20 mL of water were added and the resultant reaction mixture was stirred under reflux for 2 hours. The aqueous phase was removed and then the organic phase was washed with 20 mL of water twice, with 20 mL of a 3% by weight acetic acid aqueous solution twice, and further with 20 mL of water twice, followed by pouring the resultant solution into methanol to precipitate polymer. The polymer was filtered and then dried and the resultant polymer was dissolved in 30 mL of o-dichlorobenzene again. The resultant solution was passed through an alumina/silica gel column and the resultant solution was added into methanol to precipitate polymer, followed by filtering and then drying the polymer to obtain 280 mg of purified polymer. Hereinafter, the polymer is called polymer E. The molecular weight of the polymer E measured by GPC (in terms of polystyrene) corresponded to Mw=30,000 and Mn=14,000.

Comparative Example 2

In the same manner as in Example 10, except that the polymer E was used instead of the polymer B, the preparation and evalutation of the cell were carried out. The result is listed in Table 1.

Example 18

In the same manner as in Example 10, except that the polymer A was used instead of the polymer B, the preparation and evalutation of the cell were carried out. The result is listed in Table 1.

Example 19

Synthesis of Compound 7c

[Chemical Formula 89]

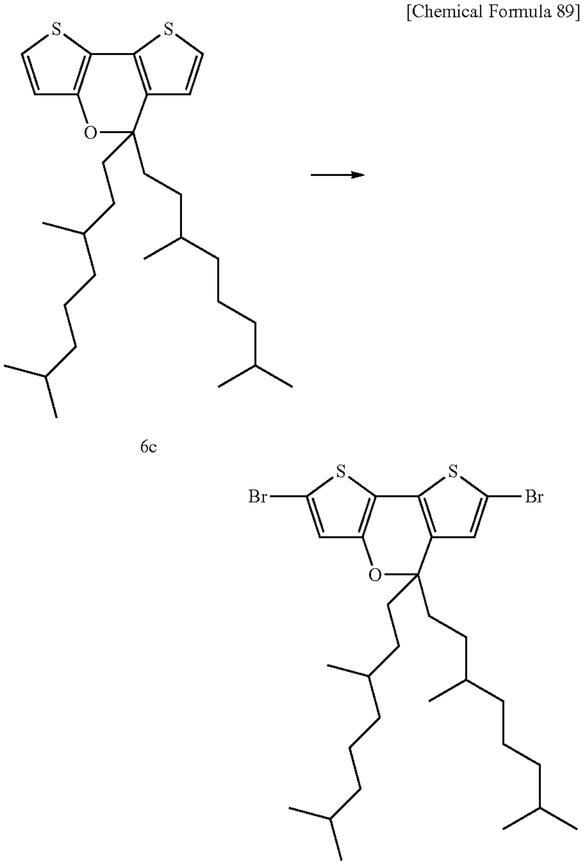

6c

7c

Into a 200 mL flask in which a gas in the flask was replaced by argon, 1.33 g (2.80 mmol) of the compound 6c and 20 mL of anhydrous DMF were charged to prepare a homogeneous solution. The solution was maintained at −30° C. and thereto, 1,040 mg (5.84 mmol) of NBS was added. The temperature of the reaction mixture was elevated from −30° C. to −10° C. over 30 minutes. After the confirmation of the disappearance of the compound 6c by liquid chromatography (LC), to the reaction mixture, 50 mL of a 1 M sodium thiosulfate aqueous solution was added to terminate the reaction and the reaction product was extracted with ether. The organic phase that was an ether solution was washed with a saturated sodium chloride aqueous solution, was dried over magnesium sulfate, and was filtered, and from the filtrate, the solvent was evaporated to obtain a crude product. The crude product was purified by a silica gel column (solvent: hexane) to obtain 1.65 g (93%) of compound 7c.

$^1$H NMR in $CDCl_3$ (ppm): 6.66 (1H), 6.63 (1H), 1.90 (m, 4H), 1.56-1.02 (b, 20H), 0.87 (s, 6H), 0.85 (s, 12H)

Example 20

Synthesis of Polymer F

[Chemical Formula 90]

7c

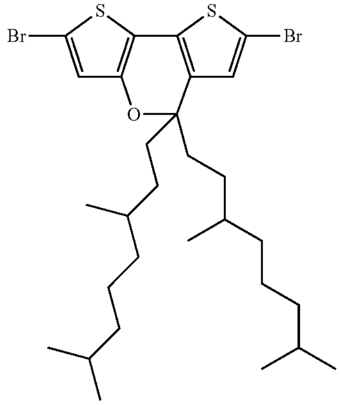

8

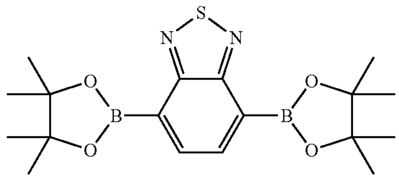

In the same manner as in Example 9, except that the compound 7c was used instead of the compound 7b, the synthesis was performed to obtain polymer F. The molecular weight of the polymer F measured by GPC (in terms of polystyrene) corresponded to Mw=54,000 and Mn=21,000. The light absorbing terminal wavelength of the polymer F was 930 nm.

Example 21

In the same manner as in Example 10, except that the polymer F was used instead of the polymer B, the preparation and evalutation of the cell were carried out. The result is listed in Table 1.

Example 22

Synthesis of Polymer G

[Chemical Formula 91]

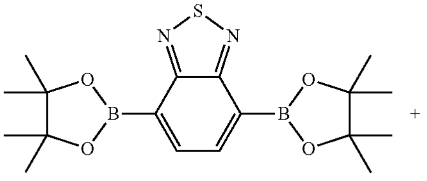

8

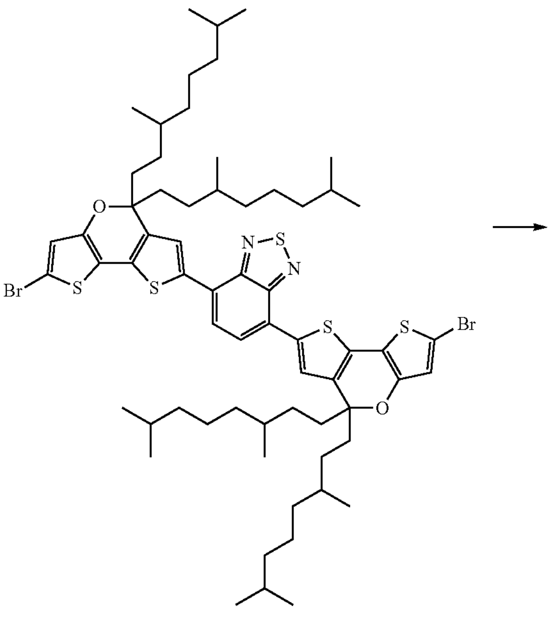

13

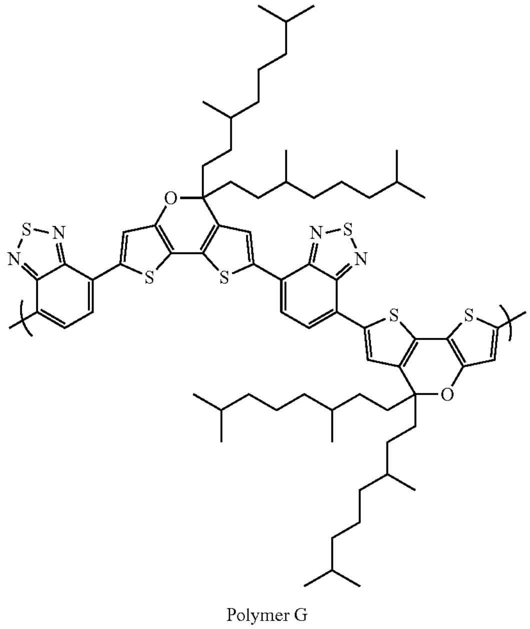

Polymer G

Into a 200 mL flask in which a gas in the flask was replaced by argon, the compound 8 (101.7 mg, 0.262 mmol), the compound 13 (343.1 mg, 0.276 mmol), and THF (10 mL) were charged to prepare a homogeneous solution and the resultant reaction mixture was subjected to argon bubbling at 25° C. for 30 minutes. The temperature of the reaction mixture was elevated to 60° C. and thereto, tris (dibenzylideneacetone) palladium (5.49 mg, 0.006 mmol) and [tri(tert-butyl)phosphonium]tetrafluoroborate (6.96 mg, 0.024 mmol) were added. Then, while stirring the reaction mixture at a reflux temperature of THF, a potassium carbonate aqueous solution (27.6% by weight, 1.50 g, 3.00 mmol) was dropped into the reaction mixture over 30 minutes. After 30 minutes, to the reaction solution, phenylboric acid (3.66 mg, 0.03 mmol) was added, the resultant reaction mixture was stirred further for 1 hour, and then the reaction was terminated. Then, to the reaction solution, 2 g of sodium diethyldithiocarbamate and 20 mL of water were added and the resultant reaction mixture was stirred under reflux for 2 hours. The aqueous phase was removed and the organic phase was washed with 20 mL of water twice, with 20 mL of a 3% by weight acetic acid aqueous solution twice, and further with 20 mL of water twice, followed by pouring the resultant solution into methanol to precipitate polymer. The polymer was filtered and then dried and the resultant polymer was dissolved in 30 mL of o-dichlorobenzene again. The resultant solution was passed through an alumina/silica gel column and the resultant solution was added into methanol to precipitate polymer, followed by filtering and then drying the polymer to obtain 242 mg of purified polymer. Hereinafter, the polymer is called polymer G. The molecular weight of the polymer G measured by GPC (in terms of polystyrene) corresponded to Mw=39,000 and Mn=15,000. The light absorbing terminal wavelength of the polymer G was 930 nm.

Example 23

In the same manner as in Example 10, except that the polymer G was used instead of the polymer B, the preparation and evalutation of the cell were carried out. The result is listed in Table 1.

Example 24

Synthesis of Polymer H

[Chemical Formula 92]

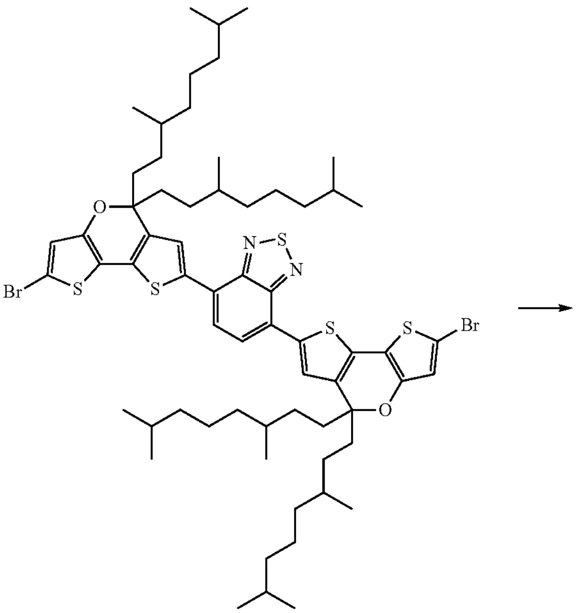

13

-continued

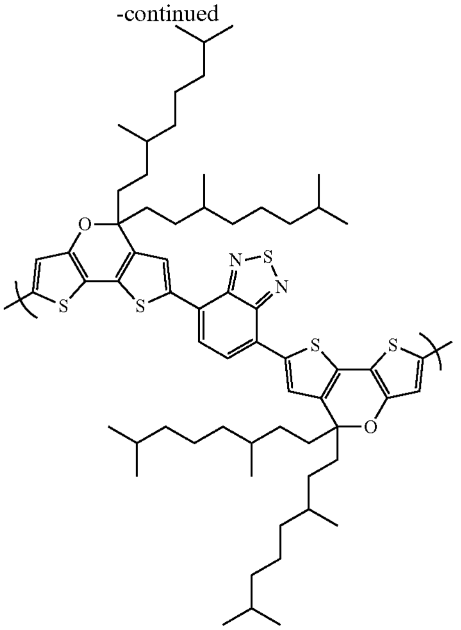

Polymer H

Into a 200 mL flask in which a gas in the flask was replaced by argon, the compound 13 (265.0 mg, 0.214 mmol), 2,2'-bipyridyl (100 mg), and toluene (10 mL) were charged and the resultant reaction mixture was subjected to argon bubbling at room temperature (25° C.) for 30 minutes. Then, to the reaction mixture, bis(1,5-cyclooctadiene) nickel (O) (177 mg, 0.643 mmol) was added and the resultant reaction mixture was stirred at room temperature (25° C.) for 30 minutes, followed by terminating the reaction.

Then, to the reaction solution, sodium diethyldithiocarbamate (1 g) and pure water (10 mL) were added and the resultant reaction mixture was stirred under reflux for 1 hour. The aqueous phase in the reaction solution was removed and then the organic phase was washed with 10 mL of water twice, with 10 mL of a 3% by weight acetic acid aqueous solution twice, and further with 10 mL of water twice, followed by pouring the resultant solution into methanol to precipitate polymer. The polymer was filtered and then dried and the resultant polymer was dissolved in toluene. The resultant solution was passed through an alumina/silica gel column and the resultant solution was added into methanol to precipitate polymer. The polymer was filtered and then dried to obtain 158 mg of polymer H.

For the molecular weight of the polymer H measured by GPC (in terms of polystyrene), the weight-average molecular weight (Mw) was 64,000 and the number average molecular weight (Mn) was 18,000. The light absorbing terminal wavelength of the polymer H was 910 nm.

Example 25

In the same manner as in Example 10, except that the polymer H was used instead of the polymer B, the preparation and evalutation of the cell were carried out. The result is listed in Table 1.

Reference Example 8

Synthesis of Compound 19

[Chemical Formula 93]

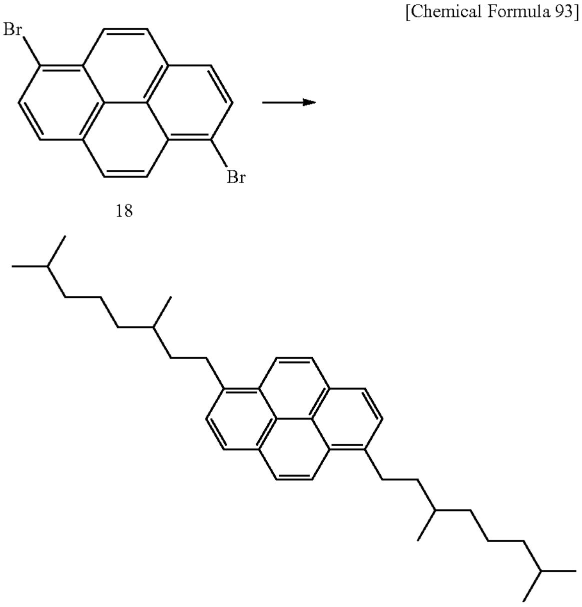

18

19

Into a 1,000 mL three-neck flask, 3.60 g (10.0 mmol) of 1,6-dibromopyrene (compound 18) and 300 mL of anhydrous THF were charged and the resultant THF solution was cooled to −78° C. and further, 15.0 mL of n-butyl lithium (1.6 M solution in hexane) was dropped into the THF solution through a syringe. While maintaining the THF solution at −78° C., the solution was stirred for 2 hours and thereinto, 5.31 g (24.0 mmol) of 1-bromo-3,7-dimethyloctane was dropped. After the completion of the dropping, the temperature of the resultant reaction mixture was elevated to room temperature (25° C.) and the reaction was carried out for 15 hours. The resultant reaction solution was slowly poured into water to terminate the reaction and the resultant reaction mixture was extracted with toluene into an organic phase. The organic phase was washed with water twice. The resultant organic phase was concentrated and recrystallized in hexane to obtain 1.20 g (2.49 mmol) of compound 19.

Reference Example 9

Synthesis of Compound 20

[Chemical Formula 94]

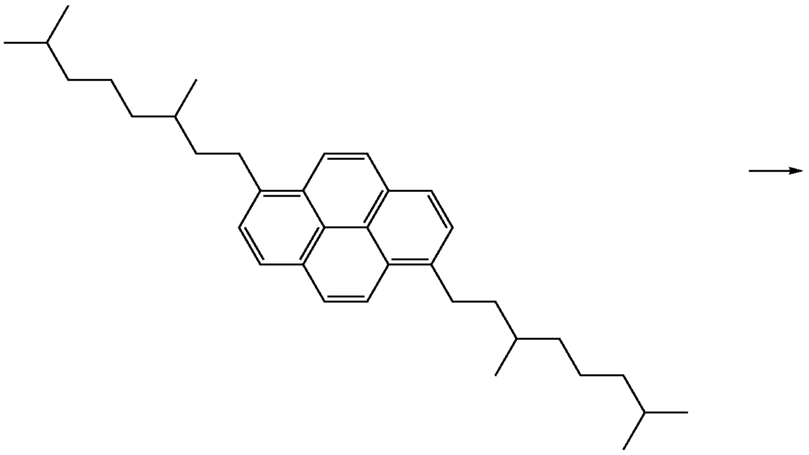

19

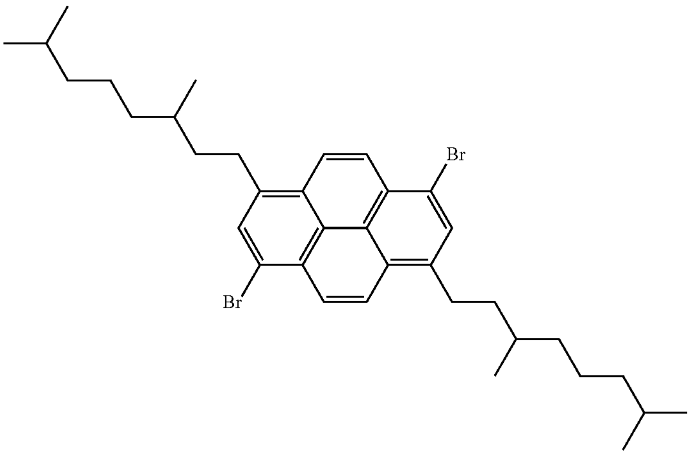

20

Into a 200 mL three-neck flask in which a gas in the flask was replaced by argon, 1.00 g (2.07 mmol) of the compound 19 and 50 mL of chloroform were charged and the resultant reaction mixture was stirred at room temperature (25° C.) to dissolve a solid. Thereinto, a solution obtained by dissolving 0.729 g (4.56 mmol) of bromine in 20 mL of chloroform was dropped at room temperature. The resultant reaction mixture was stirred for 12 hours and further thereinto, a solution obtained by dissolving 0.300 g (1.88 mmol) of bromine in 10 mL of chloroform was dropped to carry out the reaction for 5 hours. To the resultant reaction solution, 100 mL of a saturated sodium thiosulfate aqueous solution was added to terminate the reaction and the resultant reaction mixture as it was stirred at room temperature to precipitate a solid. The precipitated solid (insoluble matter) was filtered to be recovered. The resultant solid was dissolved in a solvent mixture of chloroform and THF and then the resultant solution was hot-filtered and next, recrystallized to obtain 0.95 g (1.48 mmol) of compound 20.

Reference Example 10

Synthesis of Compound 21

[Chemical Formula 95]

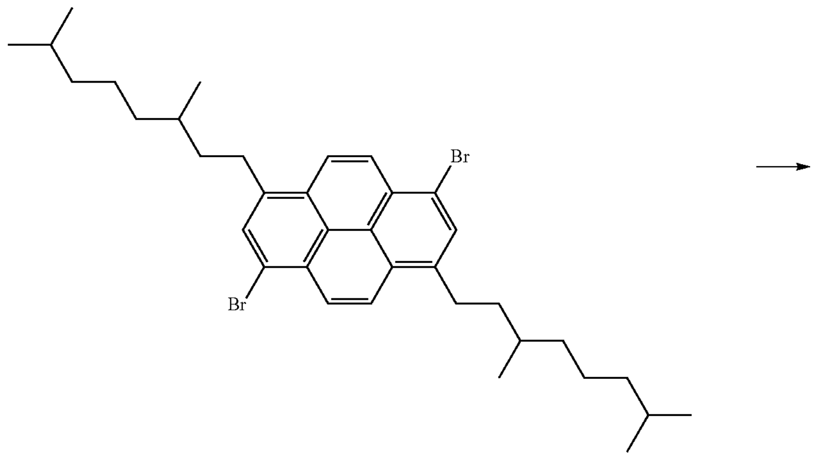

20

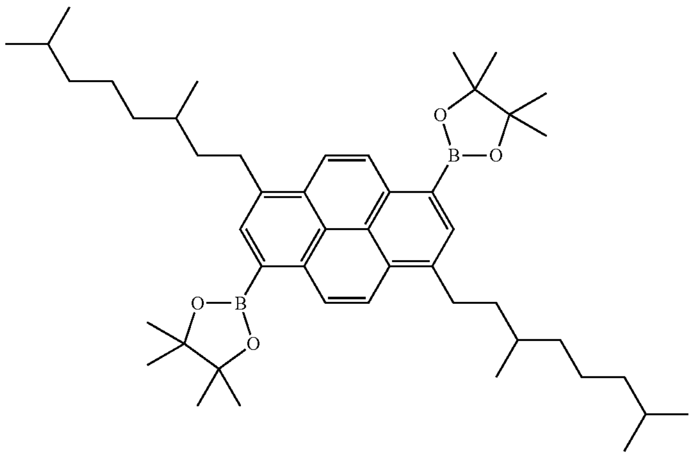

21

Into a 100 mL four-neck flask in which a gas in the flask was replaced by argon, under a nitrogen atmosphere, 0.90 g (1.40 mmol) of the compound 20, 0.78 g (3.08 mmol) of bispinacolatodiboron, 0.049 g (0.083 mmol) of 1,1'-bis (diphenylphosphino)ferrocene (dppf), 0.069 g (0.083 mmol) of $Pd(dppf)_2Cl_2$, 1.82 g (18.5 mmol) of potassium acetate, and 15 mL of 1,4-dioxane were charged, the resultant reaction mixture was heated to 100° C. and was then stirred. After 12 hours, the reaction solution was filtered with celite and from the filtrate, the solvent was removed. The residual solid was dissolved in a solvent mixture of hexane and toluene. To the resultant solution, an activated carbon was added and the resultant mixture was stirred at 90° C. for 2 hours. The resultant suspension was hot-filtered with celite and from the filtrate, the solvent was removed, followed by recrystallizing the resultant residue in hexane to obtain 0.523 g (0.71 mmol) of compound 21.

Example 26
Synthesis of Polymer I
[Chemical Formula 96]
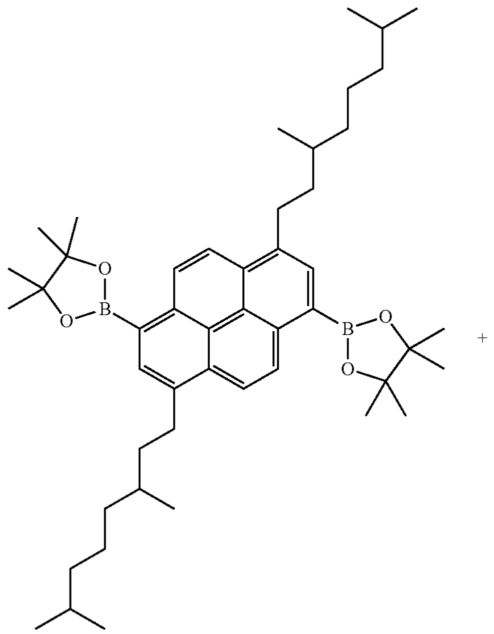
21
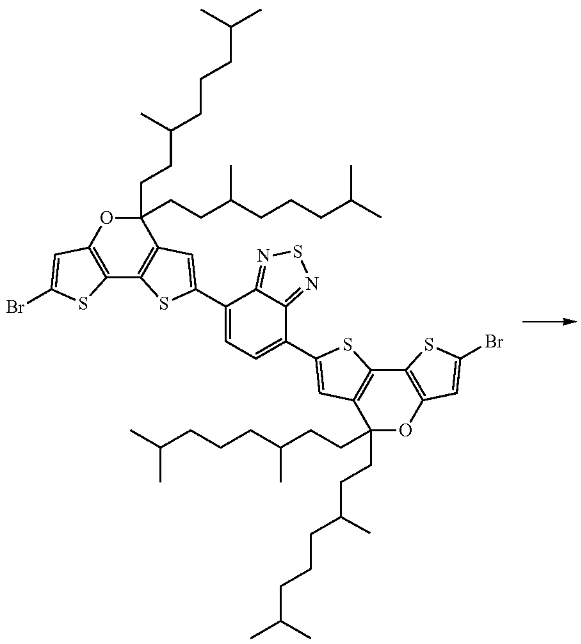
13

-continued

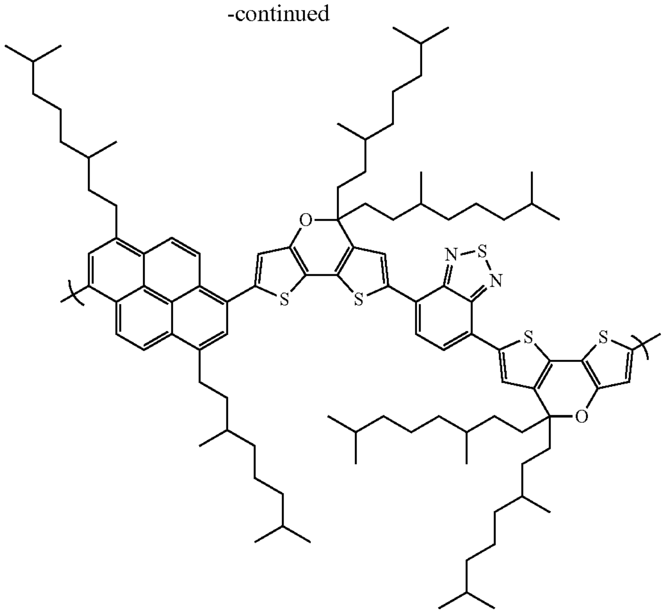

Polymer I

Into a 200 mL flask in which a gas in the flask was replaced by argon, the compound 21 (222.0 mg, 0.302 mmol), the compound 13 (395.1 mg, 0.318 mmol), toluene (10 mL), and methyltrialkylammonium chloride (trade name: Aliquat 336 (registered trademark); manufactured by Aldrich Corp.) (60.6 mg, 0.15 mmol) were charged and the resultant reaction mixture was subjected to argon bubbling at room temperature (25° C.) for 30 minutes. The temperature of the reaction mixture was elevated to 90° C. and thereto, palladium acetate (0.67 mg, 0.003 mmol) and tris (2-methoxyphenyl)phosphine (3.70 mg, 0.0105 mmol) were added. Then, while stirring the reaction mixture at 100° C., a sodium carbonate aqueous solution (16.7% by weight, 1.90 g, 3.00 mmol) was dropped into the reaction mixture over 30 minutes. After 50 minutes, to the reaction solution, phenylboric acid (3.66 mg, 0.03 mmol) was added, the resultant reaction mixture was stirred further for 1 hour, and then the reaction was terminated.

Then, to the reaction solution, sodium diethyldithiocarbamate (1 g) and pure water (10 mL) were added and the resultant reaction mixture was stirred under reflux for 1 hour. The aqueous phase in the reaction solution was removed and then the organic phase was washed with 10 mL of water twice, with 10 mL of a 3% by weight acetic acid aqueous solution twice, and further with 10 mL of water twice, followed by pouring the resultant solution into methanol to precipitate polymer. The polymer was filtered and then dried and the resultant polymer was dissolved in toluene. The resultant solution was passed through an alumina/silica gel column and the resultant solution was added into methanol to precipitate polymer. The polymer was filtered and then dried to obtain 392 mg of polymer I.

For the molecular weight of the polymer I measured by GPC (in terms of polystyrene), the weight average molecular weigh (Mw) was 103,000 and the number average molecular weight (Mn) was 50,000. The light absorbing terminal wavelength of the polymer I was 805 nm.

Example 27

In the same manner as in Example 10, except that the polymer I was used instead of the polymer B, the preparation and evalutation of the cell were carried out. The result is listed in Table 1.

Example 28

Synthesis of Compound 5d

[Chemical Formula 97]

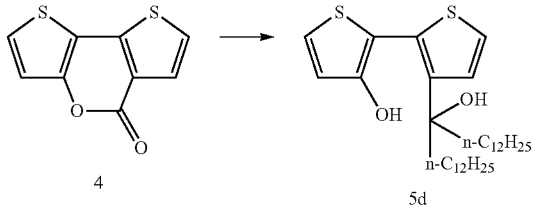

4

5d

In the same manner as in Example 12, except that the solution of n-dodecylmagnesium bromide (1 M) in ether was used instead of the solution of 3,7-dimethyloctylmagnesium bromide (1 M) in ether, the synthesis was performed to obtain compound 5d.

$^1$H NMR in $CDCl_3$ (ppm): 7.24 (d, 1H), 7.20 (d, 1H), 6.98 (d, 1H), 6.77 (d, 1H), 1.80 (b, 4H), 1.33 (b, 40H), 0.87 (s, 6H)

Example 29

Synthesis of Compound 6d

[Chemical Formula 98]

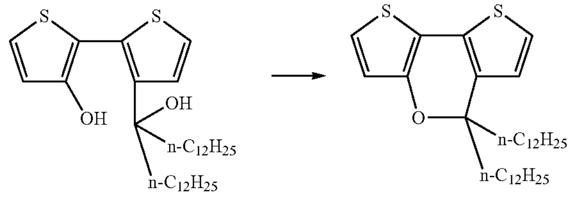

5d 6d

In the same manner as in Example 13, except that the compound 5d was used instead of the compound 5c, the synthesis was performed to obtain compound 6d.

$^1$H NMR in $CDCl_3$ (ppm): 6.99 (d, 1H), 6.93 (d, 1H), 6.68 (d, 1H), 6.59 (d, 1H), 1.79 (b, 4H), 1.31 (b, 40H), 0.85 (s, 6H)

Example 30

Synthesis of Compound 11d

[Chemical Formula 99]

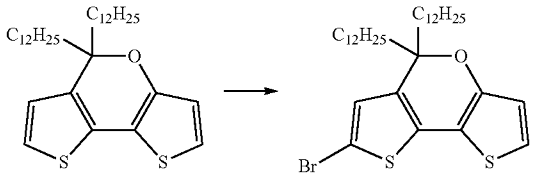

6d 11d

In the same manner as in Example 14, except that the compound 6d obtained in Example 29 was used instead of the compound 6c, the synthesis was performed to obtain compound 11d.

$^1$H-NMR ($CDCl_3$, δ (ppm)): 0.826 (t, 12H), 1.21 (m, 72H), 1.43 (m, 8H), 1.96 (t, 8H), 6.65 (d, 1H), 6.66 (s, 1H), 6.98 (s, 1H)

Example 31

Synthesis of Compound 12d

[Chemical Formula 100]

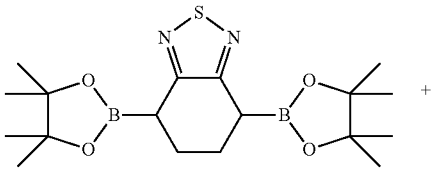

8

-continued

2

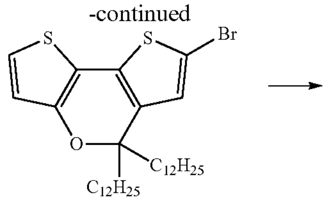

11d

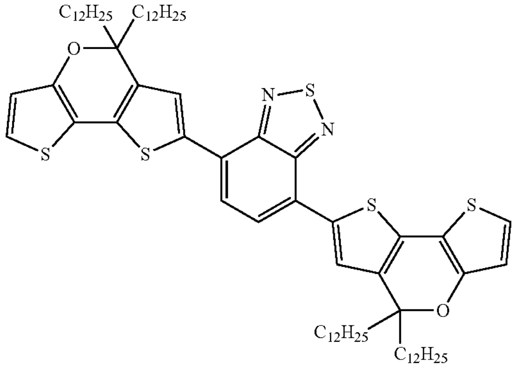

12d

In the same manner as in Example 15, except that the compound 11d was used instead of the compound 11, the synthesis was performed to obtain compound 12d.

$^1$H-NMR ($CDCl_3$, δ (ppm)): 0.862 (t, 12H), 1.213 (m, 72H), 1.432 (m, 8H), 1.968 (t, 8H), 6.715 (d, 2H), 7.045 (d, 2H), 7.786 (d, 4H)

Example 32

Synthesis of Compound 13d

[Chemical Formula 101]

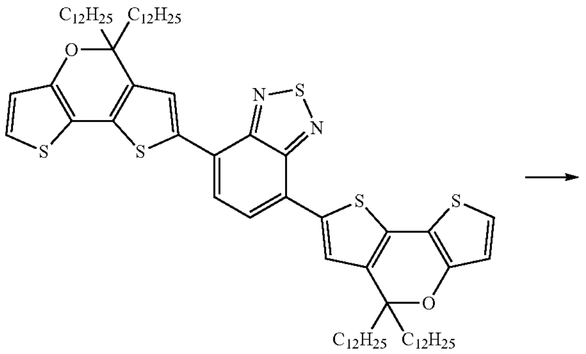

12d

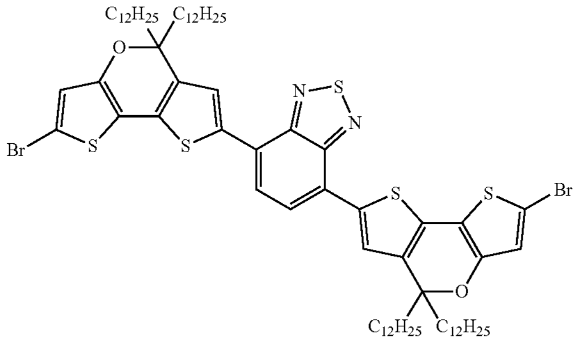

13d

In the same manner as in Example 16, except that the compound 12d was used instead of the compound 12, the synthesis was performed to obtain compound 13d.

$^1$H-NMR ($CDCl_3$, δ (ppm)): 0.860 (t, 12H), 1.213 (m, 72H), 1.427 (m, 8H), 1.949 (t, 8H), 6.710 (s, 2H), 7.756 (s, 4H)

Reference Example 11

Synthesis of Compound 23

[Chemical Formula 102]

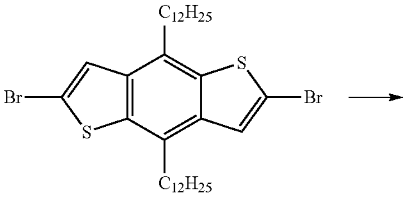

22

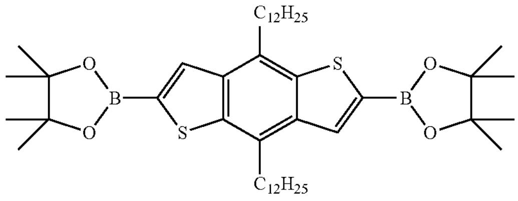

23

Into a four-neck flask, compound 22 (6.847 g, 10.00 mmol) synthesized according to a description in "Chemistry of Materials, 2006, 18 (14), pp. 3237-3241," bispinacolatodiboron (10.16 g, 40.00 mmol), and dioxane (150 mL) were charged and the resultant reaction mixture was subjected to argon bubbling at room temperature (25° C.) for 30 minutes. To the resultant reaction mixture, 1,1'-bis(diphenylphosphino)ferrocene palladium dichloride (408.3 mg, 5% by mole), 1,1'-bis(diphenylphosphino)ferrocene (277.2 mg, 5% by mole), and potassium acetate (3.926 g, 40.00 mmol), which was a base, were added and the resultant reaction mixture was refluxed with heating for 10 hours. After the reaction, the reaction solution was analyzed by HPLC to confirm the disappearance of the compound 22.

Then, using a filter, a base poorly soluble in the reaction solution was separated. Next, the solvent was evaporated with an evaporator. Then, with a silica gel column using hexane as a developing solution, the reaction product was purified and the obtained component was washed with methanol for 3 hours to obtain a light brown powder. The powder was dissolved in hexane (100 mL) and then a state in which to the resultant solution, ethanol (100 mL) was added was left to recrystallize the reaction product to obtain 1.386 g of compound 23.

Example 33

Synthesis of Polymer J

[Chemical Formula 103]

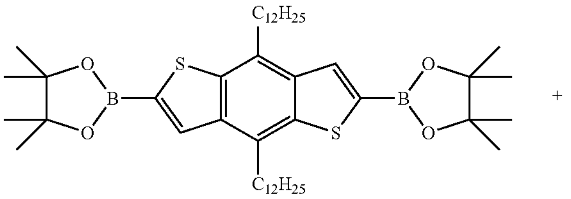

23

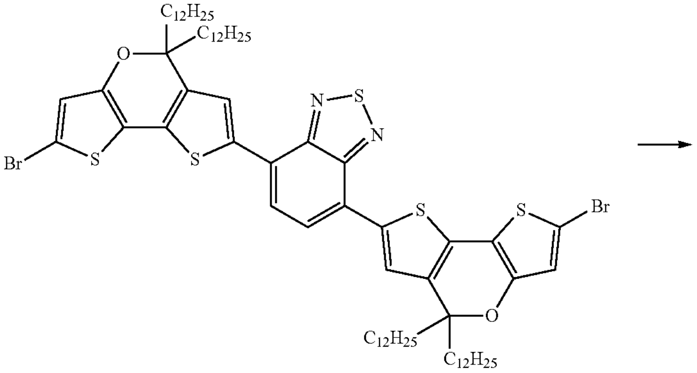

13d

-continued

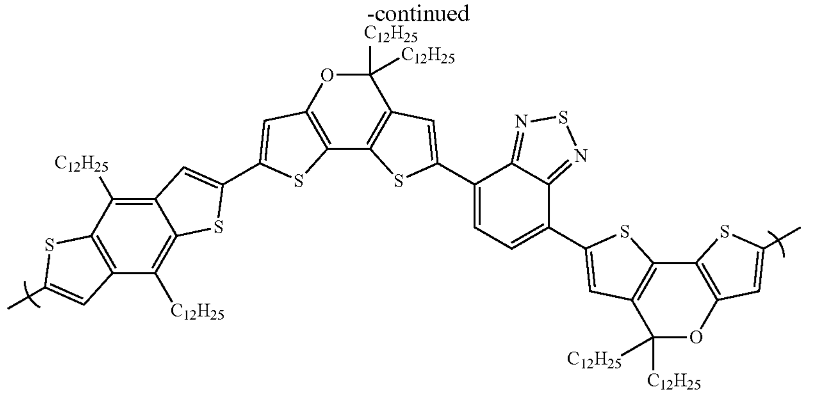

Polymer J

Into a flask in which a gas in the flask was replaced by argon, the compound 23 (223.5 mg, 0.287 mmol), the compound 13d (408.4 mg, 0.302 mmol), and THF (10 mL) were charged and the resultant reaction mixture was subjected to argon bubbling at room temperature (25° C.) for 30 minutes. Then, to the reaction solution, tris(dibenzylideneacetone) palladium (5.49 mg, 0.006 mmol) and [tri(tert-butyl)phosphonium]tetrafluoroborate (6.96 mg, 0.024 mmol) were added. While stirring the reaction mixture at 80° C., thereinto, a potassium carbonate aqueous solution (27.6% by weight, 1.50 g, 3.00 mmol) was dropped over 30 minutes. After 15 minutes, to the reaction solution, phenylboric acid (3.66 mg, 0.03 mmol) was added, the resultant reaction mixture was stirred further for 1 hour, and then the reaction was terminated.

Then, to the reaction solution, sodium diethyldithiocarbamate (1 g) and pure water (10 mL) were added and the resultant reaction mixture was stirred under reflux for 1 hour. The aqueous phase in the reaction solution was removed and then the organic phase was washed with 10 mL of water twice, with 10 mL of a 3% by weight acetic acid aqueous solution twice, and further with 10 mL of water twice, followed by pouring the resultant solution into methanol to precipitate polymer. The polymer was filtered and then dried and the resultant polymer was dissolved in toluene. The resultant solution was passed through an alumina/silica gel column and the resultant solution was poured into methanol to precipitate polymer. The polymer was filtered and then dried to obtain 359 mg of polymer J.

For the molecular weight of the polymer J measured by GPC (in terms of polystyrene), the weight average molecular weigh (Mw) was 80,000 and the number average molecular weight (Mn) was 25,000. The light absorbing terminal wavelength of the polymer J was 815 nm.

Example 34

In the same manner as in Example 10, except that the polymer J was used instead of the polymer B, the preparation and evalutation of the cell were carried out. The result is listed in Table 1.

Example 35

Synthesis of Polymer K

[Chemical Formula 104]

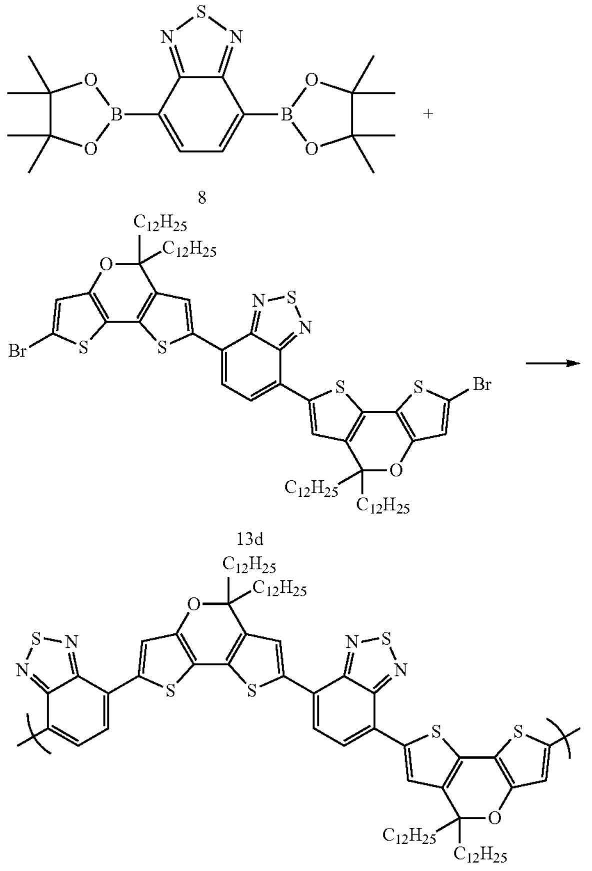

8

13d

Polymer K

In the same manner as in Example 22, except that the compound 13d was used instead of the compound 13, the synthesis was performed to obtain polymer K.

The molecular weight of the polymer K measured by GPC (in terms of polystyrene) corresponded to Mw=64,000 and Mn=22,000. The light absorbing terminal wavelength of the polymer K was 930 nm.

Example 36

In the same manner as in Example 10, except that the polymer K was used instead of the polymer B, the preparation and evalutation of the cell were carried out. The result is listed in Table 1.

Example 37

Synthesis of Compound 24

[Chemical Formula 105]

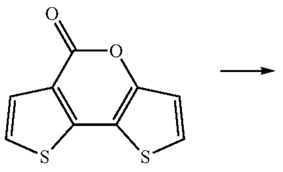

4

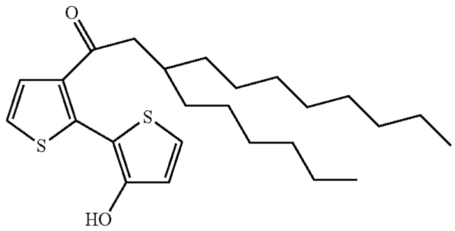

24

Into a 100 mL four-neck flask in which a gas in the flask was replaced by argon, 1.04 g (5.00 mmol) of the compound 4 and 35 mL of anhydrous THF were charged to prepare a homogeneous solution. While maintaining the flask at −20° C., to the solution, 15.0 mL of solution of 2-hexyldecylmagnesium bromide (1 M) in ether was added. Then, the temperature of the resultant reaction mixture was elevated to −5° C. over 30 minutes and the reaction mixture as it was stirred for 30 minutes. Then, the temperature of the reaction mixture was elevated to 0° C. over 10 minutes and the reaction mixture as it was stirred for 1.5 hours. Then, to the reaction mixture, water was added to terminate the reaction and the reaction product was extracted with diethyl ether. The organic phase that was a diethyl ether solution was dried over sodium sulfate and was filtered. The resultant filtrate was passed through a silica gel column using chloroform as a developing solution and the solvent of the resultant filtrate was evaporated to obtain 1.30 g of compound 24.

Example 38

Synthesis of Compound 5e

[Chemical Formula 106]

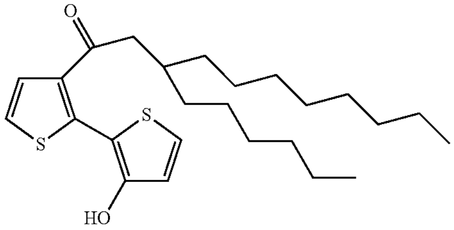

24

-continued

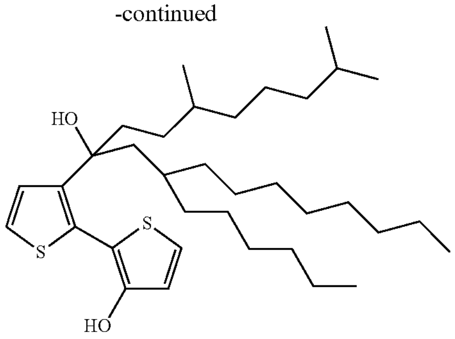

5e

Into a 100 mL four-neck flask in which a gas in the flask was replaced by argon, 1.30 g (2.99 mmol) of the compound 24 and 30 mL of anhydrous THF were charged to prepare a homogeneous solution. While maintaining the flask at −20° C., to the solution, 15.0 mL of solution of 3,7-dimethyloctylmagnesium bromide (1 M) in ether was added. Then, the temperature of the resultant reaction mixture was elevated to −5° C. over 30 minutes and the reaction mixture as it was stirred for 30 minutes. Then, the temperature of the reaction mixture was elevated to 0° C. over 10 minutes and the reaction mixture as it was stirred for 1.5 hours. Then, to the reaction mixture, water was added to terminate the reaction and the reaction product was extracted with diethyl ether. The organic phase that was a diethyl ether solution was dried over sodium sulfate and was filtered. The resultant filtrate was passed through a silica gel column using chloroform as a developing solution and the solvent of the resultant filtrate was evaporated to obtain 1.20 g of compound 5e.

Example 39

Synthesis of Compound 6e

[Chemical Formula 107]

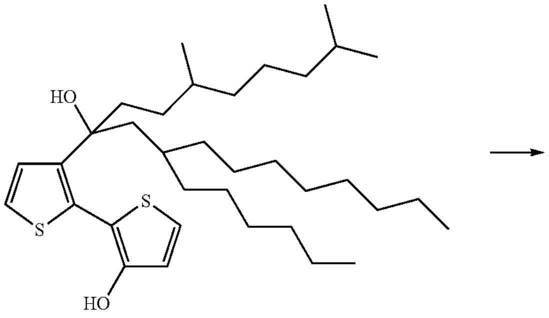

5e

-continued

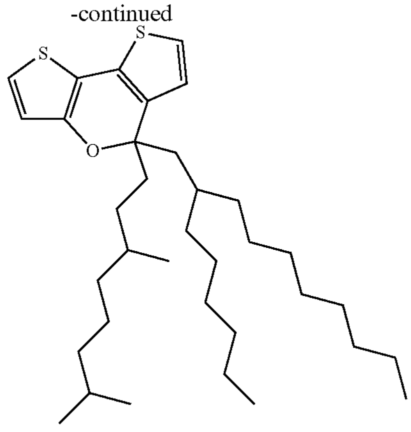

6e

Into a 200 mL flask in which a gas in the flask was replaced by argon, 1.20 g (2.08 mmol) of the compound 5e and 30 mL of toluene were charged to prepare a homogeneous solution. To the solution, 100 mg of sodium p-toluenesulfonate monohydrate was added and the resultant reaction mixture was stirred at 100° C. for 1.5 hours. The reaction solution was cooled to room temperature (25° C.) and thereto, 50 mL of water was added, followed by extracting the reaction product with toluene. The organic phase that was a toluene solution was dried over sodium sulfate and was filtered and from the resultant filtrate, the solvent was evaporated. The resultant crude product was purified by a silica gel column (solvent: hexane) to obtain 802 mg of compound 6e.

$^1$H-NMR ($CDCl_3$, δ (ppm)): 0.833 (m, 15H), 1.0-1.5 (m, 35H), 1.850 (m, 4H), 6.688 (m, 2H), 6.966 (d, 1H), 7.028 (d, 1H)

Example 40

Synthesis of Compound 7e

[Chemical Formula 108]

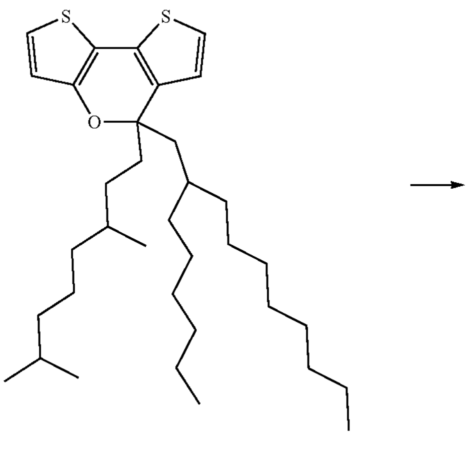

6e

-continued

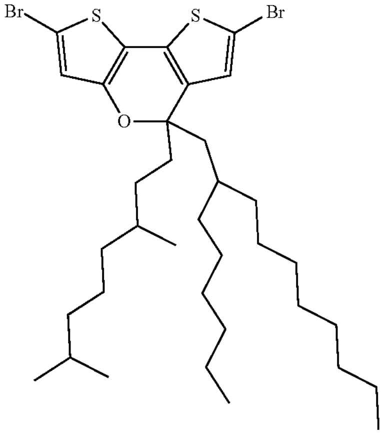

7e

Into a 300 mL flask in which a gas in the flask was replaced by argon, the compound 6e (400 mg, 0.716 mmol) and N,N-dimethylformamide (DMF) (20 mL) were charged to prepare a homogeneous solution. The solution was subjected to argon bubbling at 25° C. for 30 minutes and was then cooled to −40° C. and thereto, NBS (280.4 mg, 1.575 mmol) was added, followed by elevating the temperature of the resultant reaction mixture to 0° C. over 2 hours. To the reaction solution, 50 mL of water was added and extraction was carried out with diethyl ether. The extracted diethyl ether solution was dried over sodium sulfate and was then filtered and from the resultant filtrate, the solvent was evaporated. The resultant crude product was purified by a silica gel column using hexane as a solvent to obtain 437 mg of compound 7e.

$^1$H-NMR ($CDCl_3$, δ (ppm)): 0.833 (m, 15H), 1.0-1.5 (m, 35H), 1.850 (m, 4H), 6.660 (s, 1H), 6.980 (s, 1H)

Example 41

Synthesis of Polymer L

[Chemical Formula 109]

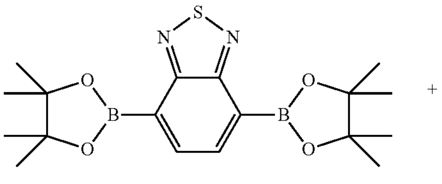

8

-continued

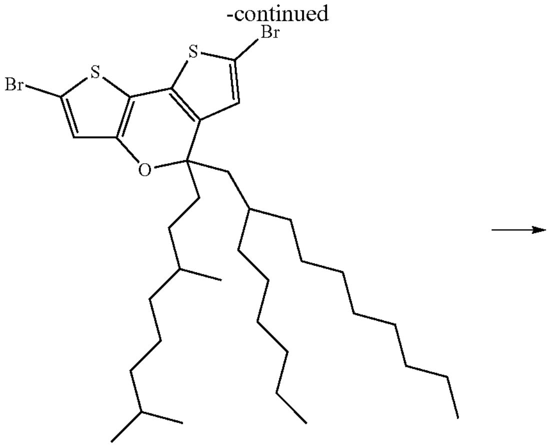

7e

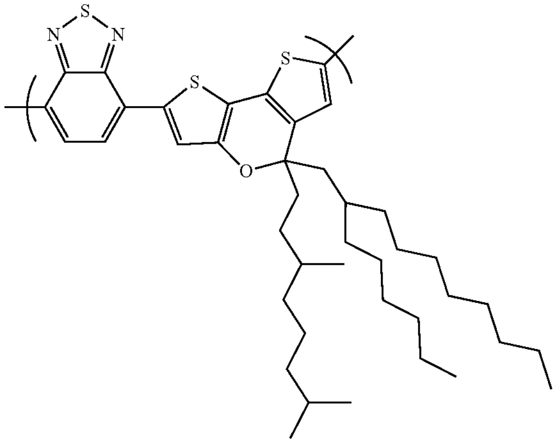

Polymer L

Into a 200 mL four-neck flask in which a gas in the flask was replaced by argon, the compound 8 (110.6 mg, 0.285 mmol), the compound 7e (215.0 mg, 0.300 mmol), and tetrahydrofuran (THF) (10 mL) were charged and the resultant reaction mixture was subjected to argon bubbling at room temperature (25° C.) for 30 minutes. Then, to the reaction solution, tris(dibenzylideneacetone) palladium (5.49 mg, 0.006 mmol) and [tri(tert-butyl)phosphonium] tetrafluoroborate (6.96 mg, 0.024 mmol) were added. While stirring the reaction mixture at 80° C., a potassium carbonate aqueous solution (27.6% by weight, 1.50 g, 3.00 mmol) was dropped into the reaction mixture over 30 minutes. After 30 minutes, to the reaction solution, phenylboric acid (3.66 mg, 0.03 mmol) was added, the resultant reaction mixture was stirred further for 1 hour, and then the reaction was terminated.

Then, to the reaction solution, sodium diethyldithiocarbamate (1 g) and pure water (10 mL) were added and the resultant reaction mixture was stirred under reflux for 1 hour. The aqueous phase in the reaction solution was removed and then the organic phase was washed with 10 mL of water twice, with 10 mL of a 3% by weight acetic acid aqueous solution twice, and further with 10 mL of water twice, followed by pouring the resultant solution into methanol to precipitate polymer. The polymer was filtered and then dried and the resultant polymer was dissolved in toluene. The resultant solution was passed through an alumina/silica gel column and the resultant solution was poured into methanol to precipitate polymer. The polymer was filtered and then dried to obtain 242 mg of polymer L. The light absorbing terminal wavelength of the polymer L was 930 nm.

Example 42

In the same manner as in Example 10, except that the polymer L was used instead of the polymer B, the preparation and evalutation of the cell were carried out. The result is listed in Table 1.

Example 43

In the same manner as in Example 10, except that the polymer D was used instead of the polymer B, the preparation and evalutation of the cell were carried out. The result is listed in Table 1.

TABLE 1

| Photovoltaic Cell Evaluation Result | | | | | |
|---|---|---|---|---|---|
| | | Short-Circuit Current Density (mA/cm$^2$) | Open-Circuit Voltage | Fill Factor | Photoelectric Conversion Efficiency (%) |
| Example 10 | Polymer B | 5.64 | 0.58 | 0.36 | 1.18 |
| Example 11 | Polymer B | 7.66 | 0.58 | 0.44 | 1.95 |
| Example 18 | Polymer A | 12.46 | 0.52 | 0.52 | 3.38 |
| Example 21 | Polymer F | 10.08 | 0.56 | 0.51 | 2.86 |
| Example 23 | Polymer G | 11.64 | 0.53 | 0.52 | 3.19 |
| Example 25 | Polymer H | 5.21 | 0.51 | 0.49 | 1.30 |
| Example 27 | Polymer I | 5.28 | 0.70 | 0.40 | 1.48 |
| Example 34 | Polymer J | 5.85 | 0.61 | 0.42 | 1.50 |
| Example 36 | Polymer K | 8.38 | 0.55 | 0.51 | 2.38 |
| Example 42 | Polymer L | 10.32 | 0.57 | 0.57 | 3.34 |
| Example 43 | Polymer D | 4.95 | 0.74 | 0.56 | 2.17 |
| Comparative Example 1 | Polymer C | 0.11 | 0.80 | 0.43 | 0.04 |
| Comparative Example 2 | Polymer E | 4.61 | 0.60 | 0.33 | 0.91 |

Example 44

(Preparation of Organic Transistor) [Polymer J]

A silicon substrate having a silicon thermal oxide film of a thickness of 300 nm and n-type silicon in which antimony was doped in a high concentration, was subjected to ultrasonic cleaning in acetone for 10 minutes and was then irradiated with ozone UV for 20 minutes. Then, the silicon substrate was spin-coated with a toluene solution in which 5 drops of octadecyltrichlorosilane were added to 10 mL of toluene with a syringe to subject the surface of the thermal oxide film to silane treatment. The silicon thermal oxide film acts as a gate insulating layer and the silicon in which antimony was doped in a high concentration acts as a gate electrode.

Next, the polymer J was dissolved in o-dichlorobenzene to prepare a solution in which concentration of polymer J is 0.5% by weight, and the solution was filtered with a membrane filter to prepare a coating liquid. The coating liquid was applied on the above silane-treated n-type silicon substrate by a spin coating method to form the coating film of polymer J having a thickness of about 60 nm. Then, the coating film was heated at 170° C. under a nitrogen atmosphere for 30 minutes to form the organic semiconductor thin film of polymer J.

Next, an organic transistor was produced by disposing a metal mask on the organic semiconductor thin film, and layering molybdenum trioxide and gold in this order on the organic semiconductor thin film by a vacuum deposition method to prepare a source electrode and a drain electrode that had a layered structure of molybdenum trioxide and gold.

The electric properties of the organic transistor were measured using a semiconductor properties evaluation system (semiconductor parameter analyzer 4200-SCS; manufactured by Keithley Instruments Inc.). When a negative gate voltage applied to a gate electrode was increased, a negative drain current also increased, so that it could be confirmed that the organic transistor was a p-type organic transistor. The electric field-effect mobility μ of a carrier in the organic transistor was calculated using Formula (a) below representing a drain current Id in a saturation region of the electric properties of the organic transistor.

$$Id=(W/2L)\mu Ci(Vg-Vt)^2 \quad (a)$$

(where L represents a channel length of the organic transistor; W represents a channel width of the organic transistor; Ci represents a capacity of the gate insulating film per unit area; Vg represents a gate voltage; and Vt represents a threshold voltage of the gate voltage).

The electric field-effect mobility of a carrier (carrier mobility) was 0.074 $cm^2/Vs$ and an ON/OFF current ratio was $10^6$.

Example 45

In the same manner as in Example 44, except that the polymer G was used instead of the polymer J, the organic transistor element was prepared and the transistor properties thereof were evaluated. The carrier mobility was 0.153 $cm^2/Vs$ and the ON/OFF current ratio was $10^6$.

Example 46

In the same manner as in Example 44, except that the polymer I was used instead of the polymer J, the organic transistor element was prepared and the transistor properties thereof were evaluated. The carrier mobility was $6.80\times10^{-4}$ $cm^2/Vs$ and the ON/OFF current ratio was $10^4$.

Example 47

In the same manner as in Example 44, except that the polymer H was used instead of the polymer J, the organic transistor element was prepared and the transistor properties thereof were evaluated. The carrier mobility was 0.029 $cm^2/Vs$ and the ON/OFF current ratio was $10^5$.

Example 48

In the same manner as in Example 44, except that the polymer L was used instead of the polymer J, the organic transistor element was prepared and the transistor properties thereof were evaluated. The carrier mobility was $5.49\times10^{-3}$ $cm^2/Vs$ and the ON/OFF current ratio was $10^4$.

Example 49

In the same manner as in Example 44, except that the polymer D was used instead of the polymer J, the organic transistor element was prepared and the transistor properties thereof were evaluated. The carrier mobility was $3.80\times10^{-3}$ $cm^2/Vs$ and the ON/OFF current ratio was $10^5$.

Example 50

In the same manner as in Example 44, except that: the polymer F was used instead of the polymer J; β-PTS (β-phenyltrichlorosilane) was used instead of octadecyltrichlorosilane; chloroform was used instead of o-dichlorobenzene; and the temperature for the thermal treatment was 120° C. instead of 170° C., the organic transistor element was prepared and the transistor properties thereof were evaluated. The carrier mobility was $7.3\times10^{-3}$ $cm^2/Vs$ and the ON/OFF current ratio was $10^4$.

TABLE 2

| Organic Transistor Element Evaluation Result | | | |
|---|---|---|---|
| | | Carrier Mobility (cm2/Vs) | ON/OFF Ratio |
| Example 44 | Polymer J | 0.074 | $10^6$ |
| Example 45 | Polymer G | 0.153 | $10^6$ |
| Example 46 | Polymer I | $6.80 \times 10^{-4}$ | $10^4$ |
| Example 47 | Polymer H | 0.029 | $10^5$ |
| Example 48 | Polymer L | $5.49 \times 10^{-3}$ | $10^4$ |
| Example 49 | Polymer D | $3.80 \times 10^{-3}$ | $10^5$ |
| Example 50 | Polymer F | $7.30 \times 10^{-3}$ | $10^4$ |

Reference Example 12

Synthesis of Compound 3-Br

[Chemical Formula 110]

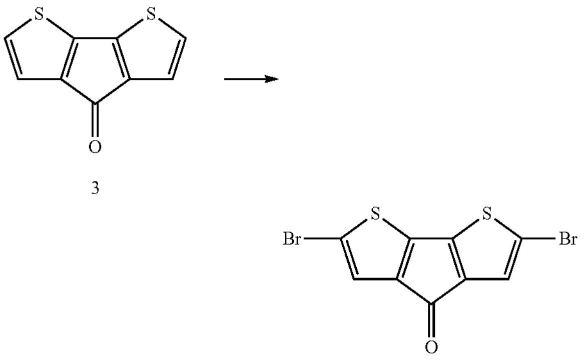

3

3-Br

Into a flask in which a gas in the flask was replaced by argon, 10.0 g (5.20 mmol) of the compound 3 and 100 mL of tetrahydrofuran (hereinafter, which may be called THF) were charged to prepare a homogeneous solution. While maintaining the flask at 0° C., to the solution, 2.31 g (1.30 mmol) of N-bromosuccinimide (hereinafter, which may be called NBS) was added over 15 minutes. Then, the resultant reaction mixture was stirred at 0° C. for 2 hours and a precipitated solid was filtered to be recovered, followed by washing the recovered solid with a sodium thiosulfate aqueous solution (10% by weight) and water. The obtained solid is called crude product 3-Br-A. Then, to the filtrate, 200 mL of the sodium thiosulfate aqueous solution (10% by weight) was added to extract the filtrate with chloroform. The organic phase that was a chloroform solution was dried over sodium sulfate and was filtered. The resultant filtrate was concentrated to recover a precipitated solid. The resultant solid is called crude product 3-Br—B. The crude product 3-Br-A and the crude product 3-Br—B were combined and the combination was purified by silica gel column chromatography (developing solution: chloroform) to obtain 17.3 g of compound 3-Br. The operations up to here were repeated by a plurality of times.

Example 51

Synthesis of Compound 4-Br

[Chemical Formula 111]

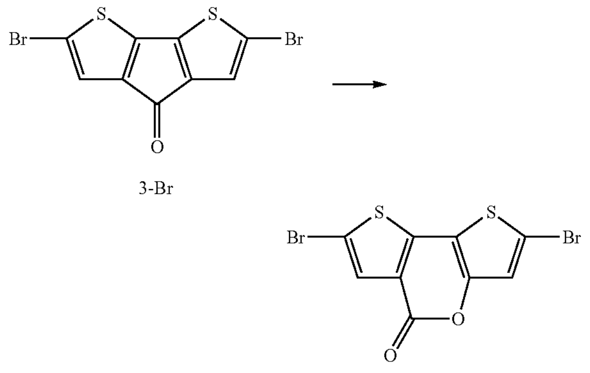

3-Br

4-Br

Into a 1,000 mL four-neck flask equipped with a mechanical stirrer in which a gas in the flask was replaced by argon, 25.0 g (71.4 mmol) of the compound 3-Br, 250 mL of chloroform, and 160 mL of trifluoroacetic acid were charged to prepare a homogeneous solution. To the solution, 21.0 g (210 mmol) of sodium perborate monohydrate was added over 35 minutes and the resultant reaction mixture was stirred at room temperature (25° C.) for 240 minutes. Then, to the reaction mixture, 500 mL of a 5% by weight sodium sulfite aqueous solution was added to terminate the reaction and to the reaction mixture, sodium hydrogen carbonate was added until pH of the reaction solution became 6. Then, the reaction product was extracted with chloroform and the organic phase that was a chloroform solution was passed through a silica gel column to obtain a filtrate. From the filtrate, the solvent was evaporated by an evaporator. The resultant residue was recrystallized in methanol to obtain 7.70 g (21.0 mmol) of compound 4-Br. The operations up to here were repeated by a plurality of times.

Example 52

Synthesis of Compound 4

[Chemical Formula 112]

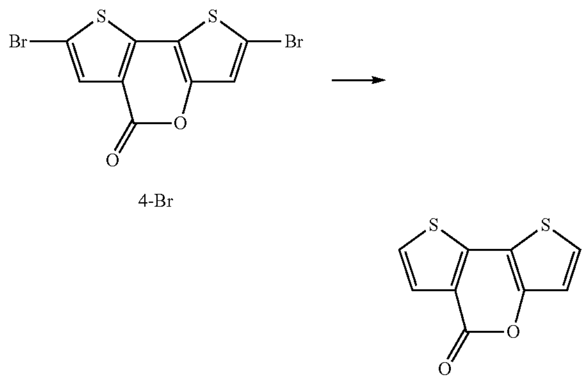

4-Br

4

Into a 2,000 mL flask in which a gas in the flask was replaced by argon, 23.1 g (63:1 mmol) of the compound 4-Br and 1,500 mL of THF were charged to prepare a homogeneous solution. The flask was cooled to −50° C. and into the solution, 190 mL of solution of n-octylmagnesium bromide (1 mol/L) in THF was dropped over 10 minutes. The resultant reaction mixture was stirred at −50° C. for 30 minutes and thereto, 500 mL of water was added to terminate the reaction. The temperature of the reaction solution was elevated to room temperature (25° C.) and therefrom, 1,000 mL of THF was evaporated by an evaporator, followed by adding 100 mL of acetic acid thereto. The reaction product was extracted with chloroform and then, the chloroform solution was dried over sodium sulfate. The chloroform solution was filtered and from the resultant filtrate, the solvent was evaporated by an evaporator. The resultant solid was washed with hexane and was dried under reduced pressure to obtain 10.9 g of compound 4.

Example 53

Synthesis of Compound 25

[Chemical Formula 113]

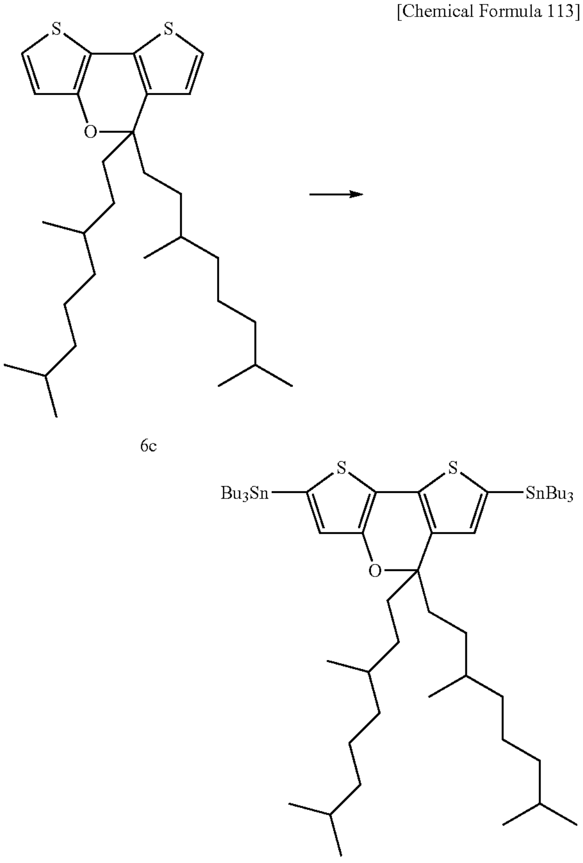

6c

25

Into a 200 mL flask in which a gas in the flask was replaced by argon, 2.16 g (4.55 mmol) of the compound 6c and 100 mL of anhydrous THF were charged to prepare a homogeneous solution. While maintaining the solution at −78° C., into the solution, 4.37 mL (11.4 mmol) of solution of n-butyllithium (2.6 M) in hexane was dropped over 10 minutes. After the dropping, the resultant reaction mixture was stirred at −78° C. for 30 minutes and then, stirred at room temperature (25° C.) for 2 hours. Then, the flask was cooled to −78° C. and to the reaction mixture, 4.07 g (12.5 mmol) of tributyltin chloride was added. After the addition, the resultant reaction mixture was stirred at −78° C. for 30 minutes and next, stirred at room temperature (25° C.) for 3 hours. Then, to the reaction mixture, 200 mL of water was added to terminate the reaction and the reaction product was extracted with ethyl acetate. The organic phase that was an ethyl acetate solution was dried over sodium sulfate and was filtered and the resultant filtrate was concentrated by an evaporator to evaporate the solvent therefrom. The resultant oily substance was purified by a silica gel column (developing solution: hexane). As the silica gel in the silica gel column, a silica gel that was immersed in hexane containing 5% by weight of triethylamine for 5 minutes previsouly and then was rinsed with hexane, was used. After the purification, 3.52 g (3.34 mmol) of compound 25 was obtained.

Reference Example 13

Synthesis of Compound 26

[Chemical Formula 114]

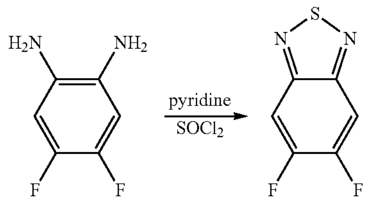

26

Into a 500 mL flask, 10.2 g (70.8 mmol) of 4,5-difluoro-1,2-diaminobenzene (manufactured by Tokyo Chemical Industry Co., Ltd.) and 150 mL of pyridine were charged to prepare a homogeneous solution. While maintaining the flask at 0° C., into the flask, 16.0 g (134 mmol) of thionyl chloride was dropped. After the dropping, the flask was warmed to 25° C. and the reaction was carried out for 6 hours. Then, 250 mL of water was added to the reaction mixture and the reaction product was extracted with chloroform. The organic phase that was a chloroform solution was dried over sodium sulfate and was filtered. The resultant filtrate was concentrated by an evaporator and the precipitated solid was purified by recrystallization. As the solvent for recrystallization, methanol was used. After the purification, 10.5 g (61.0 mmol) of compound 26 was obtained.

$^{1}H$ NMR ($CDCl_3$, ppm): 7.75 (t, 2H)

$^{19}F$ NMR ($CDCl_3$, ppm): −128.3 (s, 2F)

Reference Example 14

Synthesis of Compound 27

[Chemical Formula 115]

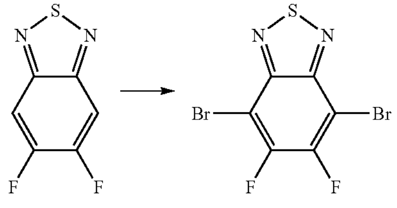

26 27

Into a 100 mL flask, 2.00 g (11.6 mmol) of the compound 26 and 0.20 g (3.58 mmol) of iron powder were charged and the flask was heated to 90° C. Into the flask, 31 g (194 mmol) of bromine was dropped over 1 hour. After the dropping, the resultant reaction mixture was stirred at 90° C. for 38 hours. Then, the flask was cooled to room temperature (25° C.) and the reaction mixture was diluted with 100 mL of chloroform. The resultant solution was added into 300 mL of a 5% by weight sodium sulfite aqueous solution and the resultant reaction mixture was stirred for 1 hour. The organic phase of the resultant mixed solution was separated by a separation funnel and the aqueous phase was extracted with chloroform three times. The resultant extract was combined with the above-separated organic phase and the combined organic phase was dried over sodium sulfate. The organic phase was filtered and the resultant filtrate was concentrated by an evaporator to evaporate the solvent therefrom. The resultant yellow solid was dissolved in 90 mL of methanol heated to 55° C. and then, the resultant solution was cooled to 25° C. A precipitated crystal was filtered to be recovered and then, the crystal was dried at room temperature (25° C.) under reduced pressure to obtain 1.50 g of compound 27.

$^{19}F$ NMR ($CDCl_3$, ppm): −118.9 (s, 2F)

Example 54

Synthesis of Polymer M

[Chemical Formula 116]

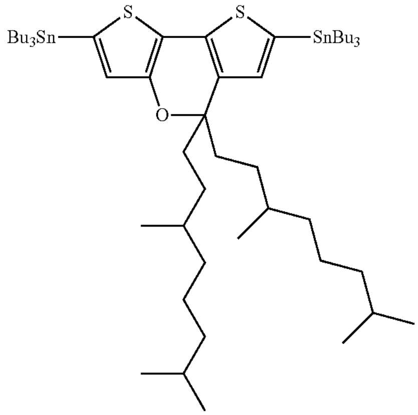

25

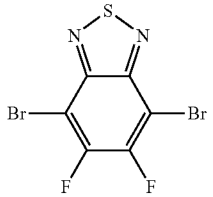

27

Into a 200 mL flask in which a gas in the flask was replaced by argon, 500 mg (0.475 mmol) of the compound 25, 141 mg (0.427 mmol) of the compound 27, and 32 mL of toluene were charged to prepare a homogeneous solution. The resultant toluene solution was bubbled with argon for 30 minutes. Then, to the toluene solution, 6.52 mg (0.007 mmol) of tris(dibenzylideneacetone) dipalladium and 13.0 mg of tris(2-tolyl)phosphine were added and the resultant reaction mixture was stirred at 100° C. for 6 hours. Then, to the resultant reaction solution, 500 mg of phenyl bromide was added and the reaction mixture was stirred further for 5 hours. Then, the flask was cooled to 25° C. and the reaction solution was added into 300 mL of methanol. A precipitated polymer was filtered to be recovered and the resultant polymer was added into a thimble to extract the polymer with methanol, acetone, and hexane using a Soxhlet extractor for 5 hours, respectively. The polymer remaining in the thimble was dissolved in 100 mL of toluene and to the resultant reaction solution, 2 g of sodium diethyldithiocarbamate and 40 mL of water were added and the resultant reaction mixture was stirred under reflux for 8 hours. The aqueous phase was removed and then the organic phase was washed with 50 mL of water twice, next with 50 mL of a 3% by weight acetic acid aqueous solution twice, next with 50 mL of water twice, next with 50 mL of a 5% potassium fluoride aqueous solution twice, and next with 50 mL of water twice, followed by pouring the resultant solution into methanol to precipitate polymer. The polymer was filtered and then dried and the resultant polymer was dissolved in 50 mL of o-dichlorobenzene again. The resultant solution was passed through an alumina/silica gel column. The resultant solution was added into methanol to precipitate polymer and the polymer was filtered and then dried to obtain 185 mg of purified polymer. Hereinafter, the polymer is called the polymer M. The molecular weight of the polymer M measured by GPC (in terms of polystyrene) corresponded to Mw=29,000 and Mn=14,000. The light absorbing terminal wavelength of the polymer M was 890 nm.

Example 55

(Production and Evaluation of Ink and Organic Thin Film Solar Cell)

A glass substrate on which an ITO film was formed by a sputtering method in a thickness of 150 nm was subjected to surface treatment by ozone UV treatment. Next, the polymer M and fullerene C60PCBM (phenyl C61-butyric acid methyl ester; manufactured by Frontier Carbon Corporation) were dissolved in o-dichlorobenzene so that the weight ratio of C60PCBM relative to the polymer M became 3 to produce an ink 2. In the ink 2, the total of the weight of the polymer M and the weight of C60PCBM was 2.0% by weight, relative to the weight of the ink 2. The ink 2 was applied on the substrate by spin-coating to prepare an organic film containing the polymer M. The organic film had a film thickness of about 100 nm. The light absorbing terminal wavelength of the organic film was measured and was 890 nm. Then, on the organic film, lithium fluoride was deposited by a vacuum deposition machine in a thickness of 2 nm and next thereon, Al was deposited in a thickness of 100 nm. The obtained organic thin film solar cell had a shape of a 2 mm×2 mm square. The obtained organic thin film solar cell was irradiated with a constant light using a solar simulator (manufactured by BUNKOUKEIKI Co., Ltd.; trade name: OTENTO-SUNII; AM 1.5G filter, irradiance: 100 mW/cm$^2$) and the generated current and voltage were measured to calculate the photoelectric conversion efficiency, the short-circuit current density, the open-circuit voltage, and the fill factor. $J_{sc}$ (short-circuit current density) was 12.2 mA/cm$^2$; Voc (open-circuit voltage) was 0.71 V; ff (fill factor) was 0.64; and photoelectric conversion efficiency (η) was 5.54%.

Example 56

(Production and Evaluation of Ink and Organic Thin Film Solar Cell)

In the same manner as in Example 54, except that fullerene C70PCBM ([6,6]-Phenyl C71 butyric acid methyl ester) was used instead of fullerene C60PCBM, the organic thin film solar cell was prepared and the photoelectric conversion efficiency, the short-circuit current density, the open-circuit voltage, and the fill factor were measured. The organic film had the light absorbing terminal wavelength of 890 nm, $J_{sc}$ (short-circuit current density) of 15.9 mA/cm$^2$, Voc (open-circuit voltage) of 0.72 V, ff (fill factor) of 0.59, and a photoelectric conversion efficiency (η) of 6.72%.

TABLE 3

Photovoltaic Cell Evaluation Result

| | | Short-Circuit Current Density (mA/cm$^2$) | Open-Circuit Voltage (V) | Fill Factor | Photoelectric Conversion Efficiency (%) | Light Absorbing Terminal Wave-length (nm) |
|---|---|---|---|---|---|---|
| Example 55 | Polymer M | 12.2 | 0.71 | 0.64 | 5.54 | 890 |
| Example 56 | Polymer M | 15.9 | 0.72 | 0.59 | 6.72 | 890 |

Example 57

Synthesis of Polymer N

[Chemical Formula 117]

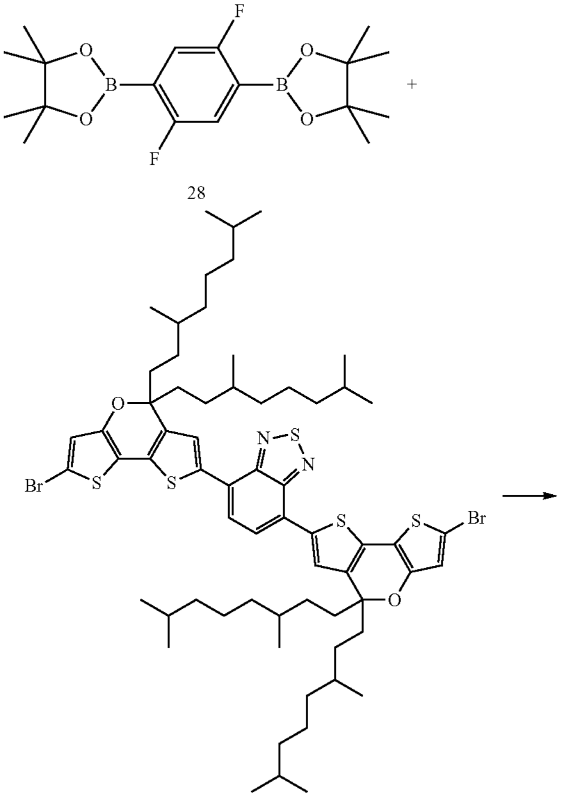

28

13

-continued

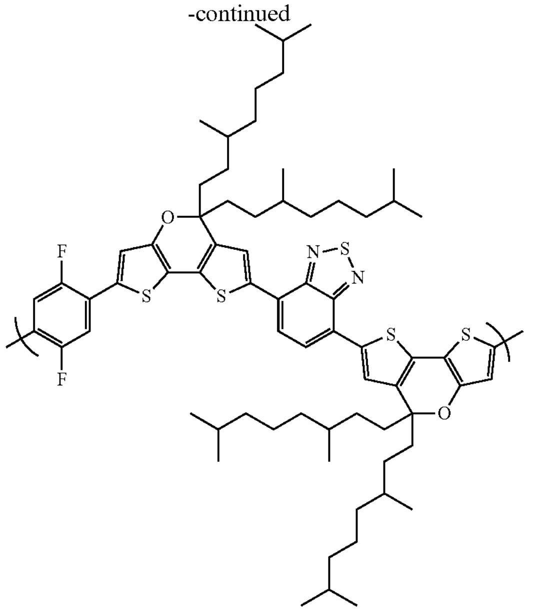

Polymer N

Into a four-neck flask, 102.5 mg (0.280 mmol) of compound 28 (manufactured by BoroPharm Inc.), 365.9 mg (0.295 mmol) of the compound 13, and 10 mL of tetrahydrofuran were charged and the resultant reaction mixture was subjected to argon bubbling at room temperature (25° C.) for 30 minutes. Then, to the reaction solution, 5.49 mg (0.006 mmol) of tris(dibenzylideneacetone) palladium and 6.96 mg (0.024 mmol) of [tri(tert-butyl)phosphonium] tetrafluoroborate were added. While stirring the resultant reaction solution at 80° C., into the reaction solution, 1.50 g (3.00 mmol) of a 27.6% by weight potassium carbonate aqueous solution was dropped over 30 minutes. After 15 minutes, to the reaction solution, 3.66 mg (0.03 mmol) of phenylboric acid was added and the reaction mixture was stirred further for 1 hour, followed by terminating the reaction. The reaction was carried out under an argon atmosphere.

Then, to the resultant reaction solution, 1 g of sodium diethyldithiocarbamate and 10 mL of pure water were added and the resultant reaction solution was stirred under reflux for 1 hour. The aqueous phase in the reaction solution was removed and then the organic phase was washed with 10 mL of water twice, with 10 mL of a 3% by weight acetic acid aqueous solution twice, and further with 10 mL of water twice, followed by pouring the resultant reaction solution into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 291 mg of polymer N.

For the molecular weight of the polymer N measured by GPC (in terms of polystyrene), the weight-average molecular weight (Mw) was 32,000 and the number average molecular weight (Mn) was 16,000. The light absorbing terminal wavelength of the polymer N was 798 nm.

Example 58

(Production and Evaluation of Ink and Organic Thin Film Solar Cell)

A glass substrate on which an ITO film was formed by a sputtering method in a thickness of 150 nm was subjected to surface treatment by ozone UV treatment. Next, the polymer N and fullerene C60PCBM (phenyl C61-butyric acid methyl ester; manufactured by Frontier Carbon Corporation) were dissolved in o-dichlorobenzene so that the weight ratio of C60PCBM relative to the weight of the polymer N became 3 to produce an ink 3. The total of the weight of the polymer N and the weight of C60PCBM was 2.0% by weight, relative to the weight of the ink 3. The ink 3 was applied on the glass substrate by spin-coating to prepare an organic film containing the polymer N. The film thickness thereof was about 100 nm. The thus prepared organic film had the light absorbing terminal wavelength of 750 nm. Then, on the organic film, lithium fluoride was deposited by a vacuum deposition machine in a thickness of 2 nm and next thereon, Al was deposited in a thickness of 100 nm to produce an organic thin film solar cell. The obtained organic thin film solar cell had a shape of a 2 mm×2 mm square. The obtained organic thin film solar cell was irradiated with a constant light using a solar simulator (manufactured by BUNKOUKEIKI Co., Ltd.; trade name: OTENTO-SUNII; AM 1.5G filter, irradiance: 100 mW/cm$^2$) and the generated current and voltage were measured to calculate the photoelectric conversion efficiency, the short-circuit current density, the open-circuit voltage, and the fill factor. $J_{sc}$ (short-circuit current density) was 9.63 mA/cm$^2$; Voc (open-circuit voltage) was 0.67 V; ff (fill factor) was 0.62; and photoelectric conversion efficiency (η) was 4.03%. The result is listed in Table 4.

Example 59

Synthesis of Polymer P

[Chemical Formula 118]

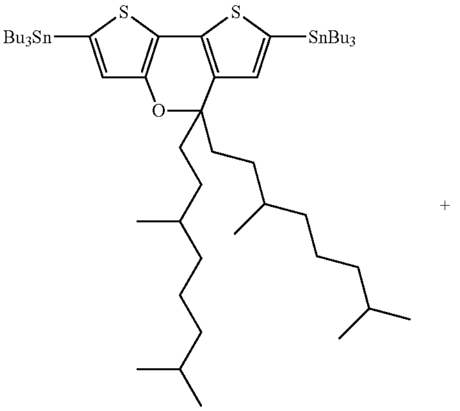

25

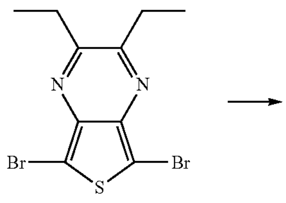

29

-continued

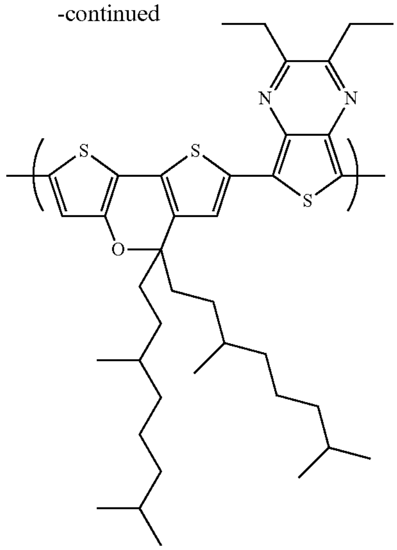

In the same manner as in Example 54, except that 149.5 mg (0.427 mmol) of compound 29 synthesized by a method described in U.S. Pat. No. 7,087,283 specification was used instead of the compound 27, 125 mg of polymer was synthesized. Hereinafter, the polymer is called polymer P. The molecular weight of the polymer P measured by GPC (in terms of polystyrene) corresponded to Mw=5,800 and Mn=4,500. The light absorbing terminal wavelength of the polymer P was 1,242 nm.

Example 60

Synthesis of Polymer Q

[Chemical Formula 119]

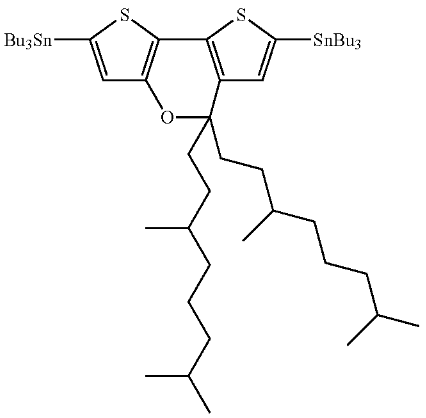

25

+

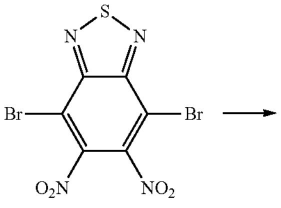

30

-continued

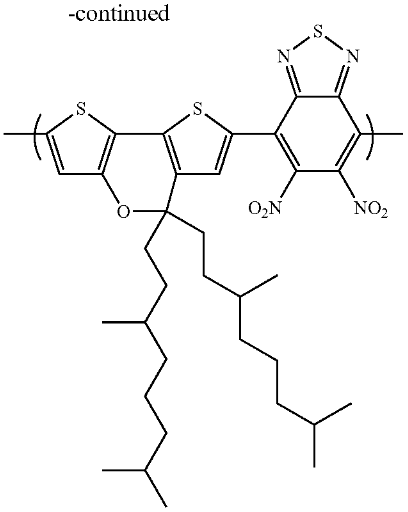

By performing the same operation as in Example 54, except that 164.0 mg (0.427 mmol) of compound 30 synthesized by a method described in "Macromolecular Rapid Communications, vol. 30, pp. 45-51 (2009)" was used instead of the compound 27, 110 mg of polymer was synthesized. Hereinafter, the polymer is called polymer Q. The molecular weight of the polymer Q measured by GPC (in terms of polystyrene) corresponded to Mw=22,000 and Mn=40,000. The light absorbing terminal wavelength of the polymer Q was 904 nm.

Reference Example 15

[Chemical Formula 120]

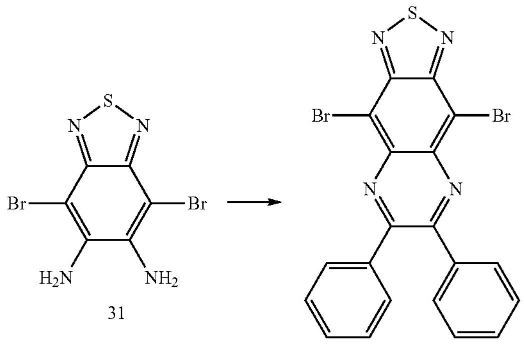

31 32

Into a 200 mL flask in which a gas in the flask was replaced by argon, 1,500 mg (1.54 mmol) of compound 3 produced by a method described in "Heterocycles, vol. 33, No. 1, pp. 337-348 (1992)", 325 mg (1.54 mmol) of benzyl, and 25 mL of acetic acid were charged and the flask was immersed in an oil bath heated to 120° C. to carry out the reaction for 2 hours. Then, the flask was cooled to room temperature (25° C.) and the reaction solution was added into 300 mL of methanol. The solid was filtered to be recovered, was washed with methanol, and was dried under vacuum to obtain 629 mg (1.26 mmol) of the objective compound 32.

Example 61

Synthesis of Polymer R

[Chemical Formula 121]

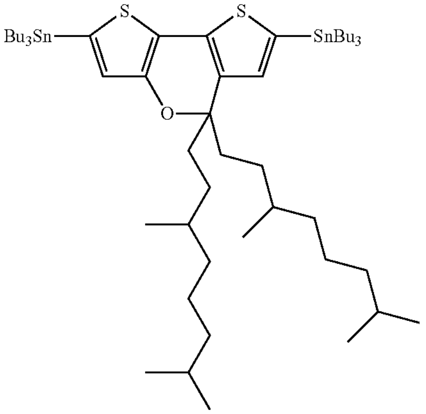

+

25

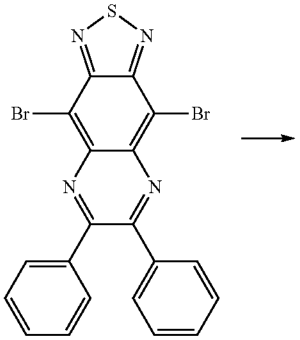

32

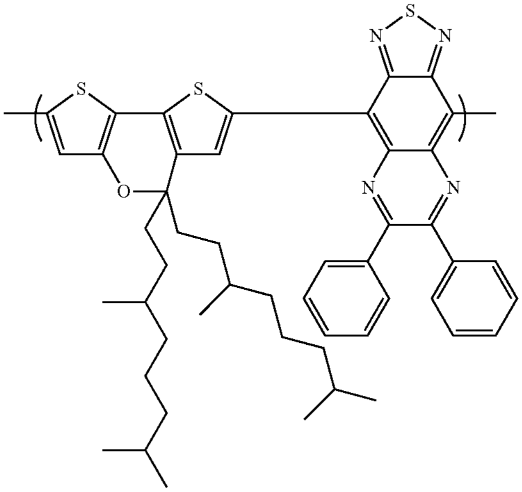

By performing the same operation as in Example 54, except that 212.7 mg (0.427 mmol) of the compound 32 was used instead of the compound 27, 132 mg of polymer was produced. Hereinafter, the polymer is called polymer R. The molecular weight of the polymer R measured by GPC (in terms of polystyrene) corresponded to Mw=11,400 and Mn=8,100. The light absorbing terminal wavelength of the polymer R was 1,898 nm.

Example 62

Synthesis of Polymer S

[Chemical Formula 122]

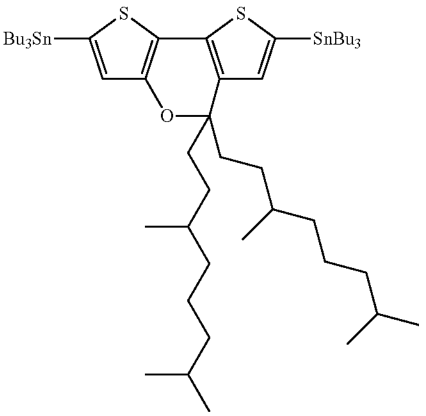

+

25

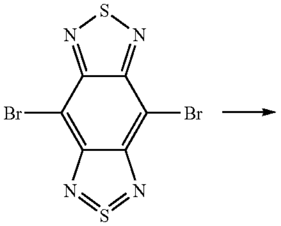

33

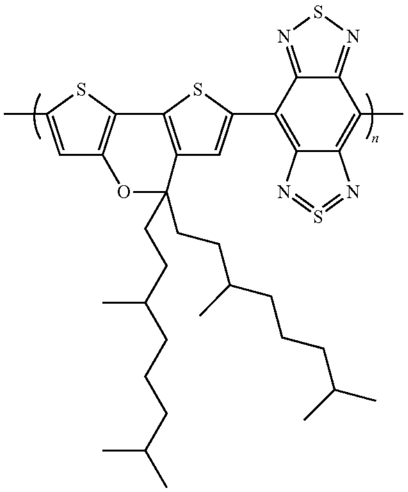

By performing the same operation as in Example 54, except that 150.3 mg (0.427 mmol) of compound 33 produced by a method described in "Tetrahedron, vol. 53, No. 29, pp. 10169-10178 (2009)" was used instead of the compound 27, 130 mg of polymer was produced. Hereinafter, the polymer is called polymer S. The molecular weight of the polymer S measured by GPC (in terms of polystyrene) corresponded to Mw=32,000 and Mn=17,000. The light absorbing terminal wavelength of the polymer S was 1,944 nm.

Example 63

Synthesis of Polymer T

[Chemical Formula 123]

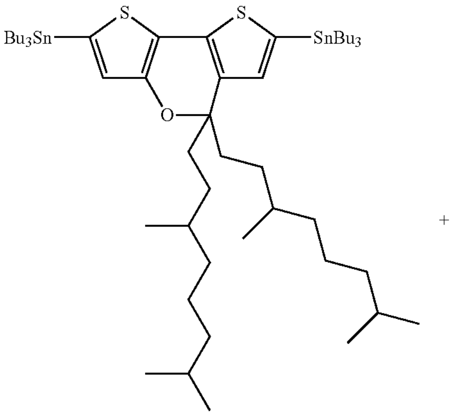

25

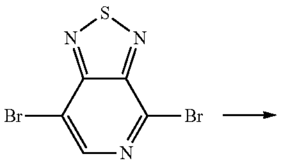

34

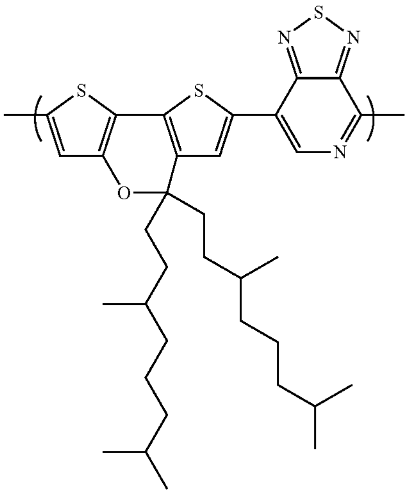

By performing the same operation as in Example 54, except that 125.9 mg (0.427 mmol) of compound 34 produced by a method described in "Journal of Polymer Science: Part A: Polymer Chemistry, vol. 46, pp. 2975-2982 (2008)" was used instead of the compound 27, 151 mg of polymer was produced. Hereinafter, the polymer is called polymer T. The molecular weight of the polymer T measured by GPC (in terms of polystyrene) corresponded to Mw=246,000 and Mn=23,500. The light absorbing terminal wavelength of the polymer T was 1,060 nm.

Example 64

Synthesis of Polymer U

[Chemical Formula 124]

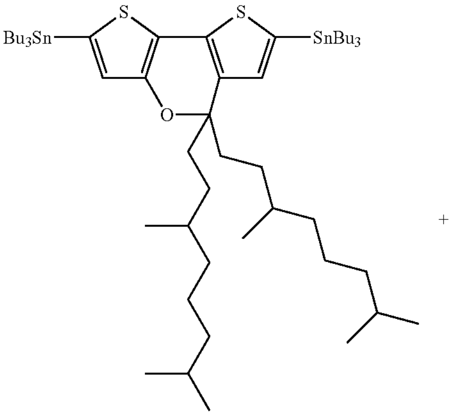

25

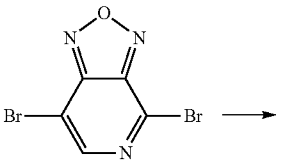

35

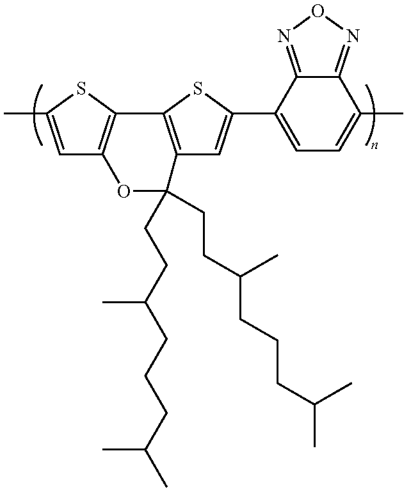

By performing the same operation as in Example 54, except that 125.9 mg (0.427 mmol) of compound 35 produced by a method described in "Journal of the American Chemical Society, vol. 130, pp. 732-742 (2008)" was used instead of the compound 27, 151 mg of polymer was produced. Hereinafter, the polymer is called polymer U. The molecular weight of the polymer U measured by GPC (in terms of polystyrene) corresponded to Mw=72,000 and Mn=17,200. The light absorbing terminal wavelength of the polymer U was 1,060 nm.

Example 65

(Production and Evaluation of Organic Thin Film Solar Cell)

In the same manner as in Example 58, except that the polymer T was used instead of the polymer N, the production and evaluation of the cell were carried out. The result is listed in Table 4.

Example 66

Production and Evaluation of Organic Thin Film Solar Cell

In the same manner as in Example 58, except that the polymer U was used instead of the polymer N, the production and evaluation of the cell were carried out. The result is listed in Table 4.

TABLE 4

Photovoltaic Cell Evaluation Result

| | | Short-Circuit Current Density (mA/cm$^2$) | Open-Circuit Voltage (V) | Fill Factor | Photoelectric Conversion Efficiency (%) |
|---|---|---|---|---|---|
| Example 58 | Polymer N | 9.63 | 0.67 | 0.62 | 4.03 |
| Example 65 | Polymer T | 10.8 | 0.58 | 0.44 | 2.80 |
| Example 66 | Polymer U | 2.85 | 0.63 | 0.59 | 1.05 |

Reference Example 16

Synthesis of Compound 36

[Chemical Formula 125]

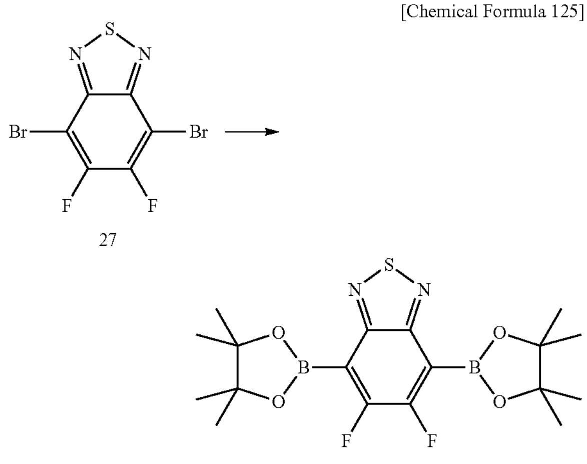

27

36

Into a four-neck flask, 12.30 g (37.28 mmol) of the compound 27, 23.67 g (93.20 mmol) of bis(pinacolato) diboron, 9.15 g (93.20 mmol) of potassium acetate, and 500 mL of dioxane were charged and the resultant reaction mixture was subjected to argon bubbling at room temperature (25° C.) for 30 minutes. To the resultant reaction solution, 1.52 g (1.86 mmol) of diphenylphosphinoferrocene palladium dichloride and 1.03 mg (1.86 mmol) of diphenylphosphinoferrocene were added and the resultant reaction mixture was refluxed with heating for 60 hours. After the reflux, the disappearance of the raw material was confirmed by liquid chromatography. The reaction solution was filtered with celite to separate insoluble contents and the filtrate was dried to remove the solvent to obtain a brown solid. To the obtained brown solid, 200 mL of hot hexane was added and the resultant mixture was filtered to dry the filtrate, followed by removing the solvent to obtain a crude crystal. Subsequently, the crude crystal was recrystallized in hexane. The recrystallization was performed twice to obtain 3.12 g of compound 36.

$^1$H-NMR ($CDCl_3$, δ (ppm)): 1.45 (s, 24H)

$^{19}$F-NMR ($CDCl_3$, δ (ppm)): −117 (s, 2F)

Example 67

Synthesis of Compound 37

[Chemical Formula 126]

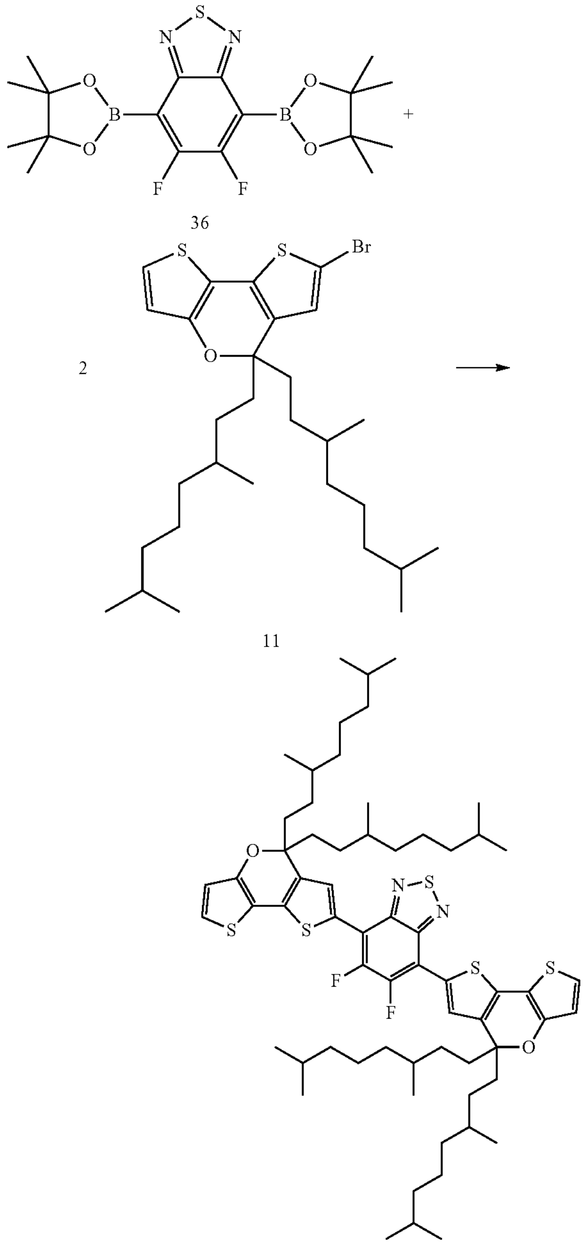

36

2

11

37

A four-neck flask was used. Thereinto, the compound 11 (1.352 g, 2.442 mmol) and tetrahydrofuran (25 mL) were charged and the resultant reaction mixture was subjected to argon bubbling at room temperature (25° C.) for 30 minutes. Then, to the resultant reaction solution, tris(dibenzylideneacetone) palladium (21.6 mg, 0.024 mmol), [tri(tert-butyl) phosphonium] tetrafluoroborate (27.4 mg, 0.094 mmol), and a potassium phosphate aqueous solution (2 mol/L, 5.90 g, 11.79 mmol) were added. While stirring the resultant reaction mixture at 80° C., into the reaction mixture, a solution in which the compound 36 (0.500 g, 1.179 mmol) was dissolved in tetrahydrofuran (10 mL) was dropped over 20 minutes. After 2 hours, the disappearance of the raw material was confirmed by liquid chromatography. Water was added to the system and the resultant reaction mixture was extracted with hexane, followed by subjecting the resultant extract to column-purification using hexane as a developing solution and then drying the purified extract to obtain 665 mg of compound 37.

$^{1}$H-NMR ($CDCl_3$, δ (ppm)): 0.82 (m, 36H), 1.08-1.47 (m, 40H), 1.95 (m, 8H), 6.71 (d, 2H), 7.07 (d, 2H), 7.92 (d, 2H)

$^{19}$F-NMR ($CDCl_3$, δ (ppm)): −125 (s, 2F)

Example 68

Synthesis of Compound 38

[Chemical Formula 127]

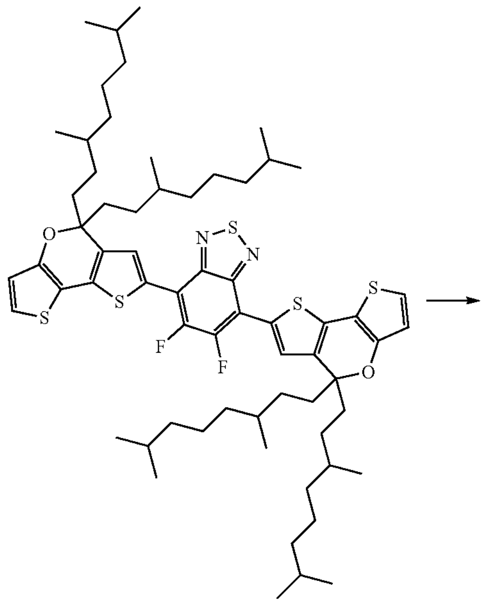

37

-continued

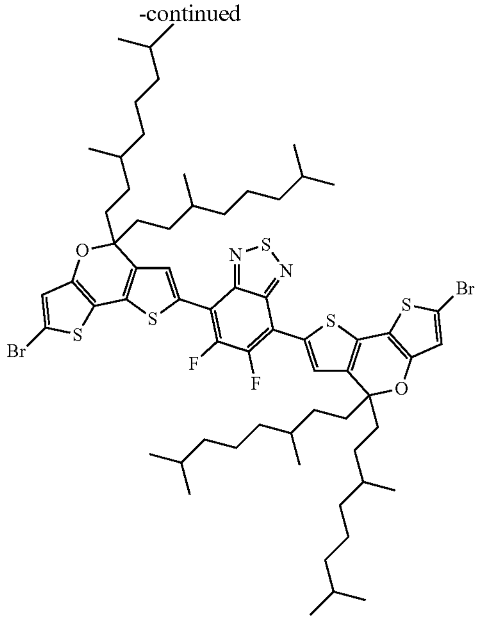

38

A four-neck flask was used. Thereinto, the compound 37 (657 mg, 0.588 mmol) and tetrahydrofuran (THF) (10 mL) were charged and the resultant reaction mixture was subjected to argon bubbling at room temperature (25° C.) for 30 minutes. The resultant reaction mixture was cooled to 0° C. and thereto, NBS (230 mg, 1.30 mmol) was added, followed by elevating the temperature of the reaction mixture to 40° C. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and a component obtained by the separation was dried to obtain 685 mg of compound 38.

$^{1}$H-NMR ($CDCl_3$, δ (ppm)): 0.82 (m, 36H), 1.08-1.47 (m, 40H), 1.95 (m, 8H), 6.73 (s, 2H), 7.90 (s, 2H)

$^{19}$F-NMR ($CDCl_3$, δ (ppm)): −129 (s, 2F)

Example 69

Synthesis of Compound 39

[Chemical Formula 128]

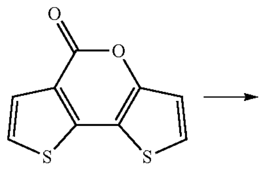

4

-continued

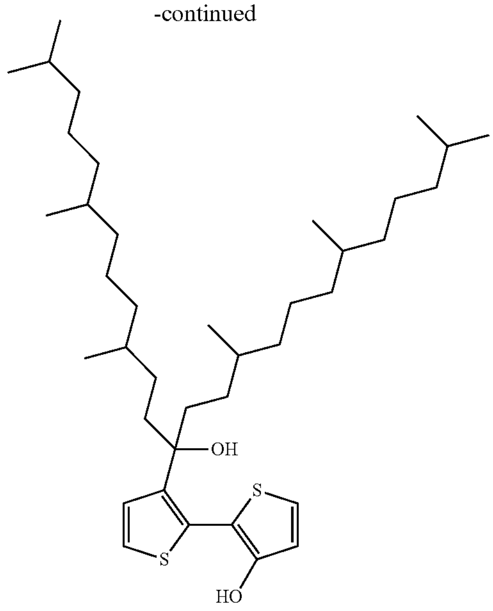

39

-continued

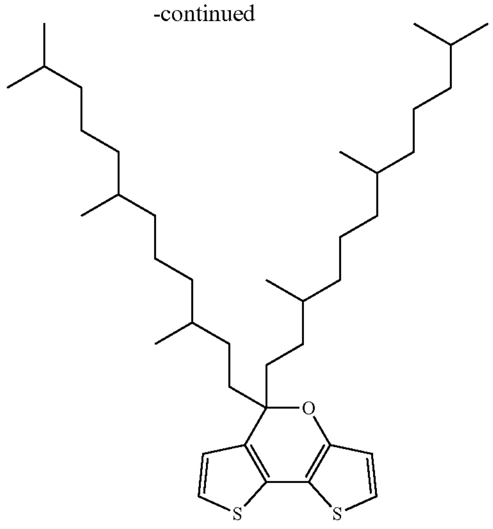

40

A four-neck flask was used. Thereinto, magnesium (3.50 g, 144.1 mmol), tetrahydrofuran (72 mL), and 3,7,11-trimethyldodecyl bromide (20.98 g, 72.03 mmol) were charged to prepare a Grignard reagent (1 mol/L). Into another four-neck flask, the compound 4 (5.00 g, 24.01 mmol) and tetrahydrofuran (200 mL) were added and the resultant reaction mixture was subjected to argon bubbling at room temperature (25° C.) for 30 minutes. The resultant reaction mixture was cooled to −40° C. and thereto, the above-prepared Grignard reagent was added. While elevating the temperature of the resultant reaction mixture to 0° C., the reaction mixture was stirred and after 3 hours, the disappearance of the raw material was confirmed.

Water was added to the system and the resultant reaction mixture was extracted with chloroform, followed by subjecting the resultant extract to column-purification using chloroform and then drying the purified extract to obtain a mixed oil containing compound 39.

Example 70

Synthesis of Compound 40

[Chemical Formula 129]

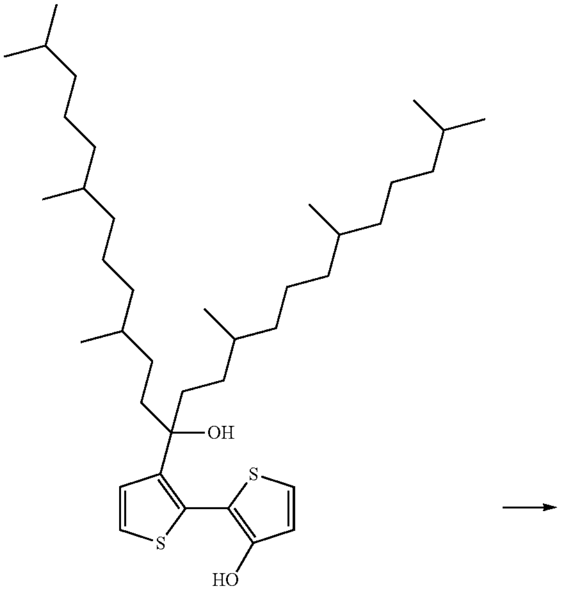

39

A four-neck flask was used. Thereinto, the whole amount of the mixed oil containing the compound 39 that was synthesized in Example 69 and toluene (100 mL) were charged and the resultant reaction mixture was subjected to argon bubbling at room temperature (25° C.) for 30 minutes. Next, to the resultant reaction mixture, p-toluenesulfonic acid monohydrate (500 mg) was added and then the temperature of the reaction mixture was elevated to 120° C., followed by stirring the reaction mixture to confirm the disappearance of the raw material after 1 hour. Water was added to the system and the resultant reaction mixture was extracted with ethyl acetate. The resultant extract was subjected to column-purification using hexane and then the purified extract was dried to obtain 15.6 g of compound 40.

$^1$H-NMR ($CDCl_3$, δ (ppm)): 0.80-0.88 (m, 24H), 0.97-1.62 (m, 34H), 1.87 (q, 4H), 6.67 (d, 1H), 6.69 (d, 1H), 6.96 (d, 1H), 7.03 (d, 1H)

Example 71

Synthesis of Compound 41

[Chemical Formula 130]

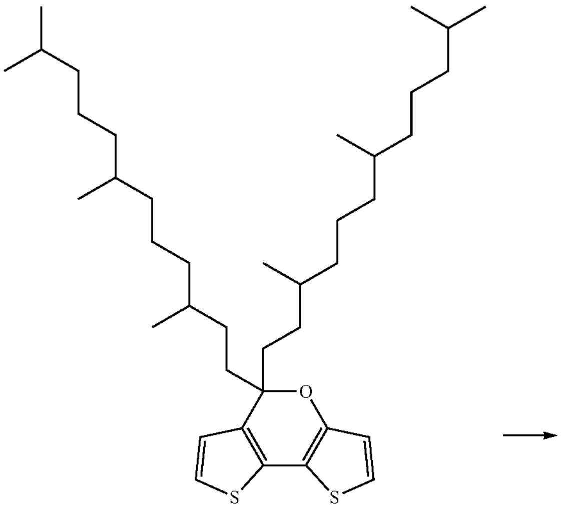

40

-continued

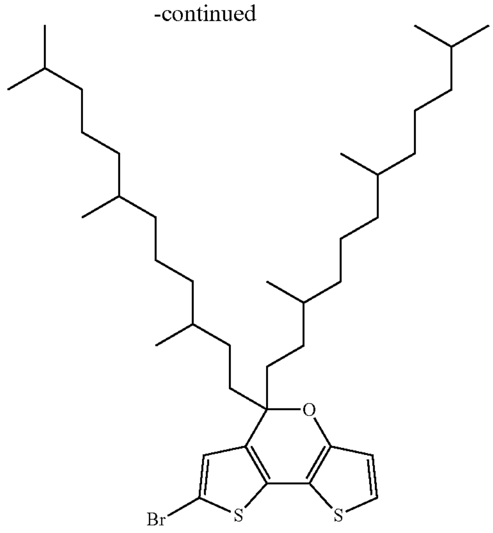

41

A four-neck flask was used. Thereinto, the compound 40 (7.995 g, 13.00 mmol) and tetrahydrofuran (160 mL) were charged and the resultant reaction mixture was subjected to argon bubbling at room temperature (25° C.) for 30 minutes. The reaction mixture was cooled to −30° C. and to the reaction mixture, N-bromosuccinimide (1.85 g, 10.4 mmol) was added. When the resultant reaction mixture was stirred at −10° C. for 2 hours, 90% of the raw material was disappeared. Accordingly, the reaction was terminated. Water was added to the system and the resultant reaction mixture was extracted with diethyl ether, followed by subjecting the resultant extract to column-purification using hexane. The purified extract was dried to obtain 7.47 g of compound 41.

$^{1}$H-NMR ($CDCl_3$, δ (ppm)): 0.82-0.88 (m, 24H), 0.95-1.60 (m, 34H), 1.82 (q, 4H), 6.64 (s, 1H), 6.65 (s, 1H), 6.98 (d, 1H)

Example 72

Synthesis of Compound 42

[Chemical Formula 131]

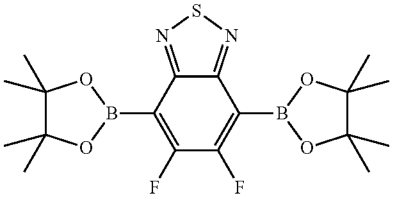

36

+

-continued

2

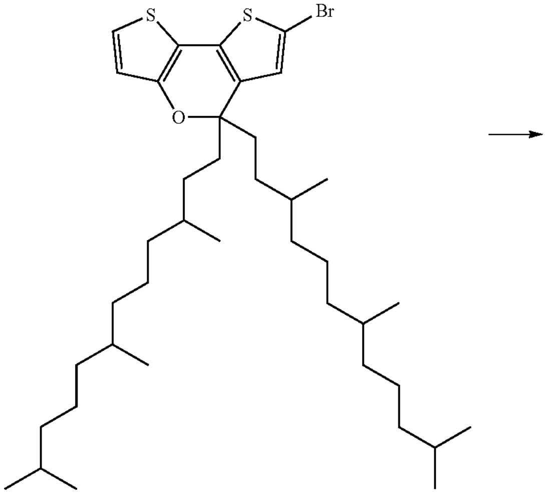

41

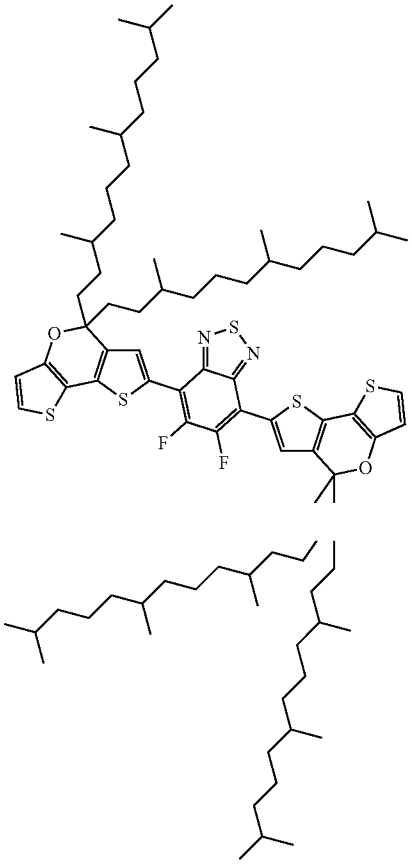

42

A four-neck flask was used. Thereinto, the compound 41 (1.729 g, 2.491 mmol) and methylene chloride (25 mL) were charged and the resultant reaction mixture was subjected to argon bubbling at room temperature (25° C.) for 30 minutes. Then, to the resultant reaction solution, tris(dibenzylideneacetone) palladium (21.6 mg, 0.024 mmol), [tri(tert-butyl)

phosphonium] tetrafluoroborate (27.4 mg, 0.094 mmol), and a potassium phosphate aqueous solution (2 mol/L, 5.90 g, 11.79 mmol) were added. While stirring the resultant reaction mixture at 45° C., into the reaction mixture, a solution in which the compound 36 (0.500 g, 1.179 mmol) was dissolved in methylene chloride (20 mL) was dropped over 20 minutes. After 2 hours, the disappearance of the raw material was confirmed by liquid chromatography. Water was added to the system and the resultant reaction mixture was extracted with hexane, followed by subjecting the resultant extract to column-purification using hexane as a developing solution and then drying the purified extract to obtain 1.21 g of compound 42.

$^{1}$H-NMR ($CDCl_3$, δ (ppm)): 0.70-0.95 (m, 48H), 0.96-1.60 (m, 68H), 1.97 (m, 8H), 6.72 (d, 2H), 7.08 (d, 2H), 7.93 (d, 2H)

$^{19}$F-NMR ($CDCl_3$, δ (ppm)): −125. (s, 2F)

Example 73

Synthesis of Compound 43

[Chemical Formula 132]

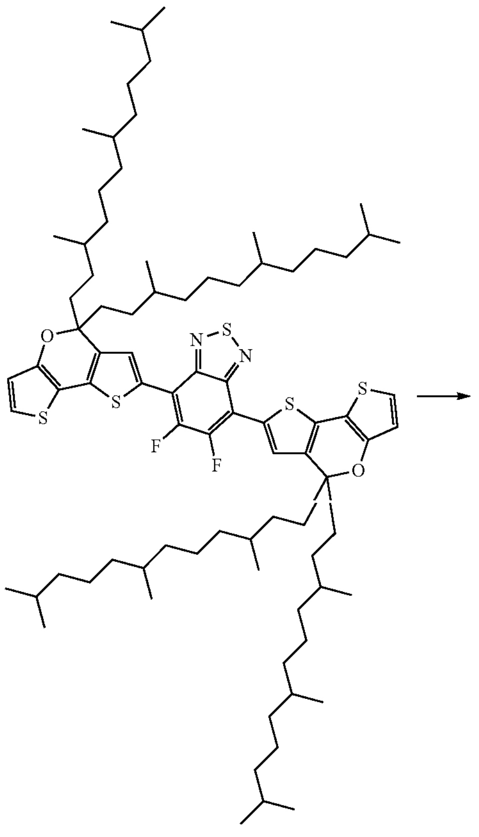

42

-continued

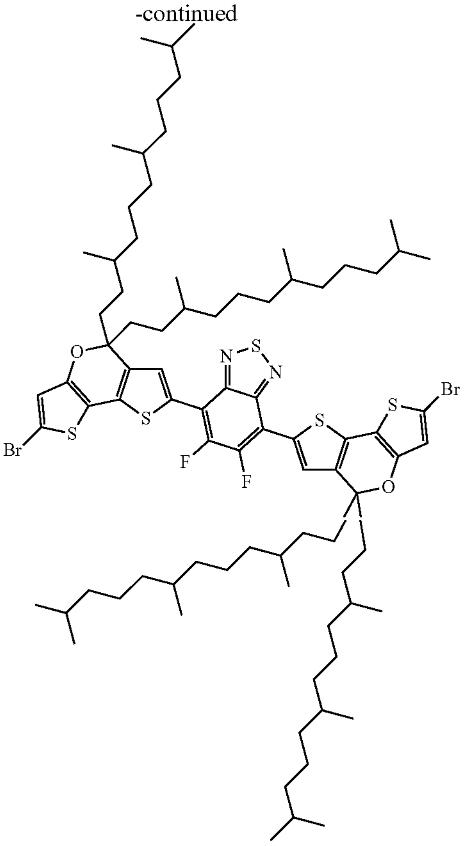

43

A four-neck flask was used. Thereinto, the compound 42 (1.214 g, 0.868 mmol) and tetrahydrofuran (THF) (40 mL) were charged and the resultant reaction mixture was subjected to argon bubbling at room temperature (25° C.) for 30 minutes. The resultant reaction mixture was cooled to 0° C. and thereto, NBS (340 mg, 1.91 mmol) was added, followed by elevating the temperature of the reaction mixture to 40° C. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 1.23 g of compound 43.

$^{1}$H-NMR ($CDCl_3$, δ (ppm)): 0.65-0.96 (m, 48H), 0.98-1.62 (m, 68H), 1.95 (m, 8H), 6.73 (s, 2H), 7.90 (s, 2H)

$^{19}$F-NMR ($CDCl_3$, δ (ppm)): −129 (s, 2F)

Example 74

Synthesis of Compound 44

[Chemical Formula 133]

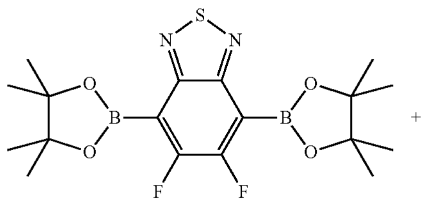

36

-continued

2

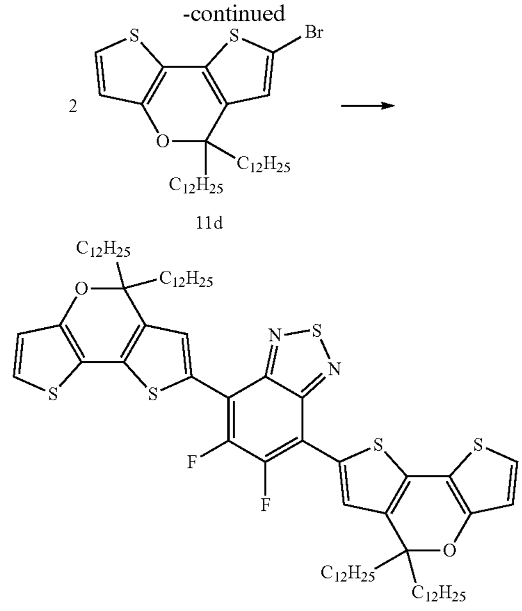

11d

44

A four-neck flask was used. Thereinto, the compound 11d (3.388 g, 5.556 mmol) and methylene chloride (50 mL) were charged and the resultant reaction mixture was subjected to argon bubbling at room temperature (25° C.) for 30 minutes. Then, to the resultant reaction solution, tris(dibenzylideneacetone) palladium (86.4 mg, 0.094 mmol), [tri(tert-butyl) phosphonium] tetrafluoroborate (109.5 mg, 0.377 mmol), and a potassium phosphate aqueous solution (2 mol/L, 11.79 g, 23.58 mmol) were added. While stirring the resultant reaction mixture at 45° C., into the reaction mixture, a solution in which the compound 36 (1.000 g, 2.358 mmol) was dissolved in methylene chloride (50 mL) was dropped over 20 minutes. After 2 hours, the disappearance of the raw material was confirmed by liquid chromatography. Water was added to the system and the resultant reaction mixture was extracted with hexane, followed by subjecting the resultant extract to column-purification using hexane as a developing solution and then drying the purified extract to obtain 1.88 g of compound 44.

$^{1}$H-NMR ($CDCl_3$, δ (ppm)): 0.86 (t, 12H), 0.95-1.50 (m, 80H), 1.97 (m, 8H), 6.71 (d, 2H), 7.07 (d, 2H), 7.92 (d, 2H)

$^{19}$F-NMR ($CDCl_3$, δ (ppm)): −125 (s, 2F)

Example 75

Synthesis of Compound 45

[Chemical Formula 134]

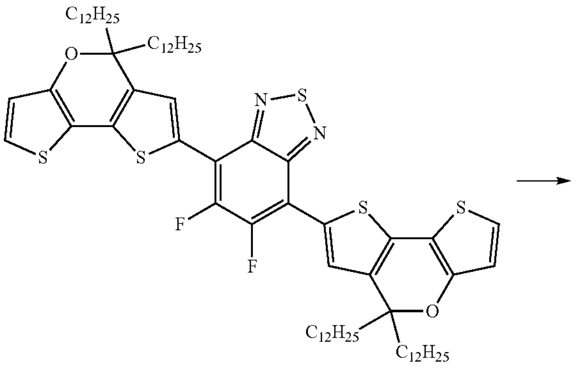

44

-continued

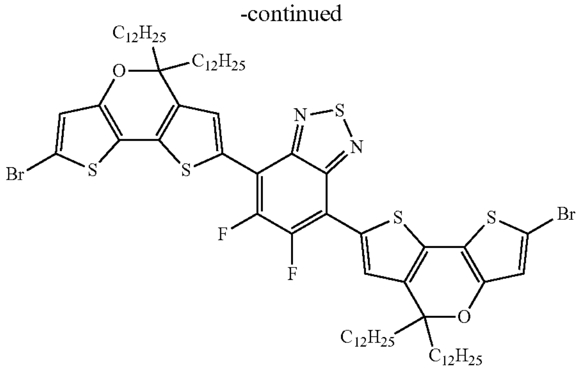

45

A four-neck flask was used. Thereinto, the compound 44 (1.884 g, 1.532 mmol) and tetrahydrofuran (THF) (60 mL) were charged and the resultant reaction mixture was subjected to argon bubbling at room temperature (25° C.) for 30 minutes. The resultant reaction mixture was cooled to 0° C. and thereto, NBS (600 mg, 3.37 mmol) was added, followed by elevating the temperature of the reaction mixture to 40° C. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 1.88 g of compound 45.

$^{1}$H-NMR ($CDCl_3$, δ (ppm)): 0.86 (t, 12H), 1.18-1.50 (m, 80H), 1.95 (m, 8H), 6.72 (s, 2H), 7.90 (s, 2H)

$^{19}$F-NMR ($CDCl_3$, δ (ppm)): −129 (s, 2F)

Example 76

Synthesis of Compound 46

[Chemical Formula 135]

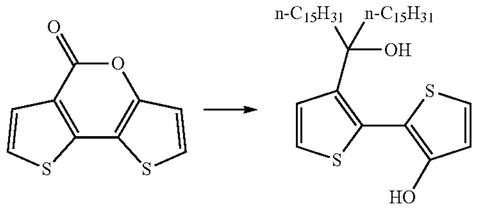

4 46

A four-neck flask was used. Thereinto, the compound 4 (6.00 g, 28.81 mmol) and tetrahydrofuran (240 mL) were charged and the resultant reaction mixture was subjected to argon bubbling at room temperature (25° C.) for 30 minutes. The resultant reaction mixture was cooled to −40° C. and thereto, n-pentadecylmagnesium bromide (0.5 mol/L tetrahydrofuran solution, 173 mL) was added. While elevating the temperature of the resultant reaction mixture to 0° C., the reaction mixture was stirred and after 3 hours, the disappearance of the raw material was confirmed.

Water was added to the system and the resultant reaction mixture was extracted with chloroform, followed by subjecting the resultant extract to column-purification using chloroform and then drying the purified extract to obtain a mixed oil containing compound 46.

Example 77

Synthesis of Compound 47

[Chemical Formula 136]

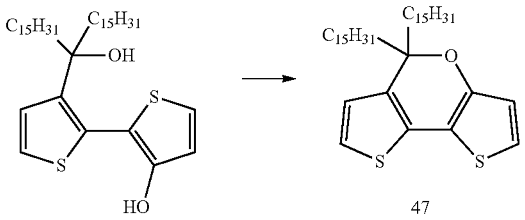

46

47

A four-neck flask was used. Thereinto, the whole amount of the mixed oil containing the compound 46 that was synthesized in Example 76 and toluene (120 mL) were charged and the resultant reaction mixture was subjected to argon bubbling at room temperature (25° C.) for 30 minutes. Next, to the resultant reaction mixture, p-toluenesulfonic acid monohydrate (600 mg) was added and then the temperature of the resultant reaction mixture was elevated to 120° C., followed by stirring the resultant reaction mixture. After 1 hour, the disappearance of the raw material was confirmed. Water was added to the system and the resultant reaction mixture was extracted with ethyl acetate. The resultant extract was subjected to column-purification using hexane and the purified extract was then dried to obtain 18.4 g of compound 47.

$^1$H-NMR ($CDCl_3$, δ (ppm)): 0.82 (t, 6H), 1.21 (m, 48H), 1.43 (m, 4H), 1.96 (t, 4H), 6.67 (d, 1H), 6.69 (d, 1H), 6.96 (d, 1H), 7.03 (d, 1H)

Example 78

Synthesis of Compound 48

[Chemical Formula 137]

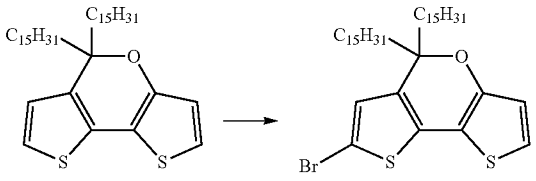

47

48

A four-neck flask was used. Thereinto, the compound 47 (23.2 g, 37.8 mmol) and tetrahydrofuran (340 mL) were charged and the resultant reaction mixture was subjected to argon bubbling at room temperature (25° C.) for 30 minutes. The resultant reaction mixture was cooled to −30° C. and thereto, N-bromosuccinimide (6.05 g, 34.0 mmol) was added. By stirring the resultant reaction mixture at −10° C. for 2 hours, 90% of the raw material was disappeared. Accordingly, the reaction was terminated. Water was added to the system and the resultant reaction mixture was extracted with diethyl ether, followed by subjecting the resultant extract to column-purification using, hexane and drying the purified extract to obtain 23.3 g of compound 48.

$^1$H-NMR ($CDCl_3$, δ (ppm)): 0.83 (t, 6H), 1.23 (m, 48H), 1.44 (m, 4H), 1.98 (t, 4H), 6.65 (d, 1H), 6.66 (s, 1H), 6.98 (s, 1H)

Example 79

Synthesis of Compound 49

[Chemical Formula 138]

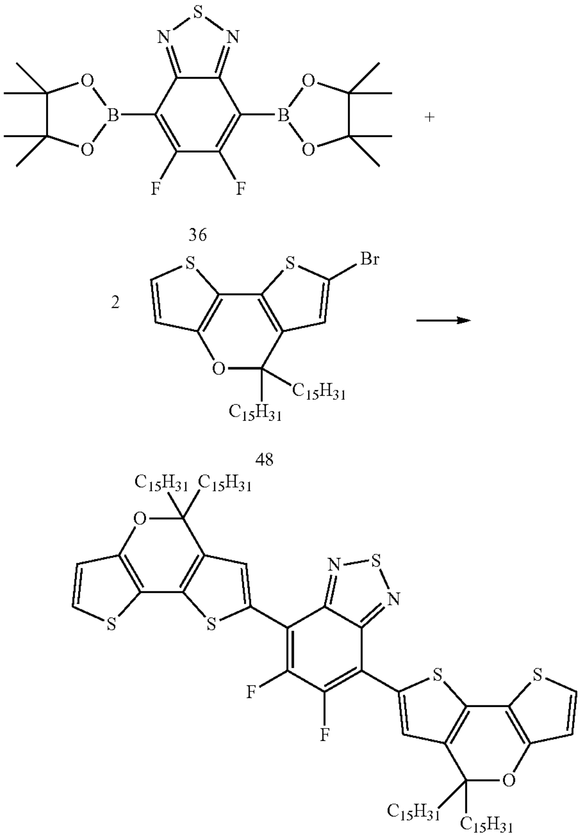

36

2

48

49

A four-neck flask was used. Thereinto, the compound 48 (1.695 g, 2.442 mmol) and methylene chloride (50 mL) were charged and the resultant reaction mixture was subjected to argon bubbling at room temperature (25° C.) for 30 minutes. Then, to the resultant reaction solution, tris(dibenzylideneacetone) palladium (21.6 mg, 0.024 mmol), [tri(tert-butyl) phosphonium] tetrafluoroborate (27.4 mg, 0.094 mmol), and a potassium phosphate aqueous solution (2 mol/L, 5.90 g, 11.79 mmol) were added. While stirring the resultant reaction mixture at 45° C., into the reaction mixture, a solution in which the compound 36 (0.500 g, 1.179 mmol) was dissolved in methylene chloride (10 mL) was dropped over 20 minutes. After 2 hours, the disappearance of the raw material was confirmed by liquid chromatography. Water was added to the system and the resultant reaction mixture was extracted with hexane, followed by subjecting the resultant extract to column-purification using hexane as a developing solution and then drying the purified extract to obtain 1.00 g of compound 49.

$^1$H-NMR ($CDCl_3$, δ (ppm)): 0.87 (t, 12H), 0.90-1.46 (m, 104H), 1.97 (m, 8H), 6.71 (d, 2H), 7.07 (d, 2H), 7.93 (s, 2H)

$^{19}$F-NMR ($CDCl_3$, δ (ppm)): −125 (s, 2F)

Example 80

Synthesis of Compound 50

[Chemical Formula 139]

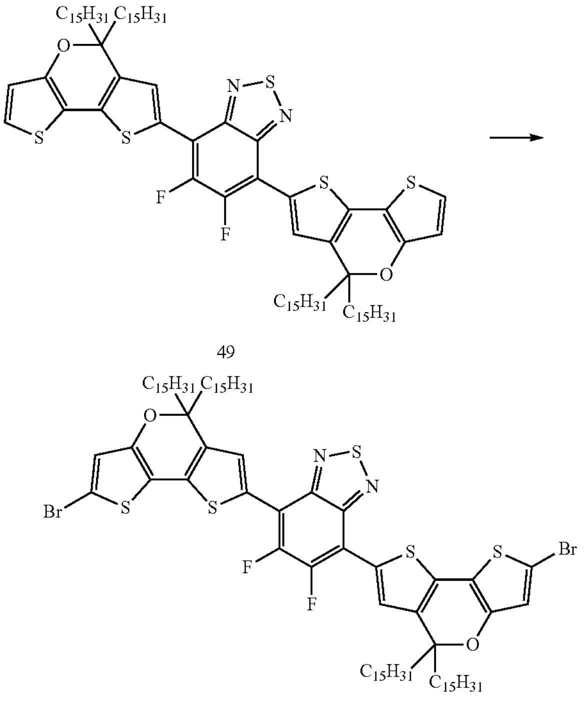

49

50

A four-neck flask was used. Thereinto, the compound 49 (1.001 g, 0.716 mmol) and tetrahydrofuran (THF) (30 mL) were charged and the resultant reaction mixture was subjected to argon bubbling at room temperature (25° C.) for 30 minutes. The resultant reaction mixture was cooled to 0° C. and thereto, NBS (280 mg, 1.573 mmol) was added, followed by elevating the temperature of the resultant reaction mixture to 40° C. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 1.04 g of compound 50.

$^1$H-NMR ($CDCl_3$, δ (ppm)): 0.87 (t, 12H), 0.95-1.50 (m, 104H), 1.95 (m, 8H), 6.72 (s, 2H), 7.90 (s, 2H)

$^{19}$F-NMR ($CDCl_3$, δ (ppm)): −129 (s, 2F)

Example 81

Synthesis of Compound 51

[Chemical Formula 140]

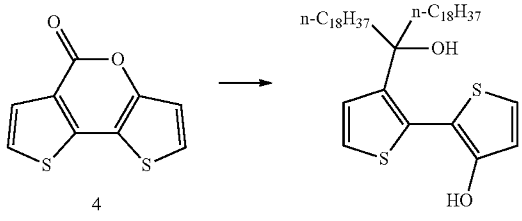

4

51

A four-neck flask was used. Thereinto, magnesium (3.50 g, 144.1 mmol), tetrahydrofuran (72 mL), and n-octadecyl bromide (24.01 g, 72.03 mmol) were charged to prepare a Grignard reagent (1 mol/L). Into another four-neck flask, the compound 4 (5.00 g, 24.01 mmol) and tetrahydrofuran (200 mL) were added and the resultant reaction mixture was subjected to argon bubbling at room temperature (25° C.) for 30 minutes. The resultant reaction mixture was cooled to −40° C. and thereto, the above-prepared Grignard reagent was added. While elevating the temperature of the reaction mixture to 0° C., the reaction mixture was stirred and after 3 hours, the disappearance of the raw material was confirmed.

Water was added to the system and the resultant reaction mixture was extracted with chloroform, followed by subjecting the resultant extract to column-purification using chloroform and then drying the purified extract to obtain a mixed oil containing compound 51.

Example 82

Synthesis of Compound 52

[Chemical Formula 141]

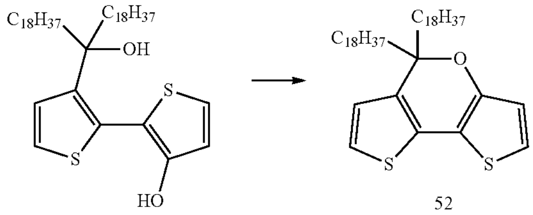

51

52

A four-neck flask was used. Thereinto, the whole amount of the mixed oil containing the compound 51 that was synthesized in Example 81 and toluene (200 mL) were charged and the resultant reaction mixture was subjected to argon bubbling at room temperature (25° C.) for 30 minutes. Next, to the resultant reaction mixture, p-toluenesulfonic acid monohydrate (1,000 mg) was added and then the temperature of the reaction mixture was elevated to 120° C., followed by stirring the reaction mixture to confirm the disappearance of the raw material after 1 hour. Water was added to the system and the resultant reaction mixture was extracted with ethyl acetate. The resultant extract was subjected to column-purification using hexane and the purified extract was then dried to obtain 23.1 g of compound 52.

$^1$H-NMR ($CDCl_3$, δ (ppm)): 0.81 (t, 6H), 1.21 (m, 60H), 1.43 (m, 4H), 1.96 (t, 4H), 6.67 (d, 1H), 6.69 (d, 1H), 6.96 (d, 1H), 7.03 (d, 1H)

Example 83

Synthesis of Compound 53

[Chemical Formula 142]

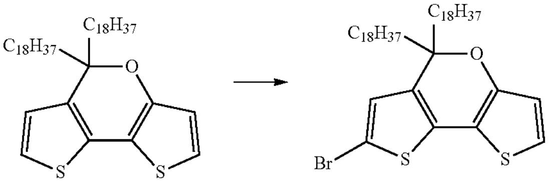

52 53

A four-neck flask was used. Thereinto, the compound 52 (1.500 g, 2.145 mmol) and tetrahydrofuran (150 mL) were charged and the resultant reaction mixture was subjected to argon bubbling at room temperature (25° C.) for 30 minutes. The resultant reaction mixture was cooled to −30° C. and thereto, N-bromosuccinimide (343.3 mg, 1.931 mmol) was added. By stirring the resultant reaction mixture at −10° C. for 2 hours, 90% of the raw material was disappeared. Accordingly, the reaction was terminated. Water was added to the system and the resultant reaction mixture was extracted with diethyl ether, followed by subjecting the resultant extract to column-purification using hexane and drying the purified extract to obtain 1.657 g of compound 53.

$^1$H-NMR ($CDCl_3$, δ (ppm)): 0.83 (t, 6H), 1.21 (m, 60H), 1.43 (m, 4H), 1.97 (t, 4H), 6.65 (d, 1H), 6.66 (s, 1H), 6.97 (s, 1H)

Example 84

Synthesis of Compound 54

[Chemical Formula 143]

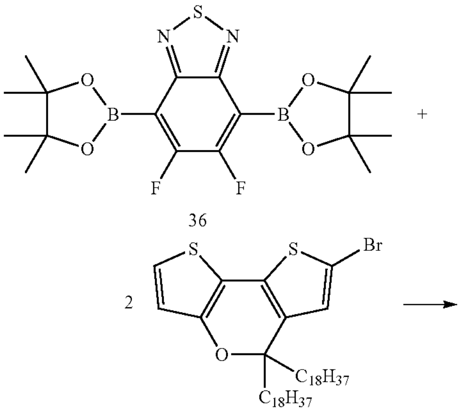

36

2

53

-continued

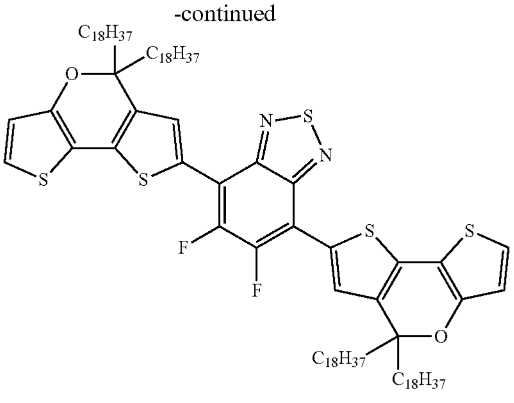

54

A four-neck flask was used. Thereinto, the compound 53 (1.657 g, 2.129 mmol) and methylene chloride (22 mL) were charged and the resultant reaction mixture was subjected to argon bubbling at room temperature (25° C.) for 30 minutes. Then, to the resultant reaction solution, tris(dibenzylideneacetone) palladium (38.8 mg, 0.042 mmol), [tri(tert-butyl) phosphonium] tetrafluoroborate (49.2 mg, 0.170 mmol), and a potassium phosphate aqueous solution (2 mol/L, 5.30 g, 10.60 mmol) were added. While stirring the resultant reaction mixture at 45° C., into the reaction mixture, a solution in which the compound 36 (0.450 g, 1.061 mmol) was dissolved in methylene chloride (20 mL) was dropped over 20 minutes. After 2 hours, the disappearance of the raw material was confirmed by liquid chromatography. Water was added to the system and the resultant reaction mixture was extracted with hexane, followed by subjecting the resultant extract to column-purification using hexane as a developing solution and then drying the purified extract to obtain 1.657 g of compound 54.

$^1$H-NMR ($CDCl_3$, δ (ppm)): 0.88 (t, 12H), 0.95-1.53 (m, 128H), 1.97 (m, 8H), 6.71 (d, 2H), 7.08 (d, 2H), 7.93 (d, 2H)

$^{19}$F-NMR ($CDCl_3$, δ (ppm)): −125 (s, 2F)

Example 85

Synthesis of Compound 55

[Chemical Formula 144]

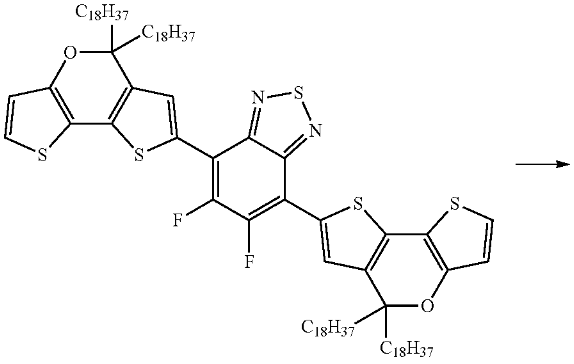

54

-continued

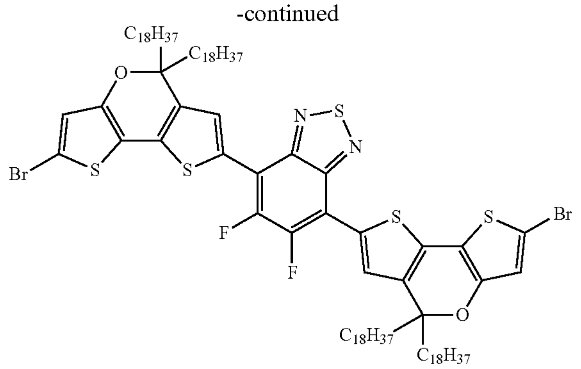

55

A four-neck flask was used. Thereinto, the compound 54 (1.166 g, 0.744 mmol) and tetrahydrofuran (THF) (120 mL) were charged and the resultant reaction mixture was subjected to argon bubbling at room temperature (25° C.) for 30 minutes. The resultant reaction mixture was cooled to 0° C. and thereto, NBS (291 mg, 1.64 mmol) was added, followed by elevating the temperature of the resultant reaction mixture to 40° C. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 1.18 g of compound 55.

$^{1}$H-NMR ($CDCl_3$, δ (ppm)): 0.87 (t, 12H), 0.95-1.50 (m, 128H), 1.95 (m, 8H), 6.72 (s, 2H), 7.90 (s, 2H)

$^{19}$F-NMR ($CDCl_3$, δ (ppm)): −129 (s, 2F)

Example 86

Synthesis of Compound 56

[Chemical Formula 145]

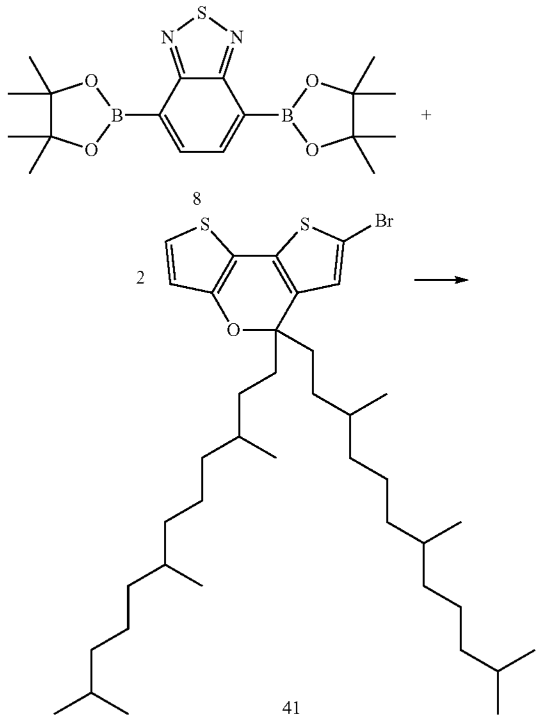

8

2

41

-continued

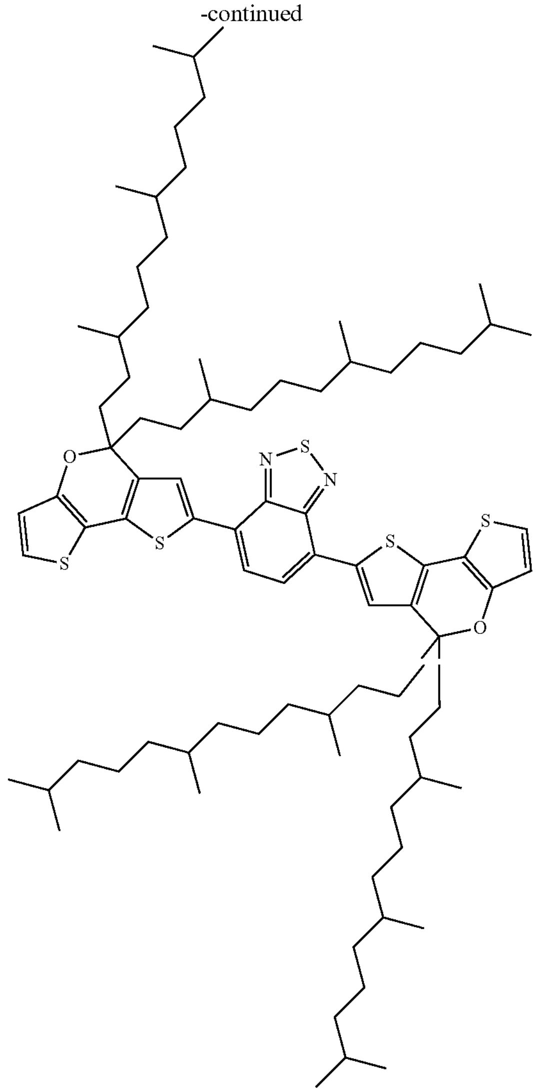

56

A four-neck flask was used. Thereinto, the compound 8 (1.501 g, 3.868 mmol), the compound 41 (6.045 g, 8.710 mmol), and tetrahydrofuran (150 mL) were charged and the resultant reaction mixture was subjected to argon bubbling at room temperature (25° C.) for 30 minutes. Then, to the resultant reaction solution, tris(dibenzylideneacetone) palladium (70.8 mg, 0.0773 mmol) and [tri(tert-butyl)phosphonium] tetrafluoroborate (89.7 mg, 0.309 mmol) were added. While stirring the resultant reaction solution at 45° C., into the reaction solution, a potassium phosphate aqueous solution (2 mol/L, 19.36 g, 38.65 mmol) was dropped over 10 minutes. After 2 hours, the disappearance of the raw material was confirmed by liquid chromatography. Water was added to the system and the resultant reaction mixture was extracted with hexane into an organic phase, followed by purifying the organic phase by a column using hexane as a developing solution and then drying the organic phase to obtain 5.432 g of compound 56.

$^{1}$H-NMR ($CDCl_3$, δ (ppm)): 0.70-0.86 (m, 48H), 0.90-1.60 (m, 68H), 1.97 (m, 8H), 6.71 (d, 2H), 7.04 (d, 2H), 7.77 (d, 2H), 7.80 (d, 2H)

Example 87

Synthesis of Compound 57

[Chemical Formula 146]

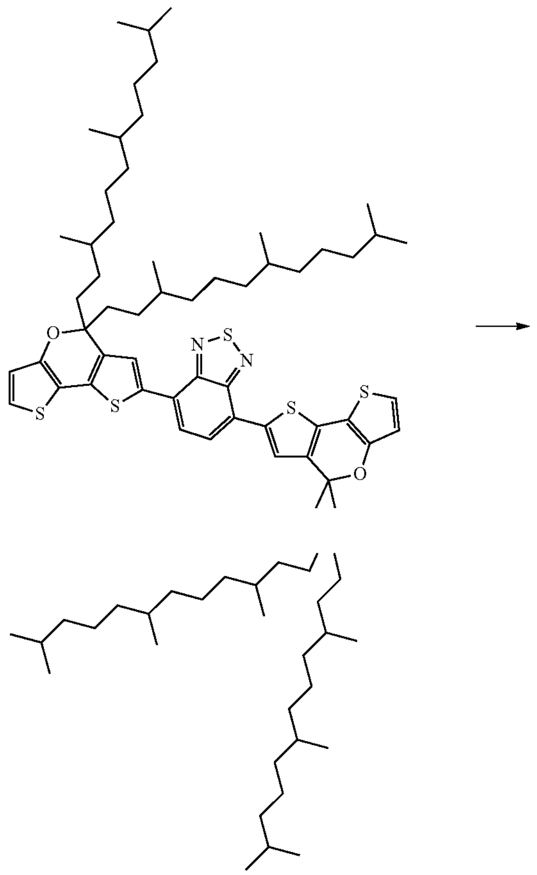

56

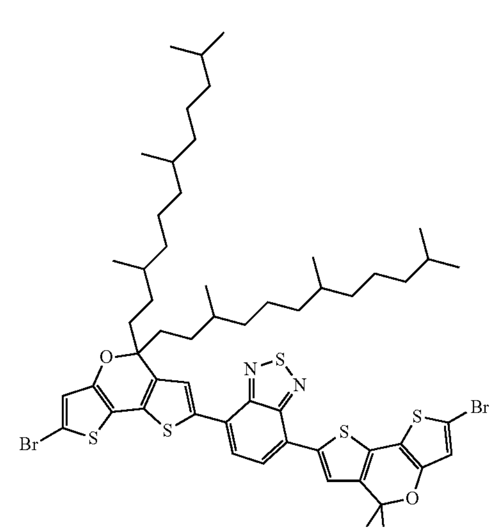

-continued

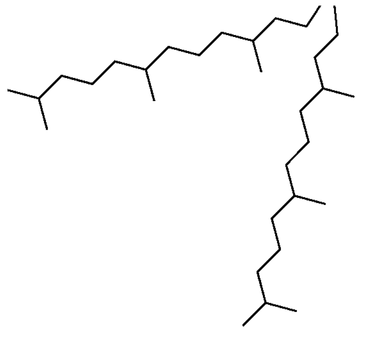

57

A four-neck flask was used. Thereinto, the compound 56 (5.265 g, 3.865 mmol) and tetrahydrofuran (THF) (100 mL) were charged and the resultant reaction mixture was subjected to argon bubbling at room temperature (25° C.) for 30 minutes. The resultant reaction solution was cooled to −30° C. and thereto, NBS (1.513 g, 8.501 mmol) was added, followed by elevating the temperature of the resultant reaction mixture to −10° C. over 30 minutes. After 1 hour, the disappearance of the raw material was confirmed by liquid chromatography. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 4.24 g of compound 57.

$^1$H-NMR ($CDCl_3$, δ (ppm)): 0.77-0.91 (m, 48H), 0.95-1.60 (m, 68H), 1.96 (m, 8H), 6.72 (s, 2H), 7.75 (s, 2H), 7.77 (s, 2H)

Example 88

Synthesis of Compound 58

[Chemical Formula 147]

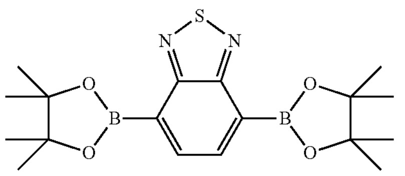

+

8

2

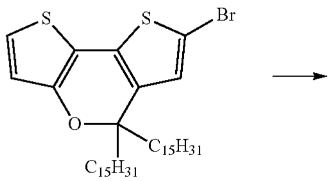

48

-continued

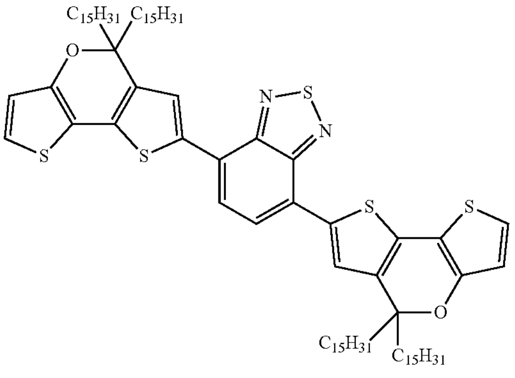

58

A four-neck flask was used. Thereinto, the compound 8 (6.36 g, 16.39 mmol), the compound 48 (23.32 g, 33.60 mmol), and tetrahydrofuran (600 mL) were charged and the resultant reaction mixture was subjected to argon bubbling at room temperature (25° C.) for 30 minutes. Then, to the resultant reaction solution, tris(dibenzylideneacetone) palladium (300.2 mg, 0.328 mmol) and [tri(tert-butyl)phosphonium] tetrafluoroborate (380.5 mg, 1.311 mmol) were added. While stirring the resultant reaction solution at 45° C., into the reaction solution, a potassium phosphate aqueous solution (2 mol/L, 81.97 g, 163.94 mmol) was dropped over 10 minutes. After 2 hours, the disappearance of the raw material was confirmed by liquid chromatography. Water was added to the system and the resultant reaction mixture was extracted with hexane into an organic phase, followed by purifying the organic phase by a column using hexane as a developing solution and then drying the organic phase to obtain 15.02 g of compound 58.

$^1$H-NMR ($CDCl_3$, δ (ppm)): 0.87 (t, 12H), 0.90-1.46 (m, 104H), 1.97 (m, 8H), 6.71 (d, 2H), 7.04 (d, 2H), 7.77 (d, 2H), 7.80 (d, 2H)

Example 89

Synthesis of Compound 59

[Chemical Formula 148]

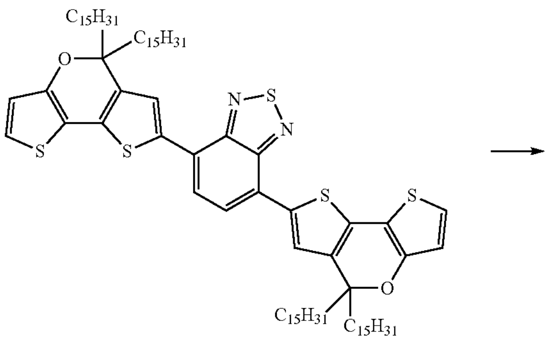

58

-continued

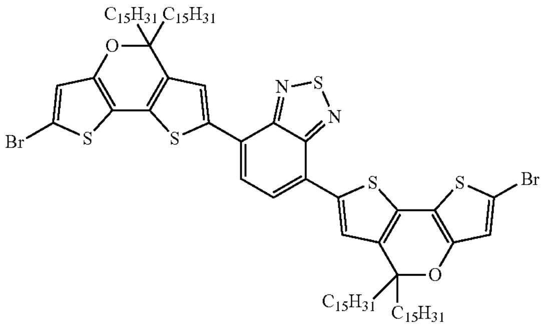

59

A four-neck flask was used. Thereinto, the compound 58 (15.89 g, 11.66 mmol) and tetrahydrofuran (THF) (320 mL) were charged and the resultant reaction mixture was subjected to argon bubbling at room temperature (25° C.) for 30 minutes. The reaction temperature was lowered to −30° C. and then, to the reaction mixture, NBS (4.57 g, 25.68 mmol) was added, followed by elevating the temperature of the resultant reaction mixture to −10° C. over 30 minutes. By liquid chromatography, after 1 hour, the disappearance of the raw material was confirmed. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 15.24 g of compound 59.

$^1$H-NMR ($CDCl_3$, δ (ppm)): 0.88 (t, 12H), 0.93-1.52 (m, 104H), 1.95 (m, 8H), 6.72 (s, 2H), 7.75 (s, 2H), 7.77 (s, 2H)

Example 90

Synthesis of Compound 60

[Chemical Formula 149]

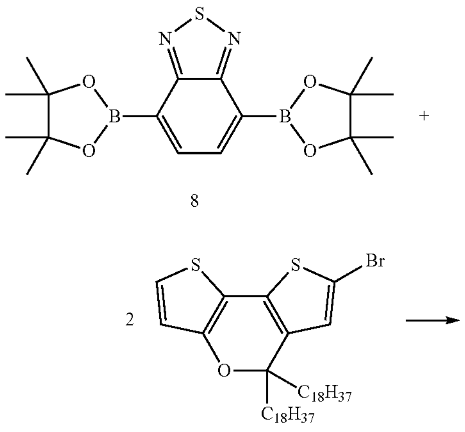

8

2

53

-continued

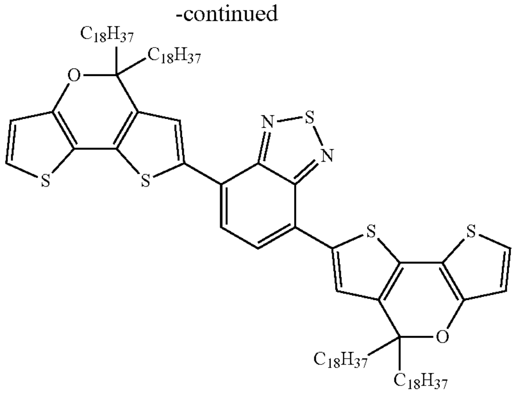

60

A four-neck flask was used. Thereinto, the compound 8 (1.164 g, 3.000 mmol), the compound 53 (4.669 g, 6.000 mmol), and tetrahydrofuran (100 mL) were charged and the resultant reaction mixture was subjected to argon bubbling at room temperature (25° C.) for 30 minutes. Then, to the resultant reaction solution, tris(dibenzylideneacetone) palladium (27.47 mg, 0.030 mmol) and [tri(tert-butyl)phosphonium] tetrafluoroborate (34.82 mg, 0.120 mmol) were added. While stirring the resultant reaction solution at 45° C., into the reaction solution, a potassium phosphate aqueous solution (2 mol/L, 15.00 g, 30.00 mmol) was dropped over 10 minutes. After 2 hours, the disappearance of the raw material was confirmed by liquid chromatography. Water was added to the system and the resultant reaction mixture was extracted with hexane into an organic phase, followed by purifying the organic phase by a column using hexane as a developing solution and then drying the organic phase to obtain 2.985 g of compound 60.

$^1$H-NMR ($CDCl_3$, δ (ppm)): 0.88 (t, 12H), 0.95-1.53 (m, 128H), 1.97 (m, 8H), 6.71 (d, 2H), 7.04 (d, 2H), 7.76 (d, 2H), 7.80 (d, 2H)

Example 91

Synthesis of Compound 61

[Chemical Formula 150]

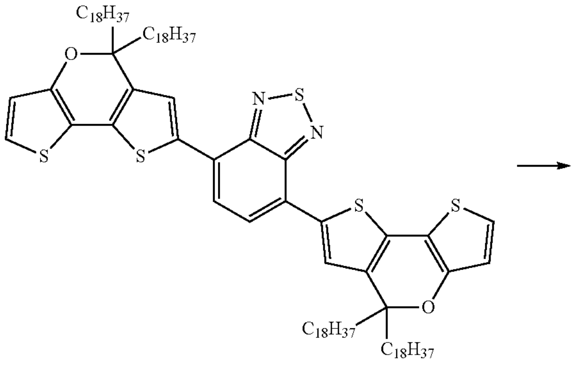

60

-continued

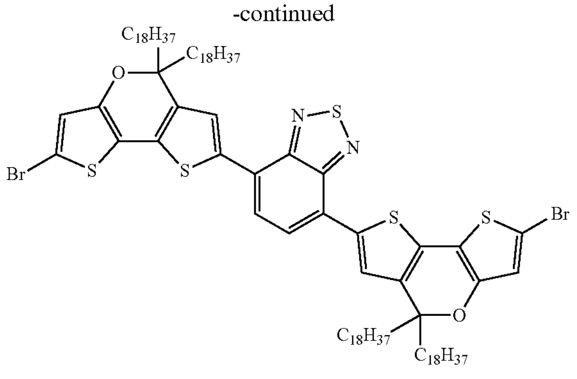

61

A four-neck flask was used. Thereinto, the compound 60 (2.985 g, 1.950 mmol) and tetrahydrofuran (THF) (60 mL) were charged and the resultant reaction mixture was subjected to argon bubbling at room temperature (25° C.) for 30 minutes. The reaction solution was cooled to −30° C. and thereto, NBS (970 mg, 4.875 mmol) was added, followed by elevating the temperature of the resultant reaction mixture to −10° C. over 30 minutes. After 1 hour, the disappearance of the raw material was confirmed by liquid chromatography. After 1 hour, the disappearance of the raw material was confirmed. Then, to the reaction solution, a sodium thiosulfate aqueous solution was added and the resultant reaction mixture was extracted with hexane into an organic phase. Then, the organic phase was separated by a column using hexane as a developing solution and the component obtained by the separation was dried to obtain 2.72 g of compound 61.

$^1$H-NMR ($CDCl_3$, δ (ppm)): 0.87 (t, 12H), 0.95-1.50 (m, 128H), 1.95 (m, 8H), 6.72 (s, 2H), 7.75 (s, 2H), 7.78 (s, 2H)

Example 92

Synthesis of Polymer V

[Chemical Formula 151]

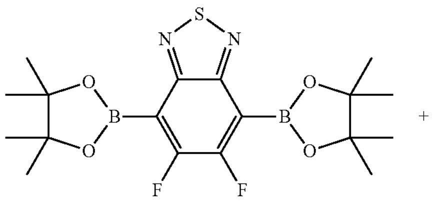

36

-continued

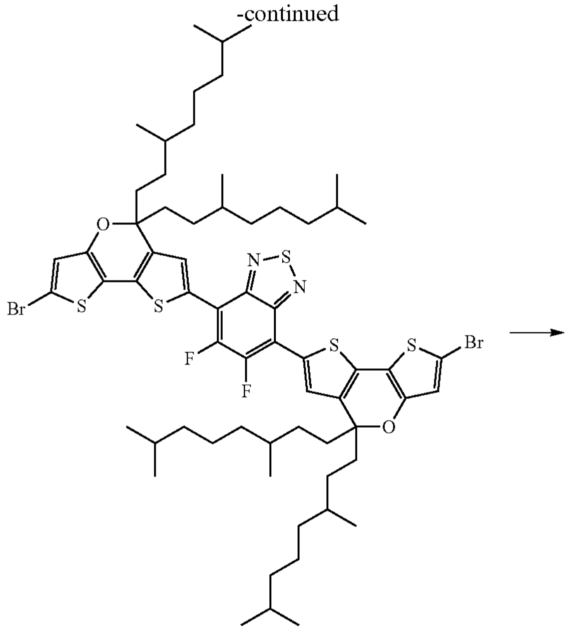

38

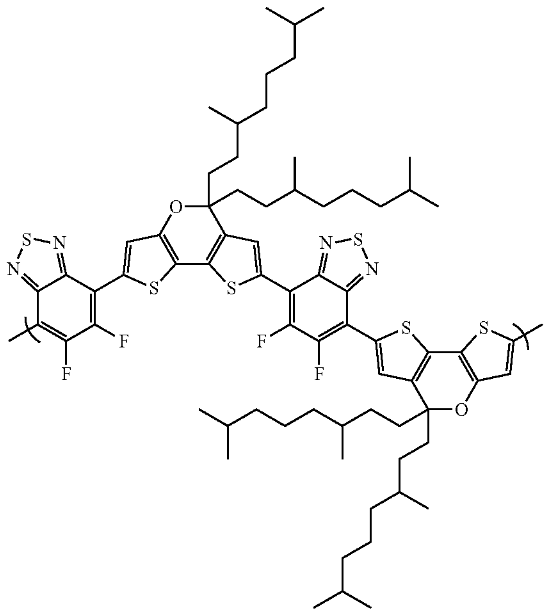

Polymer V

A four-neck flask was used. Thereinto, the compound 38 (191.3 mg, 0.150 mmol) and methylene chloride (24 mL) were charged and the resultant reaction mixture was subjected to argon bubbling at room temperature (25° C.) for 30 minutes. Then, to the resultant reaction solution, tris(dibenzylideneacetone) palladium (2.75 mg, 0.003 mmol), [tri(tert-butyl)phosphonium] tetrafluoroborate (3.48 mg, 0.012 mmol), and a potassium phosphate aqueous solution (2 mol/L, 0.8 g, 1.6 mmol) were added. While stirring the resultant reaction solution at an oil-bath temperature of 40° C., into the reaction solution, a solution in which the compound 36 (63.6 mg, 0.150 mmol) was dissolved in methylene chloride (6 mL) was dropped over 10 minutes and the resultant reaction mixture was stirred for 30 minutes. Then, to the reaction solution, phenylboric acid (15.0 mg, 0.123 mmol) was added, the resultant reaction mixture was stirred further for 1 hour, and then the reaction was terminated. The reaction was carried out under an argon atmosphere.

Then, to the resultant reaction solution, sodium diethyldithiocarbamate (1 g) and pure water (10 mL) were added and the resultant reaction mixture was stirred under reflux for 3 hours. The aqueous phase in the reaction solution was removed and then the organic phase was washed with 50 mL of water twice, with 50 mL of an acetic acid aqueous solution (3% by weight) twice, and further with 50 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 50 mg of polymer V.

For the molecular weight of the polymer V measured by GPC (in terms of polystyrene), the weight-average molecular weight (Mw) was 25,000 and the number average molecular weight (Mn) was 10,000. The light absorbing terminal wavelength of the polymer V was 940 nm.

Example 93

Synthesis of Polymer W

[Chemical Formula 152]

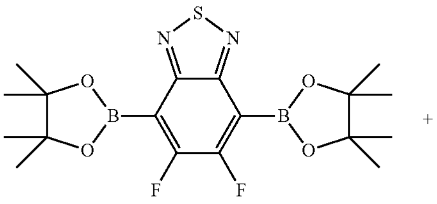

36

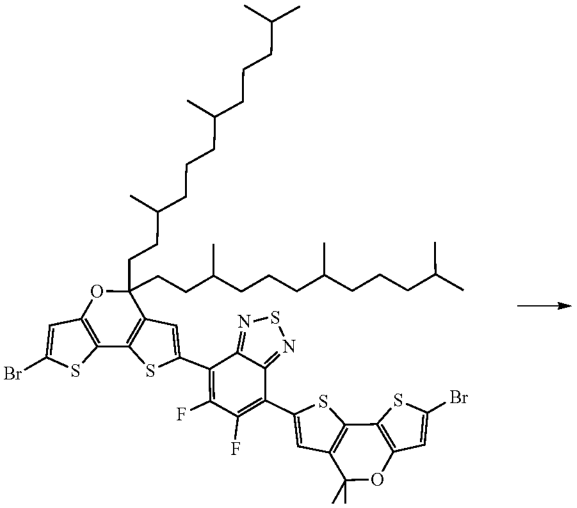

-continued

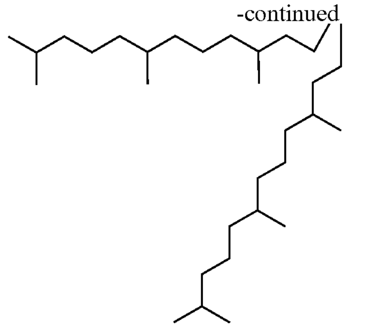

43

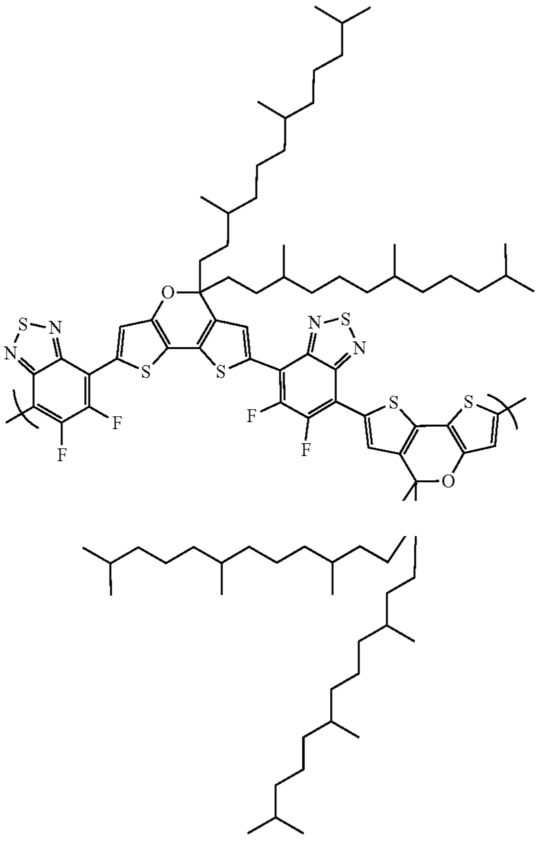

Polymer W

A four-neck flask was used. Thereinto, the compound 43 (440.0 mg, 0.280 mmol) and methylene chloride (50 mL) were charged and the resultant reaction mixture was subjected to argon bubbling at room temperature (25° C.) for 30 minutes. Then, to the resultant reaction solution, tris(dibenzylideneacetone) palladium (5.49 mg, 0.006 mmol), [tri(tert-butyl)phosphonium] tetrafluoroborate (6.96 mg, 0.024 mmol), and a potassium phosphate aqueous solution (2 mol/L, 1.5 g, 3.0 mmol) were added. While stirring the resultant reaction solution at an oil-bath temperature of 40° C., into the reaction solution, a solution in which the compound 36 (120.0 mg, 0.280 mmol) was dissolved in methylene chloride (12 mL) was dropped over 10 minutes and the resultant reaction mixture was stirred for 30 minutes. Then, to the reaction solution, phenylboric acid (150 mg, 1.23 mmol) was added, the resultant reaction mixture was stirred further for 1 hour, and then the reaction was terminated. The reaction was carried out under an argon atmosphere.

Then, to the resultant reaction solution, sodium diethyldithiocarbamate (10 g) and pure water (100 mL) were added and the resultant reaction mixture was stirred under reflux for 3 hours. The aqueous phase in the reaction solution was removed and then the organic phase was washed with 500 mL of water twice, with 200 mL of an acetic acid aqueous solution (3% by weight) twice, and further with 200 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 150 mg of polymer W.

For the molecular weight of the polymer W measured by GPC (in terms of polystyrene), the weight-average molecular weight (Mw) was 8,500 and the number average molecular weight (Mn) was 4,000. The light absorbing terminal wavelength of the polymer W was 940 nm.

Example 94

Synthesis of Polymer X

[Chemical Formula 153]

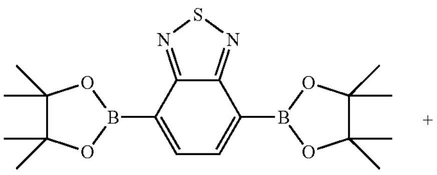

8

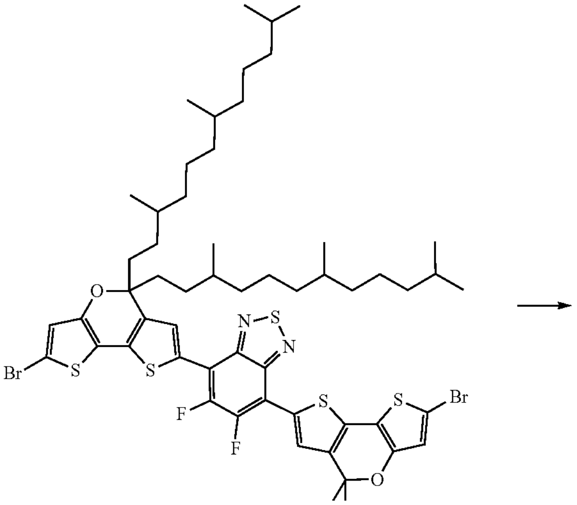

-continued

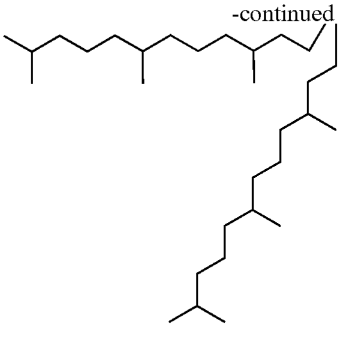

43

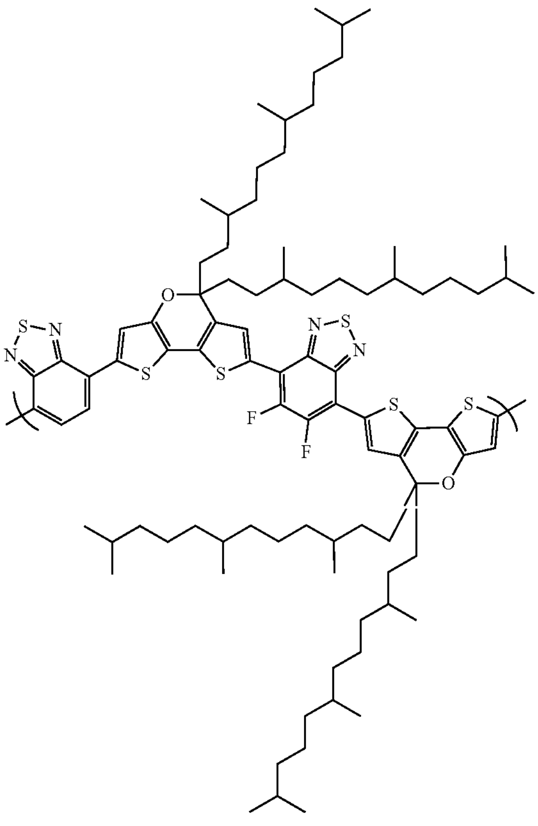

Polymer X

A four-neck flask was used. Thereinto, the compound 43 (50.5 mg, 0.032 mmol) and tetrahydrofuran (10 mL) were charged and the resultant reaction mixture was subjected to argon bubbling at room temperature (25° C.) for 30 minutes. Then, to the resultant reaction solution, tris(dibenzylideneacetone) palladium (5.49 mg, 0.006 mmol), [tri(tert-butyl) phosphonium] tetrafluoroborate (6.96 mg, 0.024 mmol), and a potassium phosphate aqueous solution (2 mol/L, 1.5 g, 3.0 mmol) were added. While stirring the resultant reaction solution at an oil-bath temperature of 40° C., into the reaction solution, a solution in which the compound 8 (12.4 mg, 0.032 mmol) was dissolved in tetrahydrofuran (5 mL) was dropped over 10 minutes and the resultant reaction mixture was stirred for 30 minutes. Then, to the reaction solution, phenylboric acid (30.0 mg, 0.246 mmol) was added, the resultant reaction mixture was stirred further for 1 hour, and then the reaction was terminated. The reaction was carried out under an argon atmosphere.

Then, to the resultant reaction solution, sodium diethyldithiocarbamate (1.5 g) and pure water (13.5 mL) were added and the resultant reaction mixture was stirred under reflux for 3 hours. The aqueous phase in the reaction solution was removed and then the organic phase was washed with 15 mL of water twice, with 15 mL of an acetic acid aqueous solution (3% by weight) twice, and further with 15 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 24 mg of polymer X.

For the molecular weight of the polymer X measured by GPC (in terms of polystyrene), the weight-average molecular weight (Mw) was 25,000 and the number average molecular weight (Mn) was 10,000. The light absorbing terminal wavelength of the polymer X was 940 nm.

Example 95

Synthesis of Polymer Y

[Chemical Formula 154]

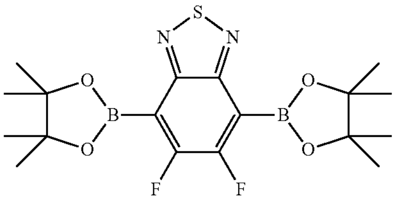

+

36

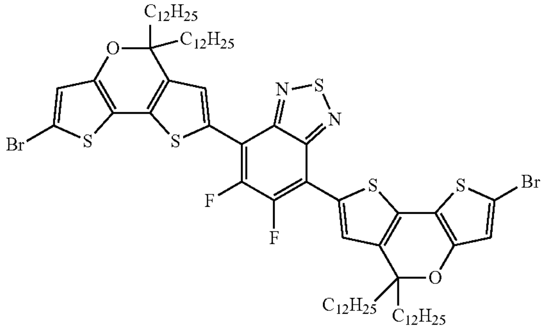

45

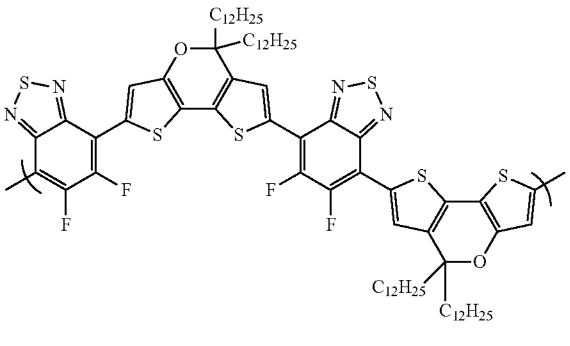

Polymer Y

A four-neck flask was used. Thereinto, the compound 45 (416.3 mg, 0.300 mmol) and methylene chloride (10 mL) were charged and the resultant reaction mixture was subjected to argon bubbling at room temperature (25° C.) for 30 minutes. Then, to the resultant reaction solution, tris(dibenzylideneacetone) palladium (10.99 mg, 0.012 mmol), [tri(tert-butyl)phosphonium] tetrafluoroborate (13.93 mg, 0.048 mmol), and a potassium phosphate aqueous solution (2 mol/L, 1.5 g, 3.0 mmol) were added. While stirring the resultant reaction solution at an oil-bath temperature of 40° C., into the reaction solution, a solution in which the compound 36 (127.2 mg, 0.300 mmol) was dissolved in methylene chloride (10 mL) was dropped over 10 minutes and the resultant reaction mixture was stirred for 30 minutes. Then, to the reaction solution, phenylboric acid (30.0 mg, 0.246 mmol) was added, the resultant reaction mixture was stirred further for 1 hour, and then the reaction was terminated. The reaction was carried out under an argon atmosphere.

Then, to the resultant reaction solution, sodium diethyldithiocarbamate (2.5 g) and pure water (22.5 mL) were added and the resultant reaction mixture was stirred under reflux for 3 hours. The aqueous phase in the reaction solution was removed and then the organic phase was washed with 30 mL of water twice, with 30 mL of an acetic acid aqueous solution (3% by weight) twice, and further with 30 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 156 mg of polymer Y.

For the molecular weight of the polymer Y measured by GPC (in terms of polystyrene), the weight-average molecular weight (Mw) was 76,000 and the number average molecular weight (Mn) was 31,000. The light absorbing terminal wavelength of the polymer Y was 940 nm.

Example 96

Synthesis of Polymer Z

[Chemical Formula 155]

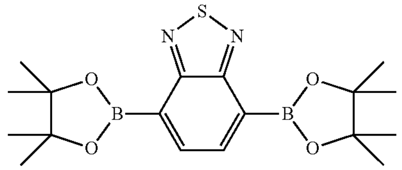

+

8

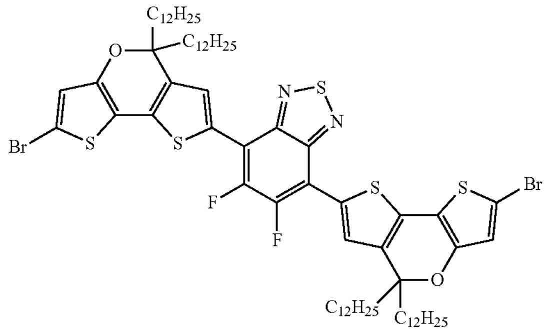

45

-continued

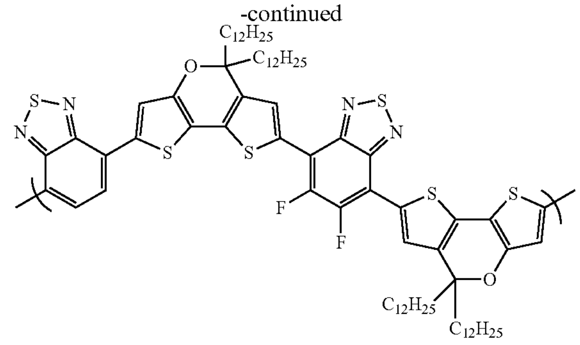

Polymer Z

A four-neck flask was used. Thereinto, the compound 45 (277.5 mg, 0.200 mmol) and tetrahydrofuran (40 mL) were charged and the resultant reaction mixture was subjected to argon bubbling at room temperature (25° C.) for 30 minutes. Then, to the resultant reaction solution, tris(dibenzylideneacetone) palladium (3.66 mg, 0.004 mmol), [tri(tert-butyl) phosphonium] tetrafluoroborate (4.64 mg, 0.016 mmol), and a potassium phosphate aqueous solution (2 mol/L, 1.0 g, 2.0 mmol) were added. While stirring the resultant reaction solution at an oil-bath temperature of 40° C., into the reaction solution, a solution in which the compound 8 (77.6 mg, 0.200 mmol) was dissolved in tetrahydrofuran (10 mL) was dropped over 10 minutes and the resultant reaction mixture was stirred for 30 minutes. Then, to the reaction solution, phenylboric acid (20.0 mg, 0.164 mmol) was added, the resultant reaction mixture was stirred further for 1 hour, and then the reaction was terminated. The reaction was carried out under an argon atmosphere.

Then, to the resultant reaction solution, sodium diethyldithiocarbamate (1.0 g) and pure water (9.0 mL) were added and the resultant reaction mixture was stirred under reflux for 3 hours. The aqueous phase in the reaction solution was removed and then the organic phase was washed with 10 mL of water twice, with 10 mL of an acetic acid aqueous solution (3% by weight) twice, and further with 10 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 44 mg of polymer Z.

For the molecular weight of the polymer Z measured by GPC (in terms of polystyrene), the weight-average molecular weight (Mw) was 35,000 and the number average molecular weight (Mn) was 15,000. The light absorbing terminal wavelength of the polymer Z was 950 nm.

Example 97

Synthesis of Polymer Z2

[Chemical Formula 156]

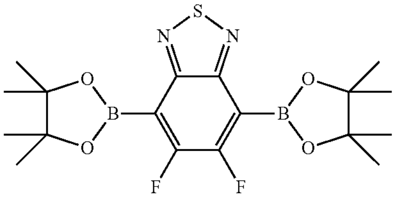

+

36

-continued

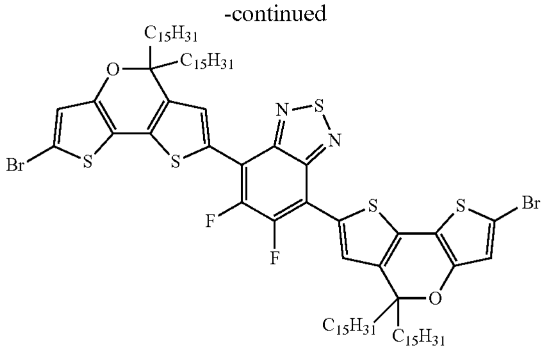

50

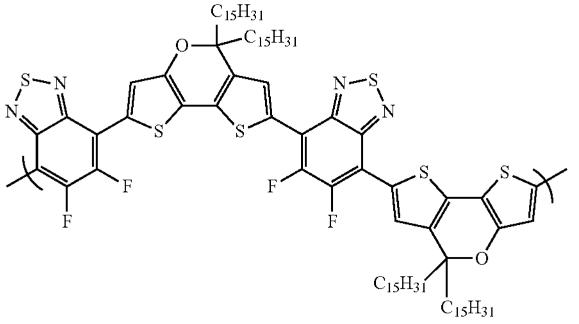

Polymer Z2

A four-neck flask was used. Thereinto, the compound 50 (311.2 mg, 0.200 mmol) and methylene chloride (10 mL) were charged and the resultant reaction mixture was subjected to argon bubbling at room temperature (25° C.) for 30 minutes. Then, to the resultant reaction solution, tris(dibenzylideneacetone) palladium (7.32 mg, 0.008 mmol), [tri(tert-butyl)phosphonium] tetrafluoroborate (9.28 mg, 0.032 mmol), and a potassium phosphate aqueous solution (2 mol/L, 1.0 g, 2.0 mmol) were added. While stirring the resultant reaction solution at an oil-bath temperature of 40° C., into the reaction solution, a solution in which the compound 36 (84.8 mg, 0.200 mmol) was dissolved in methylene chloride (10 mL) was dropped over 10 minutes and the resultant reaction mixture was stirred for 30 minutes. Then, to the reaction solution, phenylboric acid (20.0 mg, 0.164 mmol) was added, the resultant reaction mixture was stirred further for 1 hour, and then the reaction was terminated. The reaction was carried out under an argon atmosphere.

Then, to the resultant reaction solution, sodium diethyldithiocarbamate (1.7 g) and pure water (15.0 mL) were added and the resultant reaction mixture was stirred under reflux for 3 hours. The aqueous phase in the reaction solution was removed and then the organic phase was washed with 20 mL of water twice, with 20 mL of an acetic acid aqueous solution (3% by weight) twice, and further with 20 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 197 mg of polymer Z2.

For the molecular weight of the polymer Z2 measured by GPC (in terms of polystyrene), the weight-average molecular weight (Mw) was 240,000 and the number average molecular weight (Mn) was 90,000. The light absorbing terminal wavelength of the polymer Z2 was 950 nm.

Example 98

Synthesis of Polymer Z3

[Chemical Formula 157]

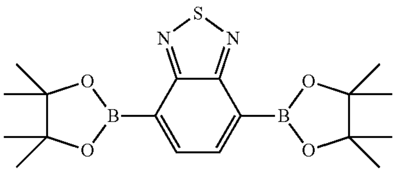

+

8

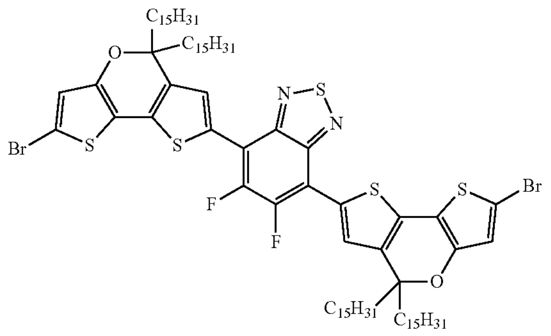

50

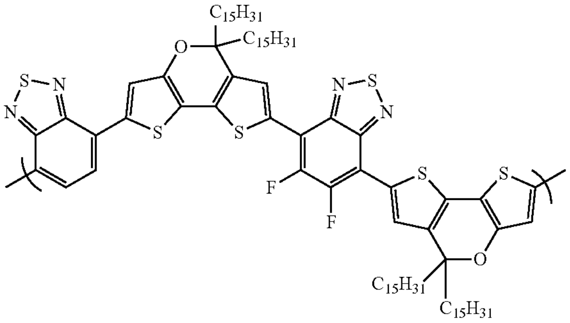

Polymer Z3

A four-neck flask was used. Thereinto, the compound 50 (252.2 mg, 0.162 mmol) and tetrahydrofuran (20 mL) were charged and the resultant reaction mixture was subjected to argon bubbling at room temperature (25° C.) for 30 minutes. Then, to the resultant reaction solution, tris(dibenzylideneacetone) palladium (3.66 mg, 0.004 mmol), [tri(tert-butyl) phosphonium] tetrafluoroborate (4.64 mg, 0.016 mmol), and a potassium phosphate aqueous solution (2 mol/L, 1.0 g, 2.0 mmol) were added. While stirring the resultant reaction solution at an oil-bath temperature of 40° C., into the reaction solution, a solution in which the compound 8 (62.9 mg, 0.162 mmol) was dissolved, in tetrahydrofuran (10 mL) was dropped over 10 minutes and the resultant reaction mixture was stirred for 30 minutes. Then, to the reaction solution, phenylboric acid (20.0 mg, 0.164 mmol) was added, the resultant reaction mixture was stirred further for 1 hour, and then the reaction was terminated. The reaction was carried out under an argon atmosphere.

Then, to the resultant reaction solution, sodium diethyldithiocarbamate (1.0 g) and pure water (9.0 mL) were added and the resultant reaction mixture was stirred under reflux for 3 hours. The aqueous phase in the reaction solution was removed and then the organic phase was washed with 10 mL of water twice, with 10 mL of an acetic acid aqueous solution (3% by weight) twice, and further with 10 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 165 mg of polymer Z3.

For the molecular weight of the polymer Z3 measured by GPC (in terms of polystyrene), the weight-average molecular weight (Mw) was 300,000 and the number average molecular weight (Mn) was 100,000. The light absorbing terminal wavelength of the polymer Z3 was 950 nm.

Example 99

Synthesis of Polymer Z4

[Chemical Formula 158]

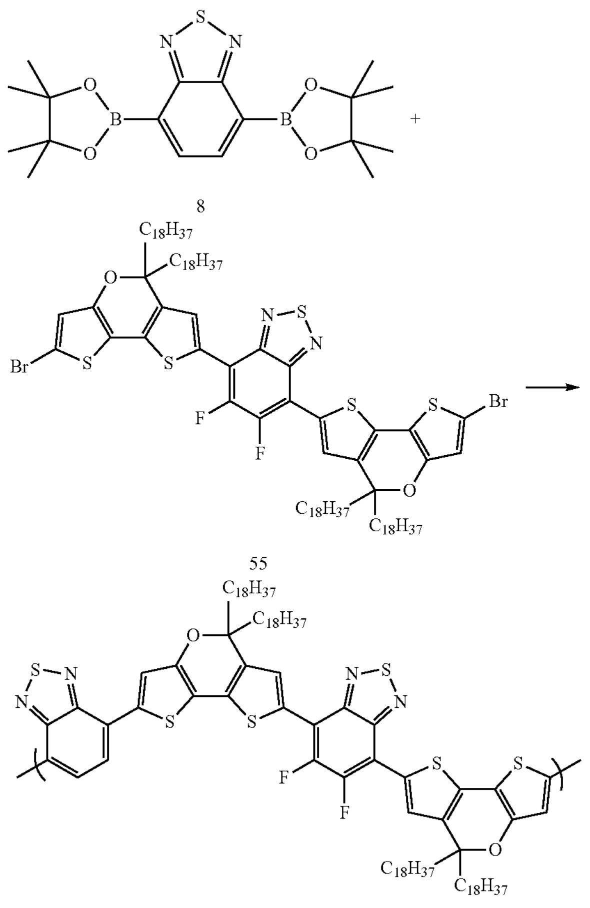

8

55

Polymer Z4

A four-neck flask was used. Thereinto, the compound 55 (344.9 mg, 0.200 mmol) and tetrahydrofuran (12 mL) were charged and the resultant reaction mixture was subjected to argon bubbling at room temperature (25° C.) for 30 minutes. Then, to the resultant reaction solution, tris(dibenzylideneacetone) palladium (3.66 mg, 0.004 mmol), [tri(tert-butyl) phosphonium] tetrafluoroborate (4.64 mg, 0.016 mmol), and a potassium phosphate aqueous solution (2 mol/L, 1.0 g, 2.0 mmol) were added. While stirring the resultant reaction solution at an oil-bath temperature of 40° C., into the reaction solution, a solution in which the compound 8 (77.6 mg, 0.200 mmol) was dissolved in tetrahydrofuran (10 mL) was dropped over 10 minutes and the resultant reaction mixture was stirred for 30 minutes. Then, to the reaction solution, phenylboric acid (20.0 mg, 0.164 mmol) was added, the resultant reaction mixture was stirred further for 1 hour, and then the reaction was terminated. The reaction was carried out under an argon atmosphere.

Then, to the resultant reaction solution, sodium diethyldithiocarbamate (1.0 g) and pure water (9.0 mL) were added and the resultant reaction mixture was stirred under reflux for 3 hours. The aqueous phase in the reaction solution was removed and then the organic phase was washed with 10 mL of water twice, with 10 mL of an acetic acid aqueous solution (3% by weight) twice, and further with 10 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 236 mg of polymer Z4.

For the molecular weight of the polymer Z4 measured by GPC (in terms of polystyrene), the weight-average molecular weight (Mw) was 101,000 and the number average molecular weight (Mn) was 32,000. The light absorbing terminal wavelength of the polymer Z4 was 940 nm.

Example 100

Synthesis of Polymer Z5

[Chemical Formula 159]

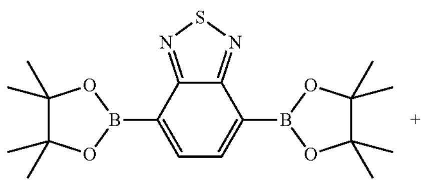

8

-continued

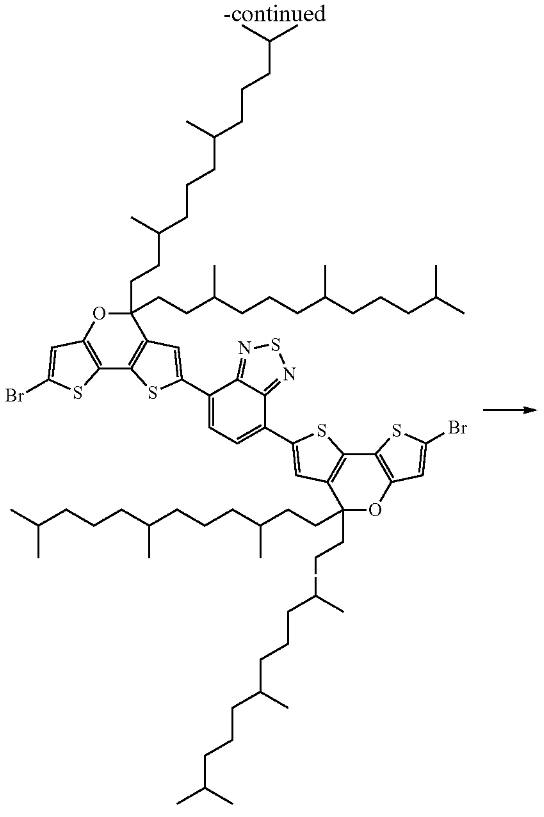

57

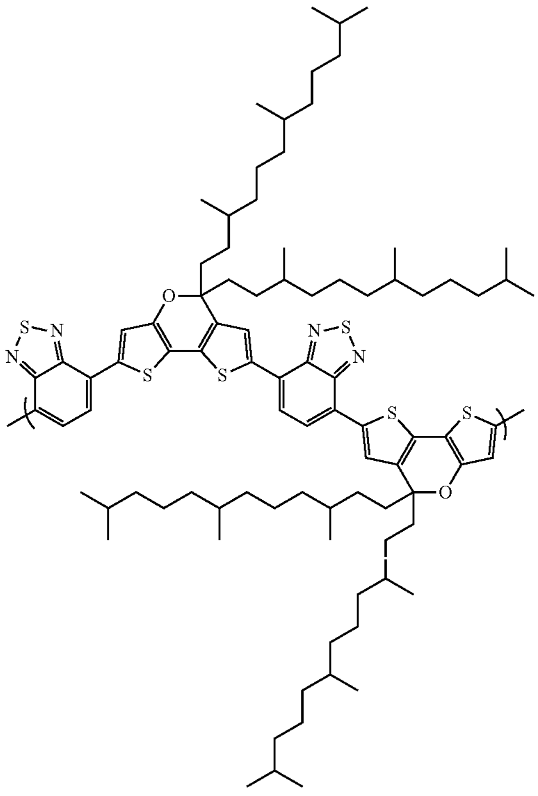

Polymer Z5

A four-neck flask was used. Thereinto, the compound 57 (455.3 mg, 0.300 mmol) and tetrahydrofuran (30 mL) were charged and the resultant reaction mixture was subjected to argon bubbling at room temperature (25° C.) for 30 minutes. Then, to the resultant reaction solution, tris(dibenzylideneacetone) palladium (5.50 mg, 0.006 mmol), [tri(tert-butyl) phosphonium] tetrafluoroborate (7.0 mg, 0.024 mmol), and a potassium phosphate aqueous solution (2 mol/L, 1.5 g, 3.0 mmol) were added. While stirring the resultant reaction solution at an oil-bath temperature of 40° C., into the reaction solution, a solution in which the compound 8 (122.3 mg, 0.315 mmol) was dissolved in tetrahydrofuran (10 mL) was dropped over 10 minutes and the resultant reaction mixture was stirred for 30 minutes. Then, to the reaction solution, phenylboric acid (30.0 mg, 0.246 mmol) was added, the resultant reaction mixture was stirred further for 1 hour, and then the reaction was terminated. The reaction was carried out under an argon atmosphere.

Then, to the resultant reaction solution, sodium diethyldithiocarbamate (2.5 g) and pure water (22.5 mL) were added and the resultant reaction mixture was stirred under reflux for 3 hours. The aqueous phase in the reaction solution was removed and then the organic phase was washed with 30 mL of water twice, with 30 mL of an acetic acid aqueous solution (3% by weight) twice, and further with 30 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 343.9 mg of polymer Z5.

For the molecular weight of the polymer Z5 measured by GPC (in terms of polystyrene), the weight-average molecular weight (Mw) was 70,000 and the number average molecular weight (Mn) was 27,000. The light absorbing terminal wavelength of the polymer Z5 was 940 nm.

Example 101

Synthesis of Polymer Z6

[Chemical Formula 160]

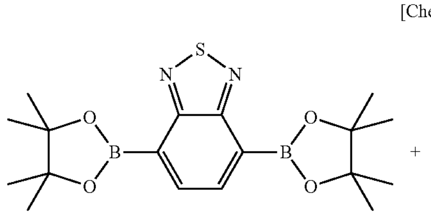

8

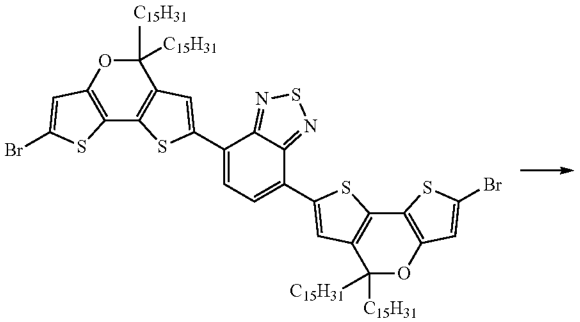

59

-continued

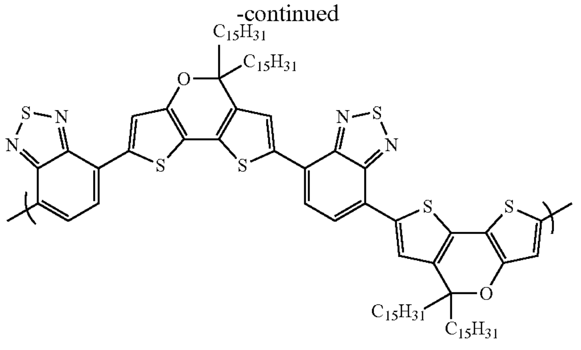

Polymer Z6

A four-neck flask was used. Thereinto, the compound 59 (912.0 mg, 0.600 mmol) and tetrahydrofuran (42 mL) were charged and the resultant reaction mixture was subjected to argon bubbling at room temperature (25° C.) for 30 minutes. Then, to the resultant reaction solution, tris(dibenzylideneacetone) palladium (5.49 mg, 0.006 mmol), [tri(tert-butyl) phosphonium] tetrafluoroborate (6.96 mg, 0.024 mmol), and a potassium phosphate aqueous solution (2 mol/L, 3.0 g, 6.0 mmol) were added. While stirring the resultant reaction solution at an oil-bath temperature of 40° C., into the reaction solution, a solution in which the compound 8 (232.9 mg, 0.600 mmol) was dissolved in tetrahydrofuran (18 mL) was dropped over 10 minutes and the resultant reaction mixture was stirred for 30 minutes. Then, to the reaction solution, phenylboric acid (60.0 mg, 0.492 mmol) was added, the resultant reaction mixture was stirred further for 1 hour, and then the reaction was terminated. The reaction was carried out under an argon atmosphere.

Then, to the resultant reaction solution, sodium diethyldithiocarbamate (5.0 g) and pure water (45.0 mL) were added and the resultant reaction mixture was stirred under reflux for 3 hours. The aqueous phase in the reaction solution was removed and then the organic phase was washed with 60 mL of water twice, with 60 mL of an acetic acid aqueous solution (3% by weight) twice, and further with 60 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 779.0 mg of polymer Z6.

For the molecular weight of the polymer Z6 measured by GPC (in terms of polystyrene), the weight-average molecular weight (Mw) was 116,000 and the number average molecular weight (Mn) was 40,000. The light absorbing terminal wavelength of the polymer Z6 was 950 nm.

Example 102

Synthesis of Polymer Z7

[Chemical Formula 161]

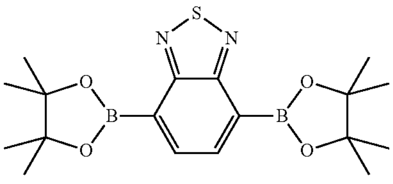

+

8

-continued

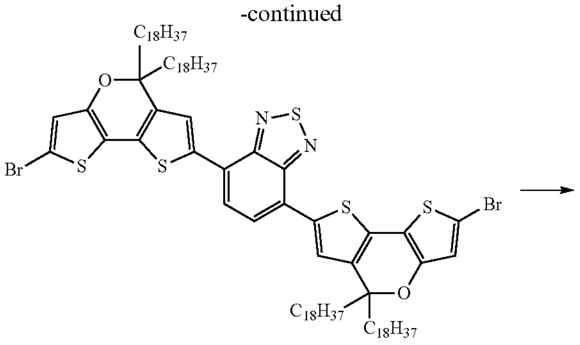

61

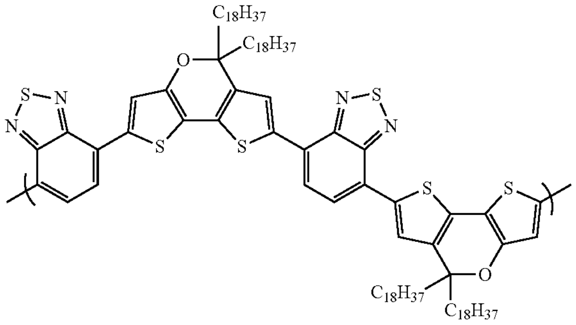

Polymer Z7

A four-neck flask was used. Thereinto, the compound 61 (506.5 mg, 0.300 mmol) and tetrahydrofuran (21 mL) were charged and the resultant reaction mixture was subjected to argon bubbling at room temperature (25° C.) for 30 minutes. Then, to the resultant reaction solution, tris(dibenzylideneacetone) palladium (2.75 mg, 0.003 mmol), [tri(tert-butyl) phosphonium] tetrafluoroborate (3.48 mg, 0.012 mmol), and a potassium phosphate aqueous solution (2 mol/L, 1.5 g, 3.0 mmol) were added. While stirring the resultant reaction solution at an oil-bath temperature of 40° C., into the reaction solution, a solution in which the compound 8 (116.4 mg, 0.300 mmol) was dissolved in tetrahydrofuran (9 mL) was dropped over 10 minutes and the resultant reaction mixture was stirred for 30 minutes. Then, to the reaction solution, phenylboric acid (30.0 mg, 0.246 mmol) was added, the resultant reaction mixture was stirred further for 1 hour, and then the reaction was terminated. The reaction was carried out under an argon atmosphere.

Then, to the resultant reaction solution, sodium diethyldithiocarbamate (2.5 g) and pure water (22.5 mL) were added and the resultant reaction mixture was stirred under reflux for 3 hours. The aqueous phase in the reaction solution was removed and then the organic phase was washed with 30 mL of water twice, with 30 mL of an acetic acid aqueous solution (3% by weight) twice, and further with 30 mL of water twice, followed by pouring the resultant reaction mixture into methanol to precipitate polymer. The polymer was filtered and then dried and the resultant polymer was dissolved in toluene. The resultant toluene solution was passed through an alumina/silica gel column and the resultant solution was added into methanol to precipitate polymer. The polymer was filtered and then dried to obtain 440.5 mg of polymer Z7.

For the molecular weight of the polymer Z7 measured by GPC (in terms of polystyrene), the weight-average molecular weight (Mw) was 55,000 and the number average molecular weight (Mn) was 20,000. The light absorbing terminal wavelength of the polymer Z7 was 940 nm.

Example 103

(Preparation of Organic Transistor)

An n-type silicon substrate having a thermal oxide film of a thickness of 300 nm which had been doped in a high concentration was subjected to ultrasonic cleaning in acetone for 10 minutes and was irradiated with ozone UV for 20 minutes. Then, the n-type silicon substrate was spin-coated with β-phenethyltrichlorosilane diluted in a ratio of 5 drops thereof (dropped by taking with a syringe) in 10 mL of toluene to subject the surface of the thermal oxide film to silane treatment.

Next, the polymer X was dissolved in o-dichlorobenzene to prepare a solution having polymer X concentration of 0.5% by weight and the solution was filtered with a membrane filter to prepare a coating liquid. The coating liquid was applied on the above surface-treated substrate by a spin coating method to form polymer X coating film (thickness: about 30 nm). Furthermore, the coating film was subjected to thermal treatment at 170° C. under a nitrogen atmosphere for 30 minutes to form polymer X organic semiconductor thin film.

Furthermore, on the organic semiconductor thin film, a source electrode and a drain electrode that had a layered structure of molybdenum trioxide and gold from the side of the organic semiconductor thin film were prepared by a vacuum deposition evaporation method using a metal mask to produce an organic transistor.

Example 104

(Evaluation of Organic Transistor)

The electric properties of the organic transistor were measured using a semiconductor parameter 4200 (manufactured by Keithley Instruments Inc.). As a result, the change curve of the drain current (Id) relative to the drain voltage (Vd) with respect to an organic transistor using the polymer X was good. When a negative gate voltage applied to a gate electrode was increased, a negative drain current also increased. Therefore, it could be confirmed that the organic transistor was a p-type organic transistor.

The electric field-effect mobility μ of a carrier in the organic transistor was calculated using Formula (a) below representing a drain current Id in a saturation region of the electric properties of the organic transistor.

$$Id=(W/2L)\mu Ci(Vg-Vt)^2 \quad (a)$$

(where L represents a channel length of the organic transistor; W represents a channel width of the organic transistor; Ci represents a capacity of the gate insulating film per unit area; Vg represents a gate voltage; and Vt represents a threshold voltage of the gate voltage.)

As a result, the electric field-effect mobility of a carrier (carrier mobility) was 0.03 $cm^2/Vs$ and an ON/OFF current ratio was $10^5$. The result is listed in Table 5.

Example 105

In the same manner as in Example 103, except that the polymer Y was used instead of the polymer X, the organic transistor element was prepared and the transistor properties thereof were evaluated in the same manner as in Example 104. The carrier mobility was 0.07 $cm^2/Vs$ and the ON/OFF current ratio was $10^6$. The result is listed in Table 5.

Example 106

In the same manner as in Example 103, except that the polymer Z was used instead of the polymer X, the organic transistor element was prepared and the transistor properties thereof were evaluated in the same manner as in Example 104. The carrier mobility was 0.06 $cm^2/Vs$ and the ON/OFF current ratio was $10^6$. The result is listed in Table 5.

Example 107

In the same manner as in Example 103, except that the polymer Z2 was used instead of the polymer X, the organic transistor element was prepared and the transistor properties thereof were evaluated in the same manner as in Example 104. The carrier mobility was 0.13 $cm^2/Vs$ and the ON/OFF current ratio was $10^6$. The result is listed in Table 5.

Example 108

In the same manner as in Example 103, except that the polymer Z3 was used instead of the polymer X, the organic transistor element was prepared and the transistor properties thereof were evaluated in the same manner as in Example 104. The carrier mobility was 0.25 $cm^2/Vs$ and the ON/OFF current ratio was $10^6$. The result is listed in Table 5.

Example 109

In the same manner as in Example 103, except that the polymer Z4 was used instead of the polymer X, the organic transistor element was prepared and the transistor properties thereof were evaluated in the same manner as in Example 104. The carrier mobility was 0.12 $cm^2/Vs$ and the ON/OFF current ratio was $10^6$. The result is listed in Table 5.

Example 110

In the same manner as in Example 103, except that the polymer Z5 was used instead of the polymer X, the organic transistor element was prepared and the transistor properties thereof were evaluated in the same manner as in Example 104. The carrier mobility was 0.04 $cm^2/Vs$ and the ON/OFF current ratio was $10^5$. The result is listed in Table 5.

Example 111

In the same manner as in Example 103, except that the polymer Z6 was used instead of the polymer X, the organic transistor element was prepared and the transistor properties thereof were evaluated in the same manner as in Example 104. The carrier mobility was 0.32 $cm^2/Vs$ and the ON/OFF current ratio was $10^6$. The result is listed in Table 5.

Example 112

In the same manner as in Example 103, except that the polymer K was used instead of the polymer X, the organic transistor element was prepared and the transistor properties thereof were evaluated in the same manner as in Example 104. The carrier mobility was 0.30 $cm^2/Vs$ and the ON/OFF current ratio was $10^6$. The result is listed in Table 5.

TABLE 5

| Organic Transistor Element Evaluation Result | | | |
|---|---|---|---|
| | | Carrier Mobility ($cm^2/Vs$) | ON/OFF Ratio |
| Example 104 | Polymer X | 0.03 | $10^5$ |
| Example 105 | Polymer Y | 0.07 | $10^6$ |
| Example 106 | Polymer Z | 0.06 | $10^6$ |
| Example 107 | Polymer Z2 | 0.13 | $10^6$ |
| Example 108 | Polymer Z3 | 0.25 | $10^6$ |
| Example 109 | Polymer Z4 | 0.12 | $10^6$ |
| Example 110 | Polymer Z5 | 0.04 | $10^5$ |
| Example 111 | Polymer Z6 | 0.32 | $10^6$ |
| Example 112 | Polymer K | 0.30 | $10^6$ |

Example 113

(Production and Evaluation of Ink and Organic Thin Film Solar Cell)

A glass substrate on which an ITO film was formed by a sputtering method in a thickness of 150 nm was subjected to surface treatment by ozone UV treatment. Next, the polymer X and fullerene C60PCBM (phenyl C61-butyric acid methyl ester; manufactured by Frontier Carbon Corporation) were dissolved in o-dichlorobenzene so that the weight ratio of C60PCBM relative to the weight of the polymer X became 3 to produce an ink. The total of the weight of the polymer X and the weight of C60PCBM was 2.0% by weight, relative to the weight of the ink. The ink was applied on the glass substrate by spin-coating to prepare an organic film containing the polymer X. The organic film had a film thickness of about 100 nm. The light absorbing terminal wavelength of the thus prepared organic film was 940 nm. Then, on the organic film, lithium fluoride was deposited by a vacuum deposition machine in a thickness of 2 nm and next thereon, Al was deposited in a thickness of 100 nm to produce an organic thin film solar cell. The obtained organic thin film solar cell had a shape of a 2 mm×2 mm square. The obtained organic thin film solar cell was irradiated with a constant light using a solar simulator (manufactured by BUNKOUKEIKI Co., Ltd.; trade name: OTENTO-SUNII; AM 1.5G filter, irradiance: 100 $mW/cm^2$) and the generated current and voltage were measured to calculate the photoelectric conversion efficiency, the short-circuit current density, the open-circuit voltage, and the fill factor. $J_{sc}$ (short-circuit current density) was 11.20 $mA/cm^2$; Voc (open-circuit voltage) was 0.62 V; ff (fill factor) was 0.67; and photoelectric conversion efficiency (11) was 4.63%. The result is listed in Table 6.

Example 114

In the same manner as in Example 113, except that the polymer Y was used instead of the polymer W, the ink and the organic thin film solar cell were prepared and evaluated. $J_{sc}$ (short-circuit current density) was 5.00 $mA/cm^2$; Voc (open-circuit voltage) was 0.69 V; ff (fill factor) was 0.56; and photoelectric conversion efficiency (η) was 1.96%. The result is listed in Table 6.

Example 115

In the same manner as in Example 113, except that the polymer Z2 was used instead of the polymer W, the ink and the organic thin film solar cell were prepared and evaluated. $J_{sc}$ (short-circuit current density) was 6.67 $mA/cm^2$; Voc (open-circuit voltage) was 0.71 V; ff (fill factor) was 0.66; and photoelectric conversion efficiency (η) was 3.11%. The result is listed in Table 6.

Example 116

In the same manner as in Example 113, except that the polymer Z3 was used instead of the polymer W, the ink and the organic thin film solar cell were prepared and evaluated. $J_{sc}$ (short-circuit current density) was 10.73 $mA/cm^2$; Voc (open-circuit voltage) was 0.58 V; ff (fill factor) was 0.65; and photoelectric conversion efficiency (η) was 4.02%. The result is listed in Table 6.

TABLE 6

| Photovoltaic Cell Evaluation Result | | | | | |
|---|---|---|---|---|---|
| | | Short-Circuit Current Density ($mA/cm^2$) | Open-Circuit Voltage (V) | Fill Factor | Photoelectric Conversion Efficiency (%) |
| Example 113 | Polymer X | 11.20 | 0.62 | 0.67 | 4.63 |
| Example 114 | Polymer Y | 5.00 | 0.69 | 0.56 | 1.96 |
| Example 115 | Polymer Z2 | 6.67 | 0.71 | 0.66 | 3.11 |
| Example 116 | Polymer Z3 | 10.73 | 0.58 | 0.65 | 4.02 |

The invention claimed is:

1. A macromolecular compound having a structural unit represented by Formula (2) and a structural unit represented by Formula 109:

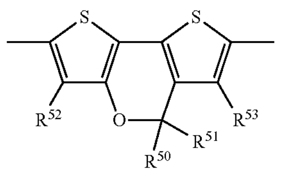

(2)

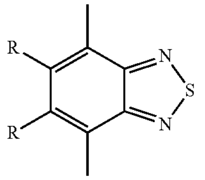

109 wherein $R^{50}$ represents an alkyl group; $R^{51}$ represents an alkyl group having 6 or more carbon atoms; $R^{52}$ and $R^{53}$ each represent a hydrogen atom;

wherein Rs are the same as or different from each other and represent a hydrogen atom or a substituent wherein Rs may be coupled with each other to form a cyclic structure.

2. The macromolecular compound according to claim 1, wherein a weight-average molecular weight in terms of polystyrene is 3,000 or more.

3. A thin film, comprising the macromolecular compound according to claim 1.

4. A composition, comprising:

the macromolecular compound according to claim 1; and an electron acceptor compound.

5. The composition according to claim 4, wherein the electron acceptor compound is a fullerene derivative.

6. A thin film, comprising the composition according to described in claim 4.

7. An ink, comprising:

the composition according to claim 4; and a solvent.

* * * * *